(12) United States Patent
Lindsley et al.

(10) Patent No.: US 11,299,481 B2
(45) Date of Patent: Apr. 12, 2022

(54) ANTAGONISTS OF THE MUSCARINIC ACETYLCHOLINE RECEPTOR M4

(71) Applicant: Vanderbilt University, Nashville, TN (US)

(72) Inventors: Craig W. Lindsley, Brentwood, TN (US); P. Jeffrey Conn, Nashville, TN (US); Darren W. Engers, Brentwood, TN (US); Julie L. Engers, Brentwood, TN (US); Kayla J. Temple, Spring Hill, TN (US); Aaron M. Bender, Spring Hill, TN (US); Logan A. Baker, Thompson's Station, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/757,245

(22) PCT Filed: Oct. 20, 2018

(86) PCT No.: PCT/US2018/056803
§ 371 (c)(1),
(2) Date: Apr. 17, 2020

(87) PCT Pub. No.: WO2019/079783
PCT Pub. Date: Apr. 25, 2019

(65) Prior Publication Data
US 2021/0188820 A1  Jun. 24, 2021

Related U.S. Application Data

(60) Provisional application No. 62/574,912, filed on Oct. 20, 2017.

(51) Int. Cl.
| | | |
|---|---|---|
| *C07D 403/14* | (2006.01) | |
| *C07D 209/52* | (2006.01) | |
| *C07D 401/14* | (2006.01) | |
| *C07D 403/12* | (2006.01) | |
| *C07D 405/14* | (2006.01) | |
| *C07D 413/14* | (2006.01) | |
| *C07D 417/12* | (2006.01) | |
| *C07D 471/04* | (2006.01) | |
| *C07D 493/08* | (2006.01) | |

(52) U.S. Cl.
CPC ......... *C07D 403/14* (2013.01); *C07D 209/52* (2013.01); *C07D 401/14* (2013.01); *C07D 403/12* (2013.01); *C07D 405/14* (2013.01); *C07D 413/14* (2013.01); *C07D 417/12* (2013.01); *C07D 471/04* (2013.01); *C07D 493/08* (2013.01)

(58) Field of Classification Search
CPC .. C07D 403/14; C07D 209/52; C07D 401/14; C07D 403/12; C07D 405/14; C07D 413/14; C07D 417/12; C07D 471/04; C07D 493/08
See application file for complete search history.

(56) References Cited

U.S. PATENT DOCUMENTS

| | | |
|---|---|---|
| 5,726,172 A | 3/1998 | Sparks et al. |
| 7,517,905 B2 | 4/2009 | Mehta et al. |
| 7,932,246 B2 | 4/2011 | Moffat et al. |
| 8,173,667 B2 | 5/2012 | Feuerbach et al. |
| 8,178,575 B2 | 5/2012 | Tang et al. |
| 2004/0044029 A1 | 3/2004 | Dart et al. |
| 2009/0258872 A1 | 10/2009 | Schwink et al. |
| 2014/0275011 A1 | 9/2014 | Mastracchio et al. |
| 2015/0284405 A1 | 10/2015 | Trzupek et al. |
| 2017/0145020 A1 | 5/2017 | Zak et al. |
| 2020/0339547 A1* | 10/2020 | Lindsley et al. ..... C07D 403/14 |

FOREIGN PATENT DOCUMENTS

| | | |
|---|---|---|
| CN | 103102352 A | 5/2013 |
| WO | 2004006846 A2 | 1/2004 |
| WO | 2004056811 A1 | 7/2004 |
| WO | 2006035280 A1 | 4/2006 |
| WO | 2006035282 A2 | 4/2006 |
| WO | 2007007281 A2 | 1/2007 |
| WO | 2007138431 A1 | 12/2007 |
| WO | 2008065500 A2 | 6/2008 |
| WO | 2005030140 A2 | 7/2011 |
| WO | 2011084796 A2 | 7/2011 |
| WO | 2015119899 A1 | 8/2015 |
| WO | 2016049165 A1 | 3/2016 |

(Continued)

OTHER PUBLICATIONS

PubChem CID 110134863—National Center for Biotechnology Information. PubChem Compound Summary for CID 110134863. https://pubchem.ncbi.nlm.nih.gov/compound/110134863. Accessed May 31, 2021, create date Jan. 18, 2016. (Year: 2016).*
European Patent Office Extended Search Report for Application No. 18869444.2 dated Apr. 14, 2021 (10 pages).
Dencker et al., "Muscarinic Acetylcholine Receptor Subtypes as Potential Drug Targets for the Treatment of Schizophrenia, Drug Abuse, and Parkinson's Disease", ACS Chemical Neuroscience, vol. 3, 2012, pp. 80-89.
PUBCHEM CID: 86299010, pp. 1-12, Create date: Dec. 31, 2014.
Croy et al., "Characterization of PCS1055, a novel muscarinic M4 receptor antagonist", European Journal of Pharmacology, vol. 782, 2016, pp. 70-76.

(Continued)

*Primary Examiner* — Laura L Stockton

(74) *Attorney, Agent, or Firm* — Michael Best & Friedrich LLP

(57) ABSTRACT

Disclosed herein are substituted hexahydro-1H-cyclopenta [c]pyrrole compounds, which may be useful as antagonists of the muscarinic acetylcholine receptor $M_4$ (mAChR $M_4$). Also disclosed herein are methods of making the compounds, pharmaceutical compositions comprising the compounds, and methods of treating disorders using the compounds and compositions.

20 Claims, No Drawings

(56) References Cited

FOREIGN PATENT DOCUMENTS

WO    2017079641 A1    5/2017
WO    2017143041 A1    8/2017

OTHER PUBLICATIONS

Betz et al., "The muscarinic receptor antagonist tropicamide suppresses tremulous jaw movements in a rodent model of parkinsonian termor: possible role of M4 receptors", Psychopharmacology, 2007, pp. 347-359.
Patent Cooperation Treaty Invitation to Pay Additional Fees for Application No. PCT/US2018/056803 dated Dec. 14, 2018 (3 pages).
International Search Report and Written Opinion for Application No. PCT/US2018/056803 dated Feb. 12, 2019 (15 pages).
International Preliminary Report on Patentability for Application No. PCT/US2018/056803 dated Apr. 21, 2020 (7 pages).

* cited by examiner

ANTAGONISTS OF THE MUSCARINIC ACETYLCHOLINE RECEPTOR M4

CROSS REFERENCE TO RELATED APPLICATIONS

This patent application is the U.S. national stage entry, under 35 U.S.C. § 371, of International Application Number PCT/US2018/056803, filed Oct. 20, 2018, which claims priority to U.S. Provisional Application No. 62/574,912, filed Oct. 20, 2017, the entire contents of each of which are hereby incorporated by reference.

TECHNICAL FIELD

The present disclosure relates to compounds, compositions, and methods for treating disorders associated with muscarinic acetylcholine receptor dysfunction.

BACKGROUND

Parkinson's disease (PD) is the second most common neurodegenerative disease with an increasing prevalence as a function of age. Moreover, early-onset PD is also increasing. A hallmark of PD is the progressive degeneration and loss of dopaminergic neurons in the substantia nigra (SN) and basal ganglia (BG), leading to pronounced motor symptoms including bradykinesia, tremor, rigidity, gait dysfunction and postural instability. At present, levodopa (L-DOPA) is the standard of care for treating the motor symptoms, but it is not curative, and prolonged use can engender L-DOPA induced dyskinesia (LID).

Prior to L-DOPA, compounds with anticholinergic activity represented the preferred mode of PD treatment. Cholinergic neurons provide important neuromodulatory control of the BG motor circuit. While the actions of cholinergic pathways on basal ganglia pathways are complex, activation of muscarinic acetylcholine receptors (mAChRs) generally have actions that oppose dopamine (DA) signaling. For instance, mAChR agonists inhibit DA release, and inhibit multiple behavioral effects of drugs that increase DA levels and signaling. Interestingly, muscarinic acetylcholine receptor (mAChR) antagonists were the first available treatments for PD and are still widely used for treatment of this disorder. While many studies of the actions of mAChR antagonists were carried out before randomized controlled trials were introduced, recent well controlled double-blind cross-over design studies demonstrate significant improvement in multiple aspects of motor function in patients receiving mAChR antagonists. Unfortunately, mAChR antagonists have a number of dose-limiting adverse effects that severely limit their clinical utility, including multiple peripheral adverse effects, as well as confusion and severe cognitive disturbances.

Because adverse effects associated with mAChR antagonists limit the doses that can be tolerated, previous clinical studies may underestimate the efficacy that could be achieved if doses of mAChR antagonists could be increased to achieve more complete blockade of specific mAChR subtypes responsible for the antiparkinsonian effects of these agents. The mAChRs include five subtypes, termed $M_1$-$M_5$. Available mAChR antagonists, such as scopolamine, are nonselective across these subtypes, and many of their adverse effects are likely mediated by mAChR subtypes that are not involved in the antiparkinsonian activity. Thus, compounds possessing a more selective profile for individual mAChRs may offer an advantage in PD, as well as related disorders such as dystonia. For example, some studies indicate that the $M_4$ mAChR subtype may play a dominant role in mAChR regulation of basal ganglia motor function.

SUMMARY

In one aspect, disclosed are compounds of formula (I),

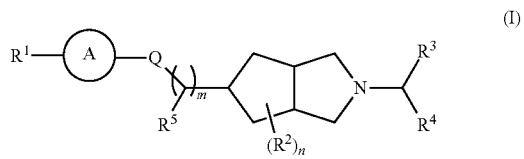

or a pharmaceutically acceptable salt thereof, wherein:

A is an arylene or a five- or six-membered heteroarylene having 1, 2, or 3 heteroatoms independently selected from N, O, and S;

Q is selected from $NR^a$, O, and —$NR^b$—C(O)—;

m is 0, 1, or 2;

$R^1$ is selected from heteroaryl, aryl, heterocyclyl, cycloalkyl, hydrogen, halo, —$OR^c$, —$NR^dR^e$, and —$NHCOR^f$;

n is 1 or 2;

each $R^2$ is independently selected from hydrogen, $C_1$-$C_4$ alkyl, halo, and —$OR^g$;

$R^3$ is selected from hydrogen and $C_1$-$C_4$ alkyl;

$R^4$ is selected from —$(CR^hR^i)_p$—Y', hydrogen, $C_1$-$C_8$ alkyl, and $C_2$-$C_8$ alkenyl;

$R^5$ is selected from hydrogen, $C_1$-$C_4$ alkyl, halo, $C_1$-$C_4$ haloalkyl, $C_1$-$C_4$ alkoxy, and $C_1$-$C_4$ haloalkoxy;

Y' is selected from cycloalkyl, cycloalkenyl, heterocycle, aryl, and heteroaryl;

each $R^a$, $R^b$, $R^c$, $R^d$, $R^e$, $R^f$, and $R^g$ is independently selected from hydrogen, $C_1$-$C_4$ alkyl, $C_3$-$C_6$ cycloalkyl, and aryl;

each $R^h$ is independently selected from hydrogen and $C_1$-$C_4$ alkyl;

each $R^i$ is independently selected from hydrogen, $C_1$-$C_4$ alkyl, $C_3$-$C_6$ cycloalkyl, and aryl; and p is 0, 1, 2, 3, or 4;

wherein each aryl, heteroaryl, arylene, heteroarylene, cycloalkyl, cycloalkenyl, and heterocycle is independently unsubstituted or substituted with 1-5 substituents.

In another aspect, the invention provides a pharmaceutical composition comprising a compound of formula (I), or a pharmaceutically acceptable salt thereof, and a pharmaceutically acceptable carrier.

In another aspect, the invention provides a method for the treatment of disorders associated with muscarinic acetylcholine receptor dysfunction, comprising administering to a subject in need thereof a therapeutically effective amount of a compound of formula (I), or a pharmaceutically acceptable salt or composition thereof.

In another aspect, the invention provides a method for antagonizing mAChR $M_4$ in a subject, comprising administering to the subject a therapeutically effective amount of a compound of formula (I), or a pharmaceutically acceptable salt or composition thereof.

In another aspect, the invention provides a method for the treatment of a neurodegenerative disorder, a movement disorder, or a brain disorder comprising administering to a subject in need thereof a therapeutically effective amount of a compound of formula (I), or a pharmaceutically acceptable salt or composition thereof.

In another aspect, the invention provides a compound of formula (I), or a pharmaceutically acceptable salt or composition thereof, for use in the treatment of a neurodegenerative disorder, a movement disorder, or a brain disorder.

In another aspect, the invention provides a compound of formula (I), or a pharmaceutically acceptable salt or composition thereof, for use in antagonizing mAChR $M_4$ in a subject.

In another aspect, the invention provides the use of a compound of formula (I), or a pharmaceutically acceptable salt or composition thereof, in the manufacture of a medicament for the treatment of a neurodegenerative disorder, a movement disorder, or a brain disorder.

In another aspect, the invention provides the use of a compound of formula (I), or a pharmaceutically acceptable salt or composition thereof, in the manufacture of a medicament for antagonizing mAChR $M_4$ in a subject.

In another aspect, the invention provides a kit comprising a compound of formula (I), or a pharmaceutically acceptable salt or composition thereof, and instructions for use.

Also disclosed are pharmaceutical compositions comprising the compounds, methods of making the compounds, kits comprising the compounds, and methods of using the compounds, compositions and kits for treatment of disorders, such as neurological and/or psychiatric disorders, associated with muscarinic acetylcholine receptor dysfunction in a mammal.

DETAILED DESCRIPTION

Disclosed herein are compounds that are antagonists of the muscarinic acetylcholine receptor $M_4$ (mAChR $M_4$), methods of making the compounds, pharmaceutical compositions comprising the compounds, and methods of treating disorders using the compounds and pharmaceutical compositions. The compounds include substituted hexahydro-1H-cyclopenta[c]pyrrole compounds.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, isopropyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, 4,4-dimethylpentan-2-yl, n-heptyl, n-octyl, n-nonyl, and n-decyl.

The term "alkenyl," as used herein, means a straight or branched, hydrocarbon chain containing at least one carbon-carbon double bond and from 2 to 10 carbon atoms.

The term "alkoxyalkyl," as used herein, refers to an alkoxy group, as defined herein, appended to the parent molecular moiety through an alkyl group, as defined herein.

The term "alkoxyfluoroalkyl," as used herein, refers to an alkoxy group, as defined herein, appended to the parent molecular moiety through a fluoroalkyl group, as defined herein.

The term "alkylene," as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH(CH_3)CH_2$—, —$CH_2CH_2CH_2CH_2$—, —$CH_2CH(CH_3)CH_2CH_2$—, and —$CH_2CH_2CH_2CH_2CH_2$—.

The term "alkylamino," as used herein, means at least one alkyl group, as defined herein, is appended to the parent molecular moiety through an amino group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino," as used herein, means —NR$_x$R$_y$, wherein R$_x$ and R$_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —NR$_x$—, wherein R$_x$ may be hydrogen, alkyl, cycloalkyl, aryl, heteroaryl, heterocycle, alkenyl, or heteroalkyl.

The term "aryl," as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, benzodioxolyl, and tetrahydroquinolinyl.

The term "cyanoalkyl," as used herein, means at least one —CN group, is appended to the parent molecular moiety through an alkylene group, as defined herein.

The term "cyanofluoroalkyl," as used herein, means at least one —CN group, is appended to the parent molecular moiety through a fluoroalkyl group, as defined herein.

The term "cycloalkoxy," as used herein, refers to a cycloalkyl group, as defined herein, appended to the parent molecular moiety through an oxygen atom.

The term "cycloalkyl," as used herein, refers to a carbocyclic ring system containing three to ten carbon atoms, zero heteroatoms and zero double bonds. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl. "Cycloalkyl" also includes carbocyclic ring systems in which a cycloalkyl group is appended to the parent molecular moiety and is fused to an aryl group as defined herein (e.g., a phenyl group), a heteroaryl group as defined herein, or a heterocycle as defined herein. Representative examples of such cycloalkyl groups include, but are not limited to, 2,3-dihydro-1H-indenyl (e.g., 2,3-dihydro-1H-inden-1-yl and 2,3-dihydro-1H-inden-2-yl), 6,7-dihydro-5H-cyclopenta[b]pyridinyl (e.g., 6,7-dihydro-5H-cyclopenta[b]pyridin-6-yl), oxaspiro[3.3]heptanyl (e.g., 2-oxaspiro[3.3]heptan-6-yl), and 5,6,7,8-tetrahydroquinolinyl (e.g., 5,6,7,8-tetrahydroquinolin-5-yl).

The term "cycloalkenyl," as used herein, means a non-aromatic monocyclic or multicyclic ring system containing at least one carbon-carbon double bond and preferably having from 5-10 carbon atoms per ring. The cycloalkenyl may be monocyclic, bicyclic, bridged, fused, or spirocyclic. Exemplary monocyclic cycloalkenyl rings include cyclopentenyl, cyclohexenyl, cycloheptenyl, and bicyclo[2.2.1]heptenyl.

The term "fluoroalkyl," as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "fluoroalkoxy," as used herein, means at least one fluoroalkyl group, as defined herein, is appended to the parent molecular moiety through an oxygen atom. Representative examples of fluoroalkoxy include, but are not limited to, difluoromethoxy, trifluoromethoxy and 2,2,2-trifluoroethoxy.

The term "halogen" or "halo," as used herein, means C$_1$, Br, I, or F.

The term "haloalkyl," as used herein, means an alkyl group, as defined herein, in which one, two, three, four, five, six, seven or eight hydrogen atoms are replaced by a halogen.

The term "haloalkoxy," as used herein, means at least one haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroalkyl," as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic ring or an aromatic bicyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a) a monocyclic cycloalkyl group, as defined herein; b) a monocyclic aryl group, as defined herein; c) a monocyclic heteroaryl group, as defined herein; d) or a monocyclic heterocycle, as defined herein; or the bicyclic heteroaryl group is exemplified by a 9-membered fused bicyclic aromatic ring system having four double bonds and a nitrogen atom at the ring junction (e.g., imidazopyridine). Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl, naphthyridinyl, pyridoimidazolyl, thiazolo[5,4-b]pyridin-2-yl, thiazolo[5,4-d]pyrimidin-2-yl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), oxabicyclo[2.2.1]heptanyl (including 7-oxabicyclo[2.2.1]heptan-3-yl) azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1³,⁷]decane), and oxa-adamantane (2-oxatricyclo[3.3.1.1³,⁷]decane). The monocyclic, bicyclic, and tricyclic heterocycles are connected to the parent molecular moiety through any carbon atom or any nitrogen atom contained within the rings, and can be unsubstituted or substituted.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxyfluoroalkyl," as used herein, means at least one —OH group, is appended to the parent molecular moiety through a fluoroalkyl group, as defined herein.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "sulfonamide," as used herein, means —S(O)$_2$NR— or —NRS(O)—, wherein R may be hydrogen, alkyl, cycloalkyl, aryl, heteroaryl, heterocycle, alkenyl, or heteroalkyl.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl. For example, if a group is described as being "optionally substituted" (such as an alkyl, alkenyl, alkynyl, aryl, heteroaryl, cycloalkyl, heteroalkyl, heterocycle or other group such as an R group), it may have 0, 1, 2, 3, 4 or 5 substituents independently selected from halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

The term "═══" designates a single bond (—) or a double bond (═).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The term "mAChR $M_4$ receptor antagonist" as used herein refers to any exogenously administered compound or agent that directly or indirectly antagonizes mAChR $M_4$, for example in an animal, in particular a mammal (e.g., a human).

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

In one aspect, disclosed is a compound of formula (I):

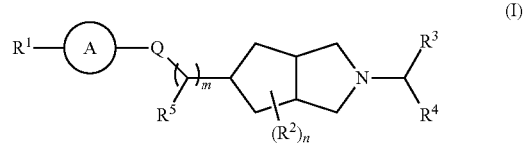

(I)

or a pharmaceutically acceptable salt thereof, wherein:

A is an arylene or a five- or six-membered heteroarylene having 1, 2, or 3 heteroatoms independently selected from N, O, and S;

Q is selected from NR$^a$, O, and —NR$^b$—C(O)—;

m is 0, 1, or 2;

R$^1$ is selected from heteroaryl, aryl, heterocyclyl, cycloalkyl, hydrogen, halo, —OR, —NR$^d$R$^e$, and —NHCOR$^f$;

n is 1 or 2;

each R$^2$ is independently selected from hydrogen, C$_1$-C$_4$ alkyl, halo, and —OR$^g$;

R$^3$ is selected from hydrogen and C$_1$-C$_4$ alkyl;

R$^4$ is selected from —(CR$^h$R$^i$)$_p$—Y', hydrogen, C$_1$-C$_8$ alkyl, and C$_2$-C$_8$ alkenyl;

R$^5$ is selected from hydrogen, C$_1$-C$_4$ alkyl, halo, C$_1$-C$_4$ haloalkyl, C$_1$-C$_4$ alkoxy, and C$_1$-C$_4$ haloalkoxy;

Y' is selected from cycloalkyl, cycloalkenyl, heterocycle, aryl, and heteroaryl; each R$^a$, R$^b$, R$^c$, R$^d$, R$^e$, R$^f$, and R$^g$ is independently selected from hydrogen, C$_1$-C$_4$ alkyl, C$_3$-C$_6$ cycloalkyl, and aryl;

each R$^h$ is independently selected from hydrogen and C$_1$-C$_4$ alkyl;

each R$^i$ is independently selected from hydrogen, C$_1$-C$_4$ alkyl, C$_3$-C$_6$ cycloalkyl, and aryl; and p is 0, 1, 2, 3, or 4;

wherein each aryl, heteroaryl, arylene, heteroarylene, cycloalkyl, cycloalkenyl, and heterocycle is independently unsubstituted or substituted with 1-5 substituents.

In some embodiments, each aryl, heteroaryl, arylene, heteroarylene, cycloalkyl, cycloalkenyl, and heterocycle in formula (I) is independently unsubstituted or substituted with 1, 2, or 3 substituents. In some embodiments, each aryl, heteroaryl, arylene, heteroarylene, cycloalkyl, cycloalkenyl, and heterocycle is independently unsubstituted or substituted with 1, 2, or 3 substituents independently selected from C$_1$-C$_4$ alkyl, halo, C$_1$-C$_4$ haloalkyl, C$_1$-C$_4$ alkoxy, C$_1$-C$_4$ haloalkoxy, C$_1$-C$_4$ hydroxyalkyl, hydroxy, cyano, —NHCOR$^f$, and benzyl.

In some embodiments, A is selected from:

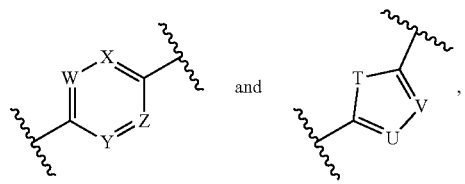

wherein:

T is selected from O, S, and NH;

U, V, W, X, Y, and Z are independently selected from N and CR; and each R$^j$ is independently selected from hydrogen, C$_1$-C$_4$ alkyl, halo, C$_1$-C$_4$ haloalkyl, C$_1$-C$_4$ alkoxy, C$_1$-C$_4$ haloalkoxy, and hydroxy.

In some embodiments, A is

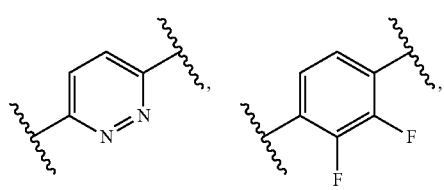

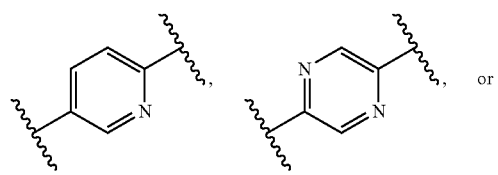

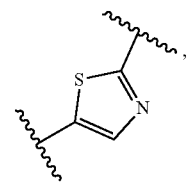

wherein R$^1$-A- is, respectively,

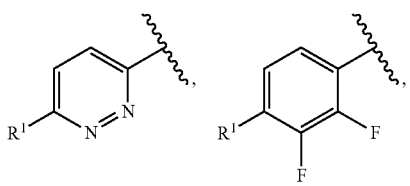

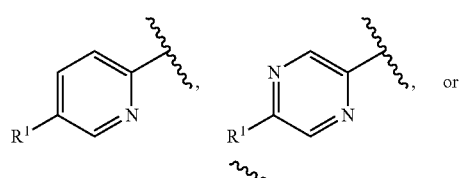

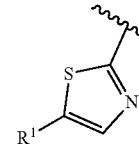

In some embodiments, A is selected from:

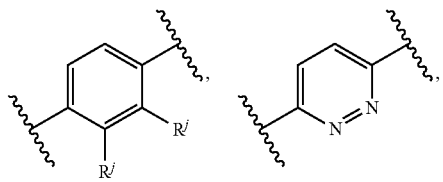

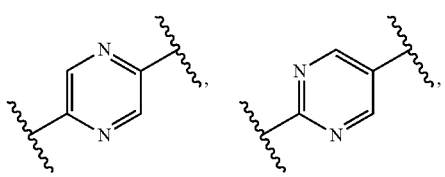

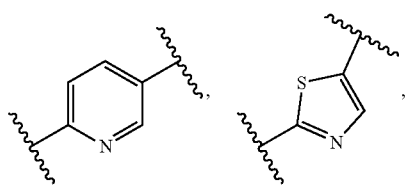

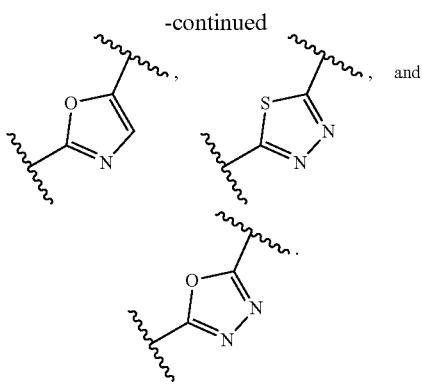

In some embodiments, A is:

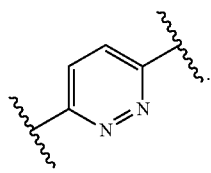 [SMILES: *c1ccc(*)nn1]

In some embodiments, Q is NR$^a$, and R$^a$ is hydrogen.

In some embodiments, Q is O.

In some embodiments, Q is —NR$^b$—C(O)—, and R$^b$ is hydrogen.

In some embodiments, Q is selected from NR$^a$ and O, wherein R$^a$ is hydrogen.

In some embodiments, m is 0.

In some embodiments, m is 1.

In some embodiments, m is 2.

In some embodiments, m is 1, and R$^5$ is hydrogen.

In some embodiments, m is 2, and each R$^5$ is hydrogen.

In the embodiments herein, R$^1$ may be heteroaryl, aryl, heterocyclyl, halo, or —OR$^c$; wherein R$^c$ is C$_1$-C$_4$ alkyl, C$_3$-C$_6$ cycloalkyl, or aryl; the heteroaryl, aryl, heterocyclyl, and cycloalkyl in R$^1$ and/or R$^c$ is optionally substituted with 1-4 substituents independently selected from the group consisting of halo (e.g., fluoro, chloro), cyano, C$_1$-C$_4$ alkyl (e.g., methyl, ethyl), C$_1$-C$_4$ haloalkyl (e.g., CF$_3$), —OR$^{10}$ (e.g., —OC$_1$-C$_4$ alkyl such as methoxy, —OC$_1$-C$_4$ haloalkyl such as difluoromethoxy), —NR$^{10}$R$^{10}$, —NR$^{10}$COR$^{10}$ (e.g., —NHCOC$_1$-C$_4$ alkyl such —NHCOCH$_3$), —CONR$^{10}$R$^{10}$ (e.g., —CON(C$_1$-C$_4$ alkyl)$_2$ such as —CON(CH$_3$)$_2$), —NR$^{10}$SO$_2$R$^{11}$ (e.g., —NHSO$_2$C$_1$-C$_4$ alkyl such —NHSO$_2$CH$_3$), —C$_1$-C$_3$alkylene-OR$^{10}$ (e.g., —C$_1$-C$_3$alkylene-OH such as —C(CH$_3$)$_2$OH), C$_3$-C$_6$ cycloalkyl (e.g., cyclopropyl), and —C$_1$-C$_3$alkylene-C$_3$-C$_6$cycloalkyl; R$^{10}$, at each occurrence, is independently hydrogen, C$_1$-C$_4$ alkyl (e.g., methyl, ethyl), C$_1$-C$_4$ haloalkyl (e.g., difluoromethyl), C$_3$-C$_6$ cycloalkyl (cyclopropyl), or —C$_1$-C$_3$alkylene-C$_3$-C$_6$ cycloalkyl; and R$^{11}$, at each occurrence, is independently C$_1$-C$_4$ alkyl (e.g., methyl, ethyl), C$_1$-C$_4$ haloalkyl, C$_3$-C$_6$ cycloalkyl, or —C$_1$-C$_3$alkylene-C$_3$-C$_6$ cycloalkyl.

In the embodiments herein, R$^1$ may be a) a 5- to 12-membered heteroaryl; b) a 6- to 12-membered aryl; c) a 4- to 12-membered heterocyclyl; d) halo; or e) —OR$^c$; wherein R$^c$ is a 6- to 12-membered aryl; the heteroaryl, aryl, and heterocyclyl in R$^1$ and/or R$^c$ is optionally substituted with 1-4 substituents independently selected from the group consisting of halo, cyano, C$_1$-C$_4$ alkyl, C$_1$-C$_4$ haloalkyl, —OR$^{10}$, —NR$^{10}$R$^{10}$, —NR$^{10}$COR$^{10}$, —CONR$^{10}$R$^{10}$, —NR$^{10}$SO$_2$R$^{11}$, —C$_1$-C$_3$alkylene-OR$^{10}$, C$_3$-C$_6$ cycloalkyl, and —C$_1$-C$_3$alkylene-C$_3$-C$_6$cycloalkyl; and R$^{10}$ and R$^{11}$ are as defined herein.

In the embodiments herein, R$^1$ may be a 5- to 6-membered monocyclic heteroaryl or an 8- to 12 membered bicyclic heteroaryl, and R$^1$ is optionally substituted with 1-4 substituents independently selected from the group consisting of halo, cyano, C$_1$-C$_4$ alkyl, C$_1$-C$_4$ haloalkyl, —OR$^{10}$, —NR$^{10}$R$^{10}$, —NR$^{10}$COR$^{10}$, —CONR$^{10}$R$^{10}$, —NR$^{10}$SO$_2$R$^{11}$, —C$_1$-C$_3$alkylene-OR$^{10}$, C$_3$-C$_6$ cycloalkyl, and —C$_1$-C$_3$alkylene-C$_3$-C$_6$cycloalkyl; and R$^{10}$ and R$^{11}$ are as defined herein. The 5- to 6-membered monocyclic heteroaryl may have 1-3 ring heteroatoms independently selected from the group consisting of O, N, and S. The 8- to 12-membered bicyclic heteroaryl may have 1-3 ring heteroatoms independently selected from the group consisting of O, N, and S. In the embodiments herein, R$^1$ may be a pyrrolyl, pyrazolyl, furanyl, thienyl, isoxazolyl, pyridinyl, or imidazopyridinyl, and R$^1$ is optionally substituted with 1-4 substituents independently selected from the group consisting of halo, cyano, C$_1$-C$_4$ alkyl, C$_1$-C$_4$ haloalkyl, —OR$^{10}$, —NR$^{10}$R$^{10}$, —NR$^{10}$COR$^{10}$, —CONR$^{10}$R$^{10}$, —NR$^{10}$SO$_2$R$^{11}$, —C$_1$-C$_3$alkylene-OR$^{10}$, C$_3$-C$_6$ cycloalkyl, and —C$_1$-C$_3$alkylene-C$_3$-C$_6$cycloalkyl; and R$^{10}$ and R$^{11}$ are as defined herein. In the embodiments herein, the heteroaryl described herein at R$^1$ is optionally substituted with 1-3 substituents independently selected from the group consisting of halo, C$_1$-C$_4$ alkyl, C$_1$-C$_4$ haloalkyl, C$_3$-C$_6$ cycloalkyl, and —OR$^{10}$. In the embodiments herein, R$^1$ may be

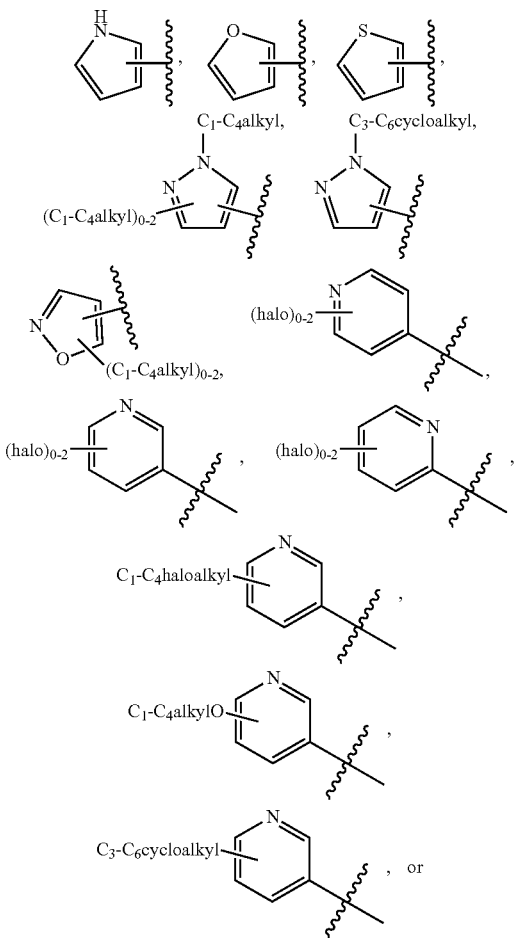

-continued

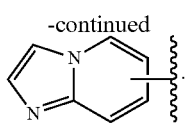

In the embodiments herein, R¹ may be

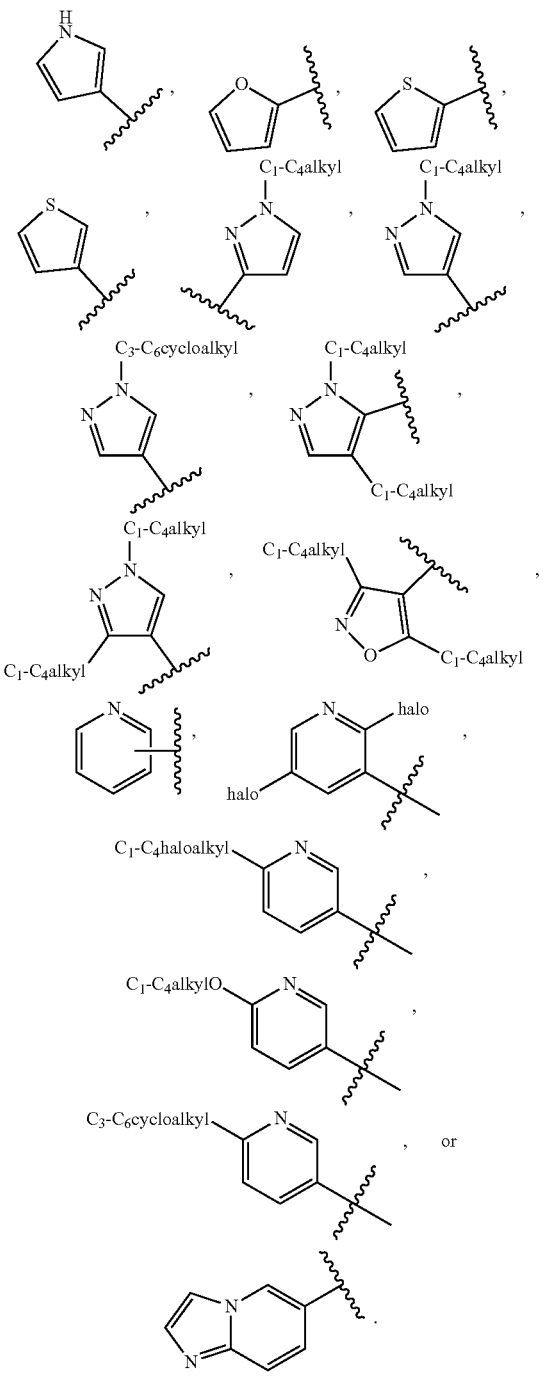

In the embodiments herein, R¹ may be a phenyl or a 9- to 12-membered aryl, and R¹ is optionally substituted with 1-4 substituents independently selected from the group consisting of halo, cyano, $C_1$-$C_4$ alkyl, $C_1$-$C_4$ haloalkyl, —$OR^{10}$, —$NR^{10}R^{10}$, —$NR^{10}COR^{10}$, —$CONR^{10}R^{10}$, —$NR^{10}SO_2R^{11}$, —$C_1$-$C_3$alkylene-$OR^{10}$, $C_3$-$C_6$ cycloalkyl, and —$C_1$-$C_3$alkylene-$C_3$-$C_6$cycloalkyl; and $R^{10}$ and $R^{11}$ are as defined herein. In the embodiments herein, R¹ may be phenyl,

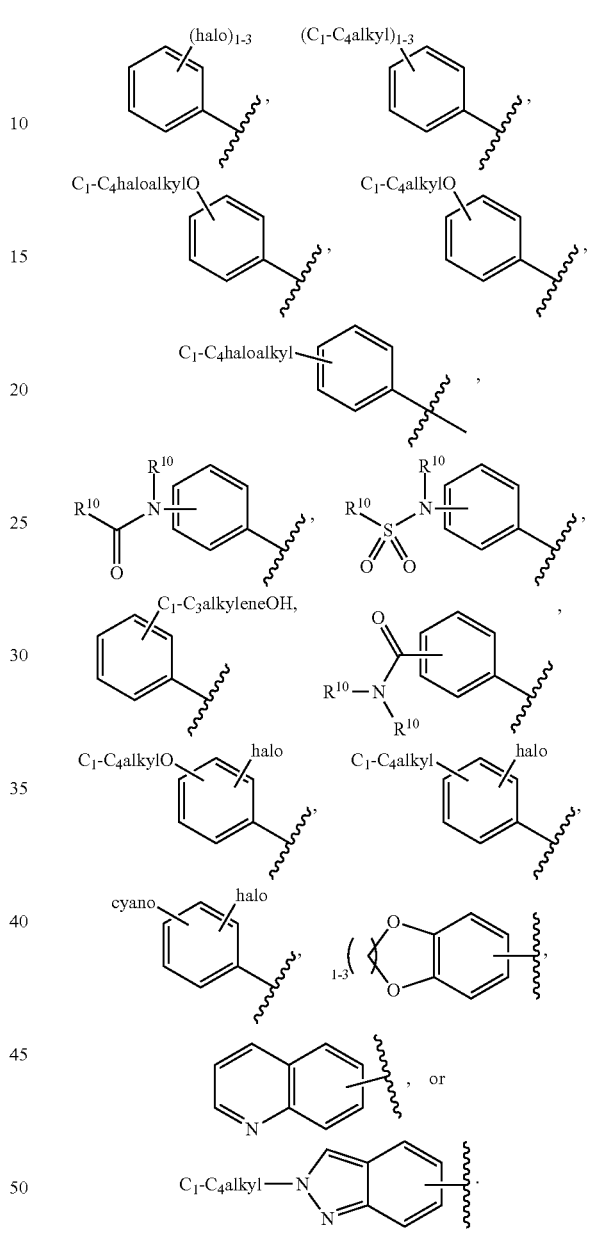

In the embodiments herein, R¹ may be phenyl,

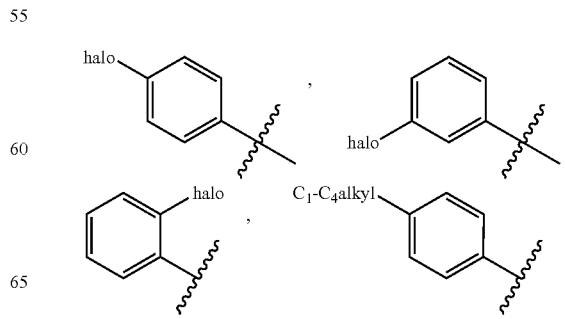

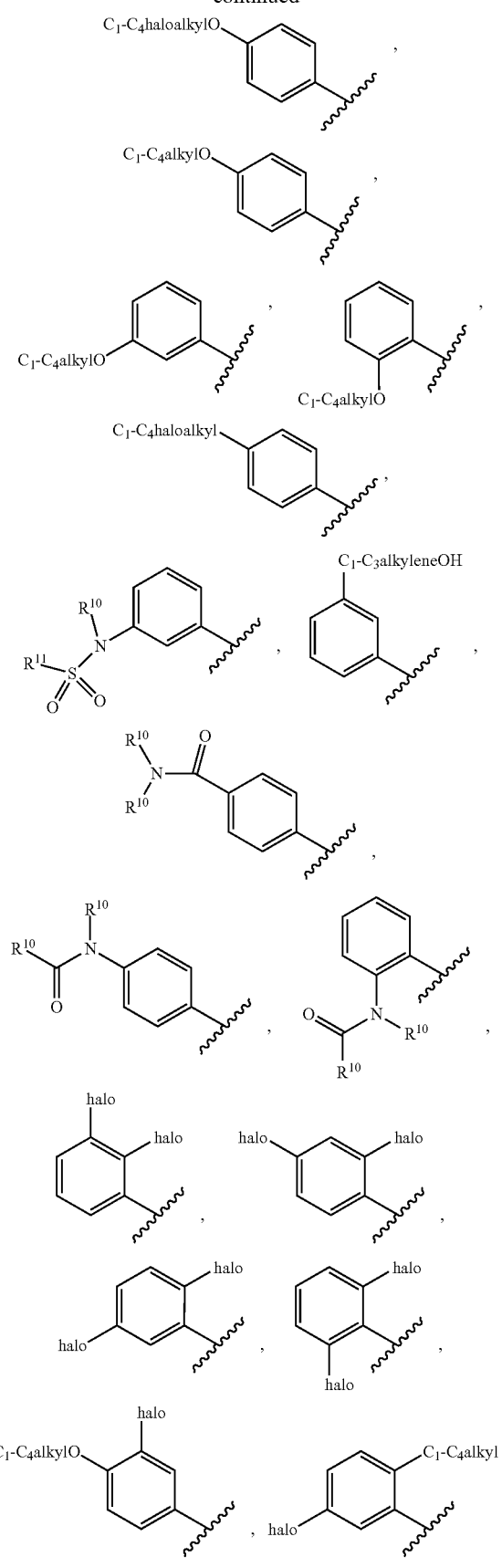

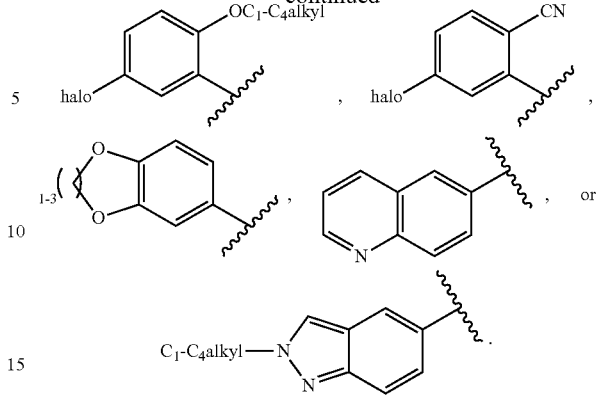

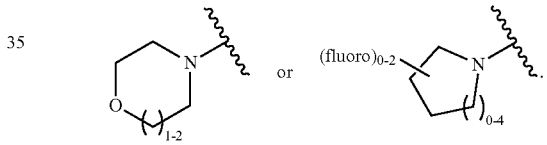

In the embodiments herein, $R^1$ may be a 4- to 8-membered heterocyclic ring optionally substituted with 1-4 substituents independently selected from the group consisting of halo, cyano, $C_1$-$C_4$ alkyl, $C_1$-$C_4$ haloalkyl, —$OR^{10}$, —$NR^{10}R^{10}$, —$NR^{10}COR^{10}$, —$CONR^{10}R^{10}$, —$NR^{10}SO_2R^{11}$, —$C_1$-$C_3$alkylene-$OR^{10}$, $C_3$-$C_6$ cycloalkyl, and —$C_1$-$C_3$alkylene-$C_3$-$C_6$cycloalkyl; and $R^{10}$ and $R^{11}$ are as defined herein. In the embodiments herein, $R^1$ may be pyrrolindinyl (e.g., pyrrolidin-1-yl), piperidinyl (piperidin-1-yl), or morpholino (e.g., morpholin-4-yl), optionally with 1-3 substituents independently selected from the group consisting of halo, $C_1$-$C_4$ alkyl, $C_1$-$C_4$ haloalkyl, $C_3$-$C_6$ cycloalkyl, and —$OR^{10}$. In the embodiments herein, $R^1$ may be In the embodiments herein, $R^1$ may be chloro.

In the embodiments herein, $R^1$ may be —$OR^c$, wherein $R^c$ is as defined herein. $R^c$ may be phenyl optionally substituted with 1-3 substituents independently selected from the group consisting of halo, cyano, $C_1$-$C_4$ alkyl, $C_1$-$C_4$ haloalkyl, —$OR^{10}$, —$NR^{10}R^{10}$, —$NR^{10}COR^{10}$, —$CONR^{10}R^{10}$, —$NR^{10}SO_2R^{11}$, —$C_1$-$C_3$alkylene-$OR^{10}$, $C_3$-$C_6$ cycloalkyl, and —$C_1$-$C_3$alkylene-$C_3$-$C_6$cycloalkyl. $R^c$ may be phenyl optionally substituted with 1-3 halo substituents (e.g., 4-fluorophenyl).

In some embodiments, $R^1$ is selected from aryl (e.g., phenyl or benzodioxolyl), heteroaryl (e.g., 5- or 6-membered heteroaryl having 1, 2, or 3 heteroatoms independently selected from N, O, and S, such as pyrazolyl or isoxazolyl), heterocyclyl (e.g., a 5- or 6-membered heterocycle having 1, 2, or 3 heteroatoms independently selected from N, O, and S, such as morpholino), and cycloalkyl (e.g., a $C_3$-$C_7$ cycloalkyl).

In some embodiments, $R^1$ is selected from phenyl, a 5- or 6-membered heteroaryl having 1, 2, or 3 heteroatoms independently selected from N, O, and S, and a 5- or 6-membered heterocycle having 1, 2, or 3 heteroatoms independently selected from N, O, and S, and the phenyl, heteroaryl, or heterocycle is unsubstituted or substituted with 1, 2, or 3 substituents independently selected from halo, $C_1$-$C_4$ alkyl, $C_1$-$C_4$ haloalkyl, and —$NHCOR^f$.

In some embodiments, $R^1$ is phenyl that is unsubstituted or substituted with 1, 2, or 3 substituents independently selected from halo, $C_1$-$C_4$ alkyl, $C_1$-$C_4$ haloalkyl, and —NHCOR$^f$. In some embodiments, $R^1$ is phenyl that is substituted with 1 or 2 substituents independently selected from halo, $C_1$-$C_4$ haloalkyl, and —NHCOR$^f$. In some embodiments, $R^1$ is phenyl that is substituted with fluoro and chloro. In some embodiments, $R^1$ is 2-chloro-5-fluoro-phenyl. In some embodiments, $R^1$ is phenyl that is substituted with an acetamido group. In some embodiments, $R^1$ is phenyl that is substituted with a trifluoromethyl group.

In some embodiments, $R^1$ is a 5- or 6-membered heteroaryl having 1, 2, or 3 heteroatoms independently selected from N, O, and S, is unsubstituted or substituted with 1, 2, or 3 substituents independently selected from halo, $C_1$-$C_4$ alkyl, $C_1$-$C_4$ haloalkyl, and —NHCOR$^f$. In some embodiments, $R^1$ is a 5-membered heteroaryl having 1, 2, or 3 heteroatoms independently selected from N and O, is substituted with 1, 2, or 3 substituents independently selected from halo, $C_1$-$C_4$ alkyl, $C_1$-$C_4$ haloalkyl, and —NHCOR$^f$. In some embodiments, $R^1$ is selected from pyrazolyl and isoxazolyl, each of which is substituted with two substituents independently selected from $C_1$-$C_4$ alkyl. In some embodiments, $R^1$ is selected from 2,4-dimethylpyrazol-3-yl, 1,3-dimethylpyrazol-4-yl, and 3,5-dimethylisoxazolyl.

In some embodiments, $R^1$ is morpholino.

In some embodiments, n is 1, and $R^2$ is hydrogen.

In some embodiments, $R^3$ is hydrogen.

In some embodiments, $R^4$ is selected from —(CR$^h$R$^i$)$_p$—Y', and $C_1$-$C_8$ alkyl.

In some embodiments, $R^4$ is $C_1$-$C_8$ alkyl, such as $C_4$-$C_6$ alkyl. In some embodiments, $R^4$ is selected from 2,2-dimethylpropyl, 3,3-dimethylbutan-2-yl, pentan-2-yl, and sec-butyl.

In some embodiments: $R^4$ is —(CR$^h$R$^i$)$_p$Y'; R$^h$ is hydrogen; R$^i$ is hydrogen; p is 0, 1, 2, or 3; and Y' is selected from: $C_3$-$C_{10}$ cycloalkyl, $C_3$-$C_8$ cycloalkenyl, aryl, a 5- or 6-membered heteroaryl having 1, 2, or 3 heteroatoms independently selected from N, O, and S, and a 5-, 6-, or 7-membered heterocycle having 1, 2, or 3 heteroatoms independently selected from N, O, and S; wherein Y' is unsubstituted or substituted with one or two substituents independently selected from halo and $C_1$-$C_4$ alkyl. In some embodiments, Y' is $C_3$-$C_{10}$ cycloalkyl (e.g., cyclohexyl, cycloheptyl, or adamantyl). In some embodiments, Y' is $C_3$-$C_8$ cycloalkenyl (e.g., bicyclo[2.2.1]heptenyl). In some embodiments, Y' is aryl (e.g., phenyl or benzodioxolyl), which may be unsubstituted or substituted with 1 or 2 substituents independently selected from halo (e.g., fluoro) and $C_1$-$C_4$ alkyl (e.g., methyl). In some embodiments, Y' is a 5- or 6-membered heteroaryl having 1, 2, or 3 heteroatoms independently selected from N, O, and S (e.g., pyridyl) which is unsubstituted or substituted with 1 or 2 substituents independently selected from halo (e.g., fluoro) and $C_1$-$C_4$ alkyl (e.g., methyl). In some embodiments, Y' is a 5-, 6-, or 7-membered heterocycle having 1, 2, or 3 heteroatoms independently selected from N, O, and S (e.g., tetrahydropyranyl or oxabicyclo[2.2.1]heptanyl).

In the embodiments herein, $R^4$ may be —(CR$^h$R$^i$)$_p$—Y'; wherein R$^h$ is hydrogen; R$^i$ is hydrogen; p is 0, 1, 2, or 3; Y' is a) $C_3$-$C_{10}$ cycloalkyl; b) $C_3$-$C_8$ cycloalkenyl; c) a 6- to 12-membered aryl; d) a 5- to 12-membered heteroaryl; or e) a 4- to 12-membered heterocyclyl; wherein Y' is optionally substituted with 1-4 substituents independently selected from the group consisting of halo, $C_1$-$C_4$ alkyl, $C_1$-$C_4$ haloalkyl, —OR$^{11}$, —NR$^{12}$R$^{12}$, —NR$^{12}$COR$^{12}$, —NR$^{12}$SO$_2$R$^{13}$; R$^{12}$, at each occurrence, is independently hydrogen, $C_1$-$C_4$ alkyl, $C_1$-$C_4$ haloalkyl, $C_3$-$C_6$ cycloalkyl, or —$C_1$-$C_3$alkylene-$C_3$-$C_6$ cycloalkyl; and R$^{13}$, at each occurrence, is independently $C_1$-$C_4$ alkyl, $C_1$-$C_4$ haloalkyl, $C_3$-$C_6$ cycloalkyl, or —$C_1$-$C_3$alkylene-$C_3$-$C_6$ cycloalkyl. In the embodiments herein p may be 0.

In the embodiments herein Y' may be $C_3$-$C_{10}$ cycloalkyl (e.g., cyclopropyl, cyclohexyl, cycloheptyl, adamantyl) optionally substituted with 1-4 substituents independently selected from the group consisting of halo, $C_1$-$C_4$ alkyl, and $C_1$-$C_4$ haloalkyl.

In the embodiments herein Y' may be $C_3$-$C_8$ cycloalkenyl (e.g., bicyclo[2.2.1]heptenyl).

In the embodiments herein, Y' may be phenyl or a 9- to 12-membered aryl, and optionally substituted with 1-4 substituents independently selected from the group consisting of halo, $C_1$-$C_4$ alkyl, $C_1$-$C_4$ haloalkyl, —OR$^{12}$, —NR$^{12}$R$^{12}$, —NR$^{12}$COR$^{12}$, —NR$^{12}$SO$_2$R$^{13}$, wherein $R^{12}$ and $R^{13}$ are as defined herein. In the embodiments herein, Y' may be

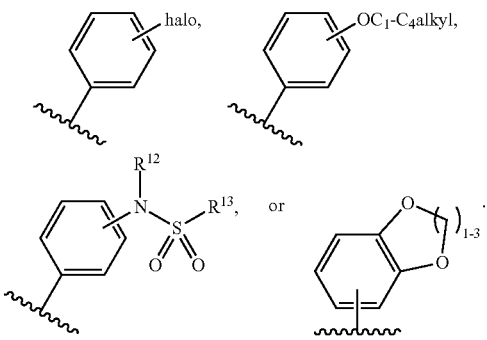

In the embodiments herein, Y' may be

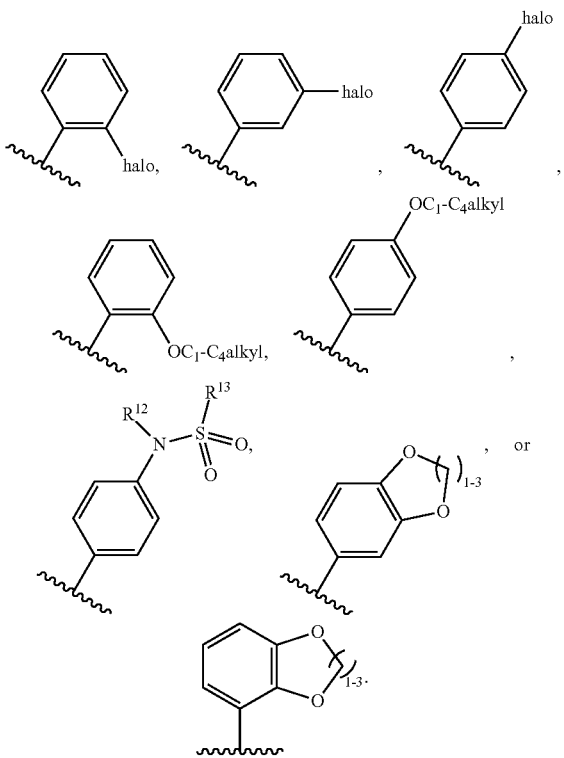

In the embodiments herein, Y' may be a 5- to 6-membered monocyclic heteroaryl or an 8- to 12 membered bicyclic heteroaryl, and optionally substituted with 1-4 substituents independently selected from the group consisting of halo, $C_1$-$C_4$ alkyl, $C_1$-$C_4$ haloalkyl, —$OR^{12}$, —$NR^{12}R^{12}$, —$NR^{12}COR^{12}$, and —$NR^{12}SO_2R^{13}$. In the embodiments herein, Y' may be

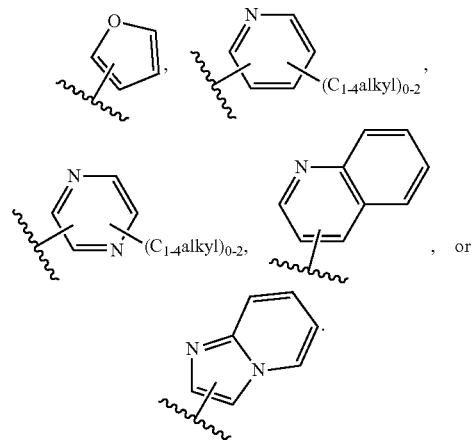

In the embodiments herein, Y' may be

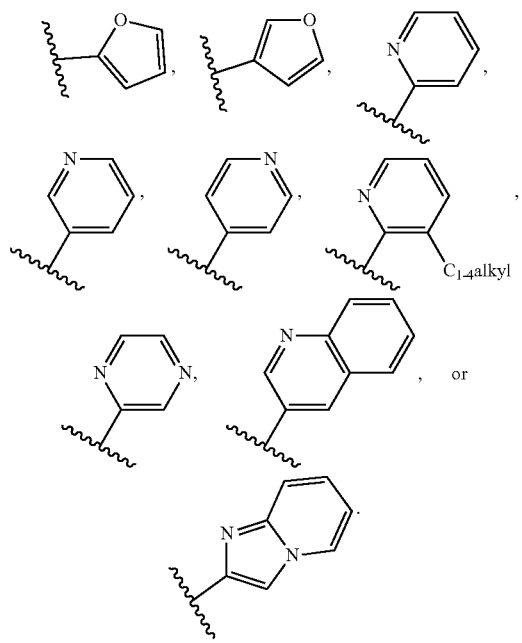

In the embodiments herein, Y' may be 4- to 10-membered monocyclic or bridged bicyclic heterocyclyl containing one oxygen atom and optionally substituted with 1-2 $C_1$-$C_4$alkyl. In the embodiments herein, Y' may be

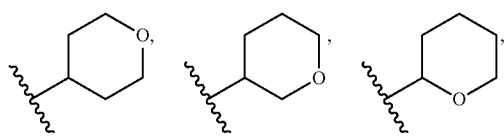

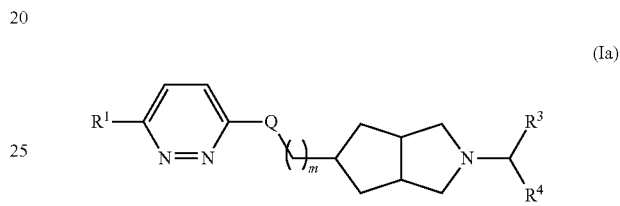

In some embodiments, each aryl, heteroaryl, arylene, heteroarylene, cycloalkyl, cycloalkenyl, and heterocycle is independently unsubstituted or substituted with 1, 2, or 3 substituents independently selected from $C_1$-$C_4$ alkyl, halo, $C_1$-$C_4$ haloalkyl, $C_1$-$C_4$ alkoxy, $C_1$-$C_4$ haloalkoxy, $C_1$-$C_4$ hydroxyalkyl, hydroxy, cyano, —$NHCOR^f$, and benzyl.

In some embodiments, each $R^5$ is hydrogen.

In some embodiments, disclosed is a compound of formula (Ia):

$$R^1 \underset{N=N}{\overset{}{\bigcirc}} Q(\phantom{x})_m \phantom{xxx} N\underset{R^4}{\overset{R^3}{}} \quad \text{(Ia)}$$

or a pharmaceutically acceptable salt thereof, wherein and m, $R^1$, $R^3$, and $R^4$ are as described herein.

In some embodiments, Q is $NR^a$, and $R^a$ is hydrogen.

In some embodiments, Q is O.

In some embodiments, Q is —$NR^b$—C(O)—, and $R^b$ is hydrogen.

In some embodiments, Q is selected from $NR^a$ and O, wherein $R^a$ is hydrogen.

In some embodiments, m is 0.

In some embodiments, m is 1.

In some embodiments, m is 2.

In some embodiments, $R^1$ is selected from aryl (e.g., phenyl or benzodioxolyl), heteroaryl (e.g., 5- or 6-membered heteroaryl having 1, 2, or 3 heteroatoms independently selected from N, O, and S, such as pyrazolyl or isoxazolyl), heterocyclyl (e.g., a 5- or 6-membered heterocycle having 1, 2, or 3 heteroatoms independently selected from N, O, and S, such as morpholino), and cycloalkyl (e.g., a $C_3$-$C_7$ cycloalkyl).

In some embodiments, $R^1$ is selected from phenyl, a 5- or 6-membered heteroaryl having 1, 2, or 3 heteroatoms independently selected from N, O, and S, and a 5- or 6-membered heterocycle having 1, 2, or 3 heteroatoms independently selected from N, O, and S, and the phenyl, heteroaryl, or heterocycle is unsubstituted or substituted with 1, 2, or 3 substituents independently selected from halo, $C_1$-$C_4$ alkyl, $C_1$-$C_4$ haloalkyl, and —$NHCOR^f$.

In some embodiments, $R^1$ is phenyl that is unsubstituted or substituted with 1, 2, or 3 substituents independently selected from halo, $C_1$-$C_4$ alkyl, $C_1$-$C_4$ haloalkyl, and —$NHCOR^f$. In some embodiments, $R^1$ is phenyl that is substituted with 1 or 2 substituents independently selected from halo, $C_1$-$C_4$ haloalkyl, and —$NHCOR^f$. In some embodiments, $R^1$ is phenyl that is substituted with fluoro and chloro. In some embodiments, $R^1$ is 2-chloro-5-fluoro-phenyl. In some embodiments, $R^1$ is phenyl that is substituted with an acetamido group. In some embodiments, $R^1$ is phenyl that is substituted with a trifluoromethyl group.

In some embodiments, R¹ is a 5- or 6-membered heteroaryl having 1, 2, or 3 heteroatoms independently selected from N, O, and S, is unsubstituted or substituted with 1, 2, or 3 substituents independently selected from halo, $C_1$-$C_4$ alkyl, $C_1$-$C_4$ haloalkyl, and —NHCOR$^f$. In some embodiments, R¹ is a 5-membered heteroaryl having 1, 2, or 3 heteroatoms independently selected from N and O, is substituted with 1, 2, or 3 substituents independently selected from halo, $C_1$-$C_4$ alkyl, $C_1$-$C_4$ haloalkyl, and —NHCOR$^f$. In some embodiments, R¹ is selected from pyrazolyl and isoxazolyl, each of which is substituted with two substituents independently selected from $C_1$-$C_4$ alkyl. In some embodiments, R¹ is selected from 2,4-dimethylpyrazol-3-yl, 1,3-dimethylpyrazol-4-yl, and 3,5-dimethylisoxazolyl.

In some embodiments, R¹ is morpholino.
In some embodiments, R³ is hydrogen.
In some embodiments, R⁴ is selected from —(CR$^h$R$^i$)$_p$—Y', and $C_1$-$C_8$ alkyl.
In some embodiments, R⁴ is $C_1$-$C_8$ alkyl, such as $C_4$-$C_6$ alkyl. In some embodiments, R⁴ is selected from 2,2-dimethylpropyl, 3,3-dimethylbutan-2-yl, pentan-2-yl, and sec-butyl.

In some embodiments: R⁴ is —(CR$^h$R$^i$)$_p$—Y'; R$^h$ is hydrogen; R$^i$ is hydrogen; p is 0, 1, 2, or 3; and Y' is selected from: $C_3$-$C_{10}$ cycloalkyl, $C_3$-$C_8$ cycloalkenyl, aryl, a 5- or 6-membered heteroaryl having 1, 2, or 3 heteroatoms independently selected from N, O, and S, and a 5-, 6-, or 7-membered heterocycle having 1, 2, or 3 heteroatoms independently selected from N, O, and S; wherein Y' is unsubstituted or substituted with one or two substituents independently selected from halo and $C_1$-$C_4$ alkyl. In some embodiments, Y' is $C_3$-$C_{10}$ cycloalkyl (e.g., cyclohexyl, cycloheptyl, or adamantyl). In some embodiments, Y' is $C_3$-$C_8$ cycloalkenyl (e.g., bicyclo[2.2.1]heptenyl). In some embodiments, Y' is aryl (e.g., phenyl or benzodioxolyl), which may be unsubstituted or substituted with 1 or 2 substituents independently selected from halo (e.g., fluoro) and $C_1$-$C_4$ alkyl (e.g., methyl). In some embodiments, Y' is a 5- or 6-membered heteroaryl having 1, 2, or 3 heteroatoms independently selected from N, O, and S (e.g., pyridyl) which is unsubstituted or substituted with 1 or 2 substituents independently selected from halo (e.g., fluoro) and $C_1$-$C_4$ alkyl (e.g., methyl). In some embodiments, Y' is a 5-, 6-, or 7-membered heterocycle having 1, 2, or 3 heteroatoms independently selected from N, O, and S (e.g., tetrahydropyranyl or oxabicyclo[2.2.1]heptanyl).

In some embodiments, each aryl, heteroaryl, arylene, heteroarylene, cycloalkyl, cycloalkenyl, and heterocycle is independently unsubstituted or substituted with 1, 2, or 3 substituents independently selected from $C_1$-$C_4$ alkyl, halo, $C_1$-$C_4$ haloalkyl, $C_1$-$C_4$ alkoxy, $C_1$-$C_4$ haloalkoxy, $C_1$-$C_4$ hydroxyalkyl, hydroxy, cyano, —NHCOR$^f$, and benzyl.

In another aspect, disclosed is a compound of formula (Ib):

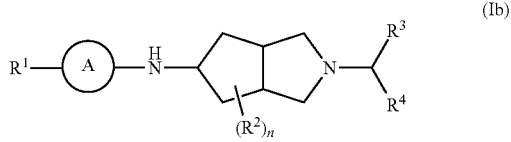

(Ib)

or a pharmaceutically acceptable salt thereof, wherein and A, n, R¹, R², R³, and R⁴ are as described herein.

In some embodiments, A is selected from:

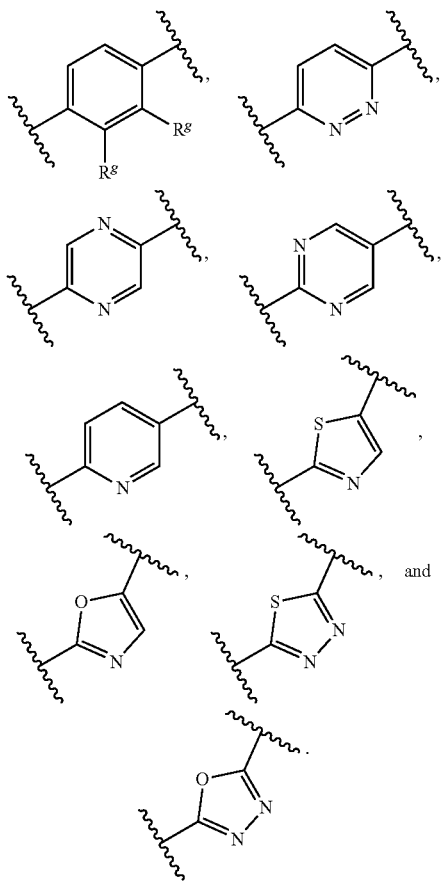

, and

In some embodiments, A is:

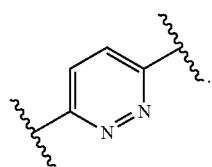 [SMILES: *c1ccc(*)nn1]

.

In some embodiments, Q is NR$^a$, and R$^a$ is hydrogen.
In some embodiments, Q is O.
In some embodiments, Q is —NR$^b$—C(O)—, and R$^b$ is hydrogen.
In some embodiments, Q is selected from NR$^a$ and O, wherein R$^a$ is hydrogen.
In some embodiments, R¹ is selected from aryl (e.g., phenyl or benzodioxolyl), heteroaryl (e.g., 5- or 6-membered heteroaryl having 1, 2, or 3 heteroatoms independently selected from N, O, and S, such as pyrazolyl or isoxazolyl), heterocyclyl (e.g., a 5- or 6-membered heterocycle having 1, 2, or 3 heteroatoms independently selected from N, O, and S, such as morpholino), and cycloalkyl (e.g., a $C_3$-$C_7$ cycloalkyl).
In some embodiments, R¹ is selected from phenyl, a 5- or 6-membered heteroaryl having 1, 2, or 3 heteroatoms independently selected from N, O, and S, and a 5- or 6-membered heterocycle having 1, 2, or 3 heteroatoms independently selected from N, O, and S, and the phenyl, heteroaryl, or heterocycle is unsubstituted or substituted with 1, 2, or 3 substituents independently selected from halo, $C_1$-$C_4$ alkyl, $C_1$-$C_4$ haloalkyl, and —NHCOR$^f$.

In some embodiments, R$^1$ is phenyl that is unsubstituted or substituted with 1, 2, or 3 substituents independently selected from halo, $C_1$-$C_4$ alkyl, $C_1$-$C_4$ haloalkyl, and —NHCOR$^f$. In some embodiments, R$^1$ is phenyl that is substituted with 1 or 2 substituents independently selected from halo, $C_1$-$C_4$ haloalkyl, and —NHCOR$^f$. In some embodiments, R$^1$ is phenyl that is substituted with fluoro and chloro. In some embodiments, R$^1$ is 2-choro-5-fluoro-phenyl. In some embodiments, R$^1$ is phenyl that is substituted with an acetamido group. In some embodiments, R$^1$ is phenyl that is substituted with a trifluoromethyl group.

In some embodiments, R$^1$ is a 5- or 6-membered heteroaryl having 1, 2, or 3 heteroatoms independently selected from N, O, and S, is unsubstituted or substituted with 1, 2, or 3 substituents independently selected from halo, $C_1$-$C_4$ alkyl, $C_1$-$C_4$ haloalkyl, and —NHCOR$^f$. In some embodiments, R$^1$ is a 5-membered heteroaryl having 1, 2, or 3 heteroatoms independently selected from N and O, is substituted with 1, 2, or 3 substituents independently selected from halo, $C_1$-$C_4$ alkyl, $C_1$-$C_4$ haloalkyl, and —NHCOR$^f$. In some embodiments, R$^1$ is selected from pyrazolyl and isoxazolyl, each of which is substituted with two substituents independently selected from $C_1$-$C_4$ alkyl. In some embodiments, R$^1$ is selected from 2,4-dimethylpyrazol-3-yl, 1,3-dimethylpyrazol-4-yl, and 3,5-dimethylisoxazolyl.

In some embodiments, R$^1$ is morpholino.
In some embodiments, n is 1, and R$^2$ is hydrogen.
In some embodiments, R$^3$ is hydrogen.
In some embodiments, R$^4$ is selected from —(CR$^h$R$^i$)$_p$—Y', and $C_1$-$C_8$ alkyl.

In some embodiments, R$^4$ is $C_1$-$C_8$ alkyl, such as $C_4$-$C_6$ alkyl. In some embodiments, R$^4$ is selected from 2,2-dimethylpropyl, 3,3-dimethylbutan-2-yl, pentan-2-yl, and sec-butyl.

In some embodiments: R$^4$ is —(CR$^h$R$^i$)$_p$—Y'; R$^h$ is hydrogen; R$^i$ is hydrogen; p is 0, 1, 2, or 3; and Y' is selected from: $C_3$-$C_{10}$ cycloalkyl, $C_3$-$C_8$ cycloalkenyl, aryl, a 5- or 6-membered heteroaryl having 1, 2, or 3 heteroatoms independently selected from N, O, and S, and a 5-, 6-, or 7-membered heterocycle having 1, 2, or 3 heteroatoms independently selected from N, O, and S; wherein Y' is unsubstituted or substituted with one or two substituents independently selected from halo and $C_1$-$C_4$ alkyl. In some embodiments, Y' is $C_3$-$C_{10}$ cycloalkyl (e.g., cyclohexyl, cycloheptyl, or adamantyl). In some embodiments, Y' is $C_3$-$C_8$ cycloalkenyl (e.g., bicyclo[2.2.1]heptenyl). In some embodiments, Y' is aryl (e.g., phenyl or benzodioxolyl), which may be unsubstituted or substituted with 1 or 2 substituents independently selected from halo (e.g., fluoro) and $C_1$-$C_4$ alkyl (e.g., methyl). In some embodiments, Y' is a 5- or 6-membered heteroaryl having 1, 2, or 3 heteroatoms independently selected from N, O, and S (e.g., pyridyl) which is unsubstituted or substituted with 1 or 2 substituents independently selected from halo (e.g., fluoro) and $C_1$-$C_4$ alkyl (e.g., methyl). In some embodiments, Y' is a 5-, 6-, or 7-membered heterocycle having 1, 2, or 3 heteroatoms independently selected from N, O, and S (e.g., tetrahydropyranyl or oxabicyclo[2.2.1]heptanyl).

In some embodiments, each aryl, heteroaryl, arylene, heteroarylene, cycloalkyl, cycloalkenyl, and heterocycle is independently unsubstituted or substituted with 1, 2, or 3 substituents independently selected from $C_1$-$C_4$ alkyl, halo, $C_1$-$C_4$ haloalkyl, $C_1$-$C_4$ alkoxy, $C_1$-$C_4$ haloalkoxy, $C_1$-$C_4$ hydroxyalkyl, hydroxy, cyano, —NHCOR$^f$, and benzyl.

Compounds of formula (I) may have formula (I-c), (I-d), (I-e), (I-f), (I-g), (I-h), (I-i), (I-j), (I-k), or (I-l), wherein R$^1$, R$^3$, and R$^4$ are as defined herein.

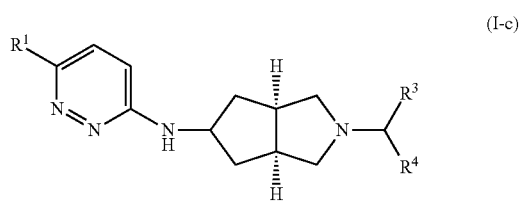

(I-c)

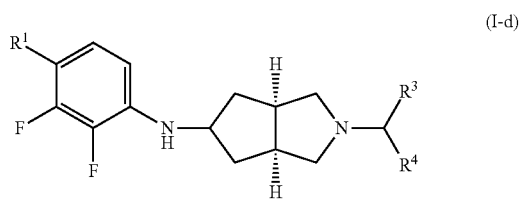

(I-d)

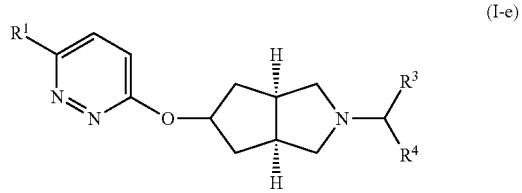

(I-e)

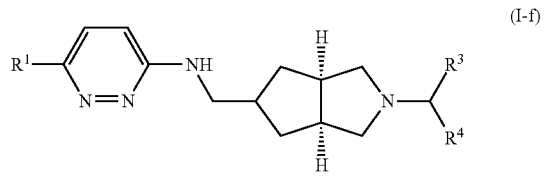

(I-f)

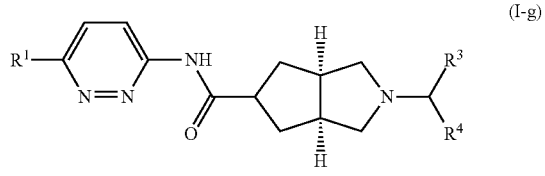

(I-g)

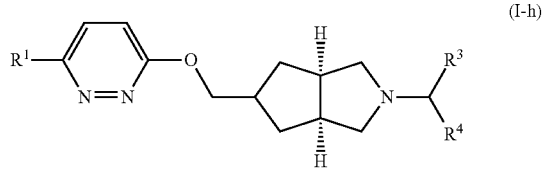

(I-h)

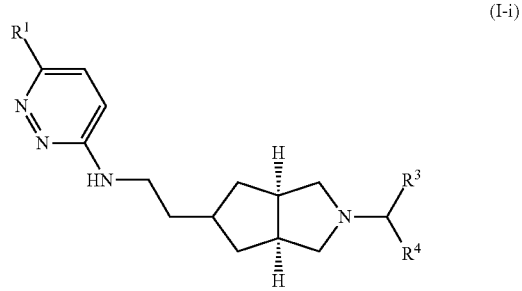

(I-i)

-continued

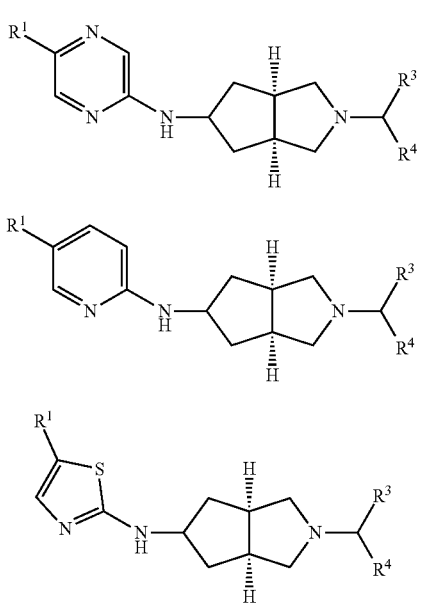

(I-j)

(I-k)

(I-l)

Representative compounds of formula (I) include, but are not limited to:

(3aR,5s,6aS)-2-(3,3-dimethylbutyl)-N-[6-(2,4-dimethylpyrazol-3-yl)pyridazin-3-yl]-3,3a,4,5,6,6a-hexahydro-1H-cyclopenta[c]pyrrol-5-amine;

(3aR,5s,6aS)-2-(5-bicyclo[2.2.1]hept-2-enylmethyl)-N-[6-(1,3-dimethylpyrazol-4-yl)pyridazin-3-yl]-3,3a,4,5,6,6a-hexahydro-1H-cyclopenta[c]pyrrol-5-amine;

(3aR,5s,6aS)-2-(3,3-dimethylbutyl)-N-[6-(1,3-dimethylpyrazol-4-yl)pyridazin-3-yl]-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-(2,3,3-trimethylbutyl)-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-(tetrahydropyran-3-ylmethyl)-3,3a,4,5,6,6a-hexahydro-1H-cyclopenta[c]pyrrol-5-amine;

(3aR,5s,6aS)-2-(cyclohexylmethyl)-N-[6-(1,3-dimethylpyrazol-4-yl)pyridazin-3-yl]-3,3a,4,5,6,6a-hexahydro-1H-cyclopenta[c]pyrrol-5-amine;

(3aR,5s,6aS)-2-benzyl-N-[6-(1,3-dimethylpyrazol-4-yl)pyridazin-3-yl]-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-(2-pyridylmethyl)-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-[(2-fluorophenyl)methyl]-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-[(3-methyl-2-pyridyl)methyl]-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-(2-phenylethyl)-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-(2-methylbutyl)-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-(2-methylpentyl)-3,3a,4,5,6,6a-hexahydro-1H-cyclopenta[c]pyrrol-5-amine;

(3aR,5s,6aS)-2-(1,3-benzodioxol-5-ylmethyl)-N-[6-(1,3-dimethylpyrazol-4-yl)pyridazin-3-yl]-3,3a,4,5,6,6a-hexahydro-1H-cyclopenta[c]pyrrol-5-amine;

(3aR,5s,6aS)-2-(1-adamantylmethyl)-N-[6-(2,4-dimethylpyrazol-3-yl)pyridazin-3-yl]-3,3a,4,5,6,6a-hexahydro-1H-cyclopenta[c]pyrrol-5-amine;

(3aR,5s,6aS)-2-(5-bicyclo[2.2.1]hept-2-enylmethyl)-N-[6-(2,4-dimethylpyrazol-3-yl)pyridazin-3-yl]-3,3a,4,5,6,6a-hexahydro-1H-cyclopenta[c]pyrrol-5-amine;

(3aR,5s,6aS)—N-[6-(2,4-dimethylpyrazol-3-yl)pyridazin-3-yl]-2-(2-methylbutyl)-3,3a,4,5,6,6a-hexahydro-1H-cyclopenta[c]pyrrol-5-amine;

(3aR,5s,6aS)—N-[6-(2,4-dimethylpyrazol-3-yl)pyridazin-3-yl]-2-(2-methylpentyl)-3,3a,4,5,6,6a-hexahydro-1H-cyclopenta[c]pyrrol-5-amine;

(3aR,5s,6aS)-2-(cyclohexylmethyl)-N-[6-(2,4-dimethylpyrazol-3-yl)pyridazin-3-yl]-3,3a,4,5,6,6a-hexahydro-1H-cyclopenta[c]pyrrol-5-amine;

(3aR,5s,6aS)—N-[6-(2,4-dimethylpyrazol-3-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2,4-dimethylpyrazol-3-yl)pyridazin-3-yl]-2-(tetrahydropyran-3-ylmethyl)-3,3a,4,5,6,6a-hexahydro-1H-cyclopenta[c]pyrrol-5-amine;

(3aR,5s,6aS)-2-benzyl-N-[6-(2,4-dimethylpyrazol-3-yl)pyridazin-3-yl]-3,3a,4,5,6,6a-hexahydro-1H-cyclopenta[c]pyrrol-5-amine;

(3aR,5s,6aS)—N-[6-(2,4-dimethylpyrazol-3-yl)pyridazin-3-yl]-2-[(3-methyl-2-pyridyl)methyl]-3,3a,4,5,6,6a-hexahydro-1H-cyclopenta[c]pyrrol-5-amine;

(3aR,5s,6aS)—N-[6-(2,4-dimethylpyrazol-3-yl)pyridazin-3-yl]-2-[(2-fluorophenyl)methyl]-3,3a,4,5,6,6a-hexahydro-1H-cyclopenta[c]pyrrol-5-amine;

(3aR,5s,6aS)-2-(1-adamantylmethyl)-N-[6-(2-chloro-5-fluoro-phenyl)pyridazin-3-yl]-3,3a,4,5,6,6a-hexahydro-1H-cyclopenta[c]pyrrol-5-amine;

(3aR,5s,6aS)-2-(5-bicyclo[2.2.1]hept-2-enylmethyl)-N-[6-(2-chloro-5-fluoro-phenyl)pyridazin-3-yl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(3,3-dimethylbutyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(2-methylbutyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(2-methylpentyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(cyclohexylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(tetrahydropyran-3-ylmethyl)-3,3a,4,5,6,6a-hexahydro-1H-cyclopenta[c]pyrrol-5-amine;

(3aR,5s,6aS)-2-benzyl-N-[6-(2-chloro-5-fluoro-phenyl)pyridazin-3-yl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-[(3-methyl-2-pyridyl)methyl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-[(2-fluorophenyl)methyl]-3,3a,4,5,6,6a-hexahydro-1H-cyclopenta[c]pyrrol-5-amine;

(3aR,5s,6aS)-2-(1-adamantylmethyl)-N-[6-(1,3-dimethylpyrazol-4-yl)pyridazin-3-yl]-3,3a,4,5,6,6a-hexahydro-1H-cyclopenta[c]pyrrol-5-amine;

(3aR,5s,6aS)—N-[6-(2,4-dimethylpyrazol-3-yl)pyridazin-3-yl]-2-(tetrahydropyran-2-ylmethyl)-3,3a,4,5,6,6a-hexahydro-1H-cyclopenta[c]pyrrol-5-amine;

N-[4-[6-[[(3aR,5r,6aS)-2-(3,3-dimethylbutyl)-3,3a,4,5,6,6a-hexahydro-1H-cyclopenta[c]pyrrol-5-yl]amino]pyridazin-3-yl]phenyl]acetamide;

(3aR,5s,6aS)—N-[6-(2,4-dimethylpyrazol-3-yl)pyridazin-3-yl]-2-(7-oxabicyclo[2.2.1]heptan-3-ylmethyl)-3,3a,4,5,6,6a-hexahydro-1H-cyclopenta[c]pyrrol-5-amine;

(3aR,5r,6aS)-2-(3,3-dimethylbutyl)-N-[4-(1,3-dimethylpyrazol-4-yl)-2,3-difluoro-phenyl]-3,3a,4,5,6,6a-hexahydro-1H-cyclopenta[c]pyrrol-5-amine;

(3aR,5r,6aS)-2-(5-bicyclo[2.2.1]hept-2-enylmethyl)-N-[4-(1,3-dimethylpyrazol-4-yl)-2,3-difluoro-phenyl]-3,3a,4,5,6,6a-hexahydro-1H-cyclopenta[c]pyrrol-5-amine;

(3aR,5r,6aS)-2-(cyclohexylmethyl)-N-[4-(1,3-dimethylpyrazol-4-yl)-2,3-difluoro-phenyl]-3,3a,4,5,6,6a-hexahydro-1H-cyclopenta[c]pyrrol-5-amine;

(3aR,5r,6aS)-2-(cycloheptylmethyl)-N-[4-(1,3-dimethylpyrazol-4-yl)-2,3-difluoro-phenyl]-3,3a,4,5,6,6a-hexahydro-1H-cyclopenta[c]pyrrol-5-amine;

(3aR,5r,6aS)-2-(1-adamantylmethyl)-N-[4-(1,3-dimethylpyrazol-4-yl)-2,3-difluoro-phenyl]-3,3a,4,5,6,6a-hexahydro-1H-cyclopenta[c]pyrrol-5-amine;

(3aR,5r,6aS)-5-[6-(1,3-dimethylpyrazol-4-yl)pyridazin-3-yl]oxy-2-(2,3,3-trimethylbutyl)-3,3a,4,5,6,6a-hexahydro-1H-cyclopenta[c]pyrrole;

(3aR,5r,6aS)-2-(5-bicyclo[2.2.1]hept-2-enylmethyl)-5-[6-(1,3-dimethylpyrazol-4-yl)pyridazin-3-yl]oxy-3,3a,4,5,6,6a-hexahydro-1H-cyclopenta[c]pyrrole;

(3aR,5r,6aS)-2-(3,3-dimethylbutyl)-5-[6-(1,3-dimethylpyrazol-4-yl)pyridazin-3-yl]oxy-3,3a,4,5,6,6a-hexahydro-1H-cyclopenta[c]pyrrole;

(3aR,5r,6aS)-2-(cyclohexylmethyl)-5-[6-(1,3-dimethylpyrazol-4-yl)pyridazin-3-yl]oxy-3,3a,4,5,6,6a-hexahydro-1H-cyclopenta[c]pyrrole;

(3aR,5r,6aS)-5-[6-(1,3-dimethylpyrazol-4-yl)pyridazin-3-yl]oxy-2-(tetrahydropyran-4-ylmethyl)-3,3a,4,5,6,6a-hexahydro-1H-cyclopenta[c]pyrrole;

(3aR,5r,6aS)-5-[6-(1,3-dimethylpyrazol-4-yl)pyridazin-3-yl]oxy-2-(tetrahydropyran-3-ylmethyl)-3,3a,4,5,6,6a-hexahydro-1H-cyclopenta[c]pyrrole;

(3aR,5r,6aS)-5-[6-(1,3-dimethylpyrazol-4-yl)pyridazin-3-yl]oxy-2-[(3-methyl-2-pyridyl)methyl]-3,3a,4,5,6,6a-hexahydro-1H-cyclopenta[c]pyrrole;

(3aR,5r,6aS)-2-(5-bicyclo[2.2.1]hept-2-enylmethyl)-5-[6-(2-chloro-5-fluoro-phenyl)pyridazin-3-yl]oxy-3,3a,4,5,6,6a-hexahydro-1H-cyclopenta[c]pyrrole;

(3aR,5r,6aS)-5-[6-(2-chloro-5-fluoro-phenyl)pyridazin-3-yl]oxy-2-(3,3-dimethylbutyl)-3,3a,4,5,6,6a-hexahydro-1H-cyclopenta[c]pyrrole;

(3aR,5r,6aS)-5-[6-(2-chloro-5-fluoro-phenyl)pyridazin-3-yl]oxy-2-(2,3,3-trimethylbutyl)-3,3a,4,5,6,6a-hexahydro-1H-cyclopenta[c]pyrrole;

(3aR,5r,6aS)-5-[6-(2-chloro-5-fluoro-phenyl)pyridazin-3-yl]oxy-2-(cyclohexylmethyl)-3,3a,4,5,6,6a-hexahydro-1H-cyclopenta[c]pyrrole;

(3aR,5r,6aS)-5-[6-(2-chloro-5-fluoro-phenyl)pyridazin-3-yl]oxy-2-(tetrahydropyran-3-ylmethyl)-3,3a,4,5,6,6a-hexahydro-1H-cyclopenta[c]pyrrole;

(3aR,5r,6aS)-5-[6-(2-chloro-5-fluoro-phenyl)pyridazin-3-yl]oxy-2-[(3-methyl-2-pyridyl)methyl]-3,3a,4,5,6,6a-hexahydro-1H-cyclopenta[c]pyrrole;

(3aR,5r,6aS)-5-[6-(2-chloro-5-fluoro-phenyl)pyridazin-3-yl]oxy-2-(tetrahydropyran-4-ylmethyl)-3,3a,4,5,6,6a-hexahydro-1H-cyclopenta[c]pyrrole;

[(3aR,5r,6aS)-5-[6-(1,3-dimethylpyrazol-4-yl)pyridazin-3-yl]oxy-3,3a,4,5,6,6a-hexahydro-1H-cyclopenta[c]pyrrol-2-yl]-(1-adamantyl)methanone;

N-[[(3aR,5s,6aS)-2-(3,3-dimethylbutyl)-3,3a,4,5,6,6a-hexahydro-1H-cyclopenta[c]pyrrol-5-yl]methyl]-6-(2,4-dimethylpyrazol-3-yl)pyridazin-3-amine;

N-[[(3aR,6aS)-2-(5-bicyclo[2.2.1]hept-2-enylmethyl)-3,3a,4,5,6,6a-hexahydro-1H-cyclopenta[c]pyrrol-5-yl]methyl]-6-(1,3-dimethylpyrazol-4-yl)pyridazin-3-amine;

N-[[(3aR,6aS)-2-(2,3,3-trimethylbutyl)-3,3a,4,5,6,6a-hexahydro-1H-cyclopenta[c]pyrrol-5-yl]methyl]-6-(1,3-dimethylpyrazol-4-yl)pyridazin-3-amine;

N-[[(3aR,5s,6aS)-2-(5-bicyclo[2.2.1]hept-2-enylmethyl)-3,3a,4,5,6,6a-hexahydro-1H-cyclopenta[c]pyrrol-5-yl]methyl]-6-(2,4-dimethylpyrazol-3-yl)pyridazin-3-amine;

N-[[(3aR,5s,6aS)-2-(2,3,3-trimethylbutyl)-3,3a,4,5,6,6a-hexahydro-1H-cyclopenta[c]pyrrol-5-yl]methyl]-6-(2,4-dimethylpyrazol-3-yl)pyridazin-3-amine;

N-[[(3aR,5s,6aS)-2-(tetrahydropyran-4-ylmethyl)-3,3a,4,5,6,6a-hexahydro-1H-cyclopenta[c]pyrrol-5-yl]methyl]-6-(2,4-dimethylpyrazol-3-yl)pyridazin-3-amine;

N-[[(3aR,5s,6aS)-2-(tetrahydropyran-3-ylmethyl)-3,3a,4,5,6,6a-hexahydro-1H-cyclopenta[c]pyrrol-5-yl]methyl]-6-(2,4-dimethylpyrazol-3-yl)pyridazin-3-amine;

N-[[(3aR,5s,6aS)-2-[(3-methyl-2-pyridyl)methyl]-3,3a,4,5,6,6a-hexahydro-1H-cyclopenta[c]pyrrol-5-yl]methyl]-6-(2,4-dimethylpyrazol-3-yl)pyridazin-3-amine;

N-[[(3aR,5s,6aS)-2-(5-bicyclo[2.2.1]hept-2-enylmethyl)-3,3a,4,5,6,6a-hexahydro-1H-cyclopenta[c]pyrrol-5-yl]methyl]-6-(2-chloro-5-fluoro-phenyl)pyridazin-3-amine;

N-[[(3aR,5s,6aS)-2-(3,3-dimethylbutyl)-3,3a,4,5,6,6a-hexahydro-1H-cyclopenta[c]pyrrol-5-yl]methyl]-6-(2-chloro-5-fluoro-phenyl)pyridazin-3-amine;

N-[[(3aR,5s,6aS)-2-(tetrahydropyran-4-ylmethyl)-3,3a,4,5,6,6a-hexahydro-1H-cyclopenta[c]pyrrol-5-yl]methyl]-6-(2-chloro-5-fluoro-phenyl)pyridazin-3-amine;

N-[[(3aR,5s,6aS)-2-(cyclohexylmethyl)-3,3a,4,5,6,6a-hexahydro-1H-cyclopenta[c]pyrrol-5-yl]methyl]-6-(1,3-dimethylpyrazol-4-yl)pyridazin-3-amine;

N-[[(3aR,5s,6aS)-2-[(3-methyl-2-pyridyl)methyl]-3,3a,4,5,6,6a-hexahydro-1H-cyclopenta[c]pyrrol-5-yl]methyl]-6-(1,3-dimethylpyrazol-4-yl)pyridazin-3-amine;

(3aR,6aS)-2-(3,3-dimethylbutyl)-N-[6-(2,4-dimethylpyrazol-3-yl)pyridazin-3-yl]-3,3a,4,5,6,6a-hexahydro-1H-cyclopenta[c]pyrrole-5-carboxamide;

(3aR,6aS)-2-(5-bicyclo[2.2.1]hept-2-enylmethyl)-N-[6-(2-chloro-4-fluoro-phenyl)pyridazin-3-yl]-3,3a,4,5,6,6a-hexahydro-1H-cyclopenta[c]pyrrole-5-carboxamide;

N-[6-(2,4-dimethylpyrazol-3-yl)pyridazin-3-yl]-2-(2,3,3-trimethylbutyl)-3,3a,4,5,6,6a-hexahydro-1H-cyclopenta[c]pyrrole-5-carboxamide;

2-(5-bicyclo[2.2.1]hept-2-enylmethyl)-N-[6-(2,4-dimethylpyrazol-3-yl)pyridazin-3-yl]-3,3a,4,5,6,6a-hexahydro-1H-cyclopenta[c]pyrrole-5-carboxamide;

(3aR,6aS)-2-(3,3-dimethylbutyl)-5-[[6-(2,4-dimethylpyrazol-3-yl)pyridazin-3-yl]oxymethyl]-3,3a,4,5,6,6a-hexahydro-1H-cyclopenta[c]pyrrole;

(3aR,6aS)-2-(1-adamantylmethyl)-5-[[6-(2,4-dimethylpyrazol-3-yl)pyridazin-3-yl]oxymethyl]-3,3a,4,5,6,6a-hexahydro-1H-cyclopenta[c]pyrrole;

(3aR,6aS)-2-(5-bicyclo[2.2.1]hept-2-enylmethyl)-5-[[6-(2,4-dimethylpyrazol-3-yl)pyridazin-3-yl]oxymethyl]-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-(2-methylbutyl)-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-(2-methylpentyl)-3,3a,4,5,6,6a-hexahydro-1H-cyclopenta[c]pyrrole;

(3aR,6aS)-2-(cyclohexylmethyl)-5-[[6-(2,4-dimethylpyrazol-3-yl)pyridazin-3-yl]oxymethyl]-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-(tetrahydropyran-4-ylmethyl)-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-(tetrahydropyran-3-ylmethyl)-3,3a,4,5,6,6a-hexahydro-1H-cyclopenta[c]pyrrole;

(3aR,6aS)-2-benzyl-5-[[6-(2,4-dimethylpyrazol-3-yl)pyridazin-3-yl]oxymethyl]-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-[(2-fluorophenyl)methyl]-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-[(4-fluorophenyl)methyl]-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-(2-pyridylmethyl)-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-[(3-methyl-2-pyridyl)methyl]-3,3a,4,5,6,6a-hexahydro-1H-cyclopenta[c]pyrrole;

(3aR,6aS)-2-(1,3-benzodioxol-5-ylmethyl)-5-[[6-(2,4-dimethylpyrazol-3-yl)pyridazin-3-yl]oxymethyl]-3,3a,4,5,6,6a-hexahydro-1H-cyclopenta[c]pyrrole;

(3aR,6aS)-2-(3,3-dimethylbutyl)-5-[[6-(1,3-dimethylpyrazol-4-yl)pyridazin-3-yl]oxymethyl]-3,3a,4,5,6,6a-hexahydro-1H-cyclopenta[c]pyrrole;

(3aR,6aS)-2-(1-adamantylmethyl)-5-[[6-(1,3-dimethylpyrazol-4-yl)pyridazin-3-yl]oxymethyl]-3,3a,4,5,6,6a-hexahydro-1H-cyclopenta[c]pyrrole;

(3aR,6aS)-2-(5-bicyclo[2.2.2]oct-2-enylmethyl)-5-[[6-(1,3-dimethylpyrazol-4-yl)pyridazin-3-yl]oxymethyl]-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-(2-methylbutyl)-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-(2-methylpentyl)-3,3a,4,5,6,6a-hexahydro-1H-cyclopenta[c]pyrrole;

(3aR,6aS)-2-(cyclohexylmethyl)-5-[[6-(1,3-dimethylpyrazol-4-yl)pyridazin-3-yl]oxymethyl]-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-(tetrahydropyran-4-ylmethyl)-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-(tetrahydropyran-3-ylmethyl)-3,3a,4,5,6,6a-hexahydro-1H-cyclopenta[c]pyrrole;

(3aR,6aS)-2-benzyl-5-[[6-(1,3-dimethylpyrazol-4-yl)pyridazin-3-yl]oxymethyl]-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-[(2-fluorophenyl)methyl]-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-[(4-fluorophenyl)methyl]-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-(2-pyridylmethyl)-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-[(3-methyl-2-pyridyl)methyl]-3,3a,4,5,6,6a-hexahydro-1H-cyclopenta[c]pyrrole;

(3aR,6aS)-2-(1,3-benzodioxol-5-ylmethyl)-5-[[6-(1,3-dimethylpyrazol-4-yl)pyridazin-3-yl]oxymethyl]-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-(3,3-dimethylbutyl)-3,3a,4,5,6,6a-hexahydro-1H-cyclopenta[c]pyrrole;

(3aR,6aS)-2-(1-adamantylmethyl)-5-[[6-(2-chloro-5-fluoro-phenyl)pyridazin-3-yl]oxymethyl]-3,3a,4,5,6,6a-hexahydro-1H-cyclopenta[c]pyrrole;

(3aR,6aS)-2-(5-bicyclo[2.2.1]hept-2-enylmethyl)-5-[[6-(2-chloro-5-fluoro-phenyl)pyridazin-3-yl]oxymethyl]-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-(2-methylbutyl)-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-(2-methylpentyl)-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-(cyclohexylmethyl)-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-(tetrahydropyran-4-ylmethyl)-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-(tetrahydropyran-3-ylmethyl)-3,3a,4,5,6,6a-hexahydro-1H-cyclopenta[c]pyrrole;

(3aR,6aS)-2-benzyl-5-[[6-(2-chloro-5-fluoro-phenyl)pyridazin-3-yl]oxymethyl]-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-[(2-fluorophenyl)methyl]-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-[(4-fluorophenyl)methyl]-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-(2-pyridylmethyl)-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-[(3-methyl-2-pyridyl)methyl]-3,3a,4,5,6,6a-hexahydro-1H-cyclopenta[c]pyrrole;

(3aR,6aS)-2-(1,3-benzodioxol-5-ylmethyl)-5-[[6-(2-chloro-5-fluoro-phenyl)pyridazin-3-yl]oxymethyl]-3,3a,4,5,6,6a-hexahydro-1H-cyclopenta[c]pyrrole;

6-(1,4-dimethyl-1H-pyrazol-5-yl)-N-(2-((3aR,6aS)-2-(3,3-dimethylbutyl)octahydrocyclopenta[c]pyrrol-5-yl)ethyl)pyridazin-3-amine;

N-[2-[(3aR,6aS)-2-(1-adamantylmethyl)-3,3a,4,5,6,6a-hexahydro-1H-cyclopenta[c]pyrrol-5-yl]ethyl]-6-(2,4-dimethylpyrazol-3-yl)pyridazin-3-amine;

N-[2-[(3aR,6aS)-2-(tetrahydropyran-3-ylmethyl)-3,3a,4,5,6,6a-hexahydro-1H-cyclopenta[c]pyrrol-5-yl]ethyl]-6-(2,4-dimethylpyrazol-3-yl)pyridazin-3-amine;

N-[2-[(3aR,6aS)-2-(5-bicyclo[2.2.1]hept-2-enylmethyl)-3,3a,4,5,6,6a-hexahydro-1H-cyclopenta[c]pyrrol-5-yl]ethyl]-6-(2,4-dimethylpyrazol-3-yl)pyridazin-3-amine;

N-[2-[(3aR,6aS)-2-[(3-methyl-2-pyridyl)methyl]-3,3a,4,5, 6,6a-hexahydro-1H-cyclopenta[c]pyrrol-5-yl]ethyl]-6-(2, 4-dimethylpyrazol-3-yl)pyridazin-3-amine;

N-[2-[(3aR,6aS)-2-(tetrahydropyran-4-ylmethyl)-3,3a,4,5, 6,6a-hexahydro-1H-cyclopenta[c]pyrrol-5-yl]ethyl]-6-(2, 4-dimethylpyrazol-3-yl)pyridazin-3-amine;

N-[2-[(3aR,6aS)-2-benzyl-3,3a,4,5,6,6a-hexahydro-1H-cyclopenta[c]pyrrol-5-yl]ethyl]-6-(2,4-dimethylpyrazol-3-yl)pyridazin-3-amine; and N-[2-[(3aR,6aS)-2-[(2-fluorophenyl)methyl]-3,3a,4,5,6,6a-hexahydro-1H-cyclopenta[c]pyrrol-5-yl]ethyl]-6-(2,4-dimethylpyrazol-3-yl)pyridazin-3-amine, or a pharmaceutically acceptable salt thereof.

Other compounds include:

(3aR,6aS)-5-(6-chloropyridazin-3-yl)oxy-2-(3,3-dimethylbutyl)-3,3a,4,5,6,6a-hexahydro-1H-cyclopenta[c]pyrrole;

N-[4-[6-[[(3aR,6aS)-2-(3,3-dimethylbutyl)-3,3a,4,5,6,6a-hexahydro-1H-cyclopenta[c]pyrrol-5-yl]oxy]pyridazin-3-yl]phenyl]acetamide;

N-[4-[6-[[(3aR,6aS)-2-(cyclohexylmethyl)-3,3a,4,5,6,6a-hexahydro-1H-cyclopenta[c]pyrrol-5-yl]oxy]pyridazin-3-yl]phenyl]acetamide;

N-[4-[6-[[(3aR,6aS)-2-[(4-fluorophenyl)methyl]-3,3a,4,5,6, 6a-hexahydro-1H-cyclopenta[c]pyrrol-5-yl]oxy] pyridazin-3-yl]phenyl]acetamide;

N-[4-[6-[[(3aR,6aS)-2-(tetrahydropyran-4-ylmethyl)-3,3a, 4,5,6,6a-hexahydro-1H-cyclopenta[c]pyrrol-5-yl]oxy] pyridazin-3-yl]phenyl]acetamide;

N-[4-[6-[[(3aR,6aS)-2-[(3-methyl-2-pyridyl)methyl]-3,3a, 4,5,6,6a-hexahydro-1H-cyclopenta[c]pyrrol-5-yl]oxy] pyridazin-3-yl]phenyl]acetamide;

(3aR,6aS)-2-(3,3-dimethylbutyl)-5-[6-(1,3-dimethylpyrazol-4-yl)pyridazin-3-yl]oxy-3,3a,4,5,6,6a-hexahydro-1H-cyclopenta[c]pyrrole;

(3aR,6aS)-2-(3,3-dimethylbutyl)-5-[6-(2,4-dimethylpyrazol-3-yl)pyridazin-3-yl]oxy-3,3a,4,5,6,6a-hexahydro-1H-cyclopenta[c]pyrrole;

4-[6-[[(3aR,6aS)-2-(3,3-dimethylbutyl)-3,3a,4,5,6,6a-hexahydro-1H-cyclopenta[c]pyrrol-5-yl]oxy]pyridazin-3-yl]-3,5-dimethyl-isoxazole;

(3aR,6aS)-5-[6-(2-chloro-5-fluoro-phenyl)pyridazin-3-yl] oxy-2-(3,3-dimethylbutyl)-3,3a,4,5,6,6a-hexahydro-1H-cyclopenta[c]pyrrole;

(3aR,6aS)-5-[6-(1,3-benzodioxol-5-yl)pyridazin-3-yl]oxy-2-(3,3-dimethylbutyl)-3,3a,4,5,6,6a-hexahydro-1H-cyclopenta[c]pyrrole;

(3aR,6aS)-2-(3,3-dimethylbutyl)-5-[6-[4-(trifluoromethyl) phenyl]pyridazin-3-yl]oxy-3,3a,4,5,6,6a-hexahydro-1H-cyclopenta[c]pyrrole;

(3aR,6aS)-2-(3,3-dimethylbutyl)-N-(6-morpholinopyridazin-3-yl)octahydrocyclopenta[c]pyrrol-5-amine;

(3aR,5s,6aS)-5-(6-chloropyridazin-3-yl)oxy-2-(3,3-dimethylbutyl)-3,3a,4,5,6,6a-hexahydro-1H-cyclopenta[c]pyrrole;

N-[4-[6-[[(3aR,5s,6aS)-2-(3,3-dimethylbutyl)-3,3a,4,5,6, 6a-hexahydro-1H-cyclopenta[c]pyrrol-5-yl]oxy] pyridazin-3-yl]phenyl]acetamide;

N-[4-[6-[[(3aR,5s,6aS)-2-(cyclohexylmethyl)-3,3a,4,5,6, 6a-hexahydro-1H-cyclopenta[c]pyrrol-5-yl]oxy] pyridazin-3-yl]phenyl]acetamide;

N-[4-[6-[[(3aR,5s,6aS)-2-[(4-fluorophenyl)methyl]-3,3a,4, 5,6,6a-hexahydro-1H-cyclopenta[c]pyrrol-5-yl]oxy] pyridazin-3-yl]phenyl]acetamide;

N-[4-[6-[[(3aR,5s,6aS)-2-(tetrahydropyran-4-ylmethyl)-3, 3a,4,5,6,6a-hexahydro-1H-cyclopenta[c]pyrrol-5-yl]oxy] pyridazin-3-yl]phenyl]acetamide;

N-[4-[6-[[(3aR,5s,6aS)-2-[(3-methyl-2-pyridyl)methyl]-3, 3a,4,5,6,6a-hexahydro-1H-cyclopenta[c]pyrrol-5-yl]oxy] pyridazin-3-yl]phenyl]acetamide;

(3aR,5s,6aS)-2-(3,3-dimethylbutyl)-5-[6-(1,3-dimethylpyrazol-4-yl)pyridazin-3-yl]oxy-3,3a,4,5,6,6a-hexahydro-1H-cyclopenta[c]pyrrole;

(3aR,5s,6aS)-2-(3,3-dimethylbutyl)-5-[6-(2,4-dimethylpyrazol-3-yl)pyridazin-3-yl]oxy-3,3a,4,5,6,6a-hexahydro-1H-cyclopenta[c]pyrrole;

4-[6-[[(3aR,5s,6aS)-2-(3,3-dimethylbutyl)-3,3a,4,5,6,6a-hexahydro-1H-cyclopenta[c]pyrrol-5-yl]oxy]pyridazin-3-yl]-3,5-dimethyl-isoxazole;

(3aR,5s,6aS)-5-[6-(2-chloro-5-fluoro-phenyl)pyridazin-3-yl]oxy-2-(3,3-dimethylbutyl)-3,3a,4,5,6,6a-hexahydro-1H-cyclopenta[c]pyrrole;

(3aR,5s,6aS)-5-[6-(1,3-benzodioxol-5-yl)pyridazin-3-yl] oxy-2-(3,3-dimethylbutyl)-3,3a,4,5,6,6a-hexahydro-1H-cyclopenta[c]pyrrole;

(3aR,5s,6aS)-2-(3,3-dimethylbutyl)-5-[6-[4-(trifluoromethyl)phenyl]pyridazin-3-yl]oxy-3,3a,4,5,6,6a-hexahydro-1H-cyclopenta[c]pyrrole;

N-[4-[6-[[(3aR,5s,6aS)-2-(3,3-dimethylbutyl)-3,3a,4,5,6, 6a-hexahydro-1H-cyclopenta[c]pyrrol-5-yl]amino] pyridazin-3-yl]phenyl]acetamide;

(3aR,5s,6aS)—N-[6-(2-chloro-4-fluoro-phenyl)pyridazin-3-yl]-2-(3,3-dimethylbutyl)-3,3a,4,5,6,6a-hexahydro-1H-cyclopenta[c]pyrrol-5-amine;

(3aR,5s,6aS)-2-(3,3-dimethylbutyl)-N-[6-(3,5-dimethyl-isoxazol-4-yl)pyridazin-3-yl]-3,3a,4,5,6,6a-hexahydro-1H-cyclopenta[c]pyrrol-5-amine;

(3aR,5s,6aS)-2-(3,3-dimethylbutyl)-N-(6-morpholino-pyridazin-3-yl)-3,3a,4,5,6,6a-hexahydro-1H-cyclopenta[c]pyrrol-5-amine;

(3aR,5r,6aS)-2-(3,3-dimethylbutyl)-N-[6-(2,4-dimethylpyrazol-3-yl)pyridazin-3-yl]-3,3a,4,5,6,6a-hexahydro-1H-cyclopenta[c]pyrrole-5-carboxamide;

(3aR,5s,6aS)-2-(3,3-dimethylbutyl)-N-[6-(2,4-dimethylpyrazol-3-yl)pyridazin-3-yl]-3,3a,4,5,6,6a-hexahydro-1H-cyclopenta[c]pyrrole-5-carboxamide;

(3aR,5s,6aS)-2-(3,3-dimethylbutyl)-5-[[6-(2,4-dimethylpyrazol-3-yl)pyridazin-3-yl]oxymethyl]-3,3a,4,5,6,6a-hexahydro-1H-cyclopenta[c]pyrrole;

(3aR,5r,6aS)-2-(3,3-dimethylbutyl)-5-[[6-(2,4-dimethylpyrazol-3-yl)pyridazin-3-yl]oxymethyl]-3,3a,4,5,6,6a-hexahydro-1H-cyclopenta[c]pyrrole;

N-[4-[4-[[(3aR,5s,6aS)-2-(3,3-dimethylbutyl)-3,3a,4,5,6, 6a-hexahydro-1H-cyclopenta[c]pyrrol-5-yl]amino]-2,3-difluoro-phenyl]phenyl]acetamide;

(3aR,5s,6aS)-2-(3,3-dimethylbutyl)-N-[5-(1,3-dimethylpyrazol-4-yl)-2-pyridyl]-3,3a,4,5,6,6a-hexahydro-1H-cyclopenta[c]pyrrol-5-amine;

(3aR,5s,6aS)-2-(1-adamantylmethyl)-N-[5-(1,3-dimethylpyrazol-4-yl)-2-pyridyl]-3,3a,4,5,6,6a-hexahydro-1H-cyclopenta[c]pyrrol-5-amine;

(3aR,5s,6aS)-2-(5-bicyclo[2.2.1]hept-2-enylmethyl)-N-[5-(1,3-dimethylpyrazol-4-yl)-2-pyridyl]-3,3a,4,5,6,6a-hexahydro-1H-cyclopenta[c]pyrrol-5-amine;

(3aR,5s,6aS)—N-[5-(1,3-dimethylpyrazol-4-yl)-2-pyridyl]-2-(tetrahydropyran-4-ylmethyl)-3,3a,4,5,6,6a-hexahydro-1H-cyclopenta[c]pyrrol-5-amine;

(3aR,5s,6aS)-2-(3,3-dimethylbutyl)-N-[5-(1,3-dimethylpyrazol-4-yl)pyrazin-2-yl]-3,3a,4,5,6,6a-hexahydro-1H-cyclopenta[c]pyrrol-5-amine;

(3aR,5s,6aS)-2-(5-bicyclo[2.2.1]hept-2-enylmethyl)-N-[5-(1,3-dimethylpyrazol-4-yl)pyrazin-2-yl]-3,3a,4,5,6,6a-hexahydro-1H-cyclopenta[c]pyrrol-5-amine;

(3aR,5s,6aS)-2-(1-adamantylmethyl)-N-[5-(1,3-dimethylpyrazol-4-yl)pyrazin-2-yl]-3,3a,4,5,6,6a-hexahydro-1H-cyclopenta[c]pyrrol-5-amine;

N-[4-[5-[[(3aR,5s,6aS)-2-(3,3-dimethylbutyl)-3,3a,4,5,6,6a-hexahydro-1H-cyclopenta[c]pyrrol-5-yl]amino]pyrazin-2-yl]phenyl]acetamide;

N-[4-[5-[[(3aR,5s,6aS)-2-(5-bicyclo[2.2.1]hept-2-enylmethyl)-3,3a,4,5,6,6a-hexahydro-1H-cyclopenta[c]pyrrol-5-yl]amino]pyrazin-2-yl]phenyl]acetamide;

N-[4-[5-[[(3aR,5s,6aS)-2-(tetrahydropyran-4-ylmethyl)-3,3a,4,5,6,6a-hexahydro-1H-cyclopenta[c]pyrrol-5-yl]amino]pyrazin-2-yl]phenyl]acetamide;

(3aR,5r,6aS)—N-[6-(2-chloro-5-fluoro-phenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(2-pyridylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(3-pyridylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(4-pyridylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-[(4-fluorophenyl)methyl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(3-quinolylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(imidazo[1,2-a]pyridin-2-ylmethyl)-3,3a,4,5,6,6a-hexahydro-1H-cyclopenta[c]pyrrol-5-amine;

(3aR,5s,6aS)-2-(1,3-benzodioxol-5-ylmethyl)-N-[6-(2-chloro-5-fluoro-phenyl)pyridazin-3-yl]-3,3a,4,5,6,6a-hexahydro-1H-cyclopenta[c]pyrrol-5-amine;

(3aR,5s,6aS)-2-(1,3-benzodioxol-4-ylmethyl)-N-[6-(2-chloro-5-fluoro-phenyl)pyridazin-3-yl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-[(4-methoxyphenyl)methyl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(cyclopropylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(pyrazin-2-ylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-[(3-methyloxetan-3-yl)methyl]-3,3a,4,5,6,6a-hexahydro-1H-cyclopenta[c]pyrrol-5-amine;

N-[4-[[(3aR,5s,6aS)-5-[[6-(2-chloro-5-fluoro-phenyl)pyridazin-3-yl]amino]-3,3a,4,5,6,6a-hexahydro-1H-cyclopenta[c]pyrrol-2-yl]methyl]phenyl]methanesulfonamide;

(3aR,5s,6aS)—N-[6-(2-chloro-5-fluoro-phenyl)pyridazin-3-yl]-2-[(2,2-dimethyltetrahydropyran-4-yl)methyl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-[(2-methoxyphenyl)methyl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-[(3-fluorophenyl)methyl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(2-furylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-isobutyl-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(3-furylmethyl)-3,3a,4,5,6,6a-hexahydro-1H-cyclopenta[c]pyrrol-5-amine;

(3aR,5s,6aS)—N-(6-chloropyridazin-3-yl)-2-(tetrahydropyran-4-ylmethyl)-3,3a,4,5,6,6a-hexahydro-1H-cyclopenta[c]pyrrol-5-amine;

N-[4-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]phenyl]acetamide;

(3aR,5s,6aS)—N-[6-(6-quinolyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(1,3-benzodioxol-5-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-imidazo[1,2-a]pyridin-6-ylpyridazin-3-yl]-2-(tetrahydropyran-4-ylmethyl)-3,3a,4,5,6,6a-hexahydro-1H-cyclopenta[c]pyrrol-5-amine;

(3aR,5s,6aS)-2-(tetrahydropyran-4-ylmethyl)-N-[6-[4-(trifluoromethoxy)phenyl]pyridazin-3-yl]-3,3a,4,5,6,6a-hexahydro-1H-cyclopenta[c]pyrrol-5-amine;

(3aR,5s,6aS)—N-[6-(2-fluorophenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(3-fluorophenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(4-fluorophenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-furyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(3,3-difluoropyrrolidin-1-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(4,4-difluoro-1-piperidyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-(6-morpholinopyridazin-3-yl)-2-(tetrahydropyran-4-ylmethyl)-3,3a,4,5,6,6a-hexahydro-1H-cyclopenta[c]pyrrol-5-amine;

(3aR,5s,6aS)—N-(6-pyrrolidin-1-ylpyridazin-3-yl)-2-(tetrahydropyran-4-ylmethyl)-3,3a,4,5,6,6a-hexahydro-1H-cyclopenta[c]pyrrol-5-amine;

(3aR,5s,6aS)—N-[6-(1-piperidyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-[(3S)-3-fluoropyrrolidin-1-yl]pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-[(3R)-3-fluoropyrrolidin-1-yl]pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(3,3-difluoro-1-piperidyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-(6-phenylpyridazin-3-yl)-2-(tetrahydropyran-4-ylmethyl)-3,3a,4,5,6,6a-hexahydro-1H-cyclopenta[c]pyrrol-5-amine;

(3aR,5s,6aS)—N-[6-(p-tolyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-methoxyphenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(3-methoxyphenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(4-methoxyphenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-chloro-3-fluoro-phenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-chloro-4-fluoro-phenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-chloro-6-fluoro-phenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-chlorophenyl)pyridazin-3-yl]-2-(tetrahydropyran-4-ylmethyl)-3,3a,4,5,6,6a-hexahydro-1H-cyclopenta[c]pyrrol-5-amine;

N-[2-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]phenyl]acetamide;

4-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]-N,N-dimethyl-benzamide;

(3aR,5s,6aS)—N-[6-(1-methylpyrazol-4-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(1-cyclopropylpyrazol-4-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(3,5-dimethylisoxazol-4-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)-2-(tetrahydropyran-4-ylmethyl)-N-[6-[6-(trifluoromethyl)-3-pyridyl]pyridazin-3-yl]-3,3a,4,5,6,6a-hexahydro-1H-cyclopenta[c]pyrrol-5-amine;

(3aR,5s,6aS)—N-[6-(5-fluoro-2-methoxy-phenyl)pyridazin-3-yl]-2-(tetrahydropyran-4-ylmethyl)-3,3a,4,5,6,6a-hexahydro-1H-cyclopenta[c]pyrrol-5-amine;

2-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]-4-fluoro-benzonitrile;

(3aR,5s,6aS)—N-[6-(5-fluoro-2-methyl-phenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2,5-difluorophenyl)pyridazin-3-yl]-2-(tetrahydropyran-4-ylmethyl)-3,3a,4,5,6,6a-hexahydro-1H-cyclopenta[c]pyrrol-5-amine;

2-[3-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]phenyl]propan-2-ol;

N-[3-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]phenyl]methanesulfonamide;

(3aR,5s,6aS)—N-[6-(3-pyridyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(4-pyridyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-chloro-5-fluoro-3-pyridyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-methylindazol-5-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(3-fluoro-4-methoxy-phenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-[4-(difluoromethoxy)phenyl]pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(6-methoxy-3-pyridyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(4-fluorophenoxy)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)-2-(tetrahydropyran-4-ylmethyl)-N-[6-(2-thienyl)pyridazin-3-yl]-3,3a,4,5,6,6a-hexahydro-1H-cyclopenta[c]pyrrol-5-amine;

(3aR,5s,6aS)-2-(tetrahydropyran-4-ylmethyl)-N-[6-(3-thienyl)pyridazin-3-yl]-3,3a,4,5,6,6a-hexahydro-1H-cyclopenta[c]pyrrol-5-amine;

(3aR,5s,6aS)—N-[6-(1-ethylpyrazol-3-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(1H-pyrrol-3-yl)pyridazin-3-yl]-2-(tetrahydropyran-4-ylmethyl)-3,3a,4,5,6,6a-hexahydro-1H-cyclopenta[c]pyrrol-5-amine;

N-[(3aR,5s,6aS)-2-(tetrahydropyran-4-ylmethyl)-3,3a,4,5,6,6a-hexahydro-1H-cyclopenta[c]pyrrol-5-yl]-5-phenyl-thiazol-2-amine;

N-[(3aR,5s,6aS)-2-(4-pyridylmethyl)-3,3a,4,5,6,6a-hexahydro-1H-cyclopenta[c]pyrrol-5-yl]-5-phenyl-thiazol-2-amine; and (3aR,5s,6aS)—N-[6-(6-cyclopropyl-3-pyridyl)pyridazin-3-yl]-2-(tetrahydropyran-4-ylmethyl)-3,3a,4,5,6,6a-hexahydro-1H-cyclopenta[c]pyrrol-5-amine, or a pharmaceutically acceptable salt thereof.

Compound names and/or structures can be assigned/determined by using the Struct=Name naming algorithm as part of CHEMDRAW® ULTRA.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

Compounds have a 3,3a,4,5,6,6a-hexahydro-1H-cyclopenta[c]pyrrole core structure that can have a plane of symmetry as in the following two representative structures.

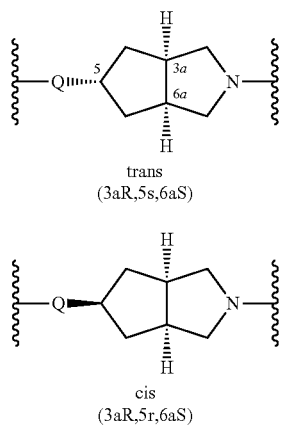

These structures are considered meso since their mirror images are superimposable. The 3a, 5, and 6a stereochemical designations are used herein for symmetrical structures of type A and B to designate relative stereochemistry between the ring fusion and the 5-position. Thus, when drawn in the orientation depicted above 3aR,5s,6aS refers to trans relative stereochemistry between the 5-position substituent and the ring fusion, and 3aR,5r,6aS refers to cis relative stereochemistry between the 5-position substituent and the ring fusion. The lower case s and r designations at the 5-position refer to pseudo asymmetry as described by G. P. Moss in "Basic terminology of stereochemistry (IUPAC Recommendations)" in Pure and Applied Chemistry (1996), 68 (12) 2193-2222. The person skilled in the art will understand that when structures A and B are drawn as the mirror images, chemical naming programs may, depending on the program, reverse the stereochemical designation for 3a and 6 positions from R to S and S to R, respectively, but that the pseudo asymmetry at the 5-position remains invariant. Compounds of formula (I) may have a 5-position substituent in a trans configuration

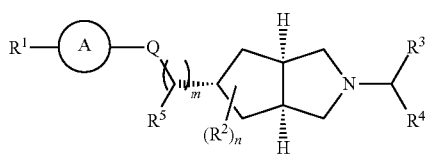

or a cis configuration

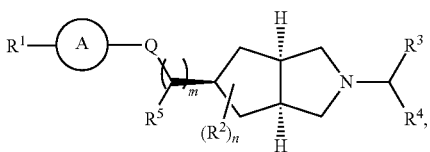

or may be prepared as a mixture of trans and cis.

It should be understood that the compound may possess tautomeric forms, as well as geometric isomers, and that these also constitute embodiments of the disclosure.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{5}N$, $^{18}O$, $^{17}O$, $^{31}P$, $^{32}P$, $^{18}F$, and $^{36}Cl$, respectively. Substitution with heavier isotopes such as deuterium, i.e. $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

a. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

b. General Synthesis

Compounds of formula (I) may be prepared by synthetic processes or by metabolic processes. Preparation of the compounds by metabolic processes includes those occurring in the human or animal body (in vivo) or processes occurring in vitro.

Abbreviations used in the descriptions of the Schemes that follow are: AcOH is acetic acid; BMS is borane dimethyl sulfide complex; Boc is tert-butyloxycarbonyl; BrettPhos-Pd-G3 is [(2-di-cyclohexylphosphino-3,6-dimethoxy-2',4',6'-triisopropyl-1,1'-biphenyl)-2-(2'-amino-1,1'-biphenyl)]palladium(II) methanesulfonate (CAS Number 1470372-59-8); DCE is 1,2-dichloroethane; DCM is dichloromethane; DIEA and DIPEA both refer to N,N-diisopropylethylamine; DMF is N,N-dimethylformamide; HATU is 2-(7-aza-1H-benzotriazole-1-yl)-1,1,3,3-tetramethyluronium hexafluorophosphate; MeOH is methanol; MsCl is methanesulfonyl chloride; $NaBH(OAc)_3$ and STAB both refer to sodium triacetoxyborohydride; rt or r.t. is room temperature; RuPhos-Pd-G3 is (2-dicyclohexylphosphino-2',6'-diisopropoxy-1,1'-biphenyl)[2-(2'-amino-1,1'-biphenyl)]palladium(II) methanesulfonate (CAS Number 1445085-77-7); t-BuOH is tert-butyl alcohol; t-BuOK is potassium tert-butoxide; THF is tetrahydrofuran; and TosMIC is toluenesulfonylmethyl isocyanide.

Compounds of formula (I) can be synthesized as shown in the following schemes.

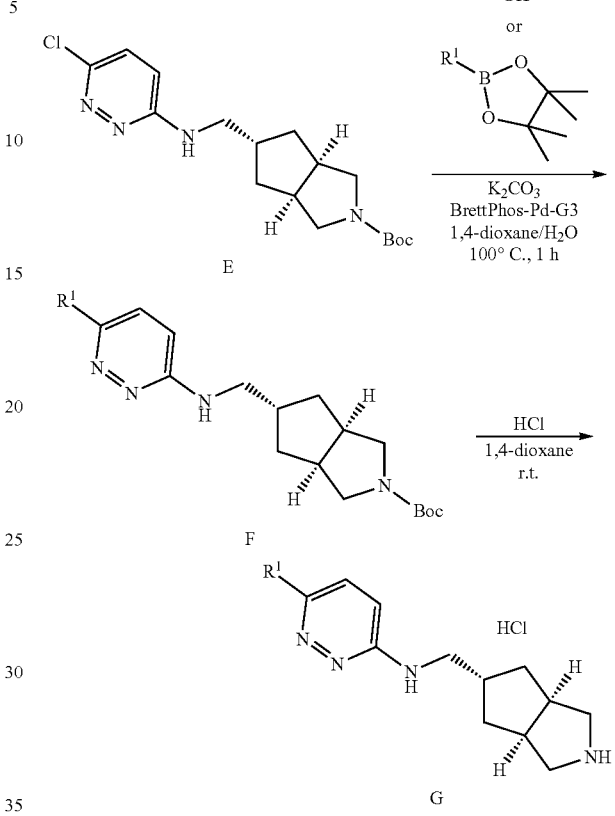

As shown in Scheme 1, cis-tert-butyl 5-oxohexahydrocyclopenta[c]pyrrole-2(1H)-carboxylate (compound A; CAS #146231-54-1, Synthonix, Catalog #B8253) can be converted to the corresponding nitrile using TosMIC to generate compound B, which can be reduced to the corresponding amine compound C. Reaction of compound C with 3,6-dichloropyridazine (compound D) can generate compound E. Coupling with a suitable boronic acid or ester provides compound F, which can be deprotected (e.g., with hydrochloric acid) to generate compound G.

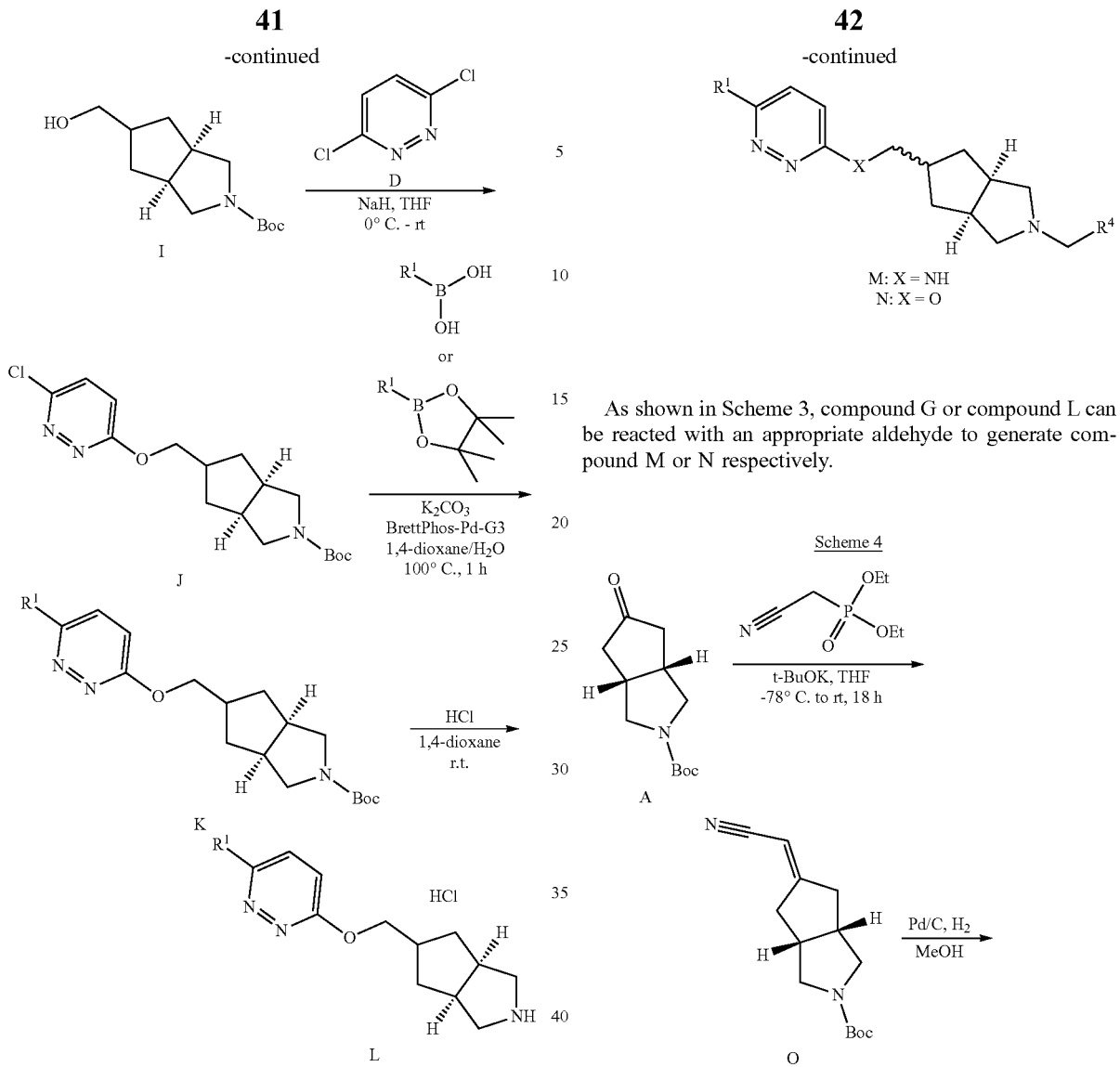

As shown in Scheme 2, cis-tert-butyl 5-oxohexahydrocyclopenta[c]pyrrole-2(1H)-carboxylate (compound A) can be converted to the corresponding alkene using methyl(triphenyl)phosphonium iodide to generate compound H, which can be subjected to hydroboration-oxidation to generate the corresponding alcohol compound I. Reaction of compound I with 3,6-dichloropyridazine (compound D) can generate compound J. Coupling with a suitable boronic acid or ester provides compound K, which can be deprotected (e.g., with hydrochloric acid) to generate compound L.

As shown in Scheme 3, compound G or compound L can be reacted with an appropriate aldehyde to generate compound M or N respectively.

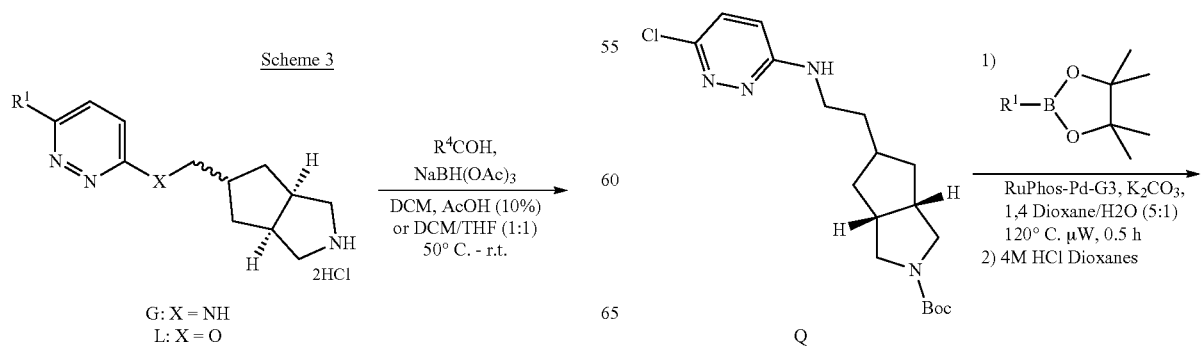

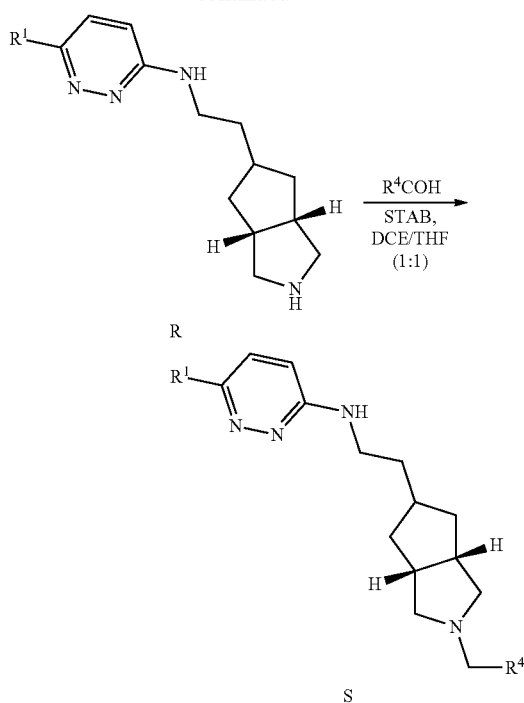

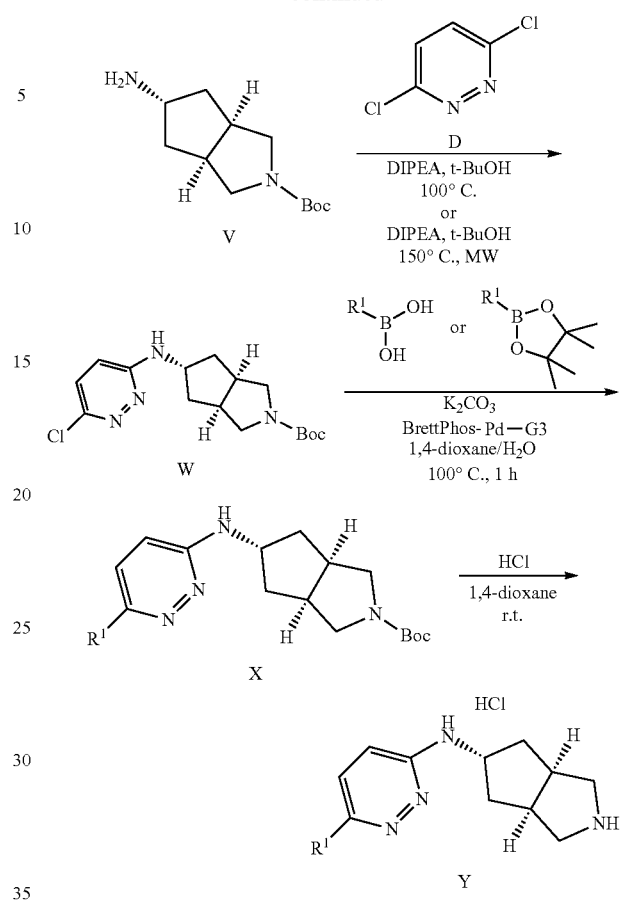

As shown in Scheme 4, cis-tert-butyl 5-oxohexahydrocyclopenta[c]pyrrole-2(1H)-carboxylate (compound A) can be converted to compound O using diethyl cyanomethylphosphonate, which can be subjected to hydrogenation to form compound P. Reduction of compound P followed by reaction with 3,6-dichloropyridazine (compound D) can generate compound Q, and reaction with a suitable boronic acid or ester followed by deprotection can provide compound R. Finally, reaction with a suitable aldehyde can provide compound S.

As shown in Scheme 5, cis-tert-butyl 5-oxohexahydrocyclopenta[c]pyrrole-2(1H)-carboxylate (compound A) can be reduced with sodium borohydride to form compound T, which can then be converted to the corresponding azide compound U. Reduction to the amine provides compound V, which can be reacted with 3,6-dichloropyridazine (compound D) to generate compound W. Coupling with a suitable boronic acid or ester provides compound X, which can be deprotected (e.g., with hydrochloric acid) to generate compound Y.

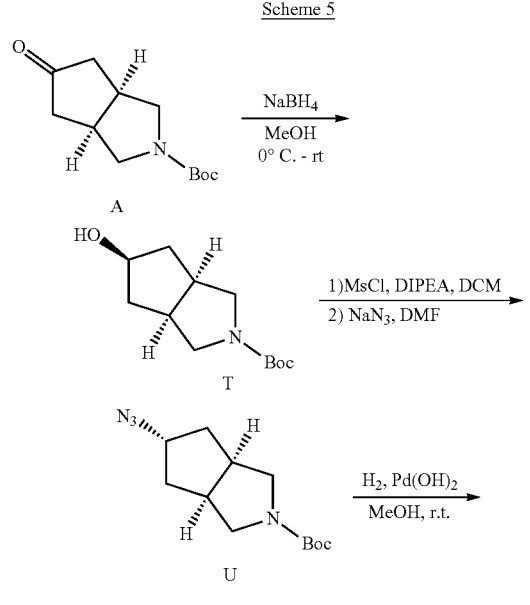

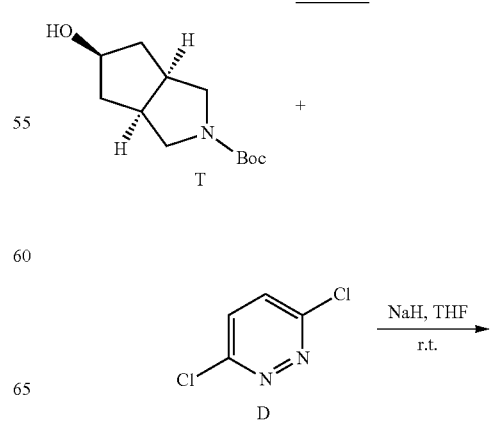

-continued

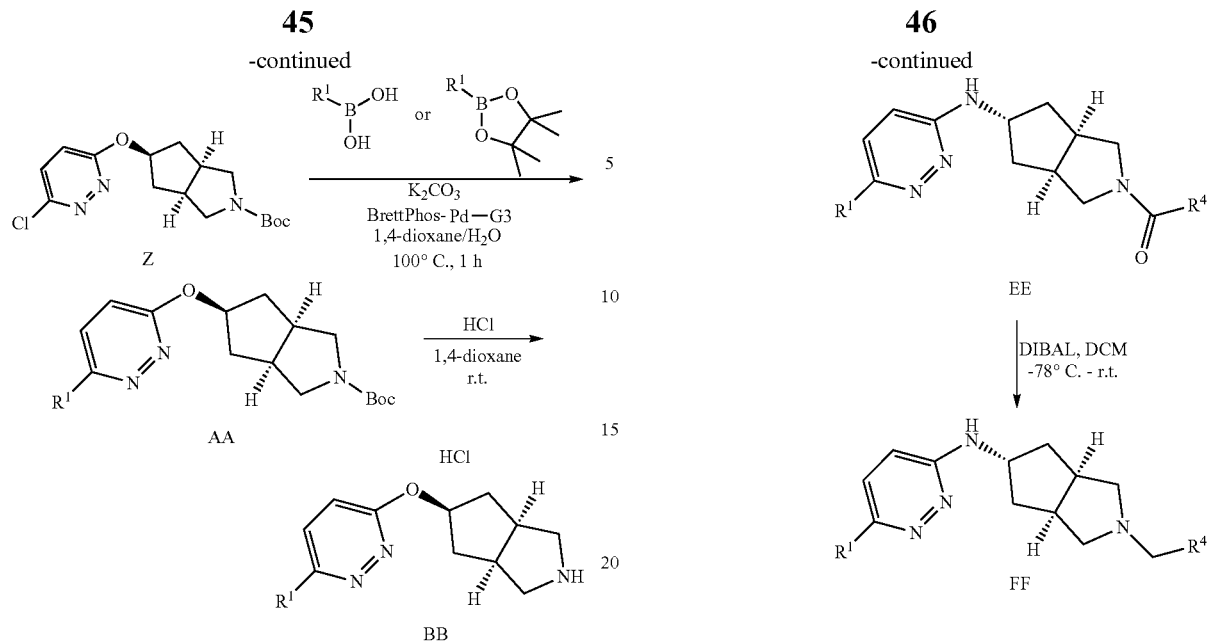

As shown in Scheme 6, compound T can be reacted with 3,6-dichloropyridazine (compound D) to generate compound Z. Coupling with a suitable boronic acid or ester provides compound AA, which can be deprotected (e.g., with hydrochloric acid) to generate compound BB.

Scheme 7

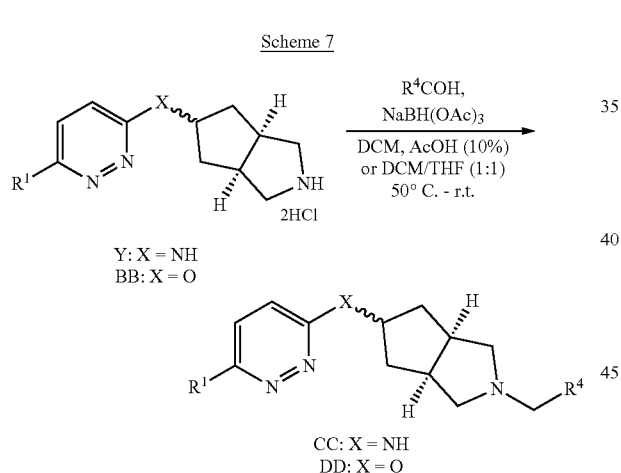

Y: X = NH
BB: X = O

CC: X = NH
DD: X = O

As shown in Scheme 7, compound Y or compound BB can be reacted with an appropriate aldehyde to generate compound CC or DD respectively.

Scheme 8

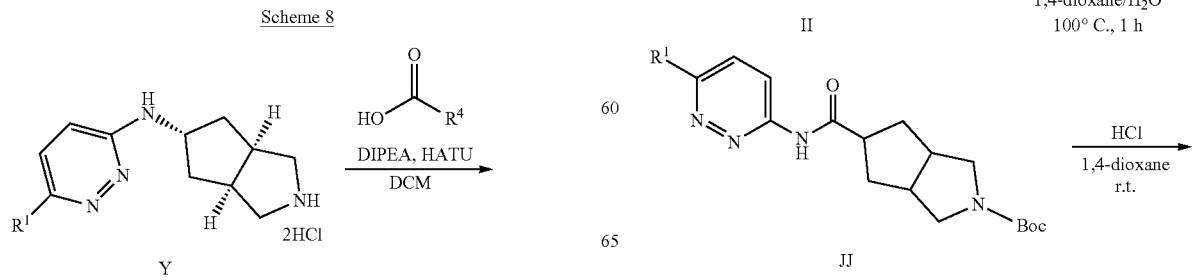

As shown in Scheme 8, compound Y can alternatively be reacted with an appropriate carboxylic acid to form amide compound EE, which can be reduced to generate compound FF.

Scheme 9

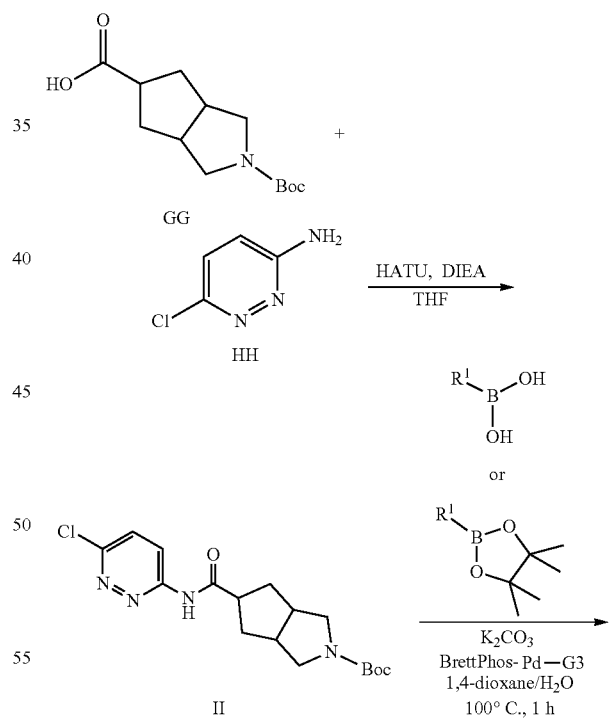

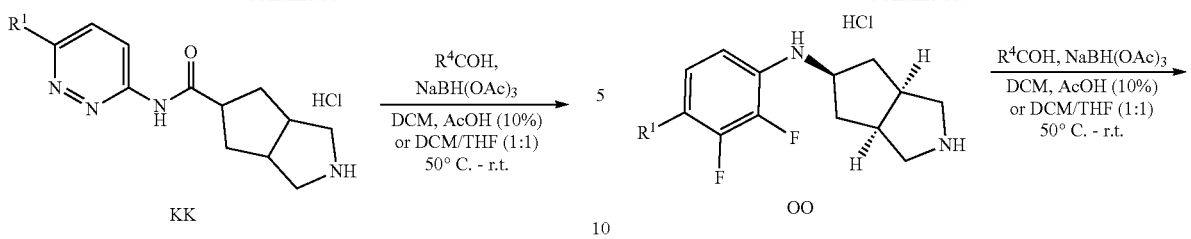

KK

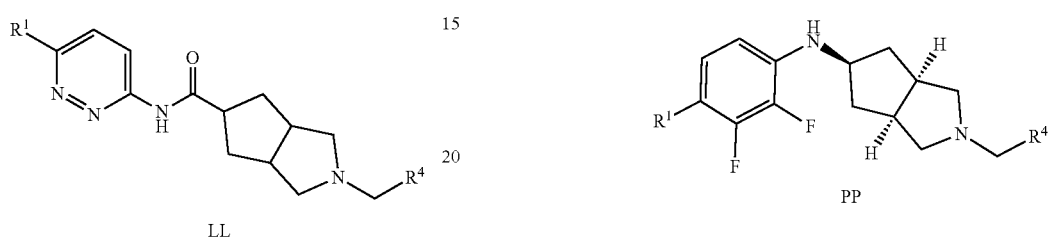

LL

As shown in Scheme 9, 2-(tert-butoxycarbonyl)octahydrocyclopenta[c]pyrrole-5-carboxylic acid (compound GG; CAS #1177319-91-3, Pharmablock, Catalog #PBN2011986) can be reacted with 3-amino-6-chloropyridazine (compound HH) to generate compound H, which can be coupled with a suitable boronic acid or ester to form compound JJ. Deprotection (e.g., with hydrochloric acid) generates compound KK, and reaction with a suitable aldehyde generates compound LL.

As shown in Scheme 10, 4-bromo-2,3-difluoroaniline can be reacted with cis-N-Boc-5-oxo-octahydrocyclopenta[c]pyrrole to generate compound MM, which can be coupled with an appropriate boronic acid or ester to form compound NN. Deprotection (e.g., with hydrochloric acid) generates compound OO, and reaction with a suitable aldehyde generates compound PP.

Scheme 10

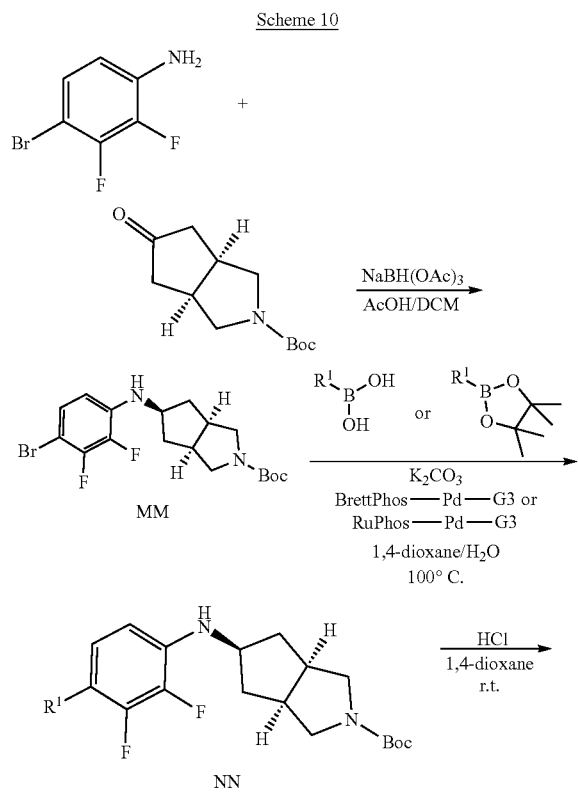

Scheme 11

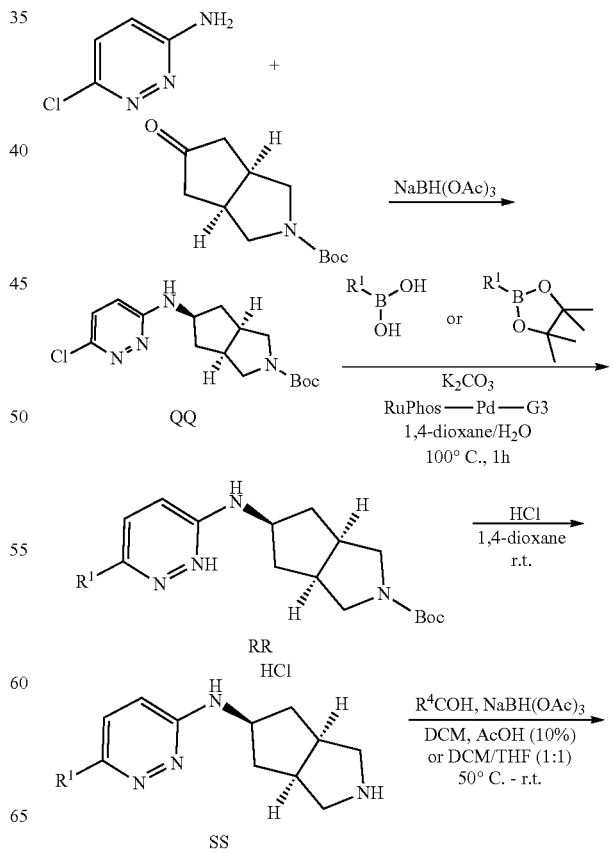

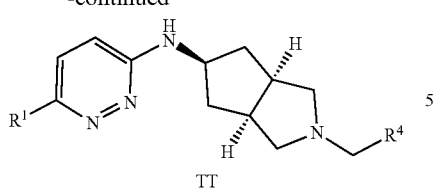

TT

As shown in Scheme 11, 3-amino-6-chloropyridazine can be reacted with cis-N-Boc-5-oxo-octahydrocyclopenta[c]pyrrole to generate compound QQ, which can be coupled with an appropriate boronic acid or ester to form compound RR. Deprotection (e.g., with hydrochloric acid) generates compound SS, and reaction with a suitable aldehyde generates compound TT.

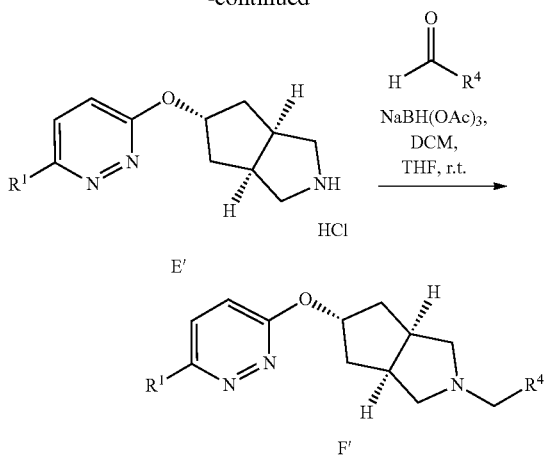

E'

F'

As shown in Scheme 12, compound T may be converted to compound A', using a Mitsunobu reaction, and cleaved to B'. Reaction of B' with 3,6-dichloropyridazine provides compound C', which can be coupled with a suitable boronic acid or ester using a Suzuki reaction to provide compound D'. Compound D' can be deprotected under acid conditions and reacted with appropriate aldehydes by reductive amination to provide compounds F'.

Scheme 12

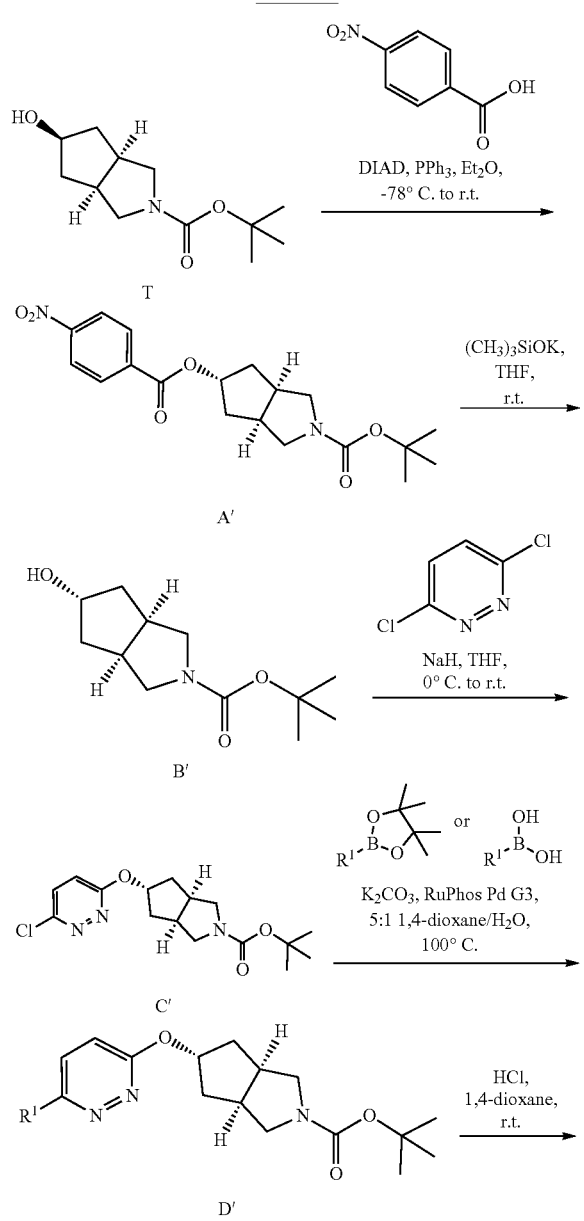

Scheme 13

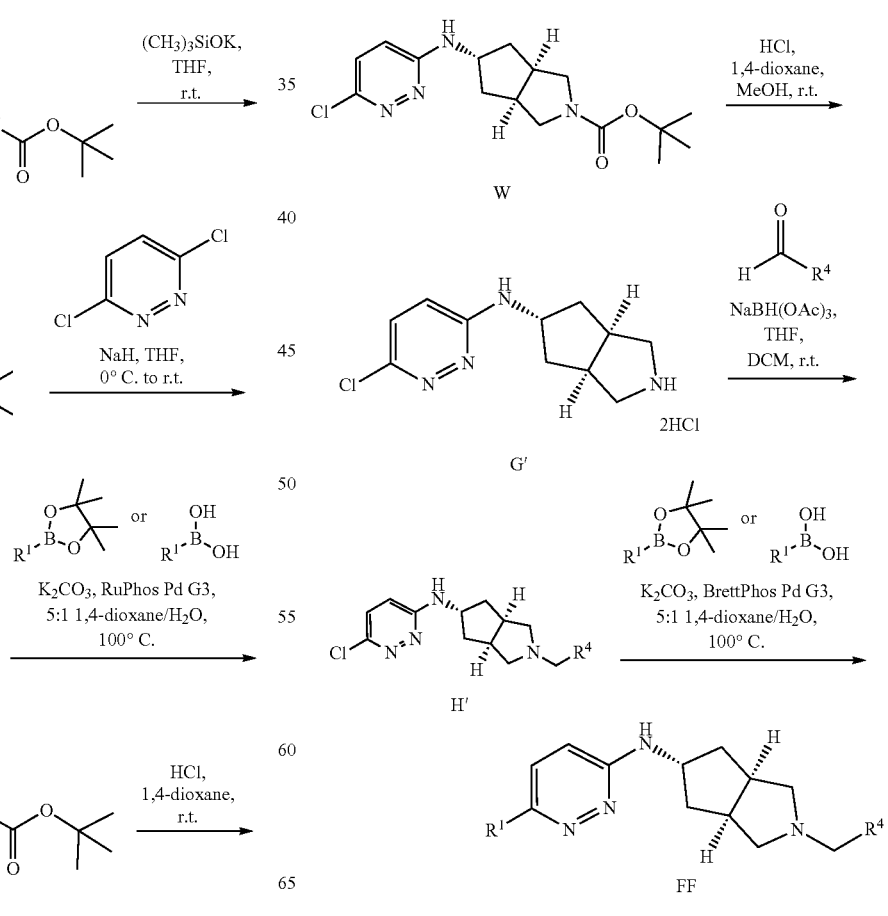

As shown in Scheme 13, compound W may be deprotected under acid conditions to provide compound G', which may be reacted with suitable aldehydes by reductive amination to provide compounds H'. Compounds H' may be coupled with suitable boronic acids or esters to provide compounds FF.

Scheme 14

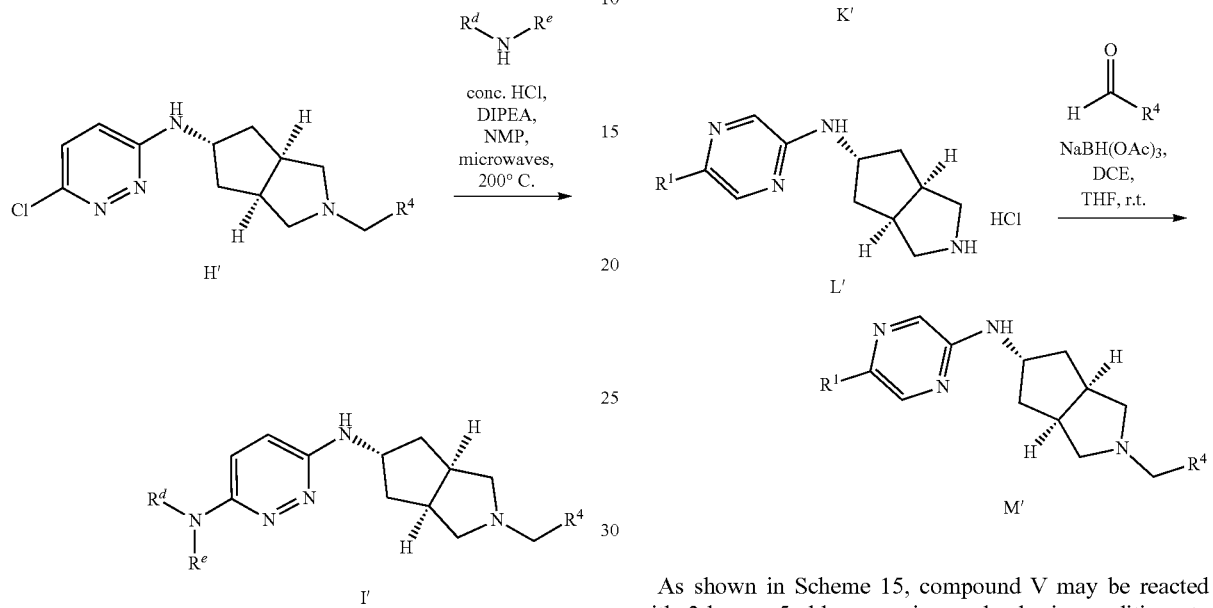

I'

As shown in Scheme 14, compounds H' may be reacted with suitable amines NHR$^d$R$^e$ to provide compounds I'. Cyclic amines, such as morpholine, piperidine, etc., may be substituted in the process of Scheme 14 to provide compounds with cyclic amine substituents.

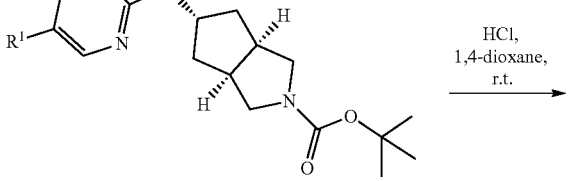

As shown in Scheme 15, compound V may be reacted with 2-bromo-5-chloropyrazine under basic conditions to provide compound J', which may be coupled with suitable boronic acids or esters to provide intermediate K'. Deprotection of K' under acid conditions may form compounds L', which can be reacted with suitable aldehydes under reductive amination conditions to provide compounds M'.

Scheme 15

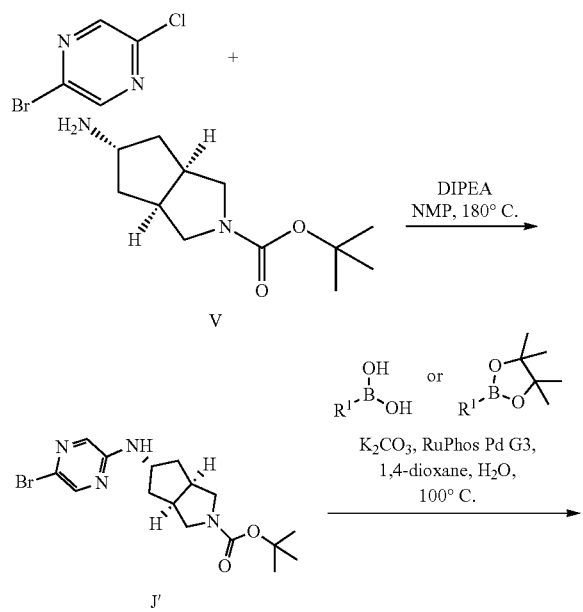

Scheme 16

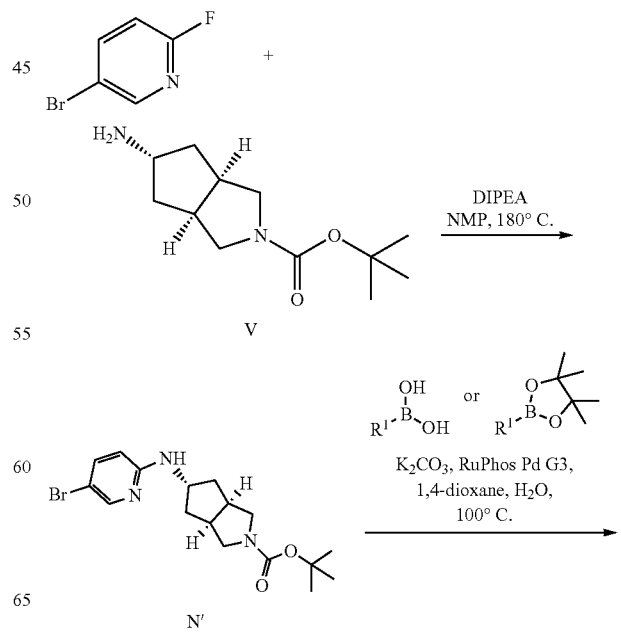

-continued

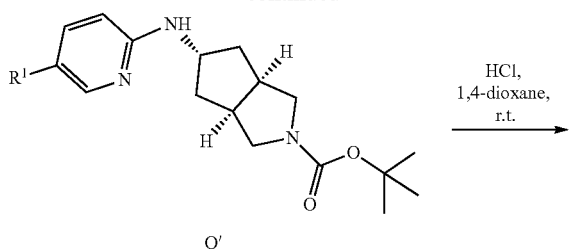

O'

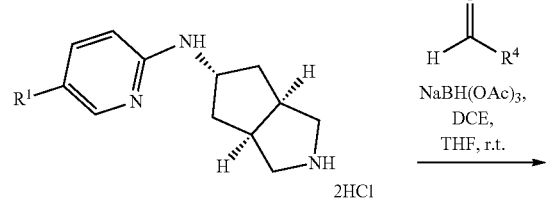

P'

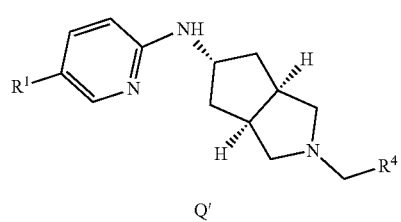

Q'

As shown in Scheme 16, compound V may be reacted with 3-bromo-6-fluoropyridine under basic conditions to form compound N', which may be coupled with suitable boronic acids or esters to provide compounds O'. Deprotection of O' under acid conditions may form compounds P', which can be reacted with suitable aldehydes under reductive amination conditions to provide compounds Q'.

Scheme 17

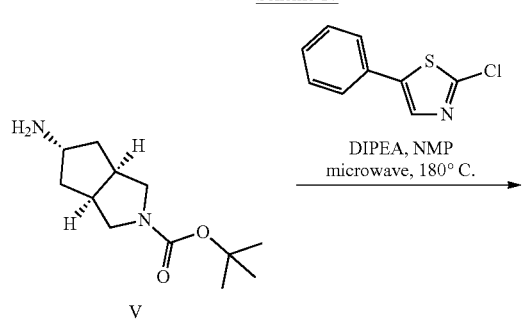

-continued

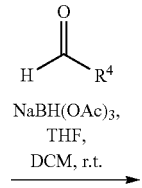

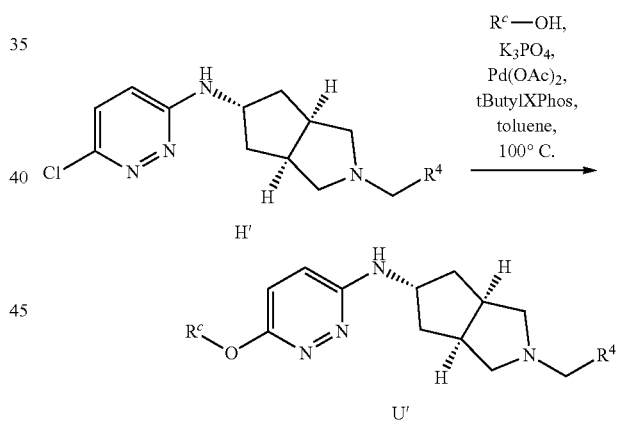

As shown in Scheme 17, compound V may be reacted with 2-chloro-5-phenylthiazole under basic conditions to form compound R', which may be deprotected under acid conditions to form S' and subjected to reductive amination to provide compounds T'.

Scheme 18

As shown in Scheme 18, compounds H' may be reacted with suitable alcohols ROH under Buchwald coupling conditions to provide compounds U'.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

c. Muscarinic Acetylcholine Receptor $M_4$ Activity $M_4$ is the most highly expressed mAChR subtype in the striatum and its expression is similar in rodents and primates. Due to a lack of selective $M_4$ antagonists, mechanistic understanding of the role of $M_4$ has been guided by biochemical and genetic studies, as well as the use of highly selective $M_4$ positive allosteric modulators (PAMs). Highly selective $M_4$ PAMs induce robust decreases in behavioral responses to psychomotor stimulants that act by increasing striatal DA levels. Furthermore, genetic deletion of $M_4$ increases exploratory locomotor activity, potentiates locomotor responses to amphetamine and other stimulants, and eliminates effects of $M_4$ PAMs on locomotor activity and these effects are also observed with selective deletion of $M_4$ from striatal spiny projection neurons that express the D1 subtype of DA receptor (D1-SPNs). In vivo microdialysis studies reveal that administration of $M_4$ PAMs reduces amphetamine-induced DA release in the dorsal and ventral striatum and fMRI studies show that $M_4$ PAMs reverse amphetamine-induced increases in cerebral blood flow (CBV) in striatum and other basal ganglia nuclei. More recently, fast-scanning cyclic voltammetry (FSCV) and genetic studies, demonstrated that $M_4$ PAMs act, at least in part, by inhibition of DA release from presynaptic DA terminals in the striatum through release of an endocannabinoid from striatal spiny projection neurons (SPNs) and activation of CB2 cannabinoid receptors on DA terminals.

$M_4$ is heavily expressed in a subset of SPNs that also express the $D_1$ subtype of DA receptor ($D_1DR$), which form the direct pathway (D1-SPNs) sending inhibitory projections to the substantia nigra pars reticulata (SNr). Interestingly, D1DRs activate a unique GTP-binding protein in D1-SPNs, termed $G_{\alpha olf}$ that couples $D_1Rs$ to activation of adenylyl cyclase, formation of cAMP, and activation of protein kinase A (PKA). This signaling pathway is critical for many of the behavioral actions of DA-mediated activation of motor activity Interestingly, $M_4$ couples to $G\alpha_{i/o}$ G proteins, which inhibit adenylyl cyclase and have the potential to directly counteract inhibit $D_1$ receptor signaling and effects on motor function. These studies raise the possibility that, in addition to inhibition of DA release, $M_4$ PAMs may directly inhibit D1R-mediated signaling in $D_1$-SPNs by direct inhibition of cAMP formation and this could also contribute to the powerful inhibitory effect of selective $M_4$ activation of DA signaling in the basal ganglia. Consistent with this, $M_4$ PAMs inhibit locomotor-stimulating effects of a direct acting $D_1$ agonist. Furthermore, a series of pharmacological, genetic, and molecular/cellular studies reveal that this response is mediated by inhibition of $D_1DR$ signaling in D1-SPNs. Thus, the primary action of $M_4$ PAMs on $D_1DR$ signaling is not in the striatum, but on GABAergic terminals of $D_1$-SPNs in the SNr, where activation of $D_1DRs$ induces a robust increase in GABA release. This challenges the widespread view that cholinergic regulation of striatal function is almost exclusively mediated through ACh released from tonically active, striatal cholinergic interneurons (ChIs) and raises the possibility that cholinergic innervation of the SNr from cholinergic projections from the pedunculopontine nucleus may also play a critical role in regulating motor activity and other functions of the basal ganglia direct pathway. Together, these data suggest that in addition to inhibiting DA release, $M_4$ activation also acts postsynaptically in $D_1$-expressing SPNs to inhibit motor function.

Consistent with a prominent role of $M_4$ as the primary mAChR subtype involved in regulating motor function, multiple reports indicate that the locomotor-activating effects of the mAChR antagonist scopolamine are dramatically reduced in $M_4$ knockout mice, but not the other four mAChR subtypes ($M_{1-3,5}$). Furthermore, haloperidol-induced catalepsy, a model of parkinsonian motor disability, is reduced in $M_4$ knockout mice as compared to wild-type controls. Evaluation of the anti-parkinsonian effects of scopolamine, by assessing effects of this compound on catalepsy induced by the DA receptor antagonist haloperidol, display robust catalepsy that was completely reversed by scopolamine in WT mice. The reversal by scopolamine was uncommonly robust and more pronounced than we observe with agents targeting a number of other targets being evaluated for potential antiparkinsonian effects, including metabotropic glutamate (mGlu) receptors $mGlu_4$ or $mGlu_5$, $A_2A$ adenosine receptors, and NMDA receptors. Importantly, scopolamine was ineffective in reducing catalepsy in $M_4$ KO mice, suggesting that the anti-cataleptic effect of scopolamine requires actions on mAChR $M_4$. Taken together with the extensive studies of $M_4$ modulation of basal ganglia and motor function, these studies provide compelling evidence that $M_4$ is the dominant mAChR subtype involved in the antiparkinsonian effects of non-selective mAChR antagonists and provide support for discovery and development of selective $M_4$ antagonists for treatment of neurodegenerative disease such as PD, dystonia, tardive dyskinesia and other movement disorders.

Despite advances in mAChR research, there is still a scarcity of compounds that are potent, efficacious and selective antagonists of the $M_4$ mAChR. Highly selective $M_4$ antagonists represent a new therapeutic approach for the treatment of neurodegenerative diseases including PD, dystonia, tardive dyskinesia and other movement disorders and may offer the clinical benefit of scopolamine, without the adverse effects mediated by pan-mAChR inhibition.

In some embodiments, the disclosed compounds are antagonists of mAChR $M_4$. Such activity can be demonstrated by methodology known in the art. For example, antagonism of mAChR $M_4$ activity can be determined by measurement of calcium flux in response to agonist, e.g. acetylcholine, in cells loaded with a $Ca^{2+}$-sensitive fluorescent dye (e.g., Fluo-4) and co-expression of a chimeric or promiscuous G protein. In some embodiments, the calcium flux can be measured as an increase in fluorescent static ratio. In some embodiments, antagonist activity can be analyzed as a concentration-dependent increase in the $EC_{80}$ acetylcholine response (i.e. the response of mAChR $M_4$ at a concentration of acetylcholine that yields 80% of the maximal response).

In some embodiments, the disclosed compounds antagonize mAChR $M_4$ as a decrease in calcium fluorescence in mAChR $M_4$-transfected CHO-K1 cells in the presence of the compound, compared to the response of equivalent CHO-K1 cells in the absence of the compound. In some embodiments, a disclosed compound antagonizes the mAChR $M_4$ response with an $IC_{50}$ of less than about 10 μM, less than about 5 μM, less than about 1 μM, less than about 500 nM, of less than about 100 nM, or less than about 50 nM. In some embodiments, the mAChR $M_4$-transfected CHO-K1 cells are transfected with human mAChR $M_4$. In some embodiments, the mAChR $M_4$-transfected CHO-K1 cells are transfected with rat mAChR $M_4$. In some embodiments, the mAChR $M_4$-transfected CHO-K1 cells are transfected with mAChR $M_4$ from dog or cynomolgus monkey.

The disclosed compounds may antagonize mAChR $M_4$ response in mAChR $M_4$-transfected CHO-K1 cells with an $IC_{50}$ less than the $IC_{50}$ for one or more of mAChR $M_1$, $M_2$, $M_3$ or $M_5$-transfected CHO-K1 cells. That is, a disclosed compound can have selectivity for the mAChR $M_4$ receptor vis-à-vis one or more of the mAChR $M_1$, $M_2$, $M_3$ or $M_5$ receptors. For example, in some embodiments, a disclosed compound can antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_1$. In some embodiments, a disclosed compound can antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_2$. In some embodiments, a disclosed compound can antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_3$. In some embodiments, a disclosed compound can antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_5$. In some embodiments, a disclosed compound can antagonize mAChR $M_4$ response with an $IC_{50}$ of 5-fold less, about 10-fold less, about 20-fold less, about 30-fold less than that for the $M_2$-$M_5$ receptors, of about 50-fold less, about 100-fold less, about 200-fold less, about 300-fold less, about 400-fold less, or greater than about 500-fold less than that for the mAChR $M_1$, $M_2$, $M_3$, or $M_5$ receptors.

The disclosed compounds may antagonize mAChR $M_4$ response in $M_4$-transfected CHO-K1 cells with an $IC_{50}$ of less than about 10 μM and exhibit a selectivity for the $M_4$ receptor vis-à-vis one or more of the mAChR $M_1$, $M_2$, $M_3$, or $M_5$ receptors. For example, in some embodiments, the compound can have an $IC_{50}$ of less than about 10 μM, of less than about 5 μM, of less than about 1 μM, of less than about 500 nM, of less than about 100 nM, or of less than about 50 nM; and the compound can also antagonize mAChR $M_4$ response with an $IC_{50}$ of about 5-fold less, 10-fold less, 20-fold less, 30-fold less, 50-fold less, 100-fold less, 200-fold less, 300-fold less, 400-fold less, or greater than about 500-fold less than that for mAChR $M_1$. In some embodiments, the compound can have an $IC_{50}$ of less than about 10 μM, of less than about 5 μM, of less than about 1 μM, of less than about 500 nM, of less than about 100 nM, or of less than about 50 nM; and the compound can also antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_2$. In some embodiments, the compound can have an $IC_{50}$ of less than about 10 μM, of less than about 5 μM, of less than about 1 μM, of less than about 500 nM, of less than about 100 nM, or of less than about 50 nM; and the compound can also antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_3$. In some embodiments, the compound can have an $IC_{50}$ of less than about 10 μM, of less than about 5 μM, of less than about 1 μM, of less than about 500 nM, of less than about 100 nM, or of less than about 50 nM; and the compound can also antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_5$. In some embodiments, the compound can have an $IC_{50}$ of less than about 10 μM, of less than about 5 μM, of less than about 1 μM, of less than about 500 nM, of less than about 100 nM, or of less than about 50 nM; and the compound can also antagonize mAChR $M_4$ response with $IC_{50}$ of 5-fold less, about 10-fold less, about 20-fold less, about 30-fold less than that for the $M_2$-$M_5$ receptors, of about 50-fold less, about 100-fold less, about 200-fold less, about 300-fold less, about 400-fold less, $M_2$, $M_3$, or $M_5$ receptors, or greater than about 500-fold less than that for the mAChR $M_1$, $M_2$, $M_3$, or $M_5$ receptors.

In vivo efficacy for disclosed compounds in models that predict antiparkinsonian activity can be measured in a number of preclinical rat models. For example, disclosed compounds may reverse deficits in motor function induced by the dopamine receptor antagonist in mice or rats. Also, these compounds may reverse deficits in motor function that are observed with other manipulations that reduce dopaminergic signaling, such as selective lesions of dopamine neurons. In addition, it is possible that these compounds will have efficacy in animal models of dystonia and may increase attention, cognitive function, and measures of motivation in animal models.

3. Pharmaceutical Compositions and Formulations

The disclosed compounds may be incorporated into pharmaceutical compositions suitable for administration to a subject (such as a patient, which may be a human or non-human). The disclosed compounds may also be provided as formulations, such as spray-dried dispersion formulations.

The pharmaceutical compositions and formulations may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (I)) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions and formulations may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I)) and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I)), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

The pharmaceutical composition or formulation may antagonize mAChR $M_4$ with an $IC_{50}$ of less than about 10 μM, less than about 5 μM, less than about 1 μM, less than about 500 nM, or less than about 100 nM. The pharmaceutical composition or formulation may antagonize mAChR $M_4$ with an $IC_{50}$ of between about 10 μM and about 1 nM, about 1 μM and about 1 nM, about 100 nM and about 1 nM, or between about 10 nM and about 1 nM.

a. Spray-Dried Dispersion Formulations

The disclosed compounds may be formulated as a spray-dried dispersion (SDD). An SDD is a single-phase, amorphous molecular dispersion of a drug in a polymer matrix. It is a solid solution with the compound molecularly "dissolved" in a solid matrix. SDDs are obtained by dissolving drug and a polymer in an organic solvent and then spray-drying the solution. The use of spray drying for pharmaceutical applications can result in amorphous dispersions with increased solubility of Biopharmaceutics Classification System (BCS) class II (high permeability, low solubility) and class IV (low permeability, low solubility) drugs. Formulation and process conditions are selected so that the solvent quickly evaporates from the droplets, thus allowing insufficient time for phase separation or crystallization. SDDs have demonstrated long-term stability and manufacturability. For example, shelf lives of more than 2 years have been demonstrated with SDDs. Advantages of SDDs include, but are not limited to, enhanced oral bioavailability of poorly water-soluble compounds, delivery using traditional solid dosage forms (e.g., tablets and capsules), a reproducible, controllable and scalable manufacturing process and broad applicability to structurally diverse insoluble compounds with a wide range of physical properties.

Thus, in one embodiment, the disclosure may provide a spray-dried dispersion formulation comprising a compound of formula (I).

4. Methods of Use

The disclosed compounds, pharmaceutical compositions and formulations may be used in methods for treatment of disorders, such as neurological and/or psychiatric disorders, associated with muscarinic acetylcholine receptor dysfunction. The disclosed compounds and pharmaceutical compositions may also be used in methods for decreasing muscarinic acetylcholine receptor activity in a mammal. The methods further include cotherapeutic methods for improving treatment outcomes. In the methods of use described herein, additional therapeutic agent(s) may be administered simultaneously or sequentially with the disclosed compounds and compositions.

a. Treating Disorders

The disclosed compounds, pharmaceutical compositions and formulations may be used in methods for treating, preventing, ameliorating, controlling, reducing, or reducing the risk of a variety of disorders, or symptoms of the disorders, in which a patient would benefit from antagonism of mAChR $M_4$. In some embodiments, the disorder may be a neurodegenerative disorder, a movement disorder, or a brain disorder. The methods may comprise administering to a subject in need of such treatment a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof.

Disorders in which a patient would benefit from antagonism of mAChR $M_4$ may include neurodegenerative disorders and movement disorders. For example, exemplary disorders may include Parkinson's disease, drug-induced Parkinsonism, dystonia, Tourette's syndrome, dyskinesias (e.g., tardive dyskinesia or levodopa-induced dyskinesia), schizophrenia, cognitive deficits associated with schizophrenia, excessive daytime sleepiness (e.g., narcolepsy), attention deficit hyperactivity disorder (ADHD), Huntington's disease, chorea (e.g., chorea associated with Huntington's disease), cerebral palsy, and progressive supranuclear palsy.

In some embodiments, the disclosure provides a method for treating motor symptoms in a subject having Parkinson's disease, comprising administering to a subject in need thereof a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. In some embodiments, the motor symptoms are selected from bradykinesia, tremor, rigidity, gait dysfunction, and postural instability. The method may treat the motor symptoms, control the motor symptoms, and/or reduce the motor symptoms in the subject.

In some embodiments, the disclosure provides a method for treating motor symptoms in a subject having dystonia, comprising administering to the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. The method may treat the motor symptoms, control the motor symptoms, and/or reduce the motor symptoms in the subject. For example, treatment may reduce muscle contractions or spasms in a subject having dystonia.

In some embodiments, the disclosure provides a method for treating motor symptoms in a subject having tardive dyskinesia, comprising administering to the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. The method may treat the motor symptoms, control the motor symptoms, and/or reduce the motor symptoms in the subject. For example, treatment may reduce involuntary movements in a subject having tardive dyskinesia.

In some embodiments, the disclosure provides a method of preventing or delaying tardive dyskinesia in a subject at risk of developing tardive dyskinesia, comprising administering to the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. For example, the subject may be a subject being treated with a neuroleptic medication (e.g., a typical antipsychotic or an atypical antipsychotic), a dopamine antagonist, or an antiemetic.

In some embodiments, the disclosure provides a method of treating catalepsy in a subject suffering from schizophrenia, comprising administering to the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. For example, the subject suffering from schizophrenia may have catalepsy induced by a neuroleptic agent (e.g., a typical antipsychotic or an atypical antipsychotic).

In some embodiments, the disclosure provides a method of treating a brain disorder characterized by altered dopamine and cholinergic signaling that could benefit from antagonism of mAChR $M_4$, comprising administering to the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. For example, the treatment may increase motivation or goal-directed behavior in patients suffering from disorders characterized by reduced motivation for goal-directed behavior, such as schizophrenia and other brain disorders.

In some embodiments, the disclosure provides a method for increasing wakefulness and/or reducing excessive daytime sleepiness in a subject in need thereof, comprising administering to the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. In some embodiments, the subject is a subject suffering from narcolepsy.

In some embodiments, the disclosure provides a method of increasing attention in a subject (e.g., a subject suffering from an attention deficit disorder such as ADHD) in a subject in need thereof, comprising administering to the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof.

In some embodiments, the disclosure provides a method for treating motor symptoms in a subject having a drug-induced movement disorder, comprising administering the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. In some embodiments, the drug-induced movement disorder is selected from drug-induced parkinsonism, tardive dyskinesia, tardive dystonia, akathisia, myoclonus, and tremor. The method may treat the motor symptoms, control the motor symptoms, and/or reduce the motor symptoms in the subject.

The compounds and compositions may be further useful in a method for the prevention, treatment, control, amelioration, or reduction of risk of the diseases, disorders and conditions noted herein. The compounds and compositions may be further useful in a method for the prevention, treatment, control, amelioration, or reduction of risk of the aforementioned diseases, disorders and conditions, in combination with other agents.

In the treatment of conditions such as those that would benefit from antagonism of mAChR $M_4$, an appropriate dosage level may be about 0.01 to 500 mg per kg patient body weight per day, which can be administered in single or multiple doses. The dosage level may be about 0.1 to about 250 mg/kg per day, or about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, or 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in some embodiments, the disclosure relates to a method for antagonizing the mAChR $M_4$ receptor in at least one cell, comprising the step of contacting the at least one cell with at least one disclosed compound or at least one product of a disclosed method in an amount effective to antagonize mAChR $M_4$ in the at least one cell. In some embodiments, the cell is mammalian, for example, human. In some embodiments, the cell has been isolated from a subject prior to the contacting step. In some embodiments, contacting is via administration to a subject.

In some embodiments, the invention relates to a method for antagonizing the mAChR $M_4$ receptor in a subject, comprising the step of administering to the subject at least one disclosed compound or at least one product of a disclosed method in a dosage and amount effective to antagonize the mAChR $M_4$ receptor in the subject. In some embodiments, the subject is mammalian, for example, human. In some embodiments, the mammal has been diagnosed with a need for mAChR $M_4$ antagonism prior to the administering step. In some embodiments, the mammal has been diagnosed with a need for mAChR $M_4$ antagonism prior to the administering step. In some embodiments, the method further comprises the step of identifying a subject in need of mAChR $M_4$ antagonism.

b. Antagonism of the Muscarinic Acetylcholine Receptor

In some embodiments, the disclosure relates to a method for antagonizing mAChR $M_4$ in a mammal, comprising the step of administering to the mammal an effective amount of at least one disclosed compound or a pharmaceutically acceptable salt thereof, or a pharmaceutical composition comprising at least one disclosed compound or pharmaceutically acceptable salt thereof.

In some embodiments, antagonism of the muscarinic acetylcholine receptor decreases muscarinic acetylcholine receptor activity.

In some embodiments, the compound administered antagonizes mAChR $M_4$ with an $IC_{50}$ of less than about 10 µM, less than about 5 µM, less than about 1 µM, less than about 500 nM, or less than about 100 nM. In some embodiments, the compound administered antagonizes mAChR $M_4$ with an $IC_{50}$ of between about 10 µM and about 1 nM, about 1 µM and about 1 nM, about 100 nM and about 1 nM, or about 10 nM and about 1 nM.

In some embodiments, the mammal is a human. In some embodiments, the mammal has been diagnosed with a need for reduction of muscarinic acetylcholine receptor activity prior to the administering step. In some embodiments, the method further comprises the step of identifying a mammal in need of reducing muscarinic acetylcholine receptor activity. In some embodiments, the antagonism of the muscarinic acetylcholine receptor treats a disorder associated with muscarinic acetylcholine receptor activity in the mammal. In some embodiments, the muscarinic acetylcholine receptor is mAChR $M_4$.

In some embodiments, antagonism of the muscarinic acetylcholine receptor in a mammal is associated with the treatment of a disorder associated with a muscarinic receptor dysfunction, such as a disorder disclosed herein. In some embodiments, the muscarinic receptor is mAChR $M_4$.

In some embodiments, the disclosure provides a method for antagonizing the muscarinic acetylcholine receptor in a cell, comprising the step of contacting the cell with an effective amount of at least one disclosed compound or a pharmaceutically acceptable salt thereof. In some embodiments, the cell is mammalian (e.g., human). In some embodiments, the cell has been isolated from a mammal prior to the contacting step. In some embodiments, contacting is via administration to a mammal.

c. Cotherapeutic Methods

The present disclosure is further directed to administration of a mAChR $M_4$ antagonist, such as a selective mAChR $M_4$ antagonist, for improving treatment outcomes. That is, in some embodiments, the disclosure relates to a cotherapeutic method comprising a step of administering to a mammal an effective amount and dosage of at least one disclosed compound, or a pharmaceutically acceptable salt thereof.

In some embodiments, administration improves treatment outcomes in the context of cognitive or behavioral therapy. Administration in connection with cognitive or behavioral therapy can be continuous or intermittent. Administration need not be simultaneous with therapy and can be before, during, and/or after therapy. For example, cognitive or behavioral therapy can be provided within 1, 2, 3, 4, 5, 6, 7 days before or after administration of the compound. As a further example, cognitive or behavioral therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

In some embodiments, administration may improve treatment outcomes in the context of physical or occupational therapy. Administration in connection with physical or occupational therapy can be continuous or intermittent. Administration need not be simultaneous with therapy and can be before, during, and/or after therapy. For example, physical or occupational therapy can be provided within 1, 2, 3, 4, 5, 6, 7 days before or after administration of the compound. As a further example, physical or occupational therapy can be provided within 1, 2, 3, or 4 weeks before or after administration of the compound. As a still further example, physical or occupational therapy can be provided before or after administration within a period of time of 1, 2, 3, 4, 5, 6, 7, 8, 9, or 10 half-lives of the administered compound.

It is understood that the disclosed cotherapeutic methods can be used in connection with the disclosed compounds, compositions, kits, and uses.

d. Combination Therapies

In the methods of use described herein, additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I). The above combinations include combinations of a compound of the present invention not only with one other active compound, but also with two or more other active compounds.

The disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefor, contemporaneously or sequentially with a disclosed compound. When a disclosed compound is used contemporaneously with one or more other drugs, a pharmaceutical composition in unit dosage form containing such drugs and the disclosed compound may be used. However, the combination therapy can also be administered on overlapping schedules. It is also envisioned that the combination of one or more active ingredients and a disclosed compound can be more efficacious than either as a single agent. Thus, when used in combination with one or more other active ingredients, the disclosed compounds and the other active ingredients can be used in lower doses than when each is used singly.

The pharmaceutical compositions and methods of the present invention can further comprise other therapeutically active compounds as noted herein which are usually applied in the treatment of the above mentioned pathological conditions.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the disclosed compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In some embodiments, the compound can be employed in combination with any other agent that is used to treat a disorder described herein, such as a standard of care therapy for a disorder that would benefit from mAChR $M_4$ antagonism, such as a disorder described herein. For example, in some embodiments, the compound can be employed in combination with a Parkinsonian drug (e.g., L-DOPA, or carbidopa/levodopa) an mGlu$_4$ positive allosteric modulator, an mGlu$_5$ negative allosteric modulator, an $A_2A$ inhibitor, a T-type calcium channel antagonist, a VMAT2 inhibitor, a muscle relaxant (e.g., baclofen), an anticholinergic agent, an antiemetic, a typical or atypical neuroleptic agent (e.g., risperidone, ziprasidone, haloperidol, pimozide, fluphenazine), an antihypertensive agent (e.g., clonidine or guanfacine), a tricyclic antidepressant (e.g., amitriptyline, butriptyline, clomipramine, desipramine, dosulepin, doxepin, imipramine, iprindole, lofepramine, nortriptyline, protriptyline, or trimipramine) an agent that increases extracellular dopamine levels (e.g., amphetamine, methylphenidate, or lisdexamfetamine), an agent for treating excessive daytime sleepiness (e.g., sodium oxybate or a wakefulness-promoting agent such as armodafinil or modafinil), and a norepinephrine reuptake inhibitor (including selective NRIs, e.g., atomoxetine, and non-selective NRIs, e.g., bupropion).

e. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

5. Kits

In one aspect, the disclosure provides a kit comprising at least one disclosed compound or a pharmaceutically acceptable salt thereof, or a pharmaceutical composition comprising at least one disclosed compound or a pharmaceutically acceptable salt thereof and one or more of:
(a) at least one agent known to increase mAChR $M_4$ activity;
(b) at least one agent known to decrease mAChR $M_4$ activity;
(c) at least one agent known to treat a disorder associated with mAChR $M_4$, such as a disorder described herein; and
(d) instructions for administering the compound.

In some embodiments, the at least one disclosed compound and the at least one agent are co-formulated. In some embodiments, the at least one disclosed compound and the at least one agent are co-packaged. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

That the disclosed kits can be employed in connection with disclosed methods of use.

The kits may further comprise information, instructions, or both that use of the kit will provide treatment for medical conditions in mammals (particularly humans). The information and instructions may be in the form of words, pictures, or both, and the like. In addition or in the alternative, the kit may include the compound, a composition, or both; and information, instructions, or both, regarding methods of application of compound, or of composition, preferably with the benefit of treating or preventing medical conditions in mammals (e.g., humans).

The compounds and processes of the invention will be better understood by reference to the following examples, which are intended as an illustration of and not a limitation upon the scope of the invention.

6. Examples

All NMR spectra were recorded on a 400 MHz AMX Bruker NMR spectrometer. $^1$H chemical shifts are reported in S values in ppm downfield with the deuterated solvent as the internal standard. Data are reported as follows: chemical shift, multiplicity (s=singlet, bs=broad singlet, d=doublet, t=triplet, q=quartet, dd=doublet of doublets, m=multiplet, ABq=AB quartet), coupling constant, integration. Reversed-phase LCMS analysis was performed using an Agilent 1200 system comprised of a binary pump with degasser, high-performance autosampler, thermostatted column compartment, C18 column, diode-array detector (DAD) and an Agilent 6150 MSD with the following parameters. The gradient conditions were 5% to 95% acetonitrile with the aqueous phase 0.1% TFA in water over 1.4 minutes. Samples were separated on a Waters Acquity UPLC BEH C18 column (1.7 µm, 1.0×50 mm) at 0.5 mL/min, with column and solvent temperatures maintained at 55° C. The DAD was set to scan from 190 to 300 nm, and the signals used were 220 nm and 254 nm (both with a band width of 4 nm). The MS detector was configured with an electrospray ionization source, and the low-resolution mass spectra were acquired by scanning from 140 to 700 AMU with a step size of 0.2 AMU at 0.13 cycles/second, and peak width of 0.008 minutes. The drying gas flow was set to 13 liters per minute at 300° C. and the nebulizer pressure was set to 30 psi. The capillary needle voltage was set at 3000 V, and the fragmentor voltage was set at 100V. Data acquisition was performed with Agilent Chemstation and Analytical Studio Reviewer software.

Abbreviations used in the examples that follow are: Boc is tert-butyloxycarbonyl; BrettPhos-Pd-G3 is [(2-di-cyclo-hexylphosphino-3,6-dimethoxy-2',4',6'-triisopropyl-1,1'-biphenyl)-2-(2'-amino-1,1'-biphenyl)]palladium(II) methanesulfonate (CAS Number 1470372-59-8); DCE is 1,2-dichloroethane; DCM is dichloromethane; DIPEA is N,N-diisopropylethylamine; DMF is N,N-dimethylformamide; EtOAc is ethyl acetate; IPA is isopropyl alcohol; MeOH is methanol; and RuPhos-Pd-G3 is (2-dicyclohexylphosphino-2',6'-diisopropoxy-1,1'-biphenyl)[2-(2'-amino-1,1'-biphenyl)]palladium(II) methanesulfonate (CAS Number 1445085-77-7).

Example 1. (3aR,5s,6aS)-2-(3,3-Dimethylbutyl)-N-[6-(2,4-dimethylpyrazol-3-yl)pyridazin-3-yl]-3,3a,4,5,6,6a-hexahydro-1H-cyclopenta[c]pyrrol-5-amine (Compound 1)

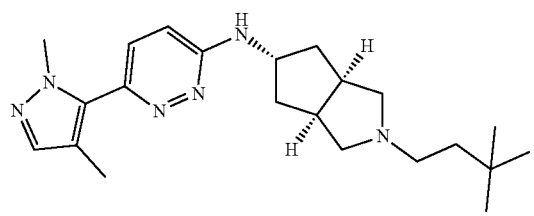

tert-Butyl(3aR,5r,6aS)-5-hydroxy-3,3a,4,5,6,6a-hexahydro-1H-cyclopenta[c]pyrrole-2-carboxylate

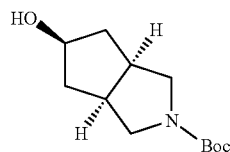

To a solution of cis-tert-butyl 5-oxohexahydrocyclopenta[c]pyrrole-2(1H)-carboxylate (2.0 g, 8.88 mmol, 1.0 eq.) in methanol (44.39 mL, 0.2 M) at 0° C. was added sodium borohydride (1.01 g, 26.63 mmol, 3.0 eq.) portionwise. After 1 h, the solvent was evaporated. The crude mixture was re-dissolved in EtOAc (100 mL) and washed with water (3×), 1M HCl and brine sequentially. The organic layer was dried over $Na_2SO_4$, filtered and concentrated to provide the title compound as a colorless oil (2.01 g, 99%) which was carried to the next stage without further purification. $^1$H-NMR (400 MHz, $CDCl_3$) 4.34-4.28 (m, 1H), 3.53-3.49 (m, 2H), 3.37-3.33 (m, 2H), 2.64-2.59 (m, 2H), 2.21-2.14 (m, 2H), 1.81-1.48 (m, 2H), 1.46 (s, 9H); ES-MS $[M+H]^+=[M+H]^+$-tButyl=172.4.

tert-Butyl (3aR,5s,6aS)-5-azido-3,3a,4,5,6,6a-hexahydro-1H-cyclopenta[c]pyrrole-2-carboxylate

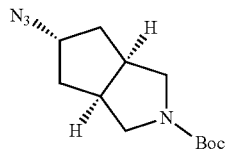

To a solution of tert-butyl (3aR,5r,6aS)-5-hydroxy-3,3a,4,5,6,6a-hexahydro-1H-cyclopenta[c]pyrrole-2-carboxylate (1.0 g, 4.40 mmol, 1.0 eq.), DIPEA (1.15 mL, 6.60 mmol, 1.5 eq.) and 4-dimethylaminopyridine (5.37 mg, 0.04 mmol, 0.01 eq.) in DCM (22.0 mL, 0.2 M) was added methanesulfonyl chloride (0.39 mL, 5.06 mmol, 1.15 eq.) dropwise. After 2 h, sat. soln. $NaHCO_3$ was added and the reaction mixture was extracted with DCM (3×). The combined extracts were washed with brine, dried over $Na_2SO_4$, filtered and concentrated to provide the mesylate intermediate as a yellow oil (1.34 g, 99%) which was carried to the next stage without further purification. ES-MS $[M+H]^+=[M+H]^+$-tButyl=250.0.

A mixture of mesylate intermediate (1.34 g, 4.39 mmol, 1.0 eq.) and sodium azide (0.713 g, 10.97 mmol, 2.5 eq.) in DMF (14.6 mL) was stirred at 60° C. After 16 h, the mixture was cooled to r.t. and diluted with EtOAc and water. The layers were separated. The aqueous layer was extracted with EtOAc (3×). The combined extracts were washed with water, dried over $Na_2SO_4$, filtered and concentrated. The crude material was purified using flash column chromatography on silica gel (0-50% EtOAc/DCM) to provide the title compound as a colorless oil (920 mg, 83%). $^1$H-NMR (400 MHz, $CDCl_3$) δ 4.14-4.10 (m, 1H), 3.50-3.48 (m, 2H), 3.22-3.16 (m, 2H), 2.84-2.78 (m, 2H), 2.03-1.97 (m, 2H), 1.76-1.68 (m, 2H), 1.46 (s, 9H); ES-MS $[M+H]^+=[M+H]^+$-tButyl=197.3.

tert-Butyl (3aR,5s,6aS)-5-amino-3,3a,4,5,6,6a-hexahydro-1H-cyclopenta[c]pyrrole-2-carboxylate

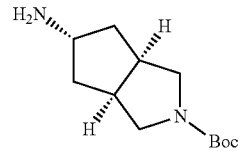 [SMILES: CC(C)(C)OC(=O)N1C[C@H]2C[C@H](N)C[C@H]2C1]

tert-butyl (3aR,5s,6aS)-5-azido-3,3a,4,5,6,6a-hexahydro-1H-cyclopenta[c]pyrrole-2-carboxylate (920 mg, 3.64 mmol, 1.0 eq.), was dissolved in methanol (10.0 mL, 0.36 M). The mixture was purged with nitrogen and palladium hydroxide on activated carbon (25% wt, 204.8 mg, 0.36 mmol, 0.1 eq.) was added. The reaction mixture was then saturated with hydrogen atmosphere. After 16 h, the mixture was filtered through a pad of Celite which was washed thoroughly with methanol. The filtrate was concentrated to provide the title compound as a viscous colorless oil (820 mg, 99%) which was carried to the next stage without further purification. $^1$H-NMR (400 MHz, MeOD) δ 3.54-3.43 (m, 3H), 3.33-3.32 (m, 2H), 3.17-3.12 (m, 2H), 2.86-2.80 (m, 2H), 1.81-1.75 (m, 2H), 1.70-1.62 (m, 2H), 1.47 (s, 9H); ES-MS $[M+H]^+=227.4$.

tert-Butyl (3aR,5s,6aS)-5-[(6-chloropyridazin-3-yl)amino]-3,3a,4,5,6,6a-hexahydro-1H-cyclopenta[c]pyrrole-2-carboxylate

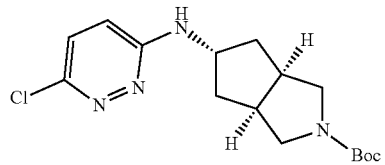 [SMILES: CC(C)(C)OC(=O)N1C[C@H]2C[C@H](Nc3ccc(Cl)nn3)C[C@H]2C1]

tert-Butyl (3aR,5s,6aS)-5-amino-3,3a,4,5,6,6a-hexahydro-1H-cyclopenta[c]pyrrole-2-carboxylate (820 mg, 3.62 mmol, 1.0 eq.) was dissolved in n-BuOH (12.1 mL, 0.3 M), and DIPEA (3.15 mL, 18.11 mmol, 5.0 eq.) was added followed by 3,6-dichloropyridazine (2.70 g, 18.11 mmol, 5.0 eq.). The resulting suspension was subjected to a microwave reactor at 150° C. After 2 h, the reaction mixture was diluted with DCM and sat. soln. $NaHCO_3$. The layers were separated. The aqueous layer was extracted with DCM (3×). The combined extracts were washed with brine, dried over $Na_2SO_4$, filtered and concentrated. The crude residue was purified by flash column chromatography on silica gel (0-40% EtOAc/hexanes then 40-80% EtOAc/DCM) to provide the title compound as a light tan solid (563 mg, 46%). $^1$H-NMR (400 MHz, $CDCl_3$) δ 7.19 (d, J=9.2 Hz, 1H), 6.64 (d, J=9.3 Hz, 1H), 4.80 (d, J=6.5 Hz, 1H), 4.38-4.29 (m, 1H), 3.62-3.56 (m, 2H), 3.33-3.18 (m, 2H), 2.88-2.83 (m, 2H), 2.08-2.02 (m, 2H), 1.87-1.80 (m, 2H), 1.49 (s, 9H); ES-MS $[M+H]^+=283.2$.

tert-Butyl(3aR,5s,6aS)-5-[[6-(2,4-dimethylpyrazol-3-yl)pyridazin-3-yl]amino]-3,3a,4,5,6,6a-hexahydro-1H-cyclopenta[c]pyrrole-2-carboxylate

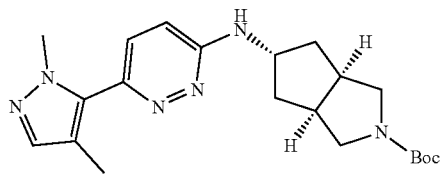 [SMILES: Cc1cnn(C)c1-c1ccc(N[C@H]2C[C@@H]3CN(C(=O)OC(C)(C)C)C[C@@H]3C2)nn1]

tert-Butyl (3aR,5s,6aS)-5-[(6-chloropyridazin-3-yl)amino]-3,3a,4,5,6,6a-hexahydro-1H-cyclopenta[c]pyrrole-2-carboxylate (280 mg, 0.826 mmol, 1.0 eq.), 1,4-dimethylpyrazole-5-boronic acid pinacol ester (367 mg, 1.65 mmol, 2.0 eq.), $K_2CO_3$ (347.8 mg, 2.48 mmol, 3.0 eq.) and BrettPhos-Pd-G3 (37.5 mg, 0.04 mmol, 0.05 eq.) were charged into a reaction vial. A degassed mixture of 1,4-dioxane/$H_2O$ (5:1 (v/v), 6.0 mL) was added. The resulting suspension was stirred at 100° C. for 1 h. After cooling to r.t., the reaction mixture was filtered through a pad of Celite which was washed thoroughly with EtOAc. The filtrate was concentrated under reduced pressure. The crude residue was purified by flash column chromatography (0-50% EtOAc/hexanes then 50-70% MeOH/DCM/$NH_4OH$ (10:89:1) in DCM) to give the title compound as a light tan material (280 mg, 85%). $^1$H-NMR (400 MHz, $CDCl_3$) δ 7.38 (s, 1H), 7.30 (d, J=9.2 Hz, 1H), 6.74 (d, J=9.2 Hz, 1H), 5.12 (d, J=6.7 Hz, 1H), 4.45 (ddd, J=12.8, 6.4, 6.4 Hz, 1H), 3.99 (s, 3H), 3.61-3.55 (m, 2H), 3.28-3.19 (m, 2H), 2.90-2.85 (m, 2H), 2.10-2.0 (m, 2H), 2.11 (s, 3H), 1.93-1.86 (m, 2H), 1.48 (s, 9H); ES-MS $[M+H]^+$=399.4.

(3aR,5s,6aS)—N-[6-(2,4-Dimethylpyrazol-3-yl)pyridazin-3-yl]-1,2,3,3a,4,5,6,6a-octahydrocyclopenta[c]pyrrol-5-amine dihydrochloride

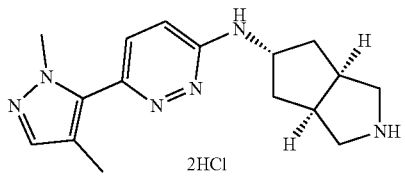 [SMILES: Cc1cnn(C)c1-c1ccc(N[C@@H]2C[C@H]3CNC[C@H]3C2)nn1]

2HCl tert-Butyl (3aR,5s,6aS)-5-[[6-(2,4-dimethylpyrazol-3-yl)pyridazin-3-yl]amino]-3,3a,4,5,6,6a-hexahydro-1H-cyclopenta[c]pyrrole-2-carboxylate (260 mg, 0.65 mmol, 1.0 eq.) was dissolved in 1,4-dioxane (3.0 mL). A 4M HCl in 1,4-dioxane solution (2.5 mL, 10.0 mmol, 15.0 eq.) was added dropwise. After stirring 1 h at r.t., the solvents were removed under reduced pressure. The crude material was azeotroped with toluene (3×) to provide the title compound as a white solid which was used without further purification as the HCl salt (242 mg, 99%). ES-MS $[M+H]^+$=313.2.

(3aR,5s,6aS)-2-(3,3-Dimethylbutyl)-N-[6-(2,4-dimethylpyrazol-3-yl)pyridazin-3-yl]-3,3a,4,5,6,6a-hexahydro-1H-cyclopenta[c]pyrrol-5-amine (Compound 1)

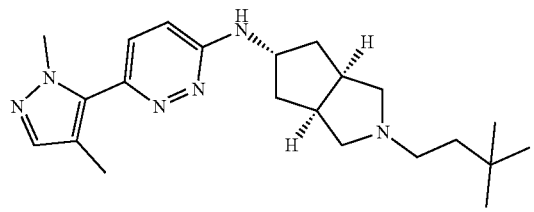

1

(3aR,5s,6aS)—N-[6-(2,4-Dimethylpyrazol-3-yl)pyridazin-3-yl]-1,2,3,3a,4,5,6,6a-octahydrocyclopenta[c]pyrrol-5-amine dihydrochloride (15 mg, 0.04 mmol, 1.0 eq.) was suspended in DCM (0.5 mL) and THF (0.5 mL). 3,3-Dimethylbutyraldehyde (25.3 µL, 0.202 mmol, 5.0 eq.) was added. The mixture was stirred at 50° C. for 30 min and sodium triacetoxyborohydride (42.8 mg, 0.202 mmol. 5.0 eq.) was added. The resulting solution was stirred at 50° C. for 2 h, after which time the reaction mixture was quenched with sat. soln. $NaHCO_3$, and extracted with chloroform/IPA (3:1, v/v). The combined extracts were filtered through a phase separator and concentrated. The crude residue was purified by RP-HPLC, and fractions containing product were basified with sat. soln. $NaHCO_3$, and extracted with chloroform/IPA (3:1, v/v). The combined extracts were filtered through a phase separator and concentrated to give the title compound as a white powder (5.9 mg, 38%). H-NMR (400 MHz, $CDCl_3$) δ 7.29 (s, 1H), 7.21 (d, J=9.2 Hz, 1H), 6.67 (d, J=9.2 Hz, 1H), 4.82 (d, J=7.2 Hz, 1H), 4.31 (ddd, J=13.2, 7.2, 7.2 Hz, 1H), 3.92 (s, 3H), 2.69-2.61 (m, 4H), 2.33-2.29 (m, 2H), 2.21-2.18 (m, 2H), 2.03 (s, 3H), 1.94-1.89 (m, 2H), 1.70-1.63 (m, 2H), 1.36-1.32 (m, 2H), 0.84 (s, 9H); ES-MS $[M+H]^+$=383.5.

The compounds shown in Table 1 were prepared similarly to the compounds described above, with appropriate starting materials.

TABLE 1

| Cpd. No. | Name | Structure | ES-MS [M + 1]$^+$ |
|---|---|---|---|
| 2 | (3aR,5s,6aS)-2-(5-bicyclo[2.2.1]hept-2-enylmethyl)-N-[6-(1,3-dimethylpyrazol-4-yl)pyridazin-3-yl]-3,3a,4,5,6,6a-hexahydro-1H-cyclopenta[c]pyrrol-5-amine | 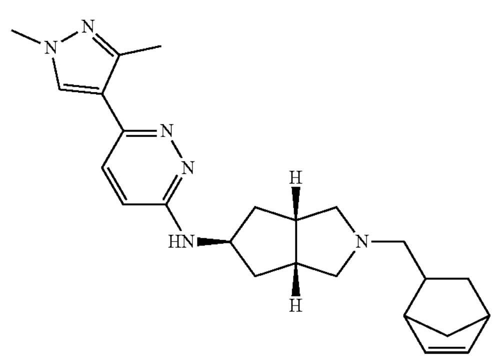 [SMILES: Cc1nn(C)cc1-c1ccc(N[C@H]2C[C@@H]3CN(CC4CC5C=CC4C5)C[C@@H]3C2)nn1] | 405.4 |

TABLE 1-continued

| Cpd. No. | Name | Structure | ES-MS [M + 1]+ |
|---|---|---|---|
| 3 | (3aR,5s,6aS)-2-(3,3-dimethylbutyl)-N-[6-(1,3-dimethylpyrazol-4-yl)pyridazin-3-yl]-3,3a,4,5,6,6a-hexahydro-1H-cyclopenta[c]pyrrol-5-amine | 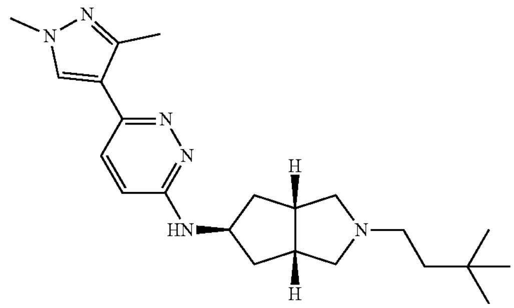 [SMILES: Cc1nn(C)cc1-c1ccc(N[C@H]2C[C@@H]3CN(CCC(C)(C)C)C[C@@H]3C2)nn1] | 383.6 |
| 4 | (3aR,5s,6aS)-N-[6-(1,3-dimethylpyrazol-4-yl)pyridazin-3-yl]-2-(2,3,3-trimethylbutyl)-3,3a,4,5,6,6a-hexahydro-1H-cyclopenta[c]pyrrol-5-amine | 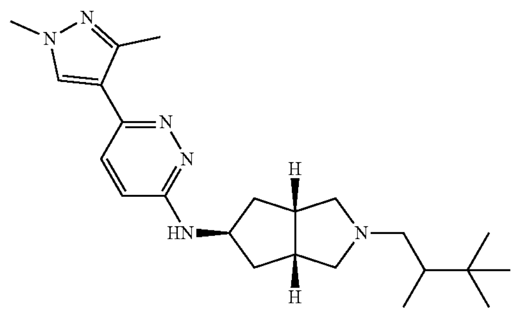 [SMILES: Cc1nn(C)cc1-c1ccc(N[C@H]2C[C@@H]3CN(CC(C)C(C)(C)C)C[C@@H]3C2)nn1] | 397.5 |
| 5 | (3aR,5s,6aS)-N-[6-(1,3-dimethylpyrazol-4-yl)pyridazin-3-yl]-2-(tetrahydropyran-4-ylmethyl)-3,3a,4,5,6,6a-hexahydro-1H-cyclopenta[c]pyrrol-5-amine | 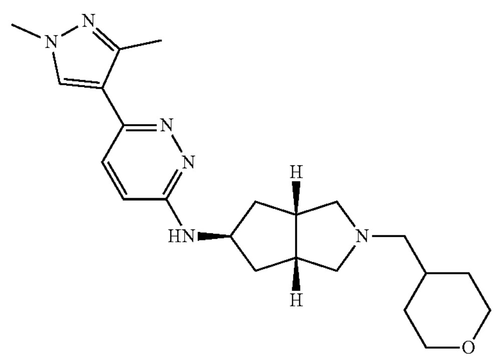 [SMILES: Cc1nn(C)cc1-c1ccc(N[C@H]2C[C@@H]3CN(CC4CCOCC4)C[C@@H]3C2)nn1] | 397.5 |
| 6 | (3aR,5s,6aS)-N-[6-(1,3-dimethylpyrazol-4-yl)pyridazin-3-yl]-2-(tetrahydropyran-3-ylmethyl)-3,3a,4,5,6,6a-hexahydro-1H-cyclopenta[c]pyrrol-5-amine | 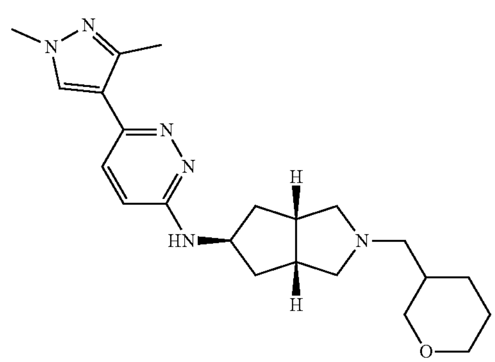 [SMILES: Cc1nn(C)cc1-c1ccc(N[C@H]2C[C@@H]3CN(CC4CCCOC4)C[C@@H]3C2)nn1] | 397.5 |

TABLE 1-continued

| Cpd. No. | Name | Structure | ES-MS [M + 1]+ |
|---|---|---|---|
| 7 | (3aR,5s,6aS)-2-(cyclohexylmethyl)-N-[6-(1,3-dimethylpyrazol-4-yl)pyridazin-3-yl]-3,3a,4,5,6,6a-hexahydro-1H-cyclopenta[c]pyrrol-5-amine | 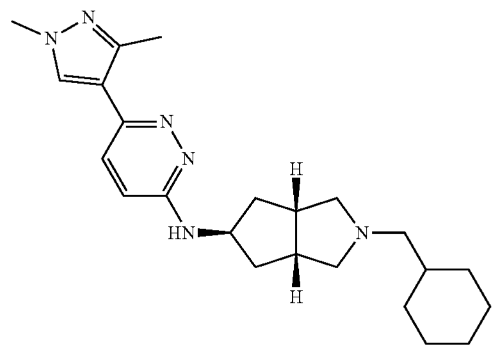 [SMILES: Cc1nn(C)cc1-c1ccc(N[C@H]2C[C@@H]3CN(CC4CCCCC4)C[C@@H]3C2)nn1] | 395.4 |
| 8 | (3aR,5s,6aS)-2-benzyl-N-[6-(1,3-dimethylpyrazol-4-yl)pyridazin-3-yl]-3,3a,4,5,6,6a-hexahydro-1H-cyclopenta[c]pyrrol-5-amine | 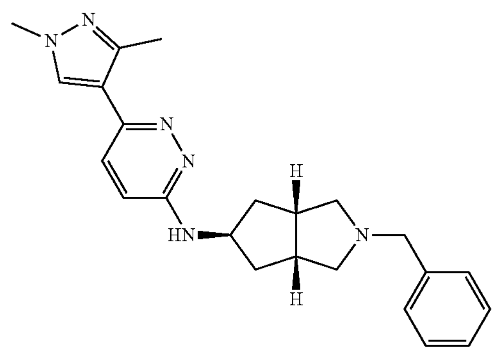 [SMILES: Cc1nn(C)cc1-c1ccc(N[C@H]2C[C@@H]3CN(Cc4ccccc4)C[C@@H]3C2)nn1] | 389.4 |
| 9 | (3aR,5s,6aS)-N-[6-(1,3-dimethylpyrazol-4-yl)pyridazin-3-yl]-2-(2-pyridylmethyl)-3,3a,4,5,6,6a-hexahydro-1H-cyclopenta[c]pyrrol-5-amine | 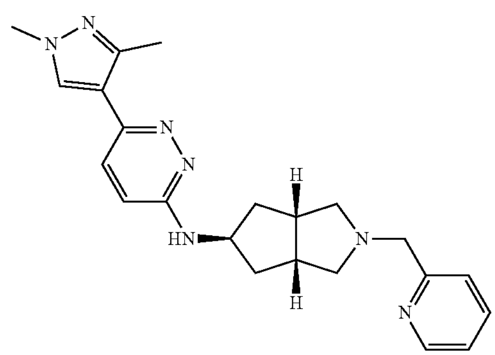 [SMILES: Cc1nn(C)cc1-c1ccc(N[C@H]2C[C@@H]3CN(Cc4ccccn4)C[C@@H]3C2)nn1] | 390.4 |
| 10 | (3aR,5s,6aS)-N-[6-(1,3-dimethylpyrazol-4-yl)pyridazin-3-yl]-2-[(2-fluorophenyl)methyl]-3,3a,4,5,6,6a-hexahydro-1H-cyclopenta[c]pyrrol-5-amine | 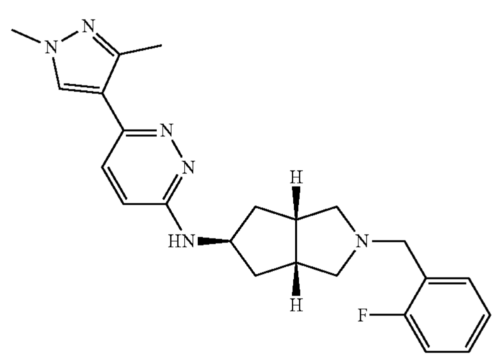 [SMILES: Cc1nn(C)cc1-c1ccc(N[C@H]2C[C@@H]3CN(Cc4ccccc4F)C[C@@H]3C2)nn1] | 407.4 |

TABLE 1-continued

| Cpd. No. | Name | Structure | ES-MS [M + 1]+ |
|---|---|---|---|
| 11 | (3aR,5s,6aS)-N-[6-(1,3-dimethylpyrazol-4-yl)pyridazin-3-yl]-2-[(3-methyl-2-pyridyl)methyl]-3,3a,4,5,6,6a-hexahydro-1H-cyclopenta[c]pyrrol-5-amine | 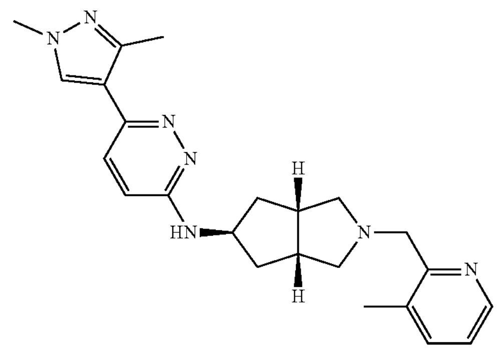 [SMILES: Cc1cccnc1CN1C[C@H]2C[C@H](Nc3ccc(-c4cn(C)nc4C)nn3)C[C@H]2C1] | 404.5 |
| 12 | (3aR,5s,6aS)-N-[6-(1,3-dimethylpyrazol-4-yl)pyridazin-3-yl]-2-(2-phenylethyl)-3,3a,4,5,6,6a-hexahydro-1H-cyclopenta[c]pyrrol-5-amine | 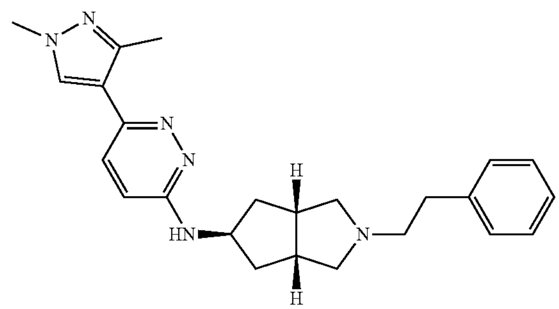 [SMILES: Cc1nn(C)cc1-c1ccc(N[C@H]2C[C@@H]3CN(CCc4ccccc4)C[C@@H]3C2)nn1] | 403.2 |
| 13 | (3aR,5s,6aS)-N-[6-(1,3-dimethylpyrazol-4-yl)pyridazin-3-yl]-2-(2-methylbutyl)-3,3a,4,5,6,6a-hexahydro-1H-cyclopenta[c]pyrrol-5-amine | 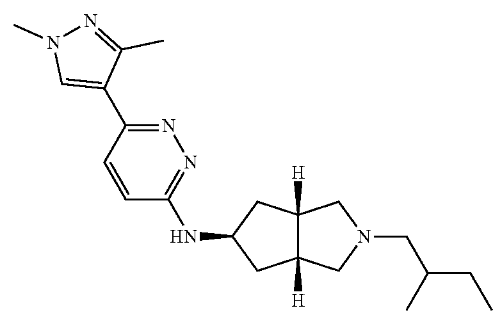 [SMILES: CCC(C)CN1C[C@H]2C[C@H](Nc3ccc(-c4cn(C)nc4C)nn3)C[C@H]2C1] | 369.4 |
| 14 | (3aR,5s,6aS)-N-[6-(1,3-dimethylpyrazol-4-yl)pyridazin-3-yl]-2-(2-methylpentyl)-3,3a,4,5,6,6a-hexahydro-1H-cyclopenta[c]pyrrol-5-amine | 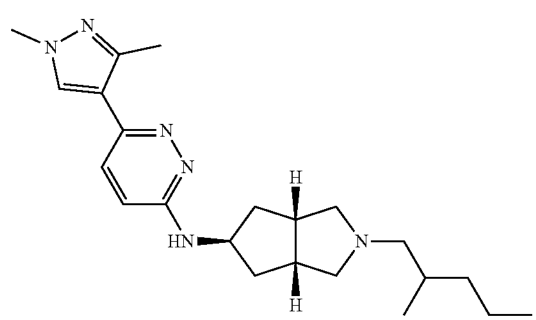 [SMILES: CCCC(C)CN1C[C@H]2C[C@H](Nc3ccc(-c4cn(C)nc4C)nn3)C[C@H]2C1] | 383.4 |
| 15 | (3aR,5s,6aS)-2-(1,3-benzodioxol-5-ylmethyl)-N-[6-(1,3-dimethylpyrazol-4-yl)pyridazin-3-yl]-3,3a,4,5,6,6a-hexahydro-1H-cyclopenta[c]pyrrol-5-amine | 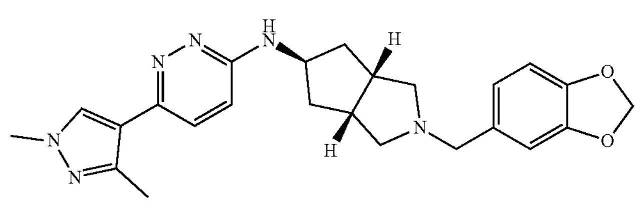 [SMILES: Cc1nn(C)cc1-c1ccc(N[C@H]2C[C@@H]3CN(Cc4ccc5c(c4)OCO5)C[C@@H]3C2)nn1] | 433.4 |

TABLE 1-continued

| Cpd. No. | Name | Structure | ES-MS [M + 1]+ |
|---|---|---|---|
| 16 | (3aR,5s,6aS)-2-(1-adamantylmethyl)-N-[6-(2,4-dimethylpyrazol-3-yl)pyridazin-3-yl]-3,3a,4,5,6,6a-hexahydro-1H-cyclopenta[c]pyrrol-5-amine | 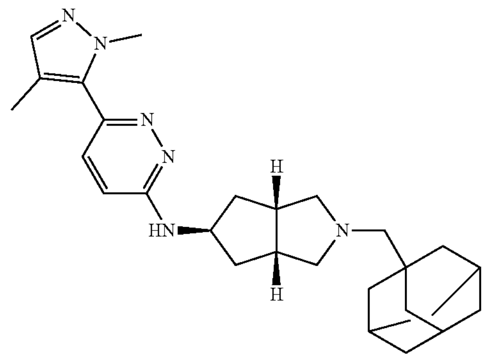 [SMILES: Cc1cnn(C)c1-c1ccc(N[C@H]2C[C@@H]3CN(CC45CC(C)CC(CC(C)C4)C5)C[C@@H]3C2)nn1] | 447.5 |
| 17 | (3aR,5s,6aS)-2-(5-bicyclo[2.2.1]hept-2-enylmethyl)-N-[6-(2,4-dimethylpyrazol-3-yl)pyridazin-3-yl]-3,3a,4,5,6,6a-hexahydro-1H-cyclopenta[c]pyrrol-5-amine | 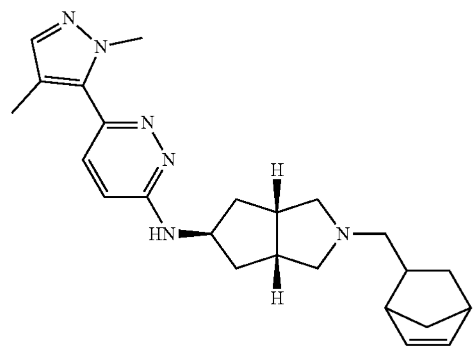 [SMILES: Cc1cnn(C)c1-c1ccc(N[C@H]2C[C@@H]3CN(CC4CC5C=CC4C5)C[C@@H]3C2)nn1] | 405.5 |
| 18 | (3aR,5s,6aS)-N-[6-(2,4-dimethylpyrazol-3-yl)pyridazin-3-yl]-2-(2-methylbutyl)-3,3a,4,5,6,6a-hexahydro-1H-cyclopenta[c]pyrrol-5-amine | 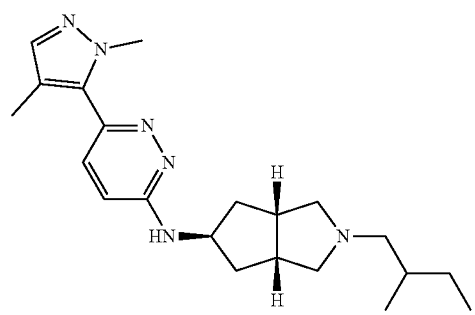 [SMILES: CCC(C)CN1C[C@H]2C[C@H](Nc3ccc(-c4c(C)cnn4C)nn3)C[C@H]2C1] | 369.5 |
| 19 | (3aR,5s,6aS)-N-[6-(2,4-dimethylpyrazol-3-yl)pyridazin-3-yl]-2-(2-methylpentyl)-3,3a,4,5,6,6a-hexahydro-1H-cyclopenta[c]pyrrol-5-amine | 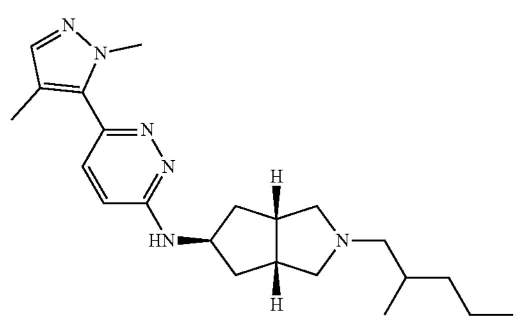 [SMILES: CCCC(C)CN1C[C@H]2C[C@H](Nc3ccc(-c4c(C)cnn4C)nn3)C[C@H]2C1] | 383.5 |

TABLE 1-continued

| Cpd. No. | Name | Structure | ES-MS [M + 1]+ |
|---|---|---|---|
| 20 | (3aR,5s,6aS)-2-(cyclohexylmethyl)-N-[6-(2,4-dimethylpyrazol-3-yl)pyridazin-3-yl]-3,3a,4,5,6,6a-hexahydro-1H-cyclopenta[c]pyrrol-5-amine | 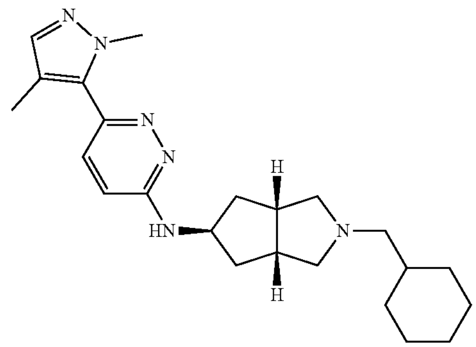 [SMILES: Cc1cnn(C)c1-c1ccc(N[C@H]2C[C@@H]3CN(CC4CCCCC4)C[C@@H]3C2)nn1] | 395.5 |
| 21 | (3aR,5s,6aS)-N-[6-(2,4-dimethylpyrazol-3-yl)pyridazin-3-yl]-2-(tetrahydropyran-4-ylmethyl)-3,3a,4,5,6,6a-hexahydro-1H-cyclopenta[c]pyrrol-5-amine | 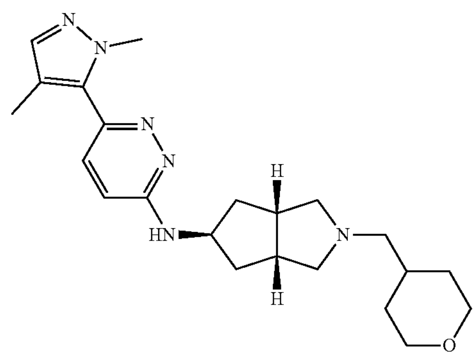 [SMILES: Cc1cnn(C)c1-c1ccc(N[C@H]2C[C@@H]3CN(CC4CCOCC4)C[C@@H]3C2)nn1] | 397.5 |
| 22 | (3aR,5s,6aS)-N-[6-(2,4-dimethylpyrazol-3-yl)pyridazin-3-yl]-2-(tetrahydropyran-3-ylmethyl)-3,3a,4,5,6,6a-hexahydro-1H-cyclopenta[c]pyrrol-5-amine | 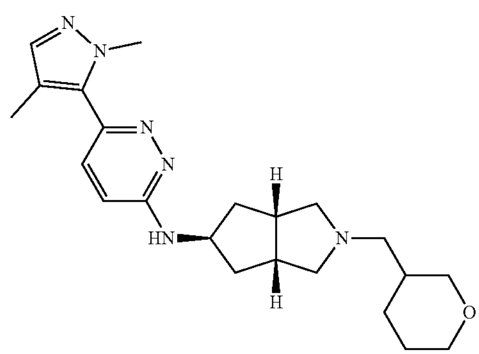 [SMILES: Cc1cnn(C)c1-c1ccc(N[C@H]2C[C@@H]3CN(CC4CCCOC4)C[C@@H]3C2)nn1] | 397.4 |
| 23 | (3aR,5s,6aS)-2-benzyl-N-[6-(2,4-dimethylpyrazol-3-yl)pyridazin-3-yl]-3,3a,4,5,6,6a-hexahydro-1H-cyclopenta[c]pyrrol-5-amine | 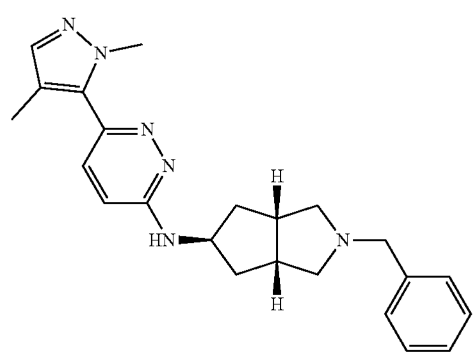 [SMILES: Cc1cnn(C)c1-c1ccc(N[C@H]2C[C@@H]3CN(Cc4ccccc4)C[C@@H]3C2)nn1] | 389.5 |

TABLE 1-continued

| Cpd. No. | Name | Structure | ES-MS [M + 1]+ |
|---|---|---|---|
| 24 | (3aR,5s,6aS)-N-[6-(2,4-dimethylpyrazol-3-yl)pyridazin-3-yl]-2-[(3-methyl-2-pyridyl)methyl]-3,3a,4,5,6,6a-hexahydro-1H-cyclopenta[c]pyrrol-5-amine | 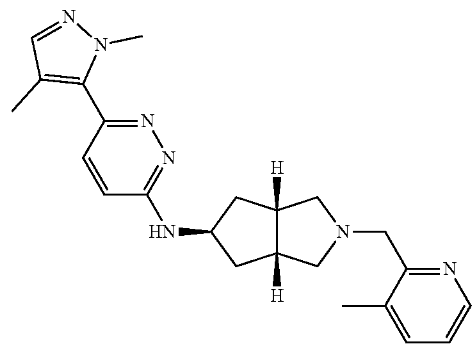 [SMILES: Cc1cccnc1CN1C[C@H]2C[C@H](Nc3ccc(-c4c(C)cnn4C)nn3)C[C@H]2C1] | 404.5 |
| 25 | (3aR,5s,6aS)-N-[6-(2,4-dimethylpyrazol-3-yl)pyridazin-3-yl]-2-[(2-fluorophenyl)methyl]-3,3a,4,5,6,6a-hexahydro-1H-cyclopenta[c]pyrrol-5-amine | 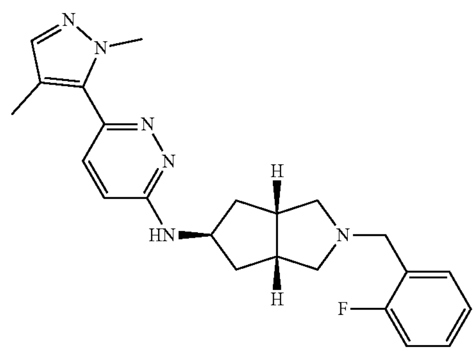 [SMILES: Cc1cnn(C)c1-c1ccc(N[C@H]2C[C@@H]3CN(Cc4ccccc4F)C[C@@H]3C2)nn1] | 407.4 |
| 26 | (3aR,5s,6aS)-2-(1-adamantylmethyl)-N-[6-(2-chloro-5-fluoro-phenyl)pyridazin-3-yl]-3,3a,4,5,6,6a-hexahydro-1H-cyclopenta[c]pyrrol-5-amine | 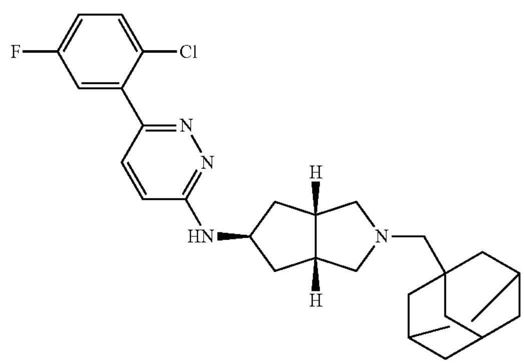 [SMILES: CC1CC2CC(C)CC(CN3C[C@H]4C[C@H](Nc5ccc(-c6cc(F)ccc6Cl)nn5)C[C@H]4C3)(C1)C2] | 481.5 |
| 27 | (3aR,5s,6aS)-2-(5-bicyclo[2.2.1]hept-2-enylmethyl)-N-[6-(2-chloro-5-fluoro-phenyl)pyridazin-3-yl]-3,3a,4,5,6,6a-hexahydro-1H-cyclopenta[c]pyrrol-5-amine | 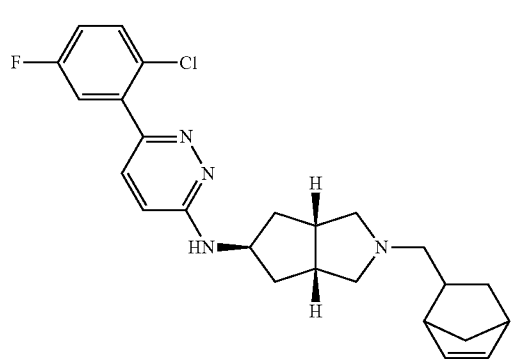 [SMILES: Fc1ccc(Cl)c(-c2ccc(N[C@H]3C[C@@H]4CN(CC5CC6C=CC5C6)C[C@@H]4C3)nn2)c1] | 439.8 |

TABLE 1-continued

| Cpd. No. | Name | Structure | ES-MS [M + 1]+ |
|---|---|---|---|
| 28 | (3aR,5s,6aS)-N-[6-(2-chloro-5-fluoro-phenyl)pyridazin-3-yl]-2-(3,3-dimethylbutyl)-3,3a,4,5,6,6a-hexahydro-1H-cyclopenta[c]pyrrol-5-amine | 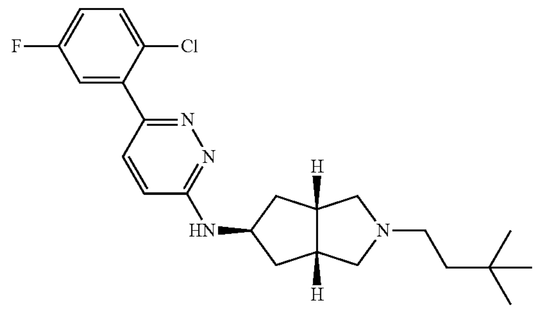 [SMILES: CC(C)(C)CCN1C[C@H]2C[C@H](Nc3ccc(-c4cc(F)ccc4Cl)nn3)C[C@H]2C1] | 417.4 |
| 29 | (3aR,5s,6aS)-N-[6-(2-chloro-5-fluoro-phenyl)pyridazin-3-yl]-2-(2-methylbutyl)-3,3a,4,5,6,6a-hexahydro-1H-cyclopenta[c]pyrrol-5-amine | 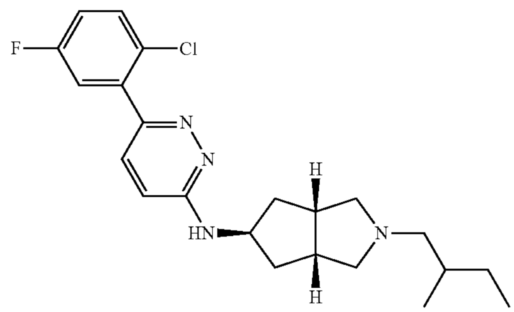 [SMILES: CCC(C)CN1C[C@H]2C[C@H](Nc3ccc(-c4cc(F)ccc4Cl)nn3)C[C@H]2C1] | 403.5 |
| 30 | (3aR,5s,6aS)-N-[6-(2-chloro-5-fluoro-phenyl)pyridazin-3-yl]-2-(2-methylpentyl)-3,3a,4,5,6,6a-hexahydro-1H-cyclopenta[c]pyrrol-5-amine | 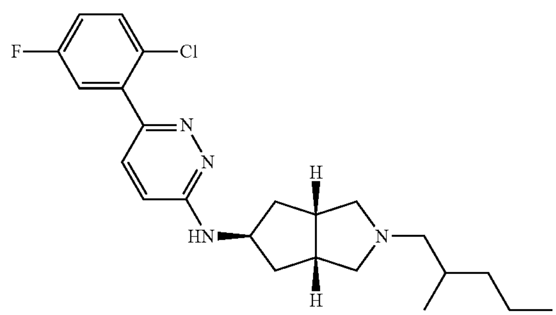 [SMILES: CCCC(C)CN1C[C@H]2C[C@H](Nc3ccc(-c4cc(F)ccc4Cl)nn3)C[C@H]2C1] | 417.4 |
| 31 | (3aR,5s,6aS)-N-[6-(2-chloro-5-fluoro-phenyl)pyridazin-3-yl]-2-(cyclohexylmethyl)-3,3a,4,5,6,6a-hexahydro-1H-cyclopenta[c]pyrrol-5-amine | 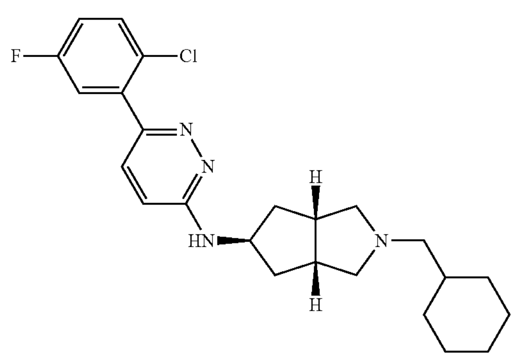 [SMILES: Fc1ccc(Cl)c(-c2ccc(N[C@H]3C[C@@H]4CN(CC5CCCCC5)C[C@@H]4C3)nn2)c1] | 429.4 |

TABLE 1-continued

| Cpd. No. | Name | Structure | ES-MS [M + 1]+ |
|---|---|---|---|
| 32 | (3aR,5s,6aS)-N-[6-(2-chloro-5-fluoro-phenyl)pyridazin-3-yl]-2-(tetrahydropyran-4-ylmethyl)-3,3a,4,5,6,6a-hexahydro-1H-cyclopenta[c]pyrrol-5-amine | 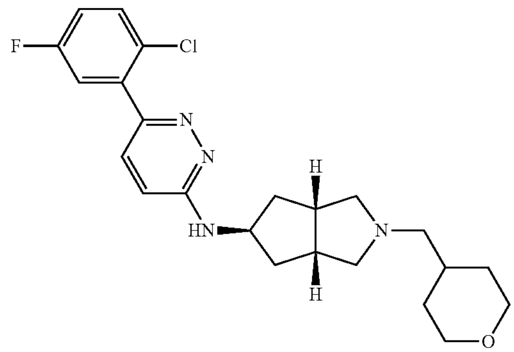 [SMILES: Fc1ccc(Cl)c(-c2ccc(N[C@H]3C[C@@H]4CN(CC5CCOCC5)C[C@@H]4C3)nn2)c1] | 431.4 |
| 33 | (3aR,5s,6aS)-N-[6-(2-chloro-5-fluoro-phenyl)pyridazin-3-yl]-2-(tetrahydropyran-3-ylmethyl)-3,3a,4,5,6,6a-hexahydro-1H-cyclopenta[c]pyrrol-5-amine | 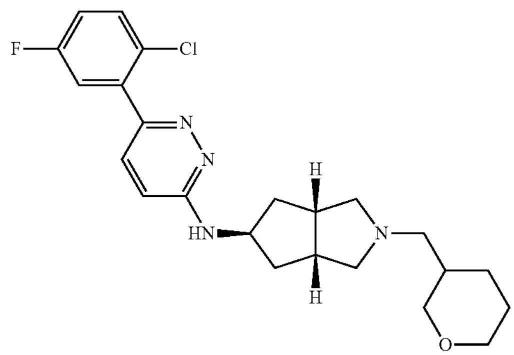 [SMILES: Fc1ccc(Cl)c(-c2ccc(N[C@H]3C[C@@H]4CN(CC5CCCOC5)C[C@@H]4C3)nn2)c1] | 431.4 |
| 34 | (3aR,5s,6aS)-2-benzyl-N-[6-(2-chloro-5-fluoro-phenyl)pyridazin-3-yl]-3,3a,4,5,6,6a-hexahydro-1H-cyclopenta[c]pyrrol-5-amine | 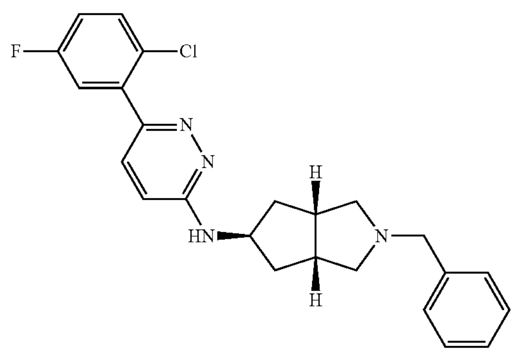 [SMILES: Fc1ccc(Cl)c(-c2ccc(N[C@H]3C[C@@H]4CN(Cc5ccccc5)C[C@@H]4C3)nn2)c1] | 423.3 |
| 35 | (3aR,5s,6aS)-N-[6-(2-chloro-5-fluoro-phenyl)pyridazin-3-yl]-2-[(3-methyl-2-pyridyl)methyl]-3,3a,4,5,6,6a-hexahydro-1H-cyclopenta[c]pyrrol-5-amine | 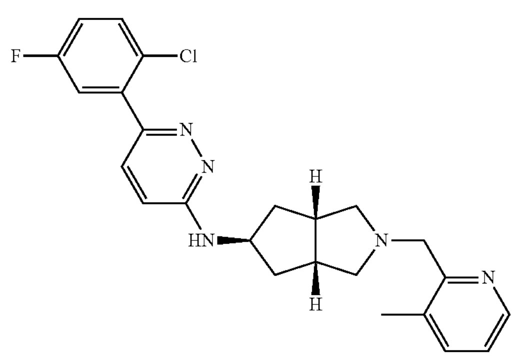 [SMILES: Cc1cccnc1CN1C[C@H]2C[C@H](Nc3ccc(-c4cc(F)ccc4Cl)nn3)C[C@H]2C1] | 438.4 |

TABLE 1-continued

| Cpd. No. | Name | Structure | ES-MS [M + 1]+ |
|---|---|---|---|
| 36 | (3aR,5s,6aS)-N-[6-(2-chloro-5-fluorophenyl)pyridazin-3-yl]-2-[(2-fluorophenyl)methyl]-3,3a,4,5,6,6a-hexahydro-1H-cyclopenta[c]pyrrol-5-amine | 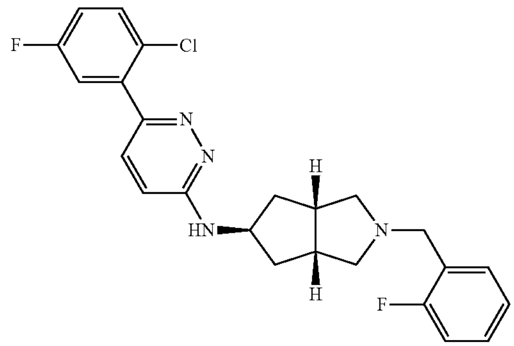 [SMILES: Fc1ccc(Cl)c(-c2ccc(N[C@H]3C[C@@H]4CN(Cc5ccccc5F)C[C@@H]4C3)nn2)c1] | 441.4 |
| 37 | (3aR,5s,6aS)-2-(1-adamantylmethyl)-N-[6-(1,3-dimethylpyrazol-4-yl)pyridazin-3-yl]-3,3a,4,5,6,6a-hexahydro-1H-cyclopenta[c]pyrrol-5-amine | 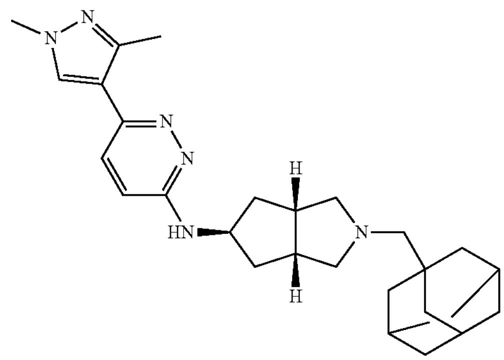 [SMILES: Cc1nn(C)cc1-c1ccc(N[C@H]2C[C@@H]3CN(CC45CC(C)CC(CC(C)C4)C5)C[C@@H]3C2)nn1] | 447.5 |
| 38 | (3aR,5s,6aS)-N-[6-(2,4-dimethylpyrazol-3-yl)pyridazin-3-yl]-2-(tetrahydropyran-2-ylmethyl)-3,3a,4,5,6,6a-hexahydro-1H-cyclopenta[c]pyrrol-5-amine | 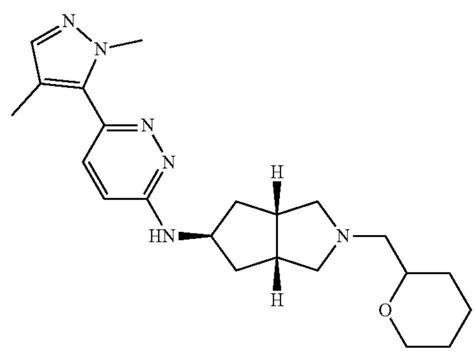 [SMILES: Cc1cnn(C)c1-c1ccc(N[C@H]2C[C@@H]3CN(CC4CCCCO4)C[C@@H]3C2)nn1] | 397.4 |

Example 2. N-[4-[6-[[(3aR,5r,6aS)-2-(3,3-Dimethylbutyl)-3,3a,4,5,6,6a-hexahydro-1H-cyclopenta[c]pyrrol-5-yl]amino]pyridazin-3-yl]phenyl]acetamide (Compound 39)

tert-Butyl(3aR,5r,6aS)-5-((6-chloropyridazin-3-yl)amino)hexahydrocyclopenta[c]pyrrole-2(1H)-carboxylate

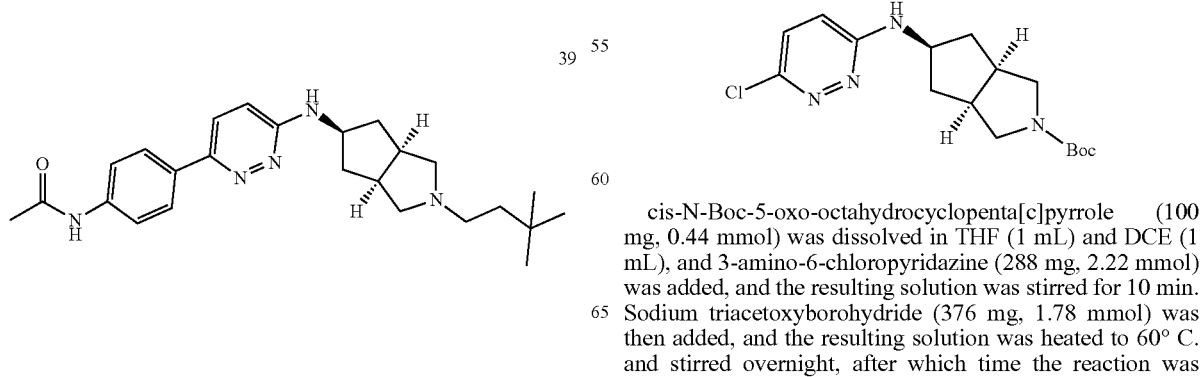

cis-N-Boc-5-oxo-octahydrocyclopenta[c]pyrrole (100 mg, 0.44 mmol) was dissolved in THF (1 mL) and DCE (1 mL), and 3-amino-6-chloropyridazine (288 mg, 2.22 mmol) was added, and the resulting solution was stirred for 10 min. Sodium triacetoxyborohydride (376 mg, 1.78 mmol) was then added, and the resulting solution was heated to 60° C. and stirred overnight, after which time the reaction was diluted with DCM and 3:1 chloroform/iPA solution, and the aqueous layer was extracted with 3:1 chloroform/iPA. The combined organic extracts were filtered through a phase separator and concentrated, and crude residue was purified by RP-HPLC. Fractions containing product were basified with sat. NaHCO₃, and extracted with 3:1 chloroform/iPA, and the combined organic extracts were filtered through a phase separator and concentrated to give the title compound as a brown oil (15.1 mg, 10%). ES-MS [M+H]⁺=339.3.

tert-Butyl (3aR,5r,6aS)-5-((6-(4-acetamidophenyl) pyridazin-3-yl)amino)hexahydrocyclopenta[c]pyrrole-2(1H)-carboxylate

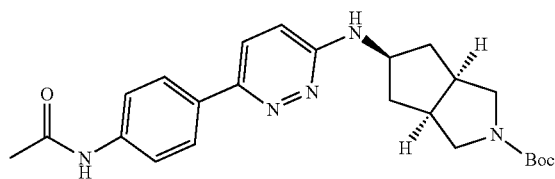 [SMILES: CC(=O)Nc1ccc(-c2ccc(N[C@@H]3C[C@@H]4CN(C(=O)OC(C)(C)C)C[C@@H]4C3)nn2)cc1]

tert-Butyl (3aR,5r,6aS)-5-((6-chloropyridazin-3-yl) amino)hexahydrocyclopenta[c]pyrrole-2(1H)-carboxylate (15.1 mg, 0.045 mmol), K₂CO₃ (18.7 mg, 0.13 mmol), 4-acetylaminophenylboronic acid (9.6 mg, 0.053 mmol) and RuPhos-Pd-G3 (3.7 mg, 0.004 mmol) were combined in a sealed vial and placed under an inert atmosphere. 5:1 1,4-dioxane/H₂O solution (0.6 mL, degassed) was then added via syringe. The resulting mixture was heated to 120° C. under microwave irradiation for 30 min, after which time the reaction was cooled to r.t. and diluted with sat. NaHCO₃, and DCM. The aqueous layer was extracted with DCM, and the combined organic extracts were filtered through a phase separator and concentrated. The crude residue was purified by column chromatography (hex/EtOAc) to give the title compound as a brown oil (3.9 mg, 20%). ES-MS [M+H]⁺=438.4.

N-(4-(6-(((3aR,5r,6aS)-Octahydrocyclopenta[c]pyrrol-5-yl)amino)pyridazin-3-yl)phenyl)acetamide dihydrochloride

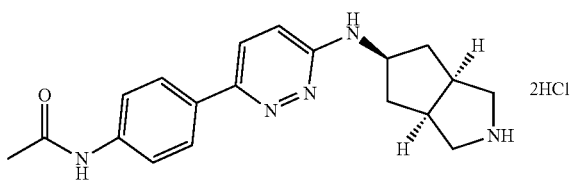 [SMILES: CC(=O)Nc1ccc(-c2ccc(N[C@H]3C[C@H]4CNC[C@H]4C3)nn2)cc1]

tert-Butyl (3aR,5r,6aS)-5-((6-(4-acetamidophenyl) pyridazin-3-yl)amino)hexahydrocyclopenta[c]pyrrole-2 (1H)-carboxylate (3.9 mg, 0.009 mmol) was dissolved in 1,4-dioxanes (0.5 mL) and 4M HCl in dioxanes solution (0.5 mL) was added dropwise. The resulting solution was stirred at r.t. for 30 min, after which time the solvents were concentrated under reduced pressure and the resulting white solid was used directly without further purification (3.9 mg, 100%). ES-MS [M+H]⁺=338.4.

N-[4-[6-[[(3aR,5r,6aS)-2-(3,3-Dimethylbutyl)-3,3a, 4,5,6,6a-hexahydro-1H-cyclopenta[c]pyrrol-5-yl] amino]pyridazin-3-yl]phenyl]acetamide (Compound 39)

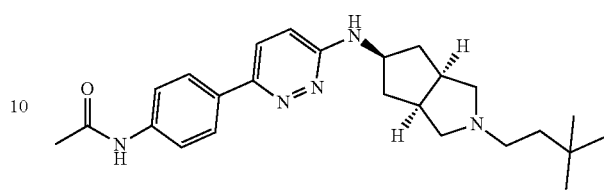

N-(4-(6-(((3aR,5r,6aS)-Octahydrocyclopenta[c]pyrrol-5-yl)amino)pyridazin-3-yl)phenyl)acetamide dihydrochloride (3.3 mg, 0.009 mmol) was dissolved in THF (0.25 mL) and DCE (0.25 mL), and 3,3-dimethylbutyraldehyde (4.3 mg, 0.004 mmol) was added. The resulting mixture was stirred at r.t. for 6 h, after which time sodium triacetoxyborohydride (9.2 mg, 0.044 mmol) was then added, and the resulting solution was stirred at r.t. overnight, after which time the solvents were concentrated, and the crude residue was purified directly by RP-HPLC. Fractions containing product were basified with sat. NaHCO₃, and the aqueous layer was extracted with 3:1 chloroform/iPA. The combined organic extracts were filtered through a phase separator and concentrated to give the title compound as a white solid (1.8 mg, 49%). ¹H-NMR (400 MHz, CDCl₃) 7.95 (d, J=8.6 Hz, 2H), 7.58 (d, J=8.6 Hz, 2H), 7.51 (d, J=9.3 Hz, 1H), 6.54 (d, J=9.3 Hz, 1H), 4.67-4.62 (m, 1H), 2.81 (d, J=9.6 Hz, 2H), 2.75-2.67 (m, 2H), 2.47-2.43 (m, 2H), 2.22-2.15 (m, 7H), 1.74-1.44 (m, 4H), 0.94 (s, 9H). ES-MS [M+H]⁺=422.4.

Example 3. (3aR,5s,6aS)—N-[6-(2,4-Dimethylpyrazol-3-yl)pyridazin-3-yl]-2-(7-oxabicyclo[2.2.1]heptan-3-ylmethyl)-3,3a,4,5,6,6a-hexahydro-1H-cyclopenta[c]pyrrol-5-amine (Compound 40)

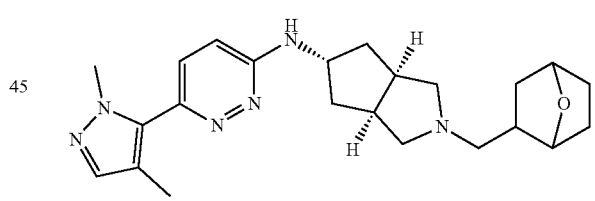

(7-Oxabicyclo[2.2.1]heptan-2-yl)((3aR,5s,6aS)-5-((6-(1,4-dimethyl-1H-pyrazol-5-yl)pyridazin-3-yl) amino)hexahydrocyclopenta[c]pyrrol-2(1H)-yl) methanone

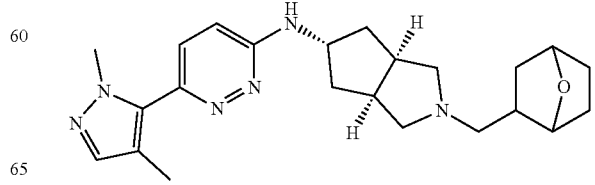

(3aR,5s,6aS)—N-[6-(2,4-Dimethylpyrazol-3-yl)
pyridazin-3-yl]-1,2,3,3a,4,5,6,6a-octahydrocyclopenta[c]
pyrrol-5-amine dihydrochloride (85 mg, 0.23 mmol) (prepared as described in Example 1) and rac-(1r,2s,4s)-7-oxabicyclo[2.2.1]heptane-2-carboxylic acid (CAS: 1048963-21-8, 39 mg, 0.28 mmol) were suspended in DCM (2 mL) and DIPEA (0.080 mL, 0.46 mmol) and HATU (174 mg, 0.46 mmol) were added. The resulting solution was stirred at r.t. for 1.5 h, after which time the reaction mixture was quenched with sat. NaHCO₃, and extracted with DCM and 3:1 chloroform/IPA. The organic extracts were filtered through a phase separator and concentrated, and the crude residue was purified by RP-HPLC (5-35% MeCN in 0.1% TFA aqueous solution over 5 min). Fractions containing product were basified with sat. NaHCO₃, and extracted with 3:1 chloroform/IPA. The combined organic extracts were filtered through a phase separator and concentrated to give the title compound as a white solid (56 mg, 57%). ES-MS [M+H]+=423.4.

(3aR,5s,6aS)—N-[6-(2,4-Dimethylpyrazol-3-yl)
pyridazin-3-yl]-2-(7-oxabicyclo[2.2.1]heptan-3-ylmethyl)-3,3a,4,5,6,6a-hexahydro-1H-cyclopenta[c]
pyrrol-5-amine (Compound 40)

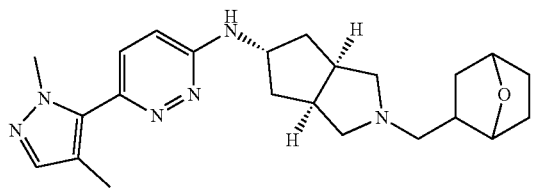 [SMILES: Cc1cnn(C)c1-c1ccc(N[C@H]2C[C@@H]3CN(CC4CC5CCC4O5)C[C@@H]3C2)nn1]

(7-Oxabicyclo[2.2.1]heptan-2-yl)((3aR,5s,6aS)-5-((6-(1,4-dimethyl-1H-pyrazol-5-yl)pyridazin-3-yl)amino)hexahydrocyclopenta[c]pyrrol-2(1H)-yl)methanone (37 mg, 0.26 mmol) was dissolved in DCM (1 mL) and cooled to −78° C. under an inert atmosphere. DIBAL (0.26 mL, 1.0 M in THF) was then added dropwise. The resulting solution was stirred at −78° C. for 15 min, after which time the reaction mixture was diluted with DCM, and MeOH and H₂O were added. The aqueous layer was extracted with DCM and 3:1 chloroform/IPA, and the organic extracts were filtered through a phase separator and concentrated. The crude residue was purified by RP-HPLC (2-32% MeCN in 0.1% TFA aqueous solution over 5 min). Fractions containing product were basified with sat. NaHCO₃, and extracted with 3:1 chloroform/IPA. The combined organic extracts were filtered through a phase separator and concentrated to give the title compound as a colorless oil (8.4 mg, 16%). ES-MS [M+H]⁺=409.4.

Example 4. (3aR,5r,6aS)-2-(3,3-Dimethylbutyl)-N-
[4-(1,3-dimethylpyrazol-4-yl)-2,3-difluoro-phenyl]-
3,3a,4,5,6,6a-hexahydro-1H-cyclopenta[c]pyrrol-5-
amine (Compound 41)

41

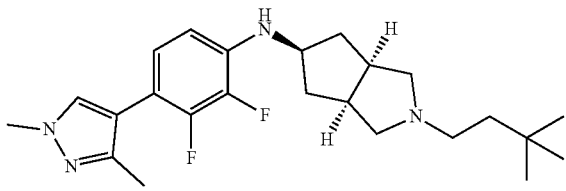

tert-Butyl (3aR,5r,6aS)-5-((4-bromo-2,3-difluoro-
phenyl)amino)hexahydrocyclopenta[c]pyrrole-2
(1H)-carboxylate

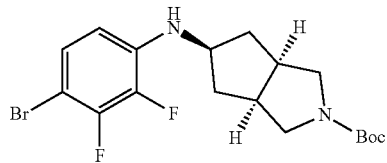 [SMILES: CC(C)(C)OC(=O)N1C[C@H]2C[C@@H](Nc3ccc(Br)c(F)c3F)C[C@H]2C1]

To a stirring solution of 4-bromo-2,3-difluoroaniline (415 mg, 2.00 mmol) in DCM (8 mL) and acetic acid (2 mL) was added cis-N-boc-5-oxo-octahydrocyclopenta[c]pyrrole (300 mg, 1.33 mmol), followed by sodium triacetoxyborohydride (423 mg, 2.00 mmol). The resulting suspension was stirred at r.t. overnight, after which time the reaction was quenched with sat. NaHCO₃, and the aqueous layer was extracted with DCM. The combined organic extracts were dried with MgSO₄, and were filtered and concentrated. The crude residue was purified by RP-HPLC (65-95% MeCN in 0.05% NH₄OH aqueous solution over 20 min), and fractions containing the product were diluted with H₂O, and extracted with DCM. The combined organic extracts were dried with MgSO₄, filtered and concentrated to give the title compound as an off white solid (142 mg, 26%). ES-MS [M+H-tbutyl]⁺=361.3.

tert-Butyl (3aR,5r,6aS)-5-((4-(1,3-dimethyl-1H-
pyrazol-4-yl)-2,3-difluorophenyl)amino)hexahydro-
cyclopenta[c]pyrrole-2(1H)-carboxylate

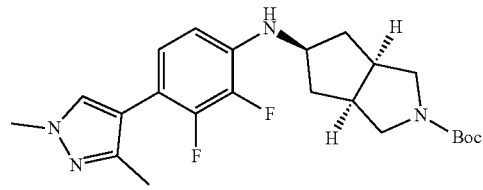 [SMILES: Cc1nn(C)cc1-c1ccc(N[C@@H]2C[C@@H]3CN(C(=O)OC(C)(C)C)C[C@@H]3C2)c(F)c1F]

tert-Butyl (3aR,5r,6aS)-5-((4-bromo-2,3-difluorophenyl)amino)hexahydrocyclopenta[c]pyrrole-2(1H)-carboxylate (114 mg, 0.27 mmol), 1,3-dimethyl-1H-pyrazole-4-boronic acid pinacol ester (73 mg, 0.33 mmol), K₂CO₃ (115 mg, 0.82 mmol) and RuPhos-Pd-G3 (23 mg, 0.03 mmol) were combined in a sealed vial, which was placed under an inert atmosphere. 5:1 1,4-dioxane/H₂O solution (2.4 mL, degassed) was then added via syringe, and the resulting solution was stirred at 100° C. for 3 h, after which time the reaction was cooled to r.t. and diluted with DCM and sat. NaHCO₃. The aqueous layer was extracted with DCM, and the combined organic extracts were filtered through a phase separator and concentrated. The crude residue was purified by column chromatography (5-100% EtOAc in hexanes) to give the title compound as a brown oil (116 mg, 98%). ES-MS [M+H]⁺=433.5.

(3aR,5r,6aS)—N-(4-(1,3-Dimethyl-1H-pyrazol-4-yl)-2,3-difluorophenyl)octahydrocyclopenta[c]pyrrol-5-amine trihydrochloride

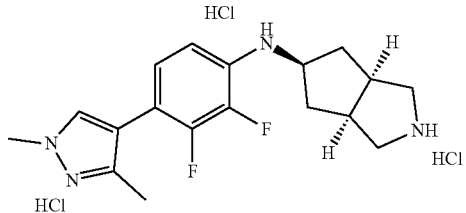 [SMILES: Cl ; Cc1nn(C)cc1-c1ccc(N[C@H]2C[C@H]3CNC[C@H]3C2)c(F)c1F ; Cl ; Cl]

tert-Butyl (3aR,5r,6aS)-5-((4-(1,3-dimethyl-1H-pyrazol-4-yl)-2,3-difluorophenyl)amino)hexahydrocyclopenta[c]pyrrole-2(1H)-carboxylate (116 mg, 0.27 mmol) was dissolved in 1,4-dioxane (2 mL) and 4M HCl in dioxanes solution (2 mL) was added dropwise. The resulting cloudy solution was stirred at r.t. for 30 min, after which time solvents were concentrated under reduced pressure to give the title compound as an off white solid which was used directly without further purification (118 mg, 100%). ES-MS [M+H]⁺=333.5.

(3aR,5r,6aS)-2-(3,3-Dimethylbutyl)-N-[4-(1,3-dimethylpyrazol-4-yl)-2,3-difluoro-phenyl]-3,3a,4,5,6,6a-hexahydro-1H-cyclopenta[c]pyrrol-5-amine (Compound 41)

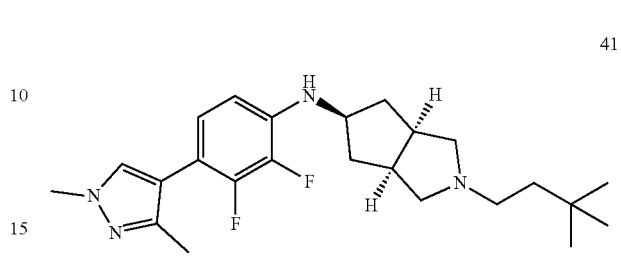

(3aR,5r,6aS)—N-(4-(1,3-Dimethyl-1H-pyrazol-4-yl)-2,3-difluorophenyl)octahydrocyclopenta[c]pyrrol-5-amine trihydrochloride (24 mg, 0.053 mmol) was dissolved in NMP (1 mL), and 3,3-dimethylbutyraldehyde (27 mg, 0.27 mmol) was added, followed by sodium triacetoxyborohydride (57 mg, 0.27 mmol). The resulting mixture was stirred at r.t. for 2 h, after which time the reaction mixture was quenched with sat. NaHCO$_3$ and diluted with 3:1 chloroform/IPA. The aqueous layer was extracted with 3:1 chloroform/IPA, and the organic extracts were filtered through a phase separator and concentrated. The crude residue was purified by RP-HPLC (20-50% MeCN in 0.1% TFA aqueous solution over 5 min), and fractions containing the product were basified with sat. NaHCO$_3$, and extracted with 3:1 chloroform/IPA. The organic extracts were filtered through a phase separator and concentrated to give the title compound as a colorless oil (7.1 mg, 32%). ES-MS [M+H]⁺=417.5.

The compounds shown in Table 2 were prepared similarly to the compounds described above, with appropriate starting materials.

TABLE 2

| Cpd. No. | Name | Structure | ES-MS [M + 1]⁺ |
|---|---|---|---|
| 42 | (3aR,5r,6aS)-2-(5-bicyclo[2.2.1]hept-2-enylmethyl)-N-[4-(1,3-dimethylpyrazol-4-yl)-2,3-difluoro-phenyl]-3,3a,4,5,6,6a-hexahydro-1H-cyclopenta[c]pyrrol-5-amine | 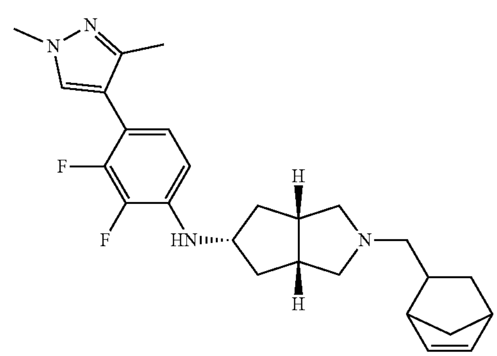 [SMILES: Cc1nn(C)cc1-c1ccc(N[C@@H]2C[C@@H]3CN(CC4CC5C=CC4C5)C[C@@H]3C2)c(F)c1F] | 439.4 |

TABLE 2-continued

| Cpd. No. | Name | Structure | ES-MS [M + 1]+ |
|---|---|---|---|
| 43 | (3aR,5r,6aS)-2-(cyclohexylmethyl)-N-[4-(1,3-dimethylpyrazol-4-yl)-2,3-difluoro-phenyl]-3,3a,4,5,6,6a-hexahydro-1H-cyclopenta[c]pyrrol-5-amine | 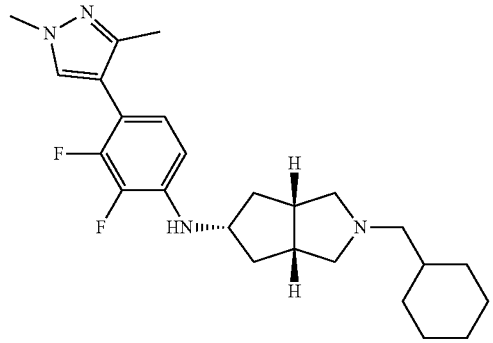 [SMILES: Cc1nn(C)cc1-c1ccc(N[C@@H]2C[C@@H]3CN(CC4CCCCC4)C[C@@H]3C2)c(F)c1F] | 429.3 |
| 44 | (3aR,5r,6aS)-2-(cycloheptylmethyl)-N-[4-(1,3-dimethylpyrazol-4-yl)-2,3-difluoro-phenyl]-3,3a,4,5,6,6a-hexahydro-1H-cyclopenta[c]pyrrol-5-amine | 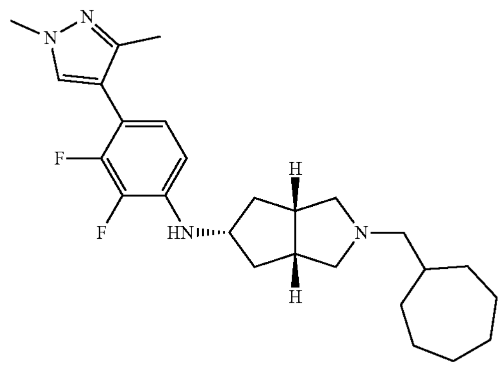 [SMILES: Cc1nn(C)cc1-c1ccc(N[C@@H]2C[C@@H]3CN(CC4CCCCCC4)C[C@@H]3C2)c(F)c1F] | 443.5 |
| 45 | (3aR,5r,6aS)-2-(1-adamantylmethyl)-N-[4-(1,3-dimethylpyrazol-4-yl)-2,3-difluoro-phenyl]-3,3a,4,5,6,6a-hexahydro-1H-cyclopenta[c]pyrrol-5-amine | 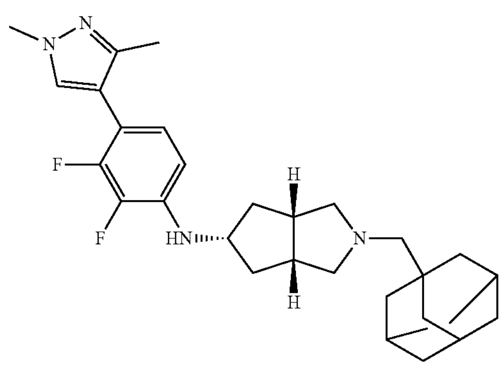 [SMILES: Cc1nn(C)cc1-c1ccc(N[C@@H]2C[C@@H]3CN(CC45CC(C)CC(CC(C)C4)C5)C[C@@H]3C2)c(F)c1F] | 481.5 |

Example 5. (3aR,5r,6aS)-5-[6-(1,3-Dimethylpyrazol-4-yl)pyridazin-3-yl]oxy-2-(2,3,3-trimethylbutyl)-3,3a,4,5,6,6a-hexahydro-1H-cyclopenta[c]pyrrole (Compound 46)

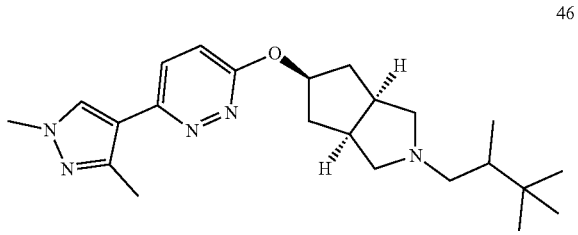 [SMILES: Cc1nn(C)cc1-c1ccc(O[C@@H]2C[C@@H]3CN(CC(C)C(C)(C)C)C[C@@H]3C2)nn1]

46 tert-Butyl (3aR,5r,6aS)-5-(6-chloropyridazin-3-yl)oxy-3,3a,4,5,6,6a-hexahydro-1H-cyclopenta[c]pyrrole-2-carboxylate

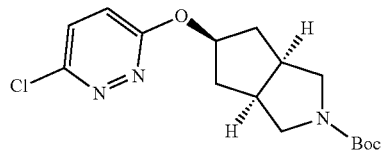 [SMILES: CC(C)(C)OC(=O)N1C[C@H]2C[C@@H](Oc3ccc(Cl)nn3)C[C@H]2C1]

To a solution of tert-butyl (3aR,5r,6aS)-5-hydroxy-3,3a,4,5,6,6a-hexahydro-1H-cyclopenta[c]pyrrole-2-carboxylate (prepared as described in Example 1) (500 mg, 2.20 mmol, 1.0 eq.) in THF (11.0 mL, 0.2 M) at 0° C. was added NaH (60% dispersion in mineral oil, 176 mg, 4.40 mmol, 2.0 eq.). After stirring for 5 min, 3,6-dichloropyridazine (491 mg, 3.30 mmol, 1.5 eq.) in THF (1.5 mL) was added. After stirring at r.t. for 16 h, the mixture was diluted with water and extracted with DCM (3×). The combined extracts were dried over Na₂SO₄, filtered and concentrated. The crude material was purified using flash chromatography on silica gel (0-40% EtOAc/hexanes) to provide the title compound as a white solid (660 mg, 89%). ¹H-NMR (400 MHz, CDCl₃) δ 7.37 (d, J=9.2 Hz, 1H), 6.93 (d, J=9.2 Hz, 1H), 5.65-5.59 (m, 1H), 3.56 (br, 2H), 3.37 (br, 2H), 2.76-2.68 (m, 2H), 2.46 (br, 2H), 1.08 (br, 2H), 1.47 (s, 9H); ES-MS [M+H]⁺=[M+H]⁺-Boc=240.4.

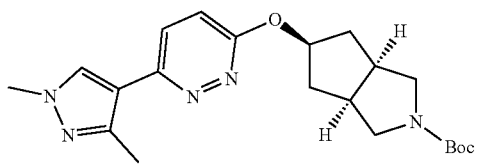 [SMILES: Cc1nn(C)cc1-c1ccc(O[C@@H]2C[C@@H]3CN(C(=O)OC(C)(C)C)C[C@@H]3C2)nn1]

tert-Butyl (3aR,5r,6aS)-5-[6-(1,3-dimethylpyrazol-4-yl)pyridazin-3-yl]oxy-3,3a,4,5,6,6a-hexahydro-1H-cyclopenta[c]pyrrole-2-carboxylate. tert-Butyl (3aR,5r,6aS)-5-(6-chloropyridazin-3-yl)oxy-3,3a,4,5,6,6a-hexahydro-1H-cyclopenta[c]pyrrole-2-carboxylate (339 mg, 1.0 mmol, 1.0 eq.), 1,3-dimethyl-1H-pyrazole-4-boronic acid pinacol ester (444.2 mg, 2.0 mmol, 2.0 eq.), K₂CO₃ (420.6 mg, 3.0 mmol, 3.0 eq.) and BrettPhos-Pd-G3 (45.4 mg, 0.05 mmol, 0.05 eq.) were charged into a reaction vial. A degassed mixture of 5:1 (v/v) 1,4-dioxane/H₂O (6.6 mL) was added. The resulting suspension was stirred at 100° C. for 1 h. After cooling to r.t., the reaction mixture was filtered through a pad of Celite which was washed thoroughly with EtOAc. The filtrate was concentrated under reduced pressure. The crude residue was purified by flash column chromatography (0-60% EtOAc/hexanes then 60-100% EtOAc/DCM) to give the title compound as a viscous oil (350 mg, 87%). ES-MS [M+H]⁺=400.4.

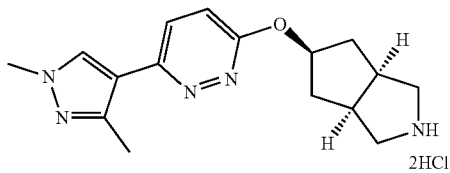

(3aR,5r,6aS)-5-[6-(1,3-Dimethylpyrazol-4-yl)pyridazin-3-yl]oxy-1,2,3,3a,4,5,6,6a-octahydrocyclopenta[c]pyrrole dihydrochloride. tert-Butyl (3aR,5r,6aS)-5-[6-(1,3-dimethylpyrazol-4-yl)pyridazin-3-yl]oxy-3,3a,4,5,6,6a-hexahydro-1H-cyclopenta[c]pyrrole-2-carboxylate (350 mg, 0.88 mmol, 1.0 eq.) was dissolved in 1,4-dioxane (4.0 mL). A 4M HCl in 1,4-dioxane solution (2.0 mL, 8.76 mmol, 10.0 eq.) was added dropwise. After stirring 1 h at r.t., solvents were removed under reduced pressure. The crude material was azeotroped with toluene (3×) to provide the title compound as a white solid which was used without further purification as the HCl salt (326 mg, 99%). ES-MS [M+H]⁺=300.4.

(3aR,5r,6aS)-5-[6-(1,3-Dimethylpyrazol-4-yl)pyridazin-3-yl]oxy-2-(2,3,3-trimethylbutyl)-3,3a,4,5,6,6a-hexahydro-1H-cyclopenta[c]pyrrole (Compound 46)

46

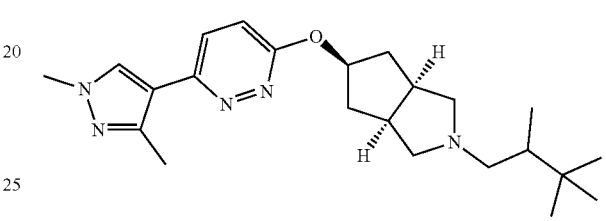

(3aR,5r,6aS)-5-[6-(1,3-Dimethylpyrazol-4-yl)pyridazin-3-yl]oxy-1,2,3,3a,4,5,6,6a-octahydrocyclopenta[c]pyrrole dihydrochloride (25 mg, 0.067 mmol, 1.0 eq.) was suspended in DCM (1.0 mL) and acetic acid (0.1 mL). 2,3,3-Trimethylbutanal (42.6 μL, 0.336 mmol, 5.0 eq.) was added. The mixture was stirred at r.t. for 30 min and sodium triacetoxyborohydride (71.2 mg, 0.336 mmol, 5.0 eq.) was added. The resulting solution was stirred at r.t. for 16 h, after which time the reaction mixture was quenched with sat. soln. NaHCO₃ and extracted with chloroform/IPA (3:1, v/v). The combined extracts were filtered through a phase separator and concentrated. The crude residue was purified by RP-HPLC, fractions containing the product were basified with sat. soln. NaHCO₃, and extracted with chloroform/IPA (3:1, v/v). The combined extracts were filtered through a phase separator and concentrated to give the title compound as a colorless soil (10.2 mg, 38). ES-MS[M+H]⁺=398.5.

The compounds shown in Table 3 were prepared similarly to the compounds described above, with appropriate starting materials.

TABLE 3

| Cpd. No. | Name | Structure | ES-MS [M + 1]⁺ |
|---|---|---|---|
| 47 | (3aR,5r,6aS)-2-(5-bicyclo[2.2.1]hept-2-enylmethyl)-5-[6-(1,3-dimethylpyrazol-4-yl)pyridazin-3-yl]oxy-3,3a,4,5,6,6a-hexahydro-1H-cyclopenta[c]pyrrole | 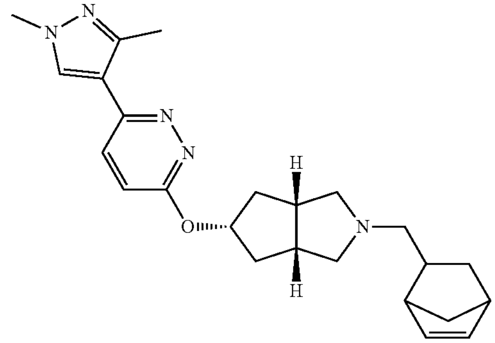 [SMILES: Cc1nn(C)cc1-c1ccc(O[C@@H]2C[C@@H]3CN(CC4CC5C=CC4C5)C[C@@H]3C2)nn1] | 406.4 |

TABLE 3-continued

| Cpd. No. | Name | Structure | ES-MS [M + 1]+ |
|---|---|---|---|
| 48 | (3aR,5r,6aS)-2-(3,3-dimethylbutyl)-5-[6-(1,3-dimethylpyrazol-4-yl)pyridazin-3-yl]oxy-3,3a,4,5,6,6a-hexahydro-1H-cyclopenta[c]pyrrole | 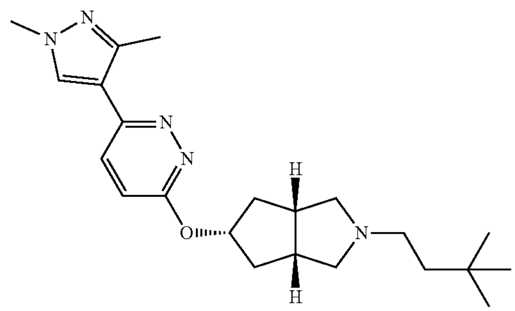 [SMILES: Cc1nn(C)cc1-c1ccc(O[C@@H]2C[C@@H]3CN(CCC(C)(C)C)C[C@@H]3C2)nn1] | 384.5 |
| 49 | (3aR,5r,6aS)-2-(cyclohexylmethyl)-5-[6-(1,3-dimethylpyrazol-4-yl)pyridazin-3-yl]oxy-3,3a,4,5,6,6a-hexahydro-1H-cyclopenta[c]pyrrole | 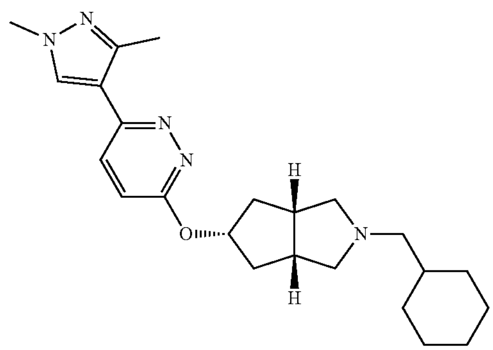 [SMILES: Cc1nn(C)cc1-c1ccc(O[C@@H]2C[C@@H]3CN(CC4CCCCC4)C[C@@H]3C2)nn1] | 396.5 |
| 50 | (3aR,5r,6aS)-5-[6-(1,3-dimethylpyrazol-4-yl)pyridazin-3-yl]oxy-2-(tetrahydropyran-4-ylmethyl)-3,3a,4,5,6,6a-hexahydro-1H-cyclopenta[c]pyrrole | 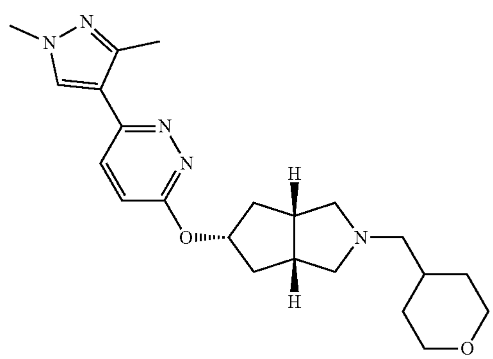 [SMILES: Cc1nn(C)cc1-c1ccc(O[C@@H]2C[C@@H]3CN(CC4CCOCC4)C[C@@H]3C2)nn1] | 398.4 |
| 51 | (3aR,5r,6aS)-5-[6-(1,3-dimethylpyrazol-4-yl)pyridazin-3-yl]oxy-2-(tetrahydropyran-3-ylmethyl)-3,3a,4,5,6,6a-hexahydro-1H-cyclopenta[c]pyrrole | 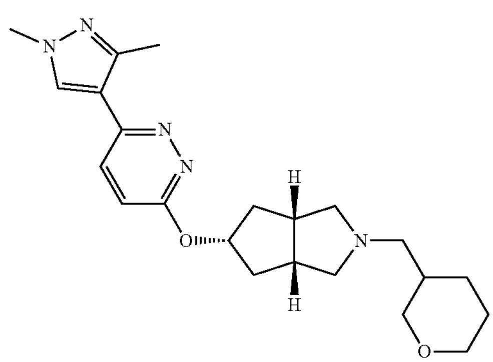 [SMILES: Cc1nn(C)cc1-c1ccc(O[C@@H]2C[C@@H]3CN(CC4CCCOC4)C[C@@H]3C2)nn1] | 398.5 |

TABLE 3-continued

| Cpd. No. | Name | Structure | ES-MS [M + 1]+ |
|---|---|---|---|
| 52 | (3aR,5r,6aS)-5-[6-(1,3-dimethylpyrazol-4-yl)pyridazin-3-yl]oxy-2-[(3-methyl-2-pyridyl)methyl]-3,3a,4,5,6,6a-hexahydro-1H-cyclopenta[c]pyrrole | 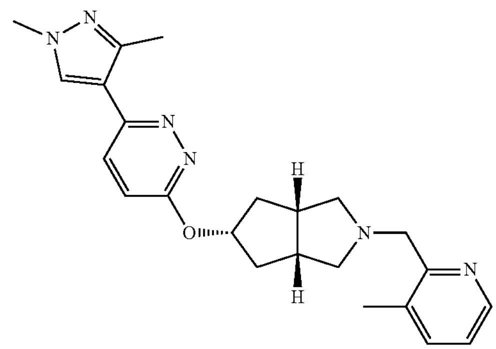 [SMILES: Cc1cccnc1CN1C[C@H]2C[C@@H](Oc3ccc(-c4cn(C)nc4C)nn3)C[C@H]2C1] | 405.5 |
| 53 | (3aR,5r,6aS)-2-(5-bicyclo[2.2.1]hept-2-enylmethyl)-5-[6-(2-chloro-5-fluoro-phenyl)pyridazin-3-yl]oxy-3,3a,4,5,6,6a-hexahydro-1H-cyclopenta[c]pyrrole | 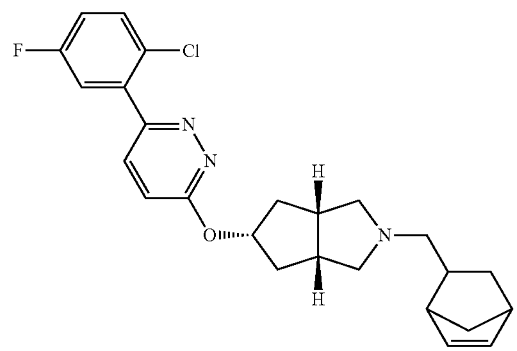 [SMILES: Fc1ccc(Cl)c(-c2ccc(O[C@@H]3C[C@@H]4CN(CC5CC6C=CC5C6)C[C@@H]4C3)nn2)c1] | 440.3 |
| 54 | (3aR,5r,6aS)-5-[6-(2-chloro-5-fluoro-phenyl)pyridazin-3-yl]oxy-2-(3,3-dimethylbutyl)-3,3a,4,5,6,6a-hexahydro-1H-cyclopenta[c]pyrrole | 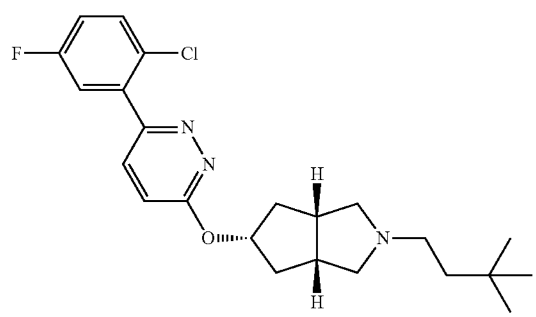 [SMILES: CC(C)(C)CCN1C[C@H]2C[C@@H](Oc3ccc(-c4cc(F)ccc4Cl)nn3)C[C@H]2C1] | 418.3 |
| 55 | (3aR,5r,6aS)-5-[6-(2-chloro-5-fluoro-phenyl)pyridazin-3-yl]oxy-2-(2,3,3-trimethylbutyl)-3,3a,4,5,6,6a-hexahydro-1H-cyclopenta[c]pyrrole | 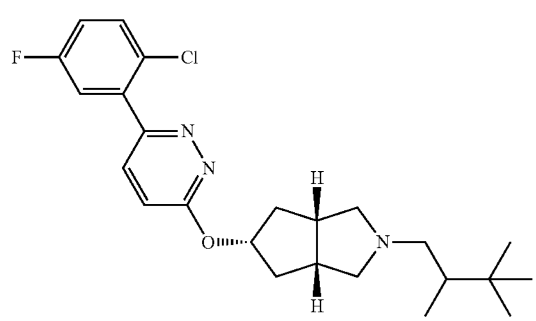 [SMILES: CC(CN1C[C@H]2C[C@@H](Oc3ccc(-c4cc(F)ccc4Cl)nn3)C[C@H]2C1)C(C)(C)C] | 432.3 |

TABLE 3-continued

| Cpd. No. | Name | Structure | ES-MS [M + 1]+ |
|---|---|---|---|
| 56 | (3aR,5r,6aS)-5-[6-(2-chloro-5-fluoro-phenyl)pyridazin-3-yl]oxy-2-(cyclohexylmethyl)-3,3a,4,5,6,6a-hexahydro-1H-cyclopenta[c]pyrrole | 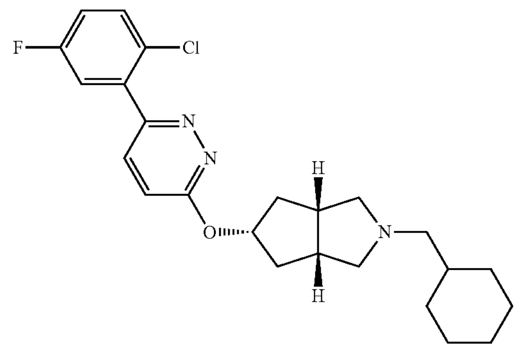 [SMILES: Fc1ccc(Cl)c(-c2ccc(O[C@@H]3C[C@@H]4CN(CC5CCCCC5)C[C@@H]4C3)nn2)c1] | 440.3 |
| 57 | (3aR,5r,6aS)-5-[6-(2-chloro-5-fluoro-phenyl)pyridazin-3-yl]oxy-2-(tetrahydropyran-3-ylmethyl)-3,3a,4,5,6,6a-hexahydro-1H-cyclopenta[c]pyrrole | 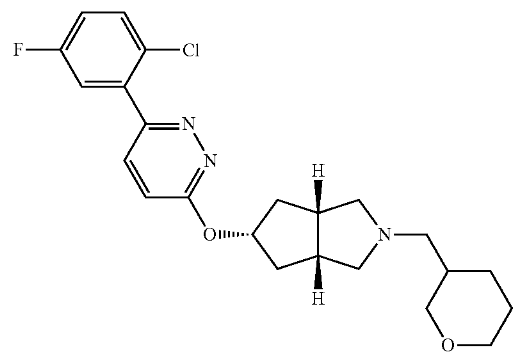 [SMILES: Fc1ccc(Cl)c(-c2ccc(O[C@@H]3C[C@@H]4CN(CC5CCCOC5)C[C@@H]4C3)nn2)c1] | 432.3 |
| 58 | (3aR,5r,6aS)-5-[6-(2-chloro-5-fluoro-phenyl)pyridazin-3-yl]oxy-2-[(3-methyl-2-pyridyl)methyl]-3,3a,4,5,6,6a-hexahydro-1H-cyclopenta[c]pyrrole | 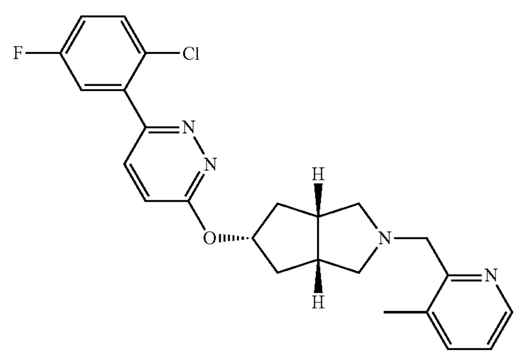 [SMILES: Cc1cccnc1CN1C[C@H]2C[C@@H](Oc3ccc(-c4cc(F)ccc4Cl)nn3)C[C@H]2C1] | 439.2 |
| 59 | (3aR,5r,6aS)-5-[6-(2-chloro-5-fluoro-phenyl)pyridazin-3-yl]oxy-2-(tetrahydropyran-4-ylmethyl)-3,3a,4,5,6,6a-hexahydro-1H-cyclopenta[c]pyrrole | 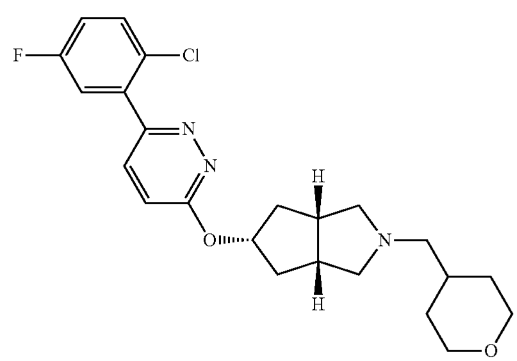 [SMILES: Fc1ccc(Cl)c(-c2ccc(O[C@@H]3C[C@@H]4CN(CC5CCOCC5)C[C@@H]4C3)nn2)c1] | 432.4 |

TABLE 3-continued

| Cpd. No. | Name | Structure | ES-MS [M + 1]+ |
|---|---|---|---|
| 60 | [(3aR,5r,6aS)-5-[6-(1,3-dimethylpyrazol-4-yl)pyridazin-3-yl]oxy-3,3a,4,5,6,6a-hexahydro-1H-cyclopenta[c]pyrrol-2-yl]-(1-adamantyl)methanone | 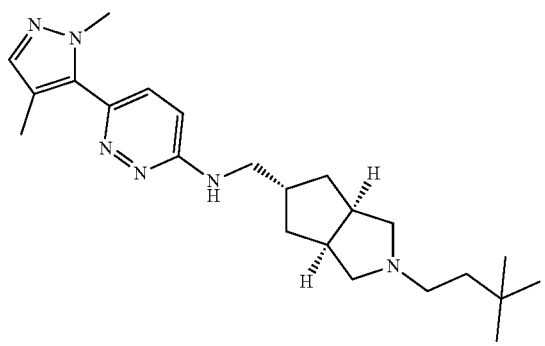 | 383 |

Example 6. N-[[(3aR,5s,6aS)-2-(3,3-Dimethyl-butyl)-3,3a,4,5,6,6a-hexahydro-1H-cyclopenta[c]pyrrol-5-yl]methyl]-6-(2,4-dimethylpyrazol-3-yl)pyridazin-3-amine (Compound 61)

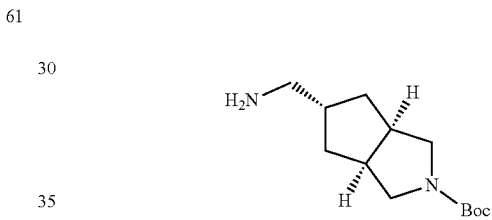

61 tert-Butyl (3aR,5s,6aS)-5-cyano-3,3a,4,5,6,6a-hexahydro-1H-cyclopenta[c]pyrrole-2-carboxylate

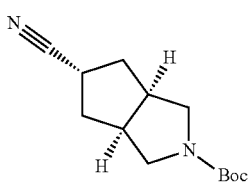 [SMILES: CC(C)(C)OC(=O)N1C[C@H]2C[C@H](C#N)C[C@H]2C1]

Solid potassium tert-butoxide (996.2 mg, 8.88 mmol, 2.0 eq.) was added portion wise to a solution of cis-tert-butyl 5-oxohexahydrocyclopenta[c]pyrrole-2(1H)-carboxylate (1.0 g, 4.44 mmol, 1.0 eq.), tosylmethyl isocyanide (870 mg, 4.44 mmol, 1.0 eq.) in monoglyme (15.52 mL, 0.285 M) and ethanol (0.44 mL, 7.55 mmol, 1.7 eq.) at 0° C. The reaction mixture was stirred for 15 min at 0° C., then warmed to r.t. and allowed to stir for additional 1.5 h. Upon completion, the precipitate (TosK) was removed via filtration and the solid was washed with EtOAc. The combined organic layers were concentrated under reduced pressure. The crude product was purified using flash column chromatography on silica gel (0-80% EtOAc/hexanes) to provide the title compound as a viscous oil (532 mg, 51%). ES-MS [M+H]+= [M+H]+-tButyl=181.2.

tert-Butyl(3aR,5s,6aS)-5-(aminomethyl)-3,3a,4,5,6,6a-hexahydro-1H-cyclopenta[c]pyrrole-2-carboxylate

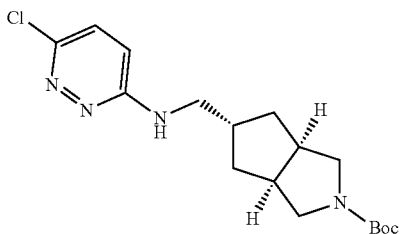 [SMILES: CC(C)(C)OC(=O)N1C[C@H]2C[C@H](CNc3ccc(Cl)nn3)C[C@H]2C1]

To a solution of tert-butyl (3aR,5s,6aS)-5-cyano-3,3a,4,5,6,6a-hexahydro-1H-cyclopenta[c]pyrrole-2-carboxylate (532 mg, 2.25 mmol, 1.0 eq.) in THF (11.24 mL, 0.2 M) at 0° C. was added dropwise a solution of lithium aluminum hydride (1M in THF, 2.25 mL, 2.25 mmol, 1.0 eq.). After 2 h at 0° C., the reaction mixture was slowly added to an aqueous saturated Rochelle's salt solution (10 mL). Ethyl acetate (20 mL) was added. The mixture was allowed to stir overnight. The organic layer was separated. The aqueous layer was extracted with EtOAc (3×). The combined extracts were dried over Na2SO4, filtered and concentrated to provide the title compound (350 mg, 65%) which was used in the next reaction without further purification. ES-MS [M+H]+=[M+H]+-tButyl=185.2.

tert-Butyl (3aR,5s,6aS)-5-[[(6-chloropyridazin-3-yl)amino]methyl]-3,3a,4,5,6,6a-hexahydro-1H-cyclopenta[c]pyrrole-2-carboxylate tert-Butyl (3aR,5s,6aS)-5-(aminomethyl)-3,3a,4,5,6,6a-hexahydro-1H-cyclopenta[c]pyrrole-2-carboxylate (350 mg, 1.45 mmol, 1.0 eq.) was dissolved in n-BuOH (7.3 mL, 0.2 M), and DIPEA (0.760 mL, 4.37 mmol, 3.0 eq.) was added followed by 3,6-dichloropyridazine (651 mg, 4.37 mmol, 3.0 eq.). The resulting suspension was heated to 100° C. overnight, after which time the reaction was cooled to r.t., and diluted with DCM and sat. soln. NaHCO$_3$. The aqueous layer was extracted with DCM (3x). The combined extracts were dried over Na$_2$SO$_4$, filtered and concentrated. The crude residue was purified by flash column chromatography on silica gel (0-30% EtOAc/hexanes then 30-50% EtOAc/DCM) to provide the title compound as a viscous oil (210 mg, 41%). ES-MS [M+H]$^+$=353.4.

tert-Butyl(3aR,5s,6aS)-5-[[[6-(2,4-dimethylpyrazol-3-yl)pyridazin-3-yl]amino]methyl]-3,3a,4,5,6,6a-hexahydro-1H-cyclopenta[c]pyrrole-2-carboxylate

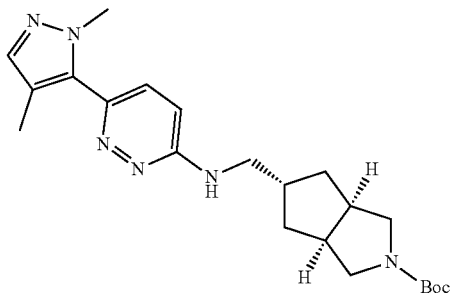 [SMILES: Cc1cnn(C)c1-c1ccc(NC[C@H]2C[C@@H]3CN(C(=O)OC(C)(C)C)C[C@@H]3C2)nn1]

tert-Butyl (3aR,5s,6aS)-5-[[(6-chloropyridazin-3-yl)amino]methyl]-3,3a,4,5,6,6a-hexahydro-1H-cyclopenta[c]pyrrole-2-carboxylate (210 mg, 0.595 mmol, 1.0 eq.), 1,4-dimethylpyrazole-5-boronic acid pinacol ester (224.7 mg, 1.01 mmol, 1.7 eq.), K$_2$CO$_3$ (250.5 mg, 1.79 mmol, 3.0 eq.) and BrettPhos-Pd-G3 (24 mg, 0.03 mmol) were charged into a reaction vial. A degassed mixture of 5:1 (v/v) 1,4-dioxane/H$_2$O (3.0 mL) was added. The resulting suspension was stirred at 100° C. for 1 h. After cooling to r.t., the reaction mixture was filtered through a pad of Celite which was washed thoroughly with EtOAc. The filtrate was concentrated under reduced pressure. The crude residue was purified by flash column chromatography (0-100% EtOAc/DCM) to give the title compound as a viscous oil (200 mg, 81%). ES-MS [M+H]$^+$=413.0.

N-[[(3aR,5s,6aS)-1,2,3,3a,4,5,6,6a-Octahydrocyclopenta[c]pyrrol-5-yl]methyl]-6-(2,4-dimethylpyrazol-3-yl)pyridazin-3-amine

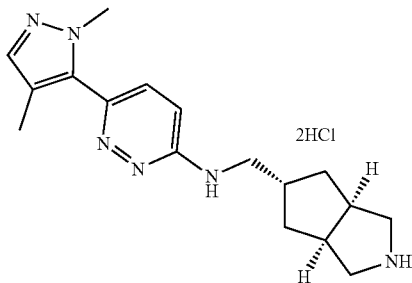 [SMILES: Cc1cnn(C)c1-c1ccc(NC[C@@H]2C[C@H]3CNC[C@H]3C2)nn1]

tert-Butyl(3aR,5s,6aS)-5-[[[6-(2,4-dimethylpyrazol-3-yl)pyridazin-3-yl]amino]methyl]-3,3a,4,5,6,6a-hexahydro-1H-cyclopenta[c]pyrrole-2-carboxylate (200 mg, 0.485 mmol, 1.0 eq.) was dissolved in 1,4-dioxane (2.0 mL). 4M HCl in 1,4-dioxane solution (1.82 mL, 7.27 mmol, 15.0 eq.) was added dropwise. After stirring 30 min at r.t., solvents were removed under reduced pressure. The crude material was azeotroped with toluene (3x) to provide the title compound as a pale yellow solid which was used without further purification as the HCl salt. ES-MS [M+H]$^+$=313.2.

N-[[(3aR,5s,6aS)-2-(3,3-Dimethylbutyl)-3,3a,4,5,6,6a-hexahydro-1H-cyclopenta[c]pyrrol-5-yl]methyl]-6-(2,4-dimethylpyrazol-3-yl)pyridazin-3-amine (Compound 61)

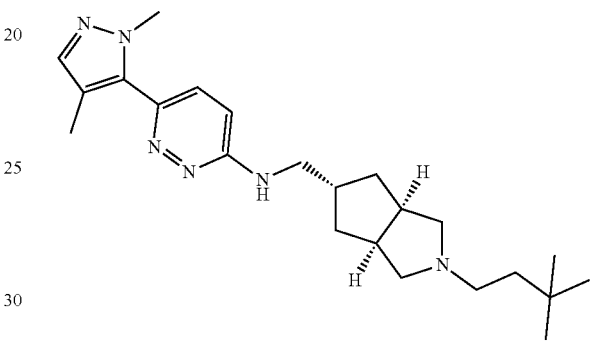

N-[[(3aR,5s,6aS)-1,2,3,3a,4,5,6,6a-Octahydrocyclopenta[c]pyrrol-5-yl]methyl]-6-(2,4-dimethylpyrazol-3-yl)pyridazin-3-amine dihydrochloride (15 mg, 0.045 mmol, 1.0 eq.) was suspended in DCM (1 mL) and acetic acid (0.1 mL). 3,3-Dimethylbutyraldehyde (28.1 μL, 0.224 mmol, 5.0 eq.) was added. The mixture was stirred at 50° C. for 30 min and sodium triacetoxyborohydride (47.5 mg, 0.224 mmol. 5.0 eq.) was added. The resulting solution was stirred at r.t. overnight, after which time the reaction mixture was quenched with sat. soln. NaHCO$_3$, and extracted with chloroform/IPA (3:1, v/v). The combined extracts were filtered through a phase separator and concentrated. The crude residue was purified by RP-HPLC, and fractions containing the product were basified with sat. soln. NaHCO$_3$, and extracted with chloroform/IPA (3:1, v/v). The combined extracts were filtered through a phase separator and concentrated to give the title compound as a colorless oil (5.2 mg, 30%). ES-MS [M+H]$^+$=397.0.

The compounds shown in Table 4 were prepared similarly to the compounds described above, with appropriate starting materials.

TABLE 4

| Cpd. No. | Name | Structure | ES-MS [M + 1]+ |
|---|---|---|---|
| 62 | N-[[(3aR,6aS)-2-(5-bicyclo[2.2.1]hept-2-enylmethyl)-3,3a,4,5,6,6a-hexahydro-1H-cyclopenta[c]pyrrol-5-yl]methyl]-6-(1,3-dimethylpyrazol-4-yl)pyridazin-3-amine | 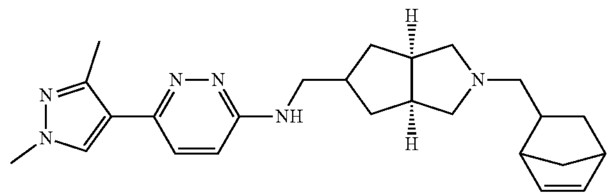 [SMILES: Cc1nn(C)cc1-c1ccc(NCC2C[C@@H]3CN(CC4CC5C=CC4C5)C[C@@H]3C2)nn1] | 419.4 |
| 63 | N-[[(3aR,6aS)-2-(2,3,3-trimethylbutyl)-3,3a,4,5,6,6a-hexahydro-1H-cyclopenta[c]pyrrol-5-yl]methyl]-6-(1,3-dimethylpyrazol-4-yl)pyridazin-3-amine | 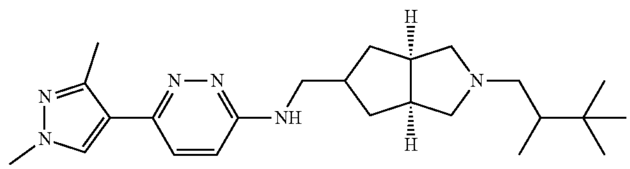 [SMILES: Cc1nn(C)cc1-c1ccc(NCC2C[C@@H]3CN(CC(C)C(C)(C)C)C[C@@H]3C2)nn1] | 411.6 |
| 64 | N-[[(3aR,5s,6aS)-2-(5-bicyclo[2.2.1]hept-2-enylmethyl)-3,3a,4,5,6,6a-hexahydro-1H-cyclopenta[c]pyrrol-5-yl]methyl]-6-(2,4-dimethylpyrazol-3-yl)pyridazin-3-amine | 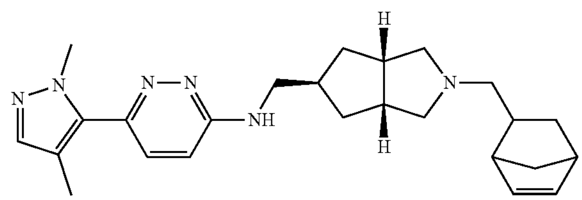 [SMILES: Cc1cnn(C)c1-c1ccc(NC[C@H]2C[C@@H]3CN(CC4CC5C=CC4C5)C[C@@H]3C2)nn1] | 419 |
| 65 | N-[[(3aR,5s,6aS)-2-(2,3,3-trimethylbutyl)-3,3a,4,5,6,6a-hexahydro-1H-cyclopenta[c]pyrrol-5-yl]methyl]-6-(2,4-dimethylpyrazol-3-yl)pyridazin-3-amine | 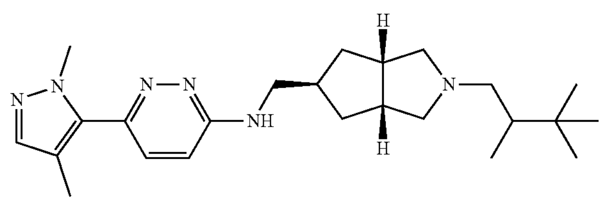 [SMILES: Cc1cnn(C)c1-c1ccc(NC[C@H]2C[C@@H]3CN(CC(C)C(C)(C)C)C[C@@H]3C2)nn1] | 411 |
| 66 | N-[[(3aR,5s,6aS)-2-(tetrahydropyran-4-ylmethyl)-3,3a,4,5,6,6a-hexahydro-1H-cyclopenta[c]pyrrol-5-yl]methyl]-6-(2,4-dimethylpyrazol-3-yl)pyridazin-3-amine | 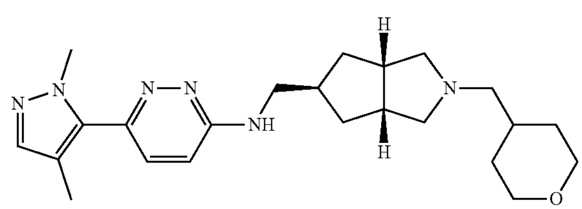 [SMILES: Cc1cnn(C)c1-c1ccc(NC[C@H]2C[C@@H]3CN(CC4CCOCC4)C[C@@H]3C2)nn1] | 411 |
| 67 | N-[[(3aR,5s,6aS)-2-(tetrahydropyran-3-ylmethyl)-3,3a,4,5,6,6a-hexahydro-1H-cyclopenta[c]pyrrol-5-yl]methyl]-6-(2,4-dimethylpyrazol-3-yl)pyridazin-3-amine | 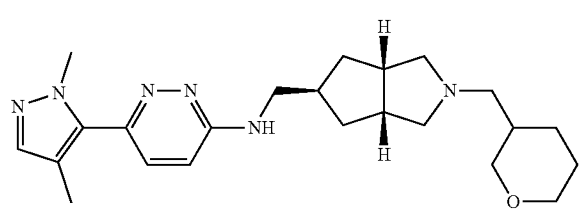 [SMILES: Cc1cnn(C)c1-c1ccc(NC[C@H]2C[C@@H]3CN(CC4CCCOC4)C[C@@H]3C2)nn1] | 411 |

TABLE 4-continued

| Cpd. No. | Name | Structure | ES-MS [M + 1]+ |
|---|---|---|---|
| 68 | N-[[(3aR,5s,6aS)-2-[(3-methyl-2-pyridyl)methyl]-3,3a,4,5,6,6a-hexahydro-1H-cyclopenta[c]pyrrol-5-yl]methyl]-6-(2,4-dimethylpyrazol-3-yl)pyridazin-3-amine | 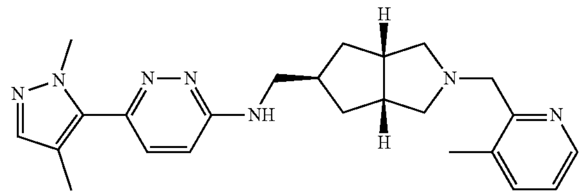 [SMILES: Cc1cccnc1CN1C[C@H]2C[C@H](CNc3ccc(-c4c(C)cnn4C)nn3)C[C@H]2C1] | 418 |
| 69 | N-[[(3aR,5s,6aS)-2-(5-bicyclo[2.2.1]hept-2-enylmethyl)-3,3a,4,5,6,6a-hexahydro-1H-cyclopenta[c]pyrrol-5-yl]methyl]-6-(2-chloro-5-fluoro-phenyl)pyridazin-3-amine | 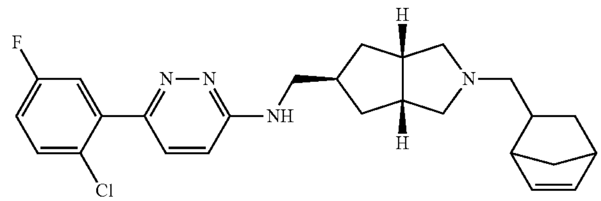 [SMILES: Fc1ccc(Cl)c(-c2ccc(NC[C@H]3C[C@@H]4CN(CC5CC6C=CC5C6)C[C@@H]4C3)nn2)c1] | 453.3 |
| 70 | N-[[(3aR,5s,6aS)-2-(3,3-dimethylbutyl)-3,3a,4,5,6,6a-hexahydro-1H-cyclopenta[c]pyrrol-5-yl]methyl]-6-(2-chloro-5-fluoro-phenyl)pyridazin-3-amine | 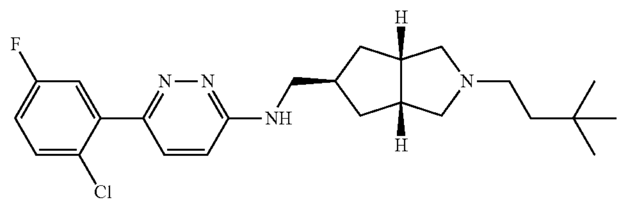 [SMILES: CC(C)(C)CCN1C[C@H]2C[C@H](CNc3ccc(-c4cc(F)ccc4Cl)nn3)C[C@H]2C1] | 431.4 |
| 71 | N-[[(3aR,5s,6aS)-2-(tetrahydropyran-4-ylmethyl)-3,3a,4,5,6,6a-hexahydro-1H-cyclopenta[c]pyrrol-5-yl]methyl]-6-(2-chloro-5-fluoro-phenyl)pyridazin-3-amine | 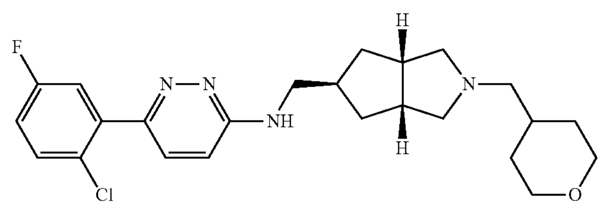 [SMILES: Fc1ccc(Cl)c(-c2ccc(NC[C@H]3C[C@@H]4CN(CC5CCOCC5)C[C@@H]4C3)nn2)c1] | 445.3 |
| 72 | N-[[(3aR,5s,6aS)-2-(cyclohexylmethyl)-3,3a,4,5,6,6a-hexahydro-1H-cyclopenta[c]pyrrol-5-yl]methyl]-6-(1,3-dimethylpyrazol-4-yl)pyridazin-3-amine | 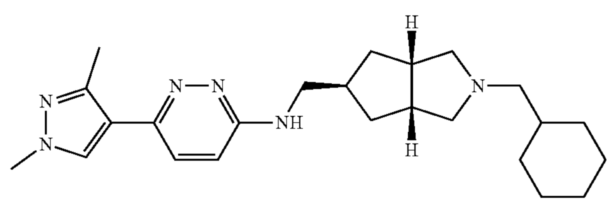 [SMILES: Cc1nn(C)cc1-c1ccc(NC[C@H]2C[C@@H]3CN(CC4CCCCC4)C[C@@H]3C2)nn1] | 409.6 |
| 73 | N-[[(3aR,5s,6aS)-2-[(3-methyl-2-pyridyl)methyl]-3,3a,4,5,6,6a-hexahydro-1H-cyclopenta[c]pyrrol-5-yl]methyl]-6-(1,3-dimethylpyrazol-4-yl)pyridazin-3-amine | 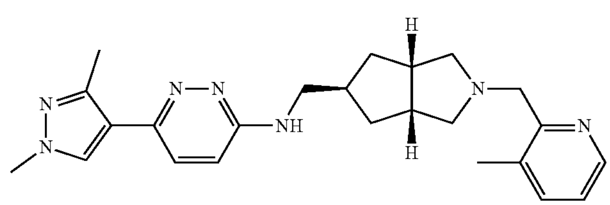 [SMILES: Cc1cccnc1CN1C[C@H]2C[C@H](CNc3ccc(-c4cn(C)nc4C)nn3)C[C@H]2C1] | 418.5 |

Example 7. (3aR,6aS)-2-(3,3-Dimethylbutyl)-N-[6-(2,4-dimethylpyrazol-3-yl)pyridazin-3-yl]-3,3a,4,5,6,6a-hexahydro-1H-cyclopenta[c]pyrrole-5-carboxamide (Compound 74)

74

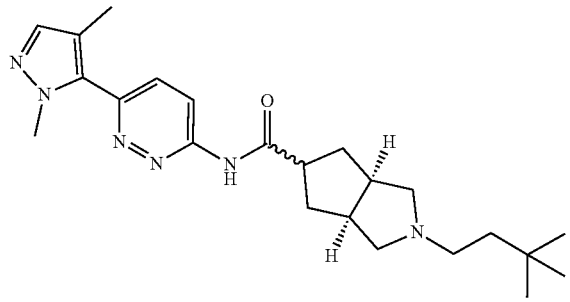

tert-Butyl 5-[[6-chloropyridazin-3-yl]carbamoyl]-3,3a,4,5,6,6a-hexahydro-1H-cyclopenta[c]pyrrole-2-carboxylate

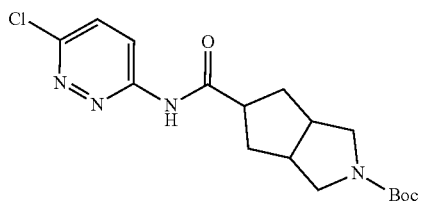 [SMILES: CC(C)(C)OC(=O)N1CC2CC(C(=O)Nc3ccc(Cl)nn3)CC2C1]

2-[(tert-Butoxy)carbonyl]-octahydrocyclopenta[c]pyrrole-5-carboxylic acid (255.3 mg, 1.0 mmol, 1.0 eq.), DIPEA (0.35 mL, 2.0 mmol, 2.0 eq.), and HATU (456.3 mg, 1.2 mol, 1.2 eq.) were dissolved in THF (5.0 mL, 0.2 M). The mixture was stirred for 15 min. 3-Amino-6-chloro-pyridazine (194.3 mg, 1.5 mmol, 1.5 eq.) was added. After 3 h at 80° C., the mixture was diluted with DCM and water. The organic layer was separated. The aqueous layer was extracted with CHCl$_3$/IPA mixture (3:1, 3×). The combined organic layers were dried over Na$_2$SO$_4$, filtered and concentrated. The crude residue was purified using flash column chromatography on silica gel (0-86% EtOAc/hexanes) to provide the title compound as a yellow powder (250 mg, 68% yield). ES-MS [M+H]$^+$=[M+H]$^+$-tButyl=311.0.

tert-Butyl 5-[[6-(2,4-dimethylpyrazol-3-yl)pyridazin-3-yl]carbamoyl]-3,3a,4,5,6,6a-hexahydro-1H-cyclopenta[c]pyrrole-2-carboxylate

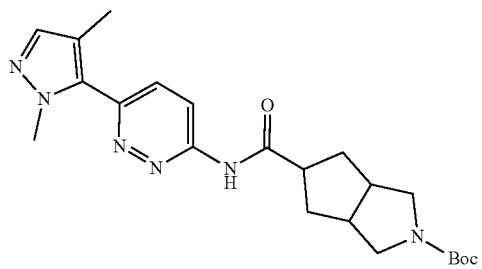 [SMILES: Cc1cnn(C)c1-c1ccc(NC(=O)C2CC3CN(C(=O)OC(C)(C)C)CC3C2)nn1]

tert-Butyl 5-[[6-chloropyridazin-3-yl]carbamoyl]-3,3a,4,5,6,6a-hexahydro-1H-cyclopenta[c]pyrrole-2-carboxylate (250 mg, 0.682 mmol, 1.0 eq.), 1,4-dimethylpyrazole-5-boronic acid pinacol ester (257.3 mg, 1.16 mmol, 1.7 eq.), K$_2$CO$_3$ (286.8 mg, 2.05 mmol, 3.0 eq.) and BrettPhos-Pd-G3 (28.5 mg, 0.03 mmol, 0.05 eq.) were charged into a reaction vial. A degassed mixture of 5:1 (v/v) 1,4-dioxane/H$_2$O (3.0 mL) was added. The resulting suspension was stirred at 100° C. for 1 h. After cooling to r.t., the reaction mixture was filtered through a pad of Celite which was washed thoroughly with EtOAc. The filtrate was concentrated under reduced pressure. The crude residue was purified by flash column chromatography (0-100% EtOAc/DCM) to give the title compound as a viscous oil (180 mg, 63% yield). ES-MS [M+H]$^+$=427.4.

N-[6-(2,4-Dimethylpyrazol-3-yl)pyridazin-3-yl]-1,2,3,3a,4,5,6,6a-octahydrocyclopenta[c]pyrrole-5-carboxamide dihydrochloride

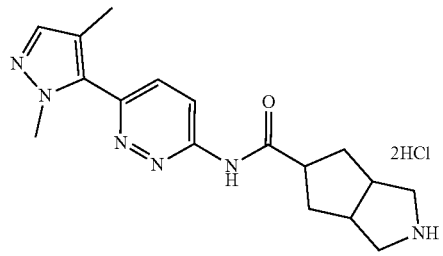 [SMILES: Cc1cnn(C)c1-c1ccc(NC(=O)C2CC3CNCC3C2)nn1]

tert-Butyl 5-[[6-(2,4-dimethylpyrazol-3-yl)pyridazin-3-yl]carbamoyl]-3,3a,4,5,6,6a-hexahydro-1H-cyclopenta[c]pyrrole-2-carboxylate (180 mg, 0.422 mmol, 1.0 eq.) was dissolved in 1,4-dioxane (2.0 mL). 4M HCl in 1,4-dioxane solution (1.0 mL, 4.0 mmol, 9.5 eq.) was added dropwise. After stirring 30 min at r.t., solvents were removed under reduced pressure. The crude material was azeotroped with toluene (3×) to provide the title compound as an off white solid which was used without further purification as the HCl salt. ES-MS [M+H]$^+$=327.4.

(3aR,6aS)-2-(3,3-Dimethylbutyl)-N-[6-(2,4-dimethylpyrazol-3-yl)pyridazin-3-yl]-3,3a,4,5,6,6a-hexahydro-1H-cyclopenta[c]pyrrole-5-carboxamide (Compound 74)

74

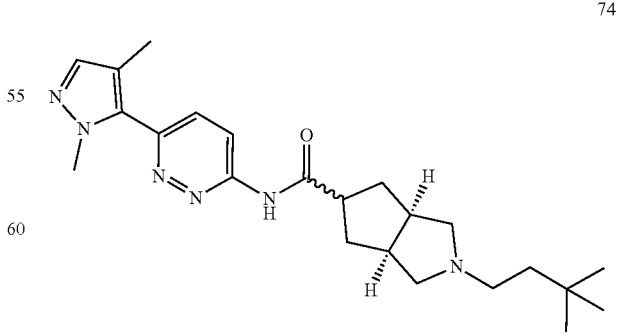

N-[6-(2,4-Dimethylpyrazol-3-yl)pyridazin-3-yl]-1,2,3,3a,4,5,6,6a-octahydrocyclopenta[c]pyrrole-5-carboxamide dihydrochloride (25 mg, 0.063 mmol, 1.0 eq.) was suspended in DCM (1.5 mL) and THF (1.5 mL). 3,3-Dimethylbutyraldehyde (39.3 µL, 0.313 mmol, 5.0 eq.) was added. The mixture was stirred at r.t. for 30 min and sodium triacetoxyborohydride (66.3 mg, 0.313 mmol, 5.0 eq.) was added. The resulting solution was stirred at r.t. overnight, after which time the reaction mixture was quenched with sat. soln. NaHCO$_3$, and extracted with chloroform/IPA (3:1, v/v). The combined extracts were filtered through a phase separator and concentrated. The crude residue was purified by RP-HPLC to provide the DP as two separable (endo and exo) isomers. Major isomer (3.5 mg, 14% yield): $^1$H-NMR (400 MHz, CDCl$_3$) δ 10.62 (s, 1H), 8.55 (d, J=9.3 Hz, 1H), 7.54 (d, J=9.2 Hz, 1H), 7.39 (s, 1H), 4.01 (s, 3H), 2.96-2.88 (m, 1H), 2.81-2.78 (m, 2H), 2.77-2.66 (m, 2H), 2.51-2.46 (m, 2H), 2.38-2.55 (m, 4H), 2.16 (s, 3H), 1.92-1.84 (m, 2H), 1.49-1.45 (m, 2H), 0.91 (s, 9H); ES-MS [M+H]$^+$=411.4. Minor isomer (1.0 mg, 4% yield): $^1$H-NMR (400 MHz, CDCl$_3$) δ 8.51 (d, J=9.2 Hz, 1H), 8.50 (s, 1H), 7.51 (d, J=9.2 Hz, 1H), 7.40 (s, 1H), 4.02 (s, 3H), 3.13-3.05 (m, 1H), 2.87-2.77 (m, 2H), 2.74-2.69 (m, 2H), 2.36-2.32 (m, 2H), 2.23-2.19 (m, 2H), 2.13 (s, 3H), 2.09-2.02 (m, 2H), 1.89-1.83 (m, 2H), 1.43-1.39 (m, 2H), 0.92 (s, 9H); ES-MS [M+H]$^+$=411.4.

The compounds shown in Table 5 were prepared similarly to the compounds described above, with appropriate starting materials.

Example 8. (3aR,6aS)-2-(3,3-Dimethylbutyl)-5-[[6-(2,4-dimethylpyrazol-3-yl)pyridazin-3-yl]oxymethyl]-3,3a,4,5,6,6a-hexahydro-1H-cyclopenta[c]pyrrole (Compound 78)

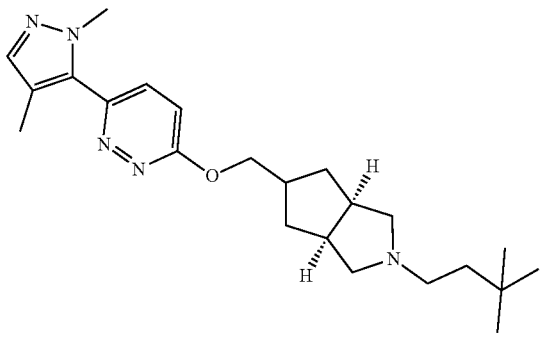

tert-Butyl(3aR,6aS)-5-methylene-1,3,3a,4,6,6a-hexahydrocyclopenta[c]pyrrole-2-carboxylate

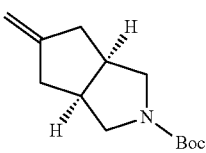

TABLE 5

| Cpd. No. | Name | Structure | ES-MS [M + 1]$^+$ |
|---|---|---|---|
| 75 | (3aR,6aS)-2-(5-bicyclo[2.2.1]hept-2-enylmethyl)-N-[6-(2-chloro-4-fluorophenyl)pyridazin-3-yl]-3,3a,4,5,6,6a-hexahydro-1H-cyclopenta[c]pyrrole-5-carboxamide | 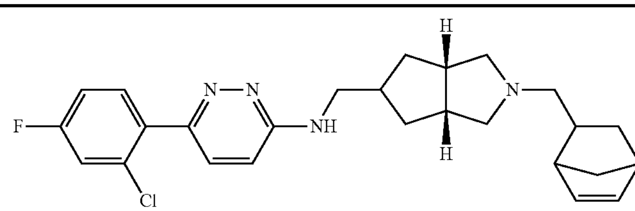 | 467.1 |
| 76 | N-[6-(2,4-dimethylpyrazol-3-yl)pyridazin-3-yl]-2-(2,3,3-trimethylbutyl)-3,3a,4,5,6,6a-hexahydro-1H-cyclopenta[c]pyrrole-5-carboxamide | 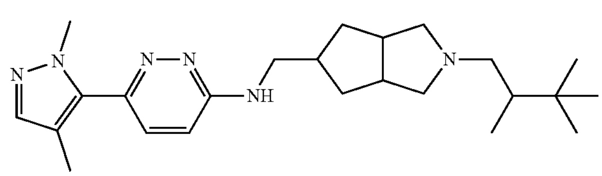 [SMILES: Cc1cnn(C)c1-c1ccc(NCC2CC3CN(CC(C)C(C)(C)C)CC3C2)nn1] | 425.5 |
| 77 | 2-(5-bicyclo[2.2.1]hept-2-enylmethyl)-N-[6-(2,4-dimethylpyrazol-3-yl)pyridazin-3-yl]-3,3a,4,5,6,6a-hexahydro-1H-cyclopenta[c]pyrrole-5-carboxamide | 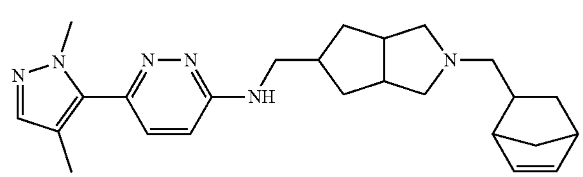 [SMILES: Cc1cnn(C)c1-c1ccc(NCC2CC3CN(CC4CC5C=CC4C5)CC3C2)nn1] | 433.5 |

To a suspension of methyl(triphenyl)phosphonium iodide (6.67 g, 16.5 mmol, 2.2 eq.) in THF (37.5 mL, 0.2 M) at 0° C. was added potassium tert-butoxide (1.68 g, 15 mmol, 2.0 eq.). After stirring at 0° C. for 30 min, the reaction mixture was allowed to warm to r.t. After 30 min, the reaction mixture was cooled back down to 0° C. and a solution of cis-tert-butyl 5-oxohexahydrocyclopenta[c]pyrrole-2(1H)-carboxylate (1.69 g, 7.5 mmol, 1.0 eq.) in THF (37.5 mL) was added. The resulting mixture was stirred at r.t. for 16 h. Diethyl ether (100 mL) was added and the mixture was filtered. The solid was washed with diethyl ether (3×). The combined filtrates were concentrated. The crude material was purified using flash column chromatography on silica gel (0-40% EtOAc/hexanes) to provide the title compound as a colorless oil (1.50 g, 89%). ¹H-NMR (400 MHz, CDCl₃) δ 4.91 (dd, J=4.0, 2.1 Hz, 2H), 3.54 (br, 2H), 3.18 (d, J=9.5 Hz, 1H), 3.09 (d, J=7.8 Hz, 1H), 2.69 (br, 2H), 2.58 (dd, J=6.6, 16.5 Hz, 2H), 2.22 (d, J=1.9 Hz, 1H), 2.19 (d, J=1.9 Hz, 1H), 1.48 (s, 9H); ES-MS [M+H]⁺=[M+H]⁺-tButyl=168.4.

tert-Butyl(3aR,6aS)-5-(hydroxymethyl)-3,3a,4,5,6,6a-hexahydro-1H-cyclopenta[c]pyrrole-2-carboxylate

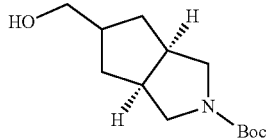 [SMILES: CC(C)(C)OC(=O)N1C[C@H]2CC(CO)C[C@H]2C1]

Under nitrogen atmosphere, borane dimethyl sulfide complex (2.0 M in THF, 15.78 mL, 31.57 mmol, 4.7 eq.) was diluted in THF (35.0 mL) and cooled to 0° C. Neat 2,3-dimethylbut-2-ene (3.77 mL, 31.57 mmol, 4.7 eq.) was added dropwise. After 3 h at 0° C., a solution of tert-butyl (3aR,6aS)-5-methylene-1,3,3a,4,6,6a-hexahydrocyclopenta[c]pyrrole-2-carboxylate (1.5 g, 6.72 mmol, 1.0 eq.) in THF (15 mL) was added slowly. The resulting mixture was warmed to r.t. and stirred for 16 h. After cooling to 0° C., a solution of 10% NaOH (15.0 mL) was added slowly followed by hydrogen peroxide solution (33% in water, 11.9 mL). The ice bath was removed. After 2 h at r.t., the solvents were removed under reduced pressure. The residue was re-dissolved in water and diethyl ether. The layers were separated. The aqueous layer was extracted with diethyl ether (3×). The combined extracts were dried over Na₂SO₄, filtered and concentrated. The crude material was purified using flash chromatography on silica gel (0-50% EtOAc/hexanes) to provide the title compound as a viscous oil (1.30 g, 78%) (mixture of endo/exo isomers, 3:1). ¹H-NMR (400 MHz, CDCl₃) (major isomer) δ 3.60 (d, J=6.1 Hz, 2H), 3.54 (d, J=6.0 Hz, 1H), 3.48-3.46 (m, 2H), 3.02 (br, 2H), 2.62 (m, 2H), 2.26-2.18 (m, 1H), 2.05 (m, 2H), 1.48 (s, 9H), 1.20-1.12 (m, 2H); ES-MS [M+H]⁺=[M+H]⁺-tButyl=186.0.

tert-Butyl (3aR,6aS)-5-[(6-chloropyridazin-3-yl)oxymethyl]-3,3a,4,5,6,6a-hexahydro-1H-cyclopenta[c]pyrrole-2-carboxylate

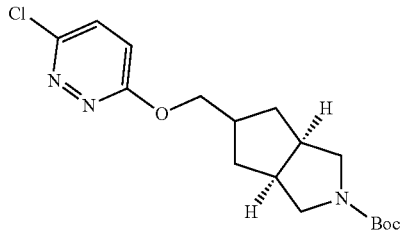 [SMILES: CC(C)(C)OC(=O)N1C[C@H]2CC(COc3ccc(Cl)nn3)C[C@H]2C1]

To a solution of tert-butyl (3aR,6aS)-5-(hydroxymethyl)-3,3a,4,5,6,6a-hexahydro-1H-cyclopenta[c]pyrrole-2-carboxylate (543 mg, 2.25 mmol, 1.0 eq.) in THF (11.25 mL, 0.2 M) at 0° C. was added NaH (60% dispersion in mineral oil, 180 mg, 4.5 mmol, 2.0 eq.). After stirring for 5 min, 3,6-dichloropyridazine (502.8 mg, 3.375 mmol, 1.5 eq.) in THF (1.5 mL) was added. After 16 h, the mixture was diluted with water and extracted with DCM (3×). The combined extracts were dried over Na₂SO₄, filtered and concentrated. The crude material was purified using flash chromatography on silica gel (0-40% EtOAc/hexanes) to provide the title compound as a white solid (580 mg, 73%) (a mixture of endo/exo isomers, 3:1). ¹H-NMR (400 MHz, CDCl₃) (major isomer) δ 7.38 (d, J=9.2 Hz, 1H), 6.97 (d, J=9.2 Hz, 1H), 4.47 (br, 2H), 3.49 (br, 2H), 3.24 (br, 2H), 2.70-2.63 (m, 1H), 2.58-2.49 (m, 1H), 2.17-2.14 (m, 2H), 1.47 (s, 9H), 1.34-1.26 (m, 2H); ES-MS [M+H]⁺=[M+H]⁺-Boc=254.0.

tert-Butyl(3aR,6aS)-5-[[6-(2,4-dimethylpyrazol-3-yl)pyridazin-3-yl]oxymethyl]-3,3a,4,5,6,6a-hexahydro-1H-cyclopenta[c]pyrrole-2-carboxylate

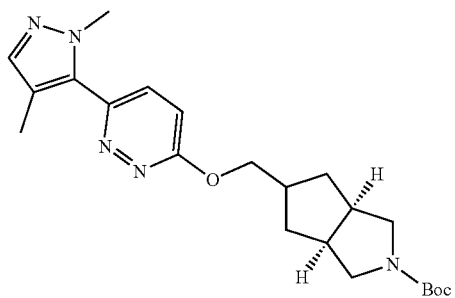 [SMILES: Cc1cnn(C)c1-c1ccc(OCC2C[C@@H]3CN(C(=O)OC(C)(C)C)C[C@@H]3C2)nn1]

tert-Butyl (3aR,6aS)-5-[(6-chloropyridazin-3-yl)oxymethyl]-3,3a,4,5,6,6a-hexahydro-1H-cyclopenta[c]pyrrole-2-carboxylate (350 mg, 0.989 mmol, 1.0 eq.), 1,4-dimethylpyrazole-5-boronic acid pinacol ester (439.4 mg, 1.97 mmol, 2.0 eq.), K₂CO₃ (416.3 mg, 2.97 mmol, 3.0 eq.) and BrettPhos-Pd-G3 (44.9 mg, 0.05 mmol, 0.05 eq.) were charged into a reaction vial. A degassed mixture of 5:1 (v/v) 1,4-dioxane/H₂O (6.5 mL) was added. The resulting suspension was stirred at 100° C. for 1 h. After cooling to r.t., the reaction mixture was filtered through a pad of Celite which was washed thoroughly with EtOAc. The filtrate was concentrated under reduced pressure. The crude residue was purified by flash column chromatography (0-100% EtOAc/DCM) to give the title compound as a light tan solid (380 mg, 93%) (mixture of endo/exo isomers, 3:1). ¹H-NMR (400 MHz, CDCl₃) (major isomer) 7.46 (d, J=9.2 Hz, 1H), 7.41 (s, 1H), 7.09 (d, J=9.1 Hz, 1H), 4.57 (br, 2H), 4.04 (s, 3H), 3.49 (br, 2H), 3.29 (br, 2H), 2.73-2.64 (m, 2H), 2.63-2.54 (m, 1H), 2.20-2.16 (m, 2H), 2.15 (s, 3H), 1.48 (s, 9H), 1.38-1.27 (m, 2H); ES-MS [M+H]⁺=414.5.

(3aR,6aS)-5-[[6-(2,4-Dimethylpyrazol-3-yl)pyridazin-3-yl]oxymethyl]-1,2,3,3a,4,5,6,6a-octahydrocyclopenta[c]pyrrole dihydrochloride

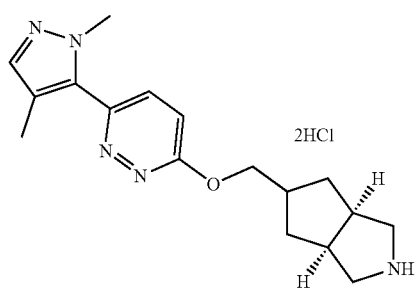 [SMILES: Cc1cnn(C)c1-c1ccc(OCC2C[C@H]3CNC[C@H]3C2)nn1]

tert-Butyl (3aR,6aS)-5-[[6-(2,4-dimethylpyrazol-3-yl)pyridazin-3-yl]oxymethyl]-3,3a,4,5,6,6a-hexahydro-1H-cyclopenta[c]pyrrole-2-carboxylate (380 mg, 0.919 mmol, 1.0 eq.) was dissolved in 1,4-dioxane (2.0 mL). 4M HCl in 1,4-dioxane solution (2.5 mL, 10.0 mmol, 10.9 eq.) was added dropwise. After stirring 30 min at r.t., solvents were removed under reduced pressure. The crude material was azeotroped with toluene (3×) to provide the title compound as a pale yellow solid which was used without further purification as the HCl salt. ES-MS [M+H]$^+$=314.2.

(3aR,6aS)-2-(3,3-Dimethylbutyl)-5-[[6-(2,4-dimethylpyrazol-3-yl)pyridazin-3-yl]oxymethyl]-3,3a,4,5,6,6a-hexahydro-1H-cyclopenta[c]pyrrole (Compound 78)

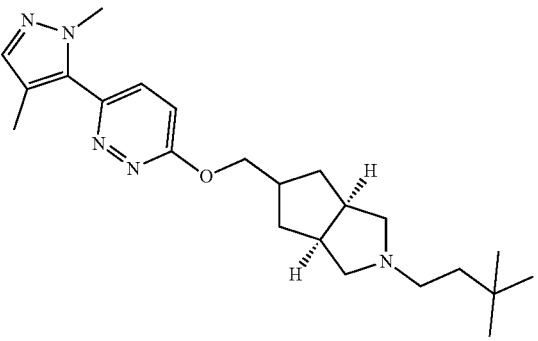

78

(3aR,6aS)-5-[[6-(2,4-Dimethylpyrazol-3-yl)pyridazin-3-yl]oxymethyl]-1,2,3,3a,4,5,6,6a-octahydrocyclopenta[c]pyrrole dihydrochloride (15 mg, 0.039 mmol, 1.0 eq.) was suspended in DCM (0.5 mL) and THF (0.5 mL). 3,3-Dimethylbutyraldehyde (24.4 µL, 0.194 mmol, 5.0 eq.) was added. The mixture was stirred at 50° C. for 30 min and sodium triacetoxyborohydride (41.1 mg, 0.194 mmol, 5.0 eq.) was added. The resulting solution was stirred at 50° C. for 2 h, after which time the reaction mixture was quenched with sat. soln. NaHCO$_3$, and extracted with chloroform/IPA (3:1, v/v). The combined extracts were filtered through a phase separator and concentrated. The crude residue was purified by RP-HPLC, and fractions containing the product were basified with sat. soln. NaHCO$_3$, and extracted with chloroform/IPA (3:1, v/v). The combined extracts were filtered through a phase separator and concentrated to give the title compound as a colorless oil (8.2 mg, 53%) (a mixture of endo/exo isomers, 3:1). $^1$H-NMR (400 MHz, CDCl$_3$) (major isomer) δ 7.41 (d, J=9.2 Hz, 1H), 7.32 (s, 1H), 6.99 (d, J=9.1 Hz, 1H), 4.49 (d, J=6.8 Hz, 2H), 3.96 (s, 3H), 2.57-2.48 (m, 4H), 2.37-2.26 (m, 5H), 2.12-2.05 (m, 2H), 2.07 (s, 3H), 1.37-1.33 (m, 2H), 1.22-1.14 (m, 2H), 0.83 (s, 9H); ES-MS [M+H]$^+$=398.4; (minor isomer) δ 7.43 (d, J=9.2 Hz, 1H), 7.32 (s, 1H), 6.99 (d, J=9.1 Hz, 1H), 4.44 (d, J=6.7 Hz, 2H), 3.96 (s, 3H), 2.92-2.85 (m, 2H), 2.72-2.66 (m, 2H), 2.59-2.51 (m, 1H), 2.36-2.31 (m, 2H), 2.07 (s, 3H), 2.01-1.94 (m, 2H), 1.68-1.63 (m, 2H), 1.54-1.46 (m, 2H), 1.38-1.34 (m, 2H), 0.83 (s, 9H); ES-MS [M+H]$^+$=398.4.

The compounds shown in Table 6 were prepared similarly to the compounds described above, with appropriate starting materials.

TABLE 6

| Cpd. No. | Name | Structure | ES-MS [M + 1]$^+$ |
|---|---|---|---|
| 79 | (3sR,6aS)-2-(1-adamantylmethyl)-5-[[6-(2,4-dimethylpyrazol-3-yl)pyridazin-3-yl]oxymethyl]-3,3a,4,5,6,6a-hexahydro-1H-cyclopenta[c]pyrrole | 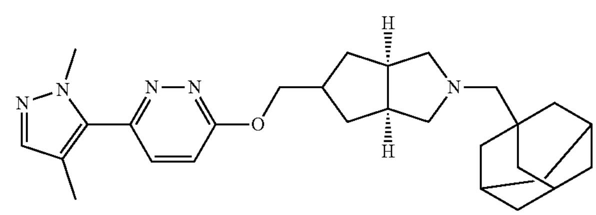 [SMILES: Cc1cnn(C)c1-c1ccc(OCC2C[C@@H]3CN(CC45CC6CC(CC(C6)C4)C5)C[C@@H]3C2)nn1] | 462.5 |
| 80 | (3aR,6aS)-2-(5-bicyclo[2.2.1]hept-2-enylmethyl)-5-[[6-(2,4-dimethylpyrazol-3-yl)pyridazin-3-yl]oxymethyl]-3,3a,4,5,6,6a-hexahydro-1H-cyclopenta[c]pyrrole | 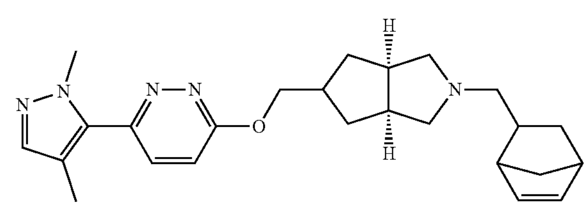 [SMILES: Cc1cnn(C)c1-c1ccc(OCC2C[C@@H]3CN(CC4CC5C=CC4C5)C[C@@H]3C2)nn1] | 420.4 |
| 81 | (3aR,6aS)-5-[[6-(2,4-dimethylpyrazol-3-yl)pyridazin-3-yl]oxymethyl]-2-(2-methylbutyl)-3,3a,4,5,6,6a-hexahydro-1H-cyclopenta[c]pyrrole | 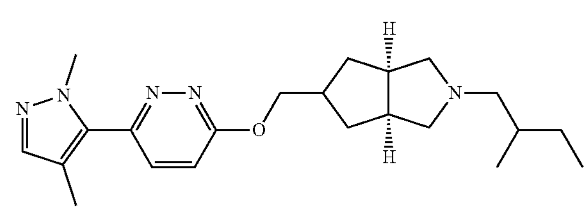 [SMILES: CCC(C)CN1C[C@H]2CC(COc3ccc(-c4c(C)cnn4C)nn3)C[C@H]2C1] | 384.5 |

TABLE 6-continued

| Cpd. No. | Name | Structure | ES-MS [M + 1]+ |
|---|---|---|---|
| 82 | (3aR,6aS)-5-[[6-(2,4-dimethylpyrazol-3-yl)pyridazin-3-yl]oxymethyl]-2-(2-methylpentyl)-3,3a,4,5,6,6a-hexahydro-1H-cyclopenta[c]pyrrole | 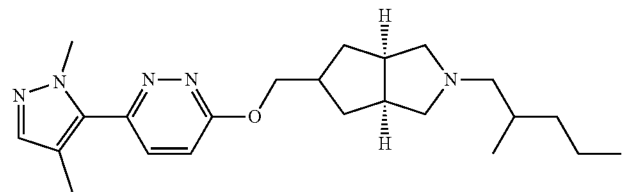 [SMILES: CCCC(C)CN1C[C@H]2CC(COc3ccc(-c4c(C)cnn4C)nn3)C[C@H]2C1] | 398.5 |
| 83 | (3aR,6aS)-2-(cyclohexylmethyl)-5-[[6-(2,4-dimethylpyrazol-3-yl)pyridazin-3-yl]oxymethyl]-3,3a,4,5,6,6a-hexahydro-1H-cyclopenta[c]pyrrole | 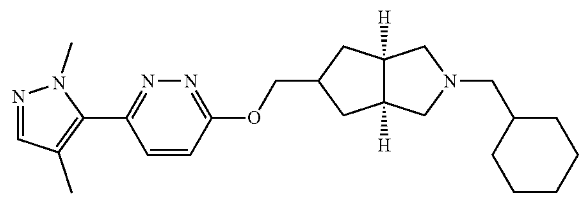 [SMILES: Cc1cnn(C)c1-c1ccc(OCC2C[C@@H]3CN(CC4CCCCC4)C[C@@H]3C2)nn1] | 410.5 |
| 84 | (3aR,6aS)-5-[[6-(2,4-dimethylpyrazol-3-yl)pyridazin-3-yl]oxymethyl]-2-(tetrahydropyran-4-ylmethyl)-3,3a,4,5,6,6a-hexahydro-1H-cyclopenta[c]pyrrole | 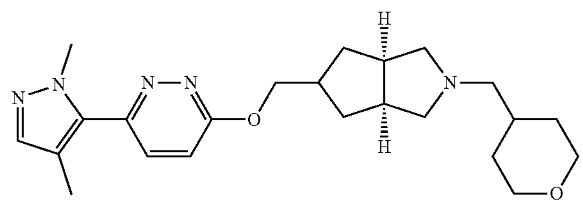 [SMILES: Cc1cnn(C)c1-c1ccc(OCC2C[C@@H]3CN(CC4CCOCC4)C[C@@H]3C2)nn1] | 412.6 |
| 85 | (3aR,6aS)-5-[[6-(2,4-dimethylpyrazol-3-yl)pyridazin-3-yl]oxymethyl]-2-(tetrahydropyran-3-ylmethyl)-3,3a,4,5,6,6a-hexahydro-1H-cyclopenta[c]pyrrole | 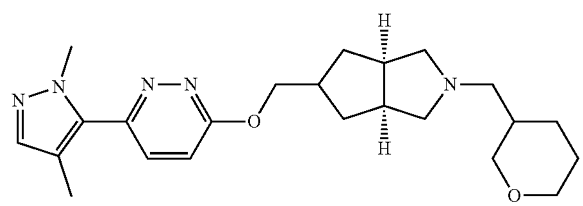 [SMILES: Cc1cnn(C)c1-c1ccc(OCC2C[C@@H]3CN(CC4CCCOC4)C[C@@H]3C2)nn1] | 412.4 |
| 86 | (3aR,6aS)-2-benzyl-5-[[6-(2,4-dimethylpyrazol-3-yl)pyridazin-3-yl]oxymethyl]-3,3a,4,5,6,6a-hexahydro-1H-cyclopenta[c]pyrrole | 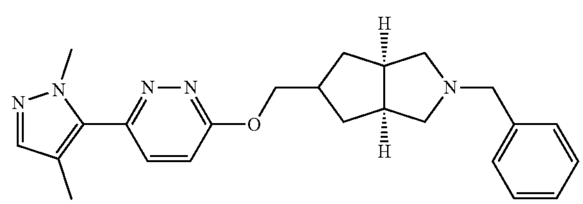 [SMILES: Cc1cnn(C)c1-c1ccc(OCC2C[C@@H]3CN(Cc4ccccc4)C[C@@H]3C2)nn1] | 404.5 |
| 87 | (3aR,6aS)-5-[[6-(2,4-dimethylpyrazol-3-yl)pyridazin-3-yl]oxymethyl]-2-[(2-fluorophenyl)methyl]-3,3a,4,5,6,6a-hexahydro-1H-cyclopenta[c]pyrrole | 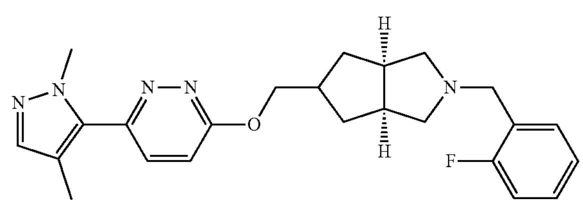 [SMILES: Cc1cnn(C)c1-c1ccc(OCC2C[C@@H]3CN(Cc4ccccc4F)C[C@@H]3C2)nn1] | 422.4 |
| 88 | (3R,6aS)-5-[[6-(2,4-dimethylpyrazol-3-yl)pyridazin-3-yl]oxymethyl]-2-[(4-fluorophenyl)methyl]-3,3a,4,5,6,6a-hexahydro-1H-cyclopenta[c]pyrrole | 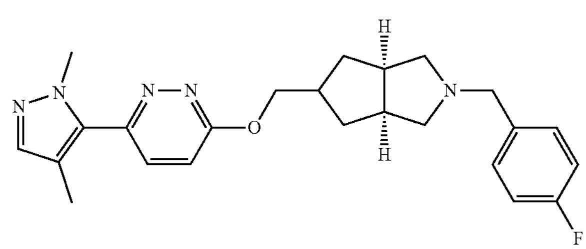 [SMILES: Cc1cnn(C)c1-c1ccc(OCC2C[C@@H]3CN(Cc4ccc(F)cc4)C[C@@H]3C2)nn1] | 422.4 |

TABLE 6-continued

| Cpd. No. | Name | ES-MS [M + 1]+ |
|---|---|---|
| 89 | (3aR,6aS)-5-[[6-(2,4-dimethylpyrazol-3-yl)pyridazin-3-yl]oxymethyl]-2-(2-pyridylmethyl)-3,3a,4,5,6,6a-hexahydro-1H-cyclopenta[c]pyrrole | 405.5 |
| 90 | (3aR,6aS)-5-[[6-(2,4-dimethylpyrazol-3-yl)pyridazin-3-yl]oxymethyl]-2-[(3-methyl-2-pyridyl)methyl]-3,3a,4,5,6,6a-hexahydro-1H-cyclopenta[c]pyrrole | 419.4 |
| 91 | (3aR,6aS)-2-(1,3-benzodioxol-5-ylmethyl)-5-[[6-(2,4-dimethylpyrazol-3-yl)pyridazin-3-yl]oxymethyl]-3,3a,4,5,6,6a-hexahydro-1H-cyclopenta[c]pyrrole | 448.4 |
| 92 | (3sR,6aS)-2-(3,3-dimethylbutyl)-5-[[6-(1,3-dimethylpyrazol-4-yl)pyridazin-3-yl]oxymethyl]-3,3a,4,5,6,6a-hexahydro-1H-cyclopenta[c]pyrrole | 398.6 |
| 93 | (3aR,6aS)-2-(1-adamantylmethyl)-5-[[6-(1,3-dimethylpyrazol-4-yl)pyridazin-3-yl]oxymethyl]-3,3a,4,5,6,6a-hexahydro-1H-cyclopenta[c]pyrrole | 462.5 |
| 94 | (3aR,6aS)-2-(5-bicyclo[2.2.2]oct-2-enylmethyl)-5-[[6-(1,3-dimethylpyrazol-4-yl)pyridazin-3-yl]oxymethyl]-3,3a,4,5,6,6a-hexahydro-1H-cyclopenta[c]pyrrole | 420.5 |
| 95 | (3aR,6aS)-5-[[6-(1,3-dimethylpyrazol-4-yl)pyridazin-3-yl]oxymethyl]-2-(2-methylbutyl)-3,3a,4,5,6,6a-hexahydro-1H-cyclopenta[c]pyrrole | 384.6 |

TABLE 6-continued

| Cpd. No. | Name | Structure | ES-MS [M + 1]+ |
|---|---|---|---|
| 96 | (3aR,6aS)-5-[[6-(1,3-dimethylpyrazol-4-yl)pyridazin-3-yl]oxymethyl]-2-(2-methylpentyl)-3,3a,4,5,6,6a-hexahydro-1H-cyclopenta[c]pyrrole | 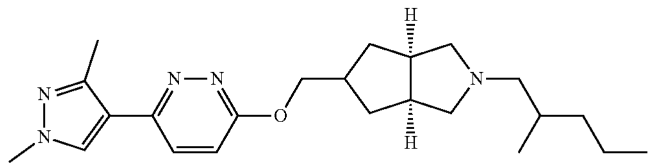 [SMILES: CCCC(C)CN1C[C@H]2CC(COc3ccc(-c4cn(C)nc4C)nn3)C[C@H]2C1] | 398.5 |
| 97 | (3aR,6aS)-2-(cyclohexylmethyl)-5-[[6-(1,3-dimethylpyrazol-4-yl)pyridazin-3-yl]oxymethyl]-3,3a,4,5,6,6a-hexahydro-1H-cyclopenta[c]pyrrole | 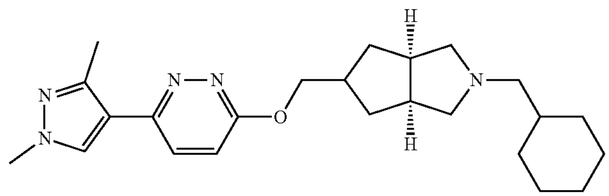 [SMILES: Cc1nn(C)cc1-c1ccc(OCC2C[C@@H]3CN(CC4CCCCC4)C[C@@H]3C2)nn1] | 410.5 |
| 98 | (3aR,6aS)-5-[[6-(1,3-dimethylpyrazol-4-yl)pyridazin-3-yl]oxymethyl]-2-(tetrahydropyran-4-ylmethyl)-3,3a,4,5,6,6a-hexahydro-1H-cyclopenta[c]pyrrole | 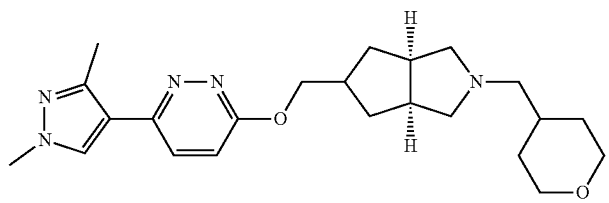 [SMILES: Cc1nn(C)cc1-c1ccc(OCC2C[C@@H]3CN(CC4CCOCC4)C[C@@H]3C2)nn1] | 412.4 |
| 99 | (3aR,6aS)-5-[[6-(1,3-dimethylpyrazol-4-yl)pyridazin-3-yl]oxymethyl]-2-(tetrahydropyran-3-ylmethyl)-3,3a,4,5,6,6a-hexahydro-1H-cyclopenta[c]pyrrole | 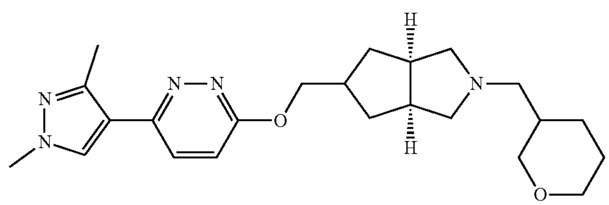 [SMILES: Cc1nn(C)cc1-c1ccc(OCC2C[C@@H]3CN(CC4CCCOC4)C[C@@H]3C2)nn1] | 412.6 |
| 100 | (3aR,6aS)-2-benzyl-5-[[6-(1,3-dimethylpyrazol-4-yl)pyridazin-3-yl]oxymethyl]-3,3a,4,5,6,6a-hexahydro-1H-cyclopenta[c]pyrrole | 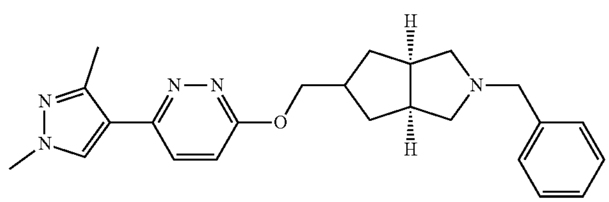 [SMILES: Cc1nn(C)cc1-c1ccc(OCC2C[C@@H]3CN(Cc4ccccc4)C[C@@H]3C2)nn1] | 404.5 |
| 101 | (3aR,6aS)-5-[[6-(1,3-dimethylpyrazol-4-yl)pyridazin-3-yl]oxymethyl]-2-[(2-fluorophenyl)methyl]-3,3a,4,5,6,6a-hexahydro-1H-cyclopenta[c]pyrrole | 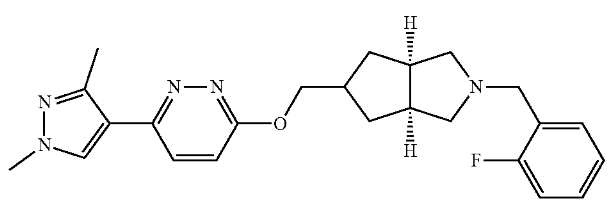 [SMILES: Cc1nn(C)cc1-c1ccc(OCC2C[C@@H]3CN(Cc4ccccc4F)C[C@@H]3C2)nn1] | 422.4 |
| 102 | (3aR,6aS)-5-[[6-(1,3-dimethylpyrazol-4-yl)pyridazin-3-yl]oxymethyl]-2-[(4-fluorophenyl)methyl]-3,3a,4,5,6,6a-hexahydro-1H-cyclopenta[c]pyrrole | 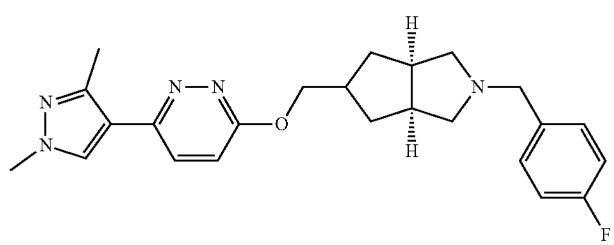 [SMILES: Cc1nn(C)cc1-c1ccc(OCC2C[C@@H]3CN(Cc4ccc(F)cc4)C[C@@H]3C2)nn1] | 422.4 |

TABLE 6-continued

| Cpd. No. | Name | Structure | ES-MS [M + 1]+ |
|---|---|---|---|
| 103 | (3aR,6aS)-5-[[6-(1,3-dimethylpyrazol-4-yl)pyridazin-3-yl]oxymethyl]-2-(2-pyridylmethyl)-3,3a,4,5,6,6a-hexahydro-1H-cyclopenta[c]pyrrole | 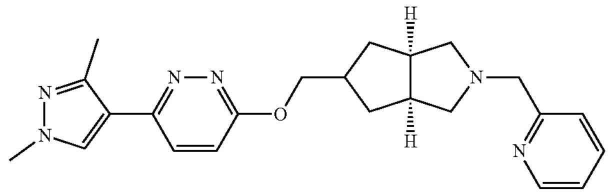 [SMILES: Cc1nn(C)cc1-c1ccc(OCC2C[C@@H]3CN(Cc4ccccn4)C[C@@H]3C2)nn1] | 405.6 |
| 104 | (3aR,6aS)-5-[[6-(1,3-dimethylpyrazol-4-yl)pyridazin-3-yl]oxymethyl]-2-[(3-methyl-2-pyridyl)methyl]-3,3a,4,5,6,6a-hexahydro-1H-cyclopenta[c]pyrrole | 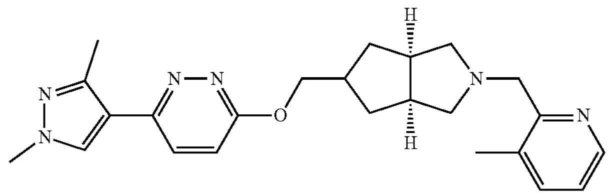 [SMILES: Cc1cccnc1CN1C[C@H]2CC(COc3ccc(-c4cn(C)nc4C)nn3)C[C@H]2C1] | 419.5 |
| 105 | (3aR,6aS)-2-(1,3-benzodioxol-5-ylmethyl)-5-[[6-(1,3-dimethylpyrazol-4-yl)pyridazin-3-yl]oxymethyl]-3,3a,4,5,6,6a-hexahydro-1H-cyclopenta[c]pyrrole | 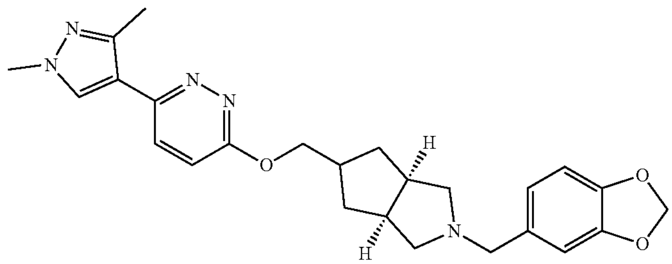 [SMILES: Cc1nn(C)cc1-c1ccc(OCC2C[C@@H]3CN(Cc4ccc5c(c4)OCO5)C[C@@H]3C2)nn1] | 448.4 |
| 106 | (3aR,6aS)-5-[[6-(2-chloro-5-fluoro-phenyl)pyridazin-3-yl]oxymethyl]-2-(3,3-dimethylbutyl)-3,3a,4,5,6,6a-hexahydro-1H-cyclopenta[c]pyrrole | 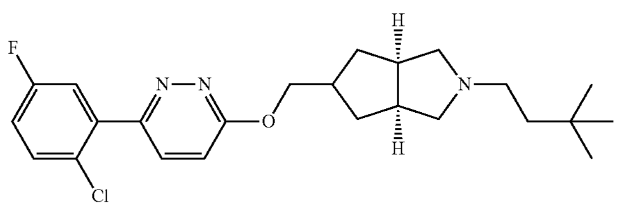 [SMILES: CC(C)(C)CCN1C[C@H]2CC(COc3ccc(-c4cc(F)ccc4Cl)nn3)C[C@H]2C1] | 432.5 |
| 107 | (3aR,6aS)-2-(1-adamantylmethyl)-5-[[6-(2-chloro-5-fluoro-phenyl)pyridazin-3-yl]oxymethyl]-3,3a,4,5,6,6a-hexahydro-1H-cyclopenta[c]pyrrole | 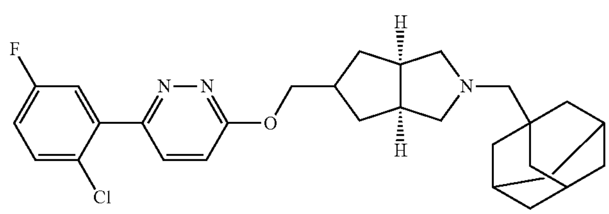 [SMILES: Fc1ccc(Cl)c(-c2ccc(OCC3C[C@@H]4CN(CC56CC7CC(CC(C7)C5)C6)C[C@@H]4C3)nn2)c1] | 496.4 |
| 108 | (3aR,6aS)-2-(5-bicyclo[2.2.1]hept-2-enylmethyl)-5-[[6-(2-chloro-5-fluoro-phenyl)pyridazin-3-yl]oxymethyl]-3,3a,4,5,6,6a-hexahydro-1H-cyclopenta[c]pyrrole | 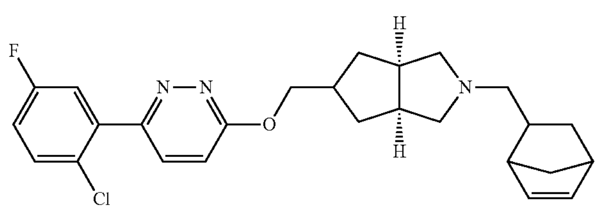 [SMILES: Fc1ccc(Cl)c(-c2ccc(OCC3C[C@@H]4CN(CC5CC6C=CC5C6)C[C@@H]4C3)nn2)c1] | 454.4 |
| 109 | (3aR,6aS)-5-[[6-(2-chloro-5-fluoro-phenyl)pyridazin-3-yl]oxymethyl]-2-(2-methylbutyl)-3,3a,4,5,6,6a-hexahydro-1H-cyclopenta[c]pyrrole | 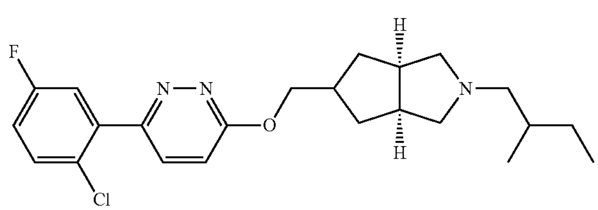 [SMILES: CCC(C)CN1C[C@H]2CC(COc3ccc(-c4cc(F)ccc4Cl)nn3)C[C@H]2C1] | 418.4 |

TABLE 6-continued

| Cpd. No. | Name | Structure | ES-MS [M + 1]+ |
|---|---|---|---|
| 110 | (3aR,6aS)-5-[[6-(2-chloro-5-fluoro-phenyl)pyridazin-3-yl]oxymethyl]-2-(2-methylpentyl)-3,3a,4,5,6,6a-hexahydro-1H-cyclopenta[c]pyrrole | 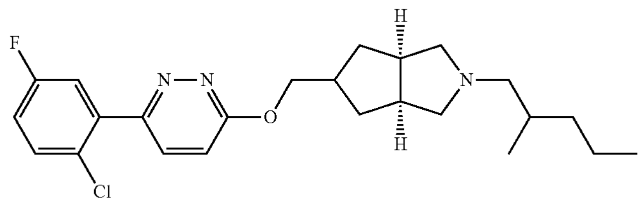 [SMILES: CCCC(C)CN1C[C@H]2CC(COc3ccc(-c4cc(F)ccc4Cl)nn3)C[C@H]2C1] | 432.4 |
| 111 | (3aR,6aS)-5-[[6-(2-chloro-5-fluoro-phenyl)pyridazin-3-yl]oxymethyl]-2-(cyclohexylmethyl)-3,3a,4,5,6,6a-hexahydro-1H-cyclopenta[c]pyrrole | 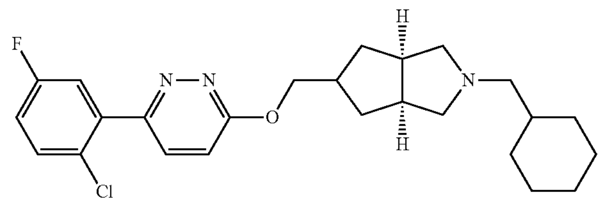 [SMILES: Fc1ccc(Cl)c(-c2ccc(OCC3C[C@@H]4CN(CC5CCCCC5)C[C@@H]4C3)nn2)c1] | 444.4 |
| 112 | (3aR,6aS)-5-[[6-(2-chloro-5-fluoro-phenyl)pyridazin-3-yl]oxymethyl]-2-(tetrahydropyran-4-ylmethyl)-3,3a,4,5,6,6a-hexahydro-1H-cyclopenta[c]pyrrole | 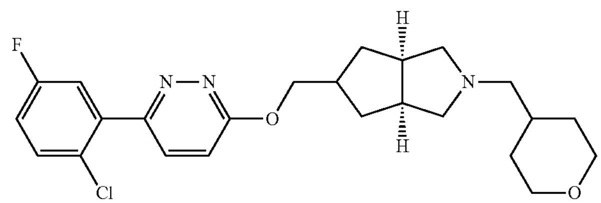 [SMILES: Fc1ccc(Cl)c(-c2ccc(OCC3C[C@@H]4CN(CC5CCOCC5)C[C@@H]4C3)nn2)c1] | 446.4 |
| 113 | (3aR,6aS)-5-[[6-(2-chloro-5-fluoro-phenyl)pyridazin-3-yl]oxymethyl]-2-(tetrahydropyran-3-ylmethyl)-3,3a,4,5,6,6a-hexahydro-1H-cyclopenta[c]pyrrole | 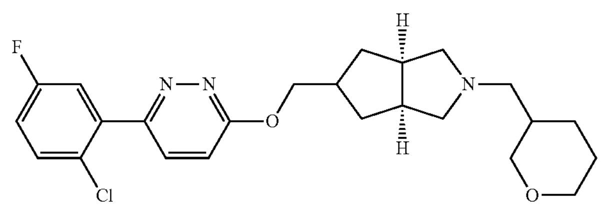 [SMILES: Fc1ccc(Cl)c(-c2ccc(OCC3C[C@@H]4CN(CC5CCCOC5)C[C@@H]4C3)nn2)c1] | 446.4 |
| 114 | (3aR,6aS)-2-benzyl-5-[[6-(2-chloro-5-fluoro-phenyl)pyridazin-3-yl]oxymethyl]-3,3a,4,5,6,6a-hexahydro-1H-cyclopenta[c]pyrrole | 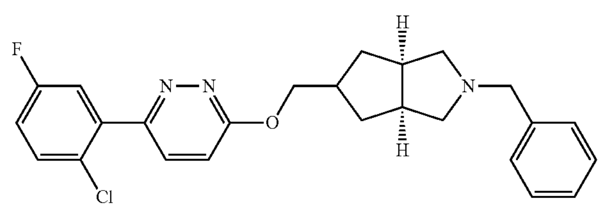 [SMILES: Fc1ccc(Cl)c(-c2ccc(OCC3C[C@@H]4CN(Cc5ccccc5)C[C@@H]4C3)nn2)c1] | 438.4 |
| 115 | (3aR,6aS)-5-[[6-(2-chloro-5-fluoro-phenyl)pyridazin-3-yl]oxymethyl]-2-[(2-fluorophenyl)methyl]-3,3a,4,5,6,6a-hexahydro-1H-cyclopenta[c]pyrrole | 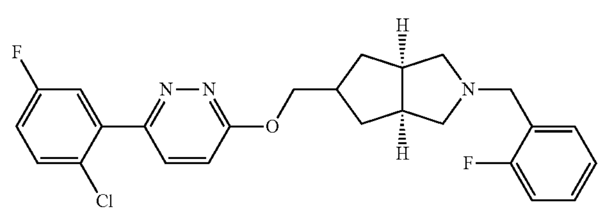 [SMILES: Fc1ccc(Cl)c(-c2ccc(OCC3C[C@@H]4CN(Cc5ccccc5F)C[C@@H]4C3)nn2)c1] | 456.4 |
| 116 | (3aR,6aS)-5-[[6-(2-chloro-5-fluoro-phenyl)pyridazin-3-yl]oxymethyl]-2-[(4-fluorophenyl)methyl]-3,3a,4,5,6,6a-hexahydro-1H-cyclopenta[c]pyrrole | 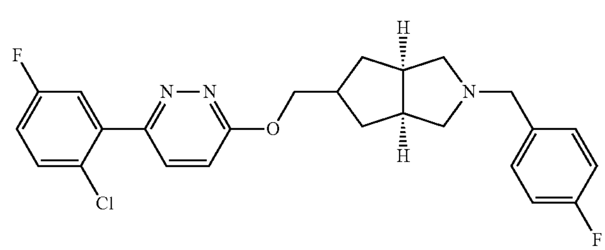 [SMILES: Fc1ccc(CN2C[C@H]3CC(COc4ccc(-c5cc(F)ccc5Cl)nn4)C[C@H]3C2)cc1] | 456.4 |

TABLE 6-continued

| Cpd. No. | Name | Structure | ES-MS [M + 1]+ |
|---|---|---|---|
| 117 | (3aR,6aS)-5-[[6-(2-chloro-5-fluoro-phenyl)pyridazin-3-yl]oxymethyl]-2-(2-pyridylmethyl)-3,3a,4,5,6,6a-hexahydro-1H-cyclopenta[c]pyrrole | 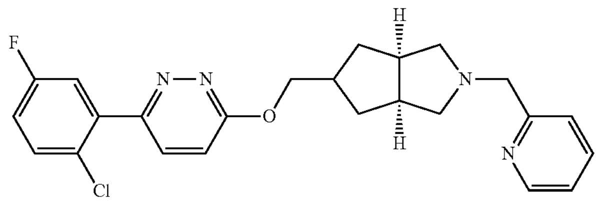 [SMILES: Fc1ccc(Cl)c(-c2ccc(OCC3C[C@@H]4CN(Cc5ccccn5)C[C@@H]4C3)nn2)c1] | 439.4 |
| 118 | (3aR,6aS)-5-[[6-(2-chloro-5-fluoro-phenyl)pyridazin-3-yl]oxymethyl]-2-[(3-methyl-2-pyridyl)methyl]-3,3a,4,5,6,6a-hexahydro-1H-cyclopenta[c]pyrrole | 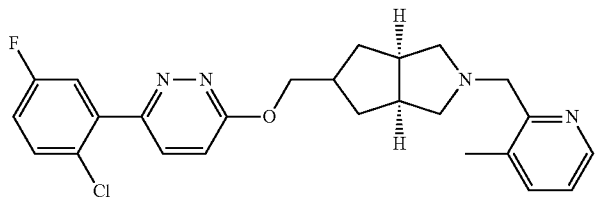 [SMILES: Cc1cccnc1CN1C[C@H]2CC(COc3ccc(-c4cc(F)ccc4Cl)nn3)C[C@H]2C1] | 453.5 |
| 119 | (3aR,6aS)-2-(1,3-benzodioxol-5-ylmethyl)-5-[[6-(2-chloro-5-fluoro-phenyl)pyridazin-3-yl]oxymethyl]-3,3a,4,5,6,6a-hexahydro-1H-cyclopenta[c]pyrrole | 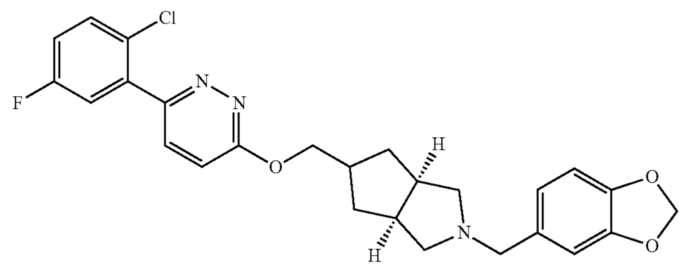 [SMILES: Fc1ccc(Cl)c(-c2ccc(OCC3C[C@@H]4CN(Cc5ccc6c(c5)OCO6)C[C@@H]4C3)nn2)c1] | 482.4 |

Example 9. 6-(1,4-Dimethyl-1H-pyrazol-5-yl)-N-(2-((3aR,6aS)-2-(3,3-dimethylbutyl)octahydrocyclopenta[c]pyrrol-5-yl)ethyl)pyridazin-3-amine (Compound 120)

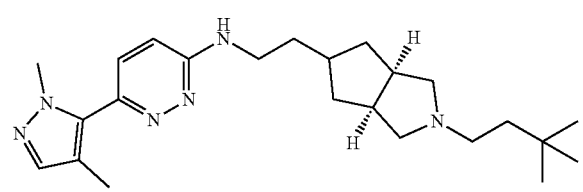

120 tert-Butyl (3aR,6aS,E)-5-(cyanomethylene)hexahydrocyclopenta[c]pyrrole-2(1H)-carboxylate To a round bottom flask, under nitrogen, was added diethyl cyanomethylphosphonate (1.6 mL, 8.9 mmol) dissolved in THF (20 mL) and cooled to −78° C. Sodium tert-butoxide (640 mg, 6.7 mmol) was added to the reaction and the mixture was stirred for 30 minutes at −78° C. At this time, a solution of cis-tert-butyl 5-oxohexahydrocyclopenta[c]pyrrole-2(1H)-carboxylate (1.0 g, 4.4 mmol) in THF (10 mL) was added and the reaction was allowed to slowly warm to room temperature over the course of 18 hours. Upon completion as determined by LCMS, the reaction was quenched by the addition of a saturated aqueous NH$_4$Cl solution and the mixture was extracted with ethyl acetate (3×35 mL). The organic layers were pooled, dried over sodium sulfate, filtered, and concentrated. The crude product was purified using Teledyne ISCO Combi-Flash system (liquid loading with DCM, 24G column, 0-60% EtOAc/Hex, 25 min run) to give the product (935 mg, 3.77 mmol, 85% yield) as a clear oil. LCMS (90 sec method): R$_T$=0.751, >95% @ 215 and 254 nM, m/z=193.2 [M+H−tBu]+. $^1$H NMR (400 MHz, chloroform-): δ 5.29-5.26 (m, 1H), 3.56 (bs, 2H), 3.17-3.06 (m, 2H), 2.92-2.72 (m, 4H), 2.59-2.55 (m, 1H); 2.46-2.40 (m. 1H), 1.45 (s, 9H).

tert-Butyl (3aR,6aS)-5-(cyanomethyl)hexahydrocyclopenta[c]pyrrole-2(1H)-carboxylate

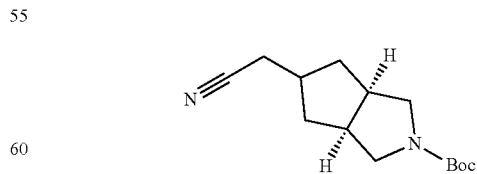

A round bottom flask containing a magnetic stir bar was equipped with a 3-way Schlenk adapter and evacuated then purged with nitrogen (×3). Palladium on activated carbon (10% by weight) (200 mg, 0.19 mmol) was added to the flask, followed by methanol (10 mL) then a solution of tert-butyl (3aR,6aS,E)-5-(cyanomethylene)hexahydrocyclopenta[c]pyrrole-2(1H)-carboxylate (935 mg, 3.8 mmol) in methanol (2 mL) The flask was equipped with a 3-way Schlenk adapter and evacuated then purged with nitrogen (×3). To the 3-way adapter was added a balloon containing H2 gas and the system was evacuated then purged with H2 (×3). The reaction was then allowed to stir 18 hours under H2 atmosphere and then analyzed by LC-MS (observe desired product [M+H−tBu]=195). Upon completion, the Pd/C catalyst was filtered off through a celite pad, the pad was washed twice with methanol, and the solvent was removed under a constant stream of air to afford tert-butyl (3aR,6aS)-5-(cyanomethyl)-3,3a,4,5,6,6a-hexahydro-1H-cyclopenta[c]pyrrole-2-carboxylate (928.9 mg, 3.71 mmol, 98% yield). The material was taken forward without further purification. LCMS (90 sec method): $R_T$=0.767, m/z=195.4 [M+H−tBu]$^+$.

tert-Butyl (3aR,6aS)-5-(2-((6-chloropyridazin-3-yl)amino)ethyl)hexahydrocyclopenta[c]pyrrole-2(1H)-carboxylate

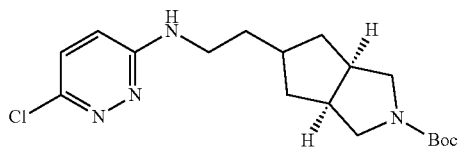 [SMILES: CC(C)(C)OC(=O)N1C[C@H]2CC(CCNc3ccc(Cl)nn3)C[C@H]2C1]

To a solution of tert-butyl (3aR,6aS)-5-(cyanomethyl)hexahydrocyclopenta[c]pyrrole-2(1H)-carboxylate (464 mg, 1.9 mmol) in THF (12.4 mL) at 0° C. was added borane dimethyl sulfide complex (2M in THF, 3.7 mL, 7.4 mmol) dropwise. The mixture was stirred for 1 h at 0° C. then added slowly to a vial containing ethanol at 0° C. to quench excess borane. The mixture was stirred for 20 minutes then allowed to warm to ambient temperature and evaporated to dryness. The crude product was used without further purification. LCMS (90 sec method): $R_T$=0.582, >95% @ 215 and 254 nM, m/z=199.4 [M+H−tBu]$^+$.

Into two 20-mL microwave vials was equally divided a solution of tert-butyl (3aR,6aS)-5-(2-aminoethyl)hexahydrocyclopenta[c]pyrrole-2(1H)-carboxylate (0.47 g, 1.9 mmol) and N,N-diisopropylethylamine (1.9 mL, 11.1 mmol) dissolved in 1-butanol (4.6 mL). Next, 3,6-dichloropyridazine (1.3 mL, 9.3 mmol) was added, the vials sealed, and the mixtures microwave irradiated for 45 minutes at 130° C. After LCMS analysis, the reaction was concentrated and crude product was purified using Teledyne ISCO Combi-Flash system (liquid loading with DCM, 24G column, 20% ethyl acetate/hexanes, 6 min; then 0-80% EtOAc/DCM, 25 min run) to afford tert-butyl (3aR,6aS)-5-[2-[(6-chloropyridazin-3-yl)amino]ethyl]-3,3a,4,5,6,6a-hexahydro-1H-cyclopenta[c]pyrrole-2-carboxylate (519 mg, 1.41 mmol, 77% yield over 2 steps). LCMS (90 sec method): $R_T$=0.768, >95% @ 215 and 254 nM, m/z=367.2 [M+H]+. $^1$H NMR (400 MHz, chloroform-d): δ 7.15 (d, J=9.3 Hz, 1H), 6.60 (d, J=9.3 Hz, 1H), 4.76 (bs, 1H), 3.55-3.35 (m, 4H), 3.21-3.07 (m, 2H), 2.74-2.53 (m, 2H), 2.15-2.07 (m, 2H), 2.04-1.94 (m, 1H), 1.72 (q, J=7.2 Hz, 2H), 1.67-1.61 (m, 2H), 1.45 (s, 9H).

tert-Butyl(3aR,6aS)-5-(2-((6-(1,4-dimethyl-1H-pyrazol-5-yl)pyridazin-3-yl)amino)ethyl)hexahydrocyclopenta[c]pyrrole-2(1H)-carboxylate

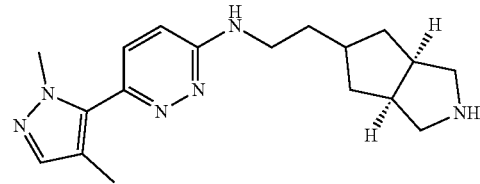 [SMILES: Cc1cnn(C)c1-c1ccc(NCCC2C[C@H]3CNC[C@H]3C2)nn1]

To a microwave vial was added 1,4-dimethylpyrazole-5-boronic acid pinacol ester (393 mg, 1.8 mmol), tert-butyl (3aR,6aS)-5-(2-((6-chloropyridazin-3-yl)amino)ethyl)hexahydrocyclopenta[c]pyrrole-2(1H)-carboxylate (259 mg, 0.71 mmol), potassium carbonate (0.22 mL, 3.5 mmol), and RuPhos-Pd-G3 (59 mg, 0.07 mmol) dissolved in 1,4-dioxane/water (4:1) (7.0 mL, degassed). The vial was purged with N$_2$, sealed, and subjected to microwave irradiation for 30 minutes at 120° C. Upon completion, as determined by LCMS, the reaction mixture was filtered over celite, the celite plug was washed with DCM, and saturated aqueous NaHCO$_3$ was added to the filtrate. The DCM layer was then isolated and the aqueous layer was extracted with chloroform/IPA (4:1) (3×10 mL). The organic layers were passed through a phase separator and concentrated. The crude product was purified using Teledyne ISCO Combi-Flash system (liquid loading with DCM, 12G column, 0-50% EtOAc/DCM, 10 min run; then 0-7% MeOH/DCM/0.1% NH$_4$OH) to afford tert-butyl (3aR,6aS)-5-[2-[[6-(2,4-dimethylpyrazol-3-yl)pyridazin-3-yl]amino]ethyl]-3,3a,4,5,6,6a-hexahydro-1H-cyclopenta[c]pyrrole-2-carboxylate (229 mg, 0.54 mmol, 76% yield). LCMS (90 sec method): $R_T$=0.802, >95% @ 215 and 254 nM, m/z=427.5 [M+H]$^+$.

To a solution of tert-butyl (3aR,6aS)-5-(2-((6-(1,4-dimethyl-1H-pyrazol-5-yl)pyridazin-3-yl)amino)ethyl)hexahydrocyclopenta[c]pyrrole-2(1H)-carboxylate (229 mg, 0.54 mmol) in DCM (2 mL) was added 4M hydrogen chloride in dioxane (0.86 mL, 3.43 mmol) and the mixture was stirred for 5 hours. Upon completion as determined by LCMS, the reaction was concentrated to afford the product (194 mg, 0.54 mmol, 98% yield). The material was carried forward without further purification. LCMS (90 sec method): $R_T$=0.372, >95% @ 215 and 254 nM, m/z=327.5 [M+H]f. $^1$H NMR (400 MHz, Methanol-d$_4$): δ 7.96 (d, J=9.7 Hz, 1H), 7.73-7.66 (m, 1H), 7.49 (s, 1H), 3.98 (s, 3H), 3.54-3.47 (m, 3H), 3.22-3.18 (m, 2H), 2.95-2.91 (m, 3H), 2.23-2.24 (m, 2H). 2.19 (s, 3H), 2.16-2.03 (m, 1H), 1.93-1.84 (m, 3H), 1.22-1.14 (m, 2H).

6-(1,4-Dimethyl-1H-pyrazol-5-yl)-N-(2-((3aR,6aS)-2-(3,3-dimethylbutyl)octahydrocyclopenta[c]pyrrol-5-yl)ethyl)pyridazin-3-amine (Compound 120)

120

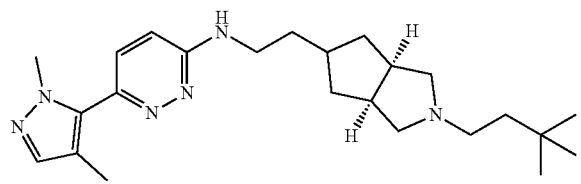

To a vial was added tert-butyl (3aR,6aS)-5-(2-((6-(1,4-dimethyl-1H-pyrazol-5-yl)pyridazin-3-yl)amino)ethyl)hexahydrocyclopenta[c]pyrrole-2(1H)-carboxylate (10 mg, 0.03 mmol) in DCE (0.5 mL)/THF (0.5 mL). Next, 3,3-dimethylbutyraldehyde (22 μL, 0.18 mmol) was added followed by sodium triacetoxyborohydride (29 mg, 0.14 mmol). The resulting suspension was stirred at ambient temperature for 18 hours then analyzed by LCMS. The reaction was quenched with a saturated aqueous NaHCO₃ solution, and extracted with 3:1 chloroform/IPA. The solvents were concentrated. The crude product was dissolved in DMSO (1 mL) and purified using the Gilson (Acidic, 30×50 mm column, 15-60% ACN/0.1% aqueous TFA, 4 min run). Fractions containing the product were basified with a saturated aqueous NaHCO₃ solution and extracted with 3:1 chloroform/IPA. The solvents were concentrated to give title compound as a white solid (74% yield). LCMS (90 sec method): $R_T$=0.693, >95% @ 215 and 254 nM, m/z=411.4 [M+H]+. ¹H NMR (400 MHz, chloroform-d): δ 7.36 (s, 1H), 7.27 (d, J=9.2 Hz, 1H), 6.69 (d, J=9.2 Hz, 1H), 4.88 (bs, 1H), 3.99 (s, 3H), 3.49-3.42 (m, 2H), 2.56-2.47 (m, 3H), 2.41-2.35 (m, 2H), 2.29-2.25 (m, 2H), 2.10 (s, 3H), 2.18-2.04 (m, 2H), 1.94-1.80 (m, 2H), 1.78-1.72 (m, 2H), 1.71-1.63 (m, 1H), 1.43-1.38 (m 2H), 1.11-1.03 (m, 2H), 0.89 (s, 9H).

The compounds shown in Table 7 were prepared similarly to the compounds described above, with appropriate starting materials.

TABLE 7

| Cpd. No. | Name | Structure | ES-MS [M + 1]+ |
|---|---|---|---|
| 121 | N-[2-[(3aR,6aS)-2-(1-adamantylmethyl)-3,3a,4,5,6,6a-hexahydro-1H-cyclopenta[c]pyrrol-5-yl]ethyl]-6-(2,4-dimethylpyrazol-3-yl)pyridazin-3-amine | 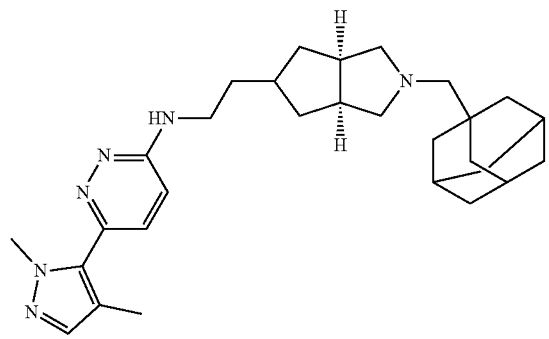 [SMILES: Cc1cnn(C)c1-c1ccc(NCCC2C[C@@H]3CN(CC45CC6CC(CC(C6)C4)C5)C[C@@H]3C2)nn1] | 475.4 |
| 122 | N-[2-[(3aR,6aS)-2-(tetrahydropyran-3-ylmethyl)-3,3a,4,5,6,6a-hexahydro-1H-cyclopenta[c]pyrrol-5-yl]ethyl]-6-(2,4-dimethylpyrazol-3-yl)pyridazin-3-amine | 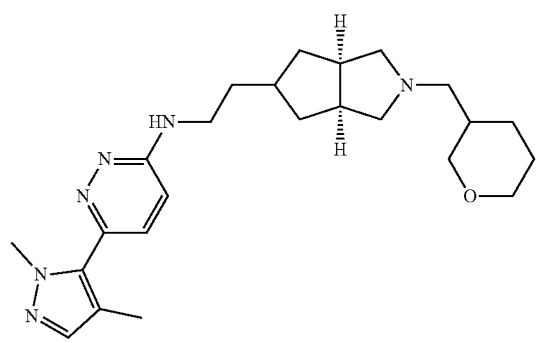 [SMILES: Cc1cnn(C)c1-c1ccc(NCCC2C[C@@H]3CN(CC4CCCOC4)C[C@@H]3C2)nn1] | 425.3 |
| 123 | N-[2-[(3aR,6aS)-2-(5-bicyclo[2.2.1]hept-2-enylmethyl)-3,3a,4,5,6,6a-hexahydro-1H-cyclopenta[c]pyrrol-5-yl]ethyl]-6-(2,4-dimethylpyrazol-3-yl)pyridazin-3-amine | 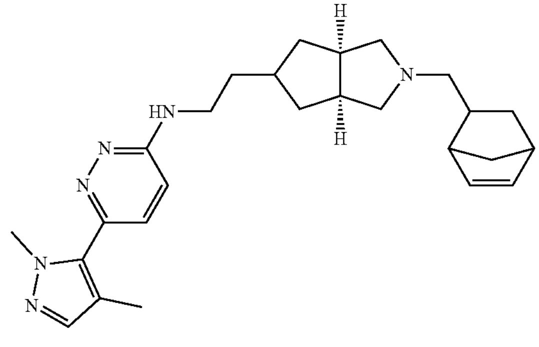 [SMILES: Cc1cnn(C)c1-c1ccc(NCCC2C[C@@H]3CN(CC4CC5C=CC4C5)C[C@@H]3C2)nn1] | 433.3 |

TABLE 7-continued

| Cpd. No. | Name | Structure | ES-MS [M + 1]+ |
|---|---|---|---|
| 124 | N-[2-[(3aR,6aS)-2-[(3-methyl-2-pyridyl)methyl]-3,3a,4,5,6,6a-hexahydro-1H-cyclopenta[c]pyrrol-5-yl]ethyl]-6-(2,4-dimethylpyrazol-3-yl)pyridazin-3-amine | 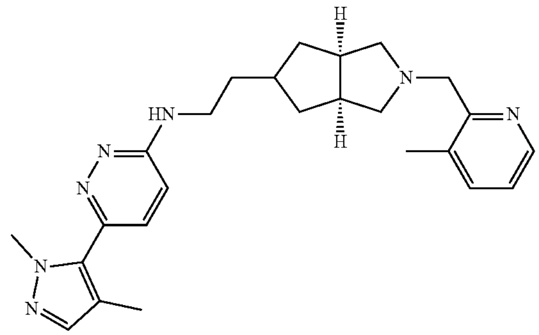 [SMILES: Cc1cccnc1CN1C[C@H]2CC(CCNc3ccc(-c4c(C)cnn4C)nn3)C[C@H]2C1] | 432.2 |
| 125 | N-[2-[(3aR,6aS)-2-(tetrahydropyran-4-ylmethyl)-3,3a,4,5,6,6a-hexahydro-1H-cyclopenta[c]pyrrol-5-yl]ethyl]-6-(2,4-dimethylpyrazol-3-yl)pyridazin-3-amine | 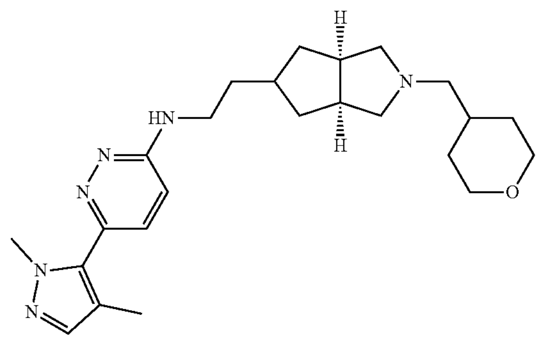 [SMILES: Cc1cnn(C)c1-c1ccc(NCCC2C[C@@H]3CN(CC4CCOCC4)C[C@@H]3C2)nn1] | 425.3 |
| 126 | N-[2-[(3aR,6aS)-2-benzyl-3,3a,4,5,6,6a-hexahydro-1H-cyclopenta[c]pyrrol-5-yl]ethyl]-6-(2,4-dimethylpyrazol-3-yl)pyridazin-3-amine | 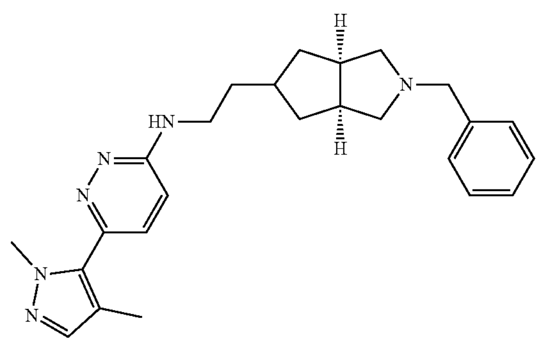 [SMILES: Cc1cnn(C)c1-c1ccc(NCCC2C[C@@H]3CN(Cc4ccccc4)C[C@@H]3C2)nn1] | 417.4 |
| 127 | N-[2-[(3aR,6aS)-2-[(2-fluorophenyl)methyl]-3,3a,4,5,6,6a-hexahydro-1H-cyclopenta[c]pyrrol-5-yl]ethyl]-6-(2,4-dimethylpyrazol-3-yl)pyridazin-3-amine | 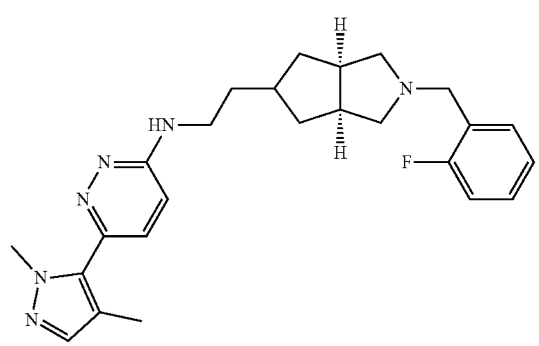 [SMILES: Cc1cnn(C)c1-c1ccc(NCCC2C[C@@H]3CN(Cc4ccccc4F)C[C@@H]3C2)nn1] | 436 |

Example 10. N-(4'-(((3aR,5s,6aS)-2-(3,3-Dimethyl-butyl)octahydrocyclopenta[c]pyrrol-5-yl)oxy)-[1,1'-biphenyl]-4-yl)acetamide

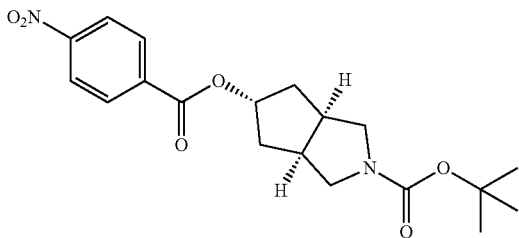 [SMILES: CC(C)(C)OC(=O)N1C[C@H]2C[C@H](OC(=O)c3ccc([N+](=O)[O-])cc3)C[C@H]2C1]

tert-Butyl (3aR,5s,6aS)-5-((4-nitrobenzoyl)oxy)hexahydrocyclopenta[c]pyrrole-2(1H)-carboxylate. To a solution of tert-butyl (3aR,5r,6aS)-5-hydroxyhexahydrocyclopenta[c]pyrrole-2(1H)-carboxylate (1.01 g, 4.44 mmol), triphenylphosphine (1.40 g, 5.33 mmol), and 4-nitrobenzoic acid (890 mg, 5.33 mmol) in diethyl ether (15 mL) was added diisopropyl azodicarboxylate (1.05 mL, 5.33 mmol) at −78° C. The reaction mixture was warmed to r.t. and stirred for 18 h, after which time the reaction mixture was quenched with the addition of MeOH (2 mL), and stirred for 15 min. Solvents were concentrated under reduced pressure, and the crude residue was purified by column chromatography (3-30% EtOAc in hexanes) to give the title compound as a colorless oil that solidified upon standing (1.67 g, 100%, 80% purity after chromatography). ES-MS [M+H-tbutyl]$^+$=321.3.

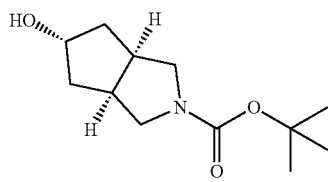 [SMILES: CC(C)(C)OC(=O)N1C[C@H]2C[C@H](O)C[C@H]2C1]

tert-Butyl (3aR,5s,6aS)-5-hydroxyhexahydrocyclopenta[c]pyrrole-2(1H)-carboxylate. tert-Butyl (3aR,5s,6aS)-5-((4-nitrobenzoyl)oxy)hexahydrocyclopenta[c]pyrrole-2(1H)-carboxylate (1.67 g, 4.44 mmol) was dissolved in THF (30 mL) and potassium trimethylsilanolate (2.85 g, 22.2 mmol) was added. The resulting cloudy brown mixture was stirred at r.t. for 2 h, after which time solvents were concentrated under reduced pressure, and the crude residue was diluted in DCM and H$_2$O. The aqueous layer was extracted with DCM, and the combined organic extracts were dried with MgSO$_4$. Solvents were filtered and concentrated under reduced pressure, and the crude residue was purified by column chromatography (0-1% MeOH in DCM) to give the title compound as a white solid (435 mg, 43%). H-NMR (400 MHz, CDCl$_3$) δ 4.50-4.45 (m, 1H), 3.54-3.46 (m, 2H), 3.16 (br, 2H), 2.89-2.79 (m, 2H), 1.92-1.86 (m, 2H), 1.73-1.66 (m, 2H), 1.45 (s, 9H). ES-MS [M+H-tbutyl]$^+$=172.4.

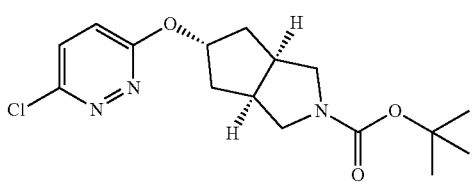 [SMILES: CC(C)(C)OC(=O)N1C[C@H]2C[C@H](Oc3ccc(Cl)nn3)C[C@H]2C1]

tert-Butyl (3aR,5s,6aS)-5-((6-chloropyridazin-3-yl)oxy)hexahydrocyclopenta[c]pyrrole-2(1H)-carboxylate. tert-Butyl (3aR,5s,6aS)-5-hydroxyhexahydrocyclopenta[c]pyrrole-2(1H)-carboxylate (430 mg, 1.89 mmol) was dissolved in THF (10 mL) and NaH (91 mg, 3.78 mmol, 60% dispersion in mineral oil) was added at 0° C. After stirring for 5 mins, 3,6-dichloropyridazine (423 mg, 2.84 mmol) was added and the resulting solution was warmed to r.t. and stirred for 70 h, after which time the reaction mixture was diluted with DCM and H$_2$O. The aqueous layer was extracted with DCM, and the combined organic extracts were dried with MgSO$_4$. Solvents were filtered and concentrated under reduced pressure, and the crude residue was purified by column chromatography (3-30% EtOAc in hexanes) to give the title compound as a white solid (477 mg, 74%). H-NMR (400 MHz, CDCl$_3$) δ 7.35 (d, J=9.2 Hz, 1H), 6.88 (d, J=9.2 Hz, 1H), 5.75-5.71 (m, 1H), 3.54 (br, 2H), 3.22 (br, 2H), 2.91-2.81 (m, 2H), 2.21-2.13 (m, 2H), 1.96 (dt, J=14.5, 5.6 Hz, 2H), 1.46 (s, 9H). ES-MS [M+H-tbutyl]$^+$=284.4.

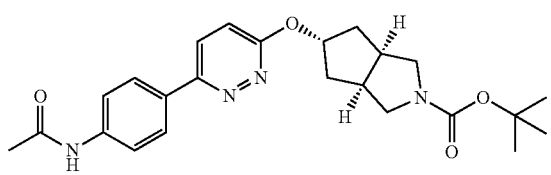 [SMILES: CC(=O)Nc1ccc(-c2ccc(O[C@H]3C[C@@H]4CN(C(=O)OC(C)(C)C)C[C@@H]4C3)nn2)cc1]

tert-Butyl (3aR,5s,6aS)-5-((6-(4-acetamidophenyl)pyridazin-3-yl)oxy)hexahydrocyclopenta[c]pyrrole-2(1H)-carboxylate. tert-Butyl (3aR,5s,6aS)-5-((6-chloropyridazin-3-yl)oxy)hexahydrocyclopenta[c]pyrrole-2(1H)-carboxylate (228 mg, 0.67 mmol), 4-acetylaminophenyl boronic acid (144 mg, 0.81 mmol), potassium carbonate (282 mg, 2.01 mmol) and RuPhos Pd G3 (56 mg, 0.067 mmol) were combined in a sealed vial, which was placed under an inert atmosphere. 5:1 dioxanes/H$_2$O solution (4 mL, degassed) was then added via syringe, and the resulting solution was stirred at 100° C. for 1 h, after which time the reaction was cooled to r.t. and diluted with DCM and sat. NaHCO$_3$. The aqueous layer was extracted with DCM, and the combined organic extracts were filtered through a phase separator and concentrated. The crude residue was purified by column chromatography (12-100% EtOAc in hexanes) to give the title compound as a white solid (94 mg, 32%). ES-MS [M+H-tbutyl]$^+$=383.3.

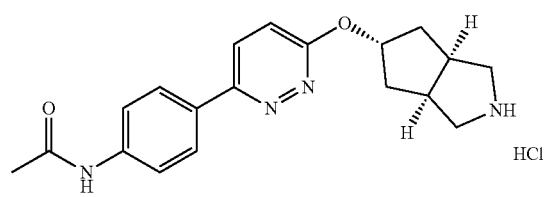 [SMILES: CC(=O)Nc1ccc(-c2ccc(O[C@@H]3C[C@H]4CNC[C@H]4C3)nn2)cc1 ; Cl]

N-(4-(6-(((3aR,5s,6aS)-Octahydrocyclopenta[c]pyrrol-5-yl)oxy)pyridazin-3-yl)phenyl)acetamide hydrochloride. tert-Butyl(3aR,5s,6aS)-5-((6-(4-acetamidophenyl)pyridazin-3-yl)oxy)hexahydrocyclopenta[c]pyrrole-2(1H)-carboxylate (94 mg, 0.21 mmol) was dissolved in 1,4-dioxane (2 mL) and 4M HCl in dioxanes solution (2 mL) was added dropwise. The resulting solution was stirred at r.t. for 30 min, after which time solvents were concentrated under reduced pressure to give the title compound as a yellow solid which was used directly without further purification (80 mg, 100%). ES-MS [M+H]⁺=339.4.

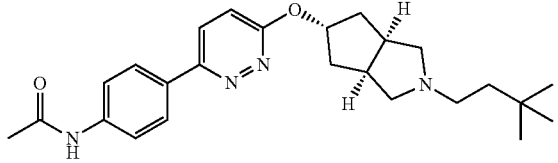 [SMILES: CC(=O)Nc1ccc(-c2ccc(O[C@H]3C[C@@H]4CN(CCC(C)(C)C)C[C@@H]4C3)nn2)cc1]

N-(4'-(((3aR,5s,6aS)-2-(3,3-Dimethylbutyl)octahydrocyclopenta[c]pyrrol-5-yl)oxy)-[1,1'-biphenyl]-4-yl)acetamide. N-(4-(6-(((3aR,5s,6aS)-Octahydrocyclopenta[c]pyrrol-5-yl)oxy)pyridazin-3-yl)phenyl)acetamide hydrochloride (16 mg, 0.043 mmol) was dissolved in THF (0.5 mL) and DCM (0.5 mL) and 3,3-dimethylbutyraldehyde (21 mg, 0.21 mmol) was added, followed by sodium triacetoxyborohydride (45 mg, 0.21 mmol). The resulting mixture was stirred at r.t. for 1 h, after which time the reaction mixture was quenched with sat. NaHCO₃ and diluted with 3:1 chloroform/IPA. The aqueous layer was extracted with 3:1 chloroform/IPA, and the organic extracts were filtered through a phase separator and concentrated. The crude residue was purified by RP-HPLC (12-42% MeCN in 0.1% TFA aqueous solution over 5 min), and fractions containing product were basified with sat. NaHCO₃, and extracted with 3:1 chloroform/IPA. The organic extracts were filtered through a phase separator and concentrated to give the title compound as a white solid (5.4 mg, 30%). ¹H-NMR (400 MHz, CDCl₃) δ 7.97 (d, J=8.6 Hz, 2H), 7.73 (d, J=9.2 Hz, 1H), 7.63 (d, J=8.6 Hz, 2H), 7.43 (s, 1H), 6.95 (d, J=9.2 Hz, 1H), 5.80 (p, J=4.7 Hz, 1H), 2.83-2.74 (m, 2H), 2.55-2.51 (m, 2H), 2.44-2.37 (m, 3H), 2.21 (s, 3H), 2.16-2.09 (m, 2H), 1.94 (dt, J=13.6, 5.0 Hz, 2H), 1.79-1.65 (m, 1H), 1.43-1.39 (m, 2H), 0.90 (s, 9H). ES-MS [M+H]⁺=423.0.

Example 11. N-(4-(6-(((3aR,5s,6aS)-2-((Tetrahydro-2H-pyran-4-yl)methyl)octahydrocyclopenta[c]pyrrol-5-yl)amino)pyridazin-3-yl)phenyl)acetamide

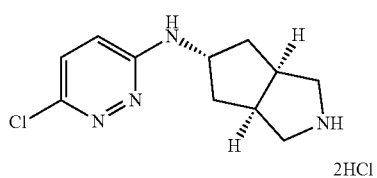 [SMILES: Clc1ccc(N[C@@H]2C[C@H]3CNC[C@H]3C2)nn1 ; "2HCl"]

2HCl (3aR,5s,6aS)—N-(6-Chloropyridazin-3-yl)octahydrocyclopenta[c]pyrrol-5-amine dihydrochloride. tert-Butyl(3aR,5s,6aS)-5-((6-chloropyridazin-3-yl)amino)hexahydrocyclopenta[c]pyrrole-2(1H)-carboxylate (2.22 g, 6.55 mmol) was dissolved in 1,4-dioxane (22 mL) and MeOH (2 mL) and 4M HCl in dioxanes solution (16 mL) was added dropwise. The resulting mixture was stirred at r.t. overnight, after which time solvents were concentrated under reduced pressure, and the resulting white solid was dried under vacuum and used directly without further purification (2.04 g, 100%). ES-MS [M+H]⁺=239.4.

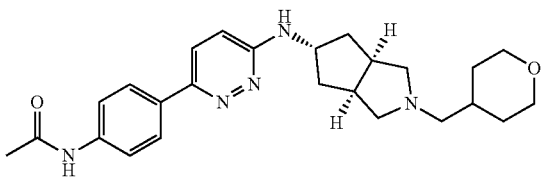 [SMILES: CC(=O)Nc1ccc(-c2ccc(N[C@H]3C[C@@H]4CN(CC5CCOCC5)C[C@@H]4C3)nn2)cc1]

(3aR,5s,6aS)—N-(6-Chloropyridazin-3-yl)-2-((tetrahydro-2H-pyran-4-yl)methyl)octahydrocyclopenta[c]pyrrol-5-amine. (3aR,5s,6aS)—N-(6-Chloropyridazin-3-yl)octahydrocyclopenta[c]pyrrol-5-amine dihydrochloride (2.04 g, 6.55 mmol) was dissolved in DCM (30 mL) and THF (30 mL) and tetrahydro-2H-pyran-4-carbaldehyde (2.05 mL, 19.7 mmol) was added, and the resulting solution was stirred for 10 mins. Sodium triacetoxyborohydride (4.17 g, 19.7 mmol) was then added. The resulting solution was stirred at r.t. for 2 h, after which time the reaction was quenched with the slow addition of sat. NaHCO₃, and the aqueous layer was extracted with 3:1 chloroform/IPA. The combined organic extracts were dried with MgSO₄, and solvents were filtered and concentrated under reduced pressure, and the resulting yellow solid was used without further purification (1.75 g, 79%). ¹H-NMR (400 MHz, CDCl₃) δ 7.15 (d, J=9.3 Hz, 1H), 6.63 (d, J=9.3 Hz, 1H), 4.84 (d, J=7.0 Hz, 1H), 4.32-4.24 (m, 1H), 3.96 (dd, J=10.9, 3.7 Hz, 2H), 3.38 (td, J=11.9, 1.9 Hz, 2H), 2.78-2.54 (m, 4H), 2.36-2.27 (m, 4H), 1.95-1.91 (m, 2H), 1.72-1.65 (m, 5H), 1.33-1.23 (m, 2H). ES-MS [M+H]⁺=337.2.

N-(4-(6-(((3aR,5s,6aS)-2-((Tetrahydro-2H-pyran-4-yl)methyl)octahydrocyclopenta[c]pyrrol-5-yl)amino)pyridazin-3-yl)phenyl)acetamide (3aR,5s,6aS)—N-(6-Chloropyridazin-3-yl)-2-((tetrahydro-2H-pyran-4-yl)methyl)octahydrocyclopenta[c]pyrrol-5-amine (20 mg, 0.059 mmol), 4-acetylaminophenyl boronic acid (15.9 mg, 0.089 mmol), potassium carbonate (25 mg, 0.18 mmol) and BrettPhos Pd G3 (5.4 mg, 0.006 mmol) were combined in a vial and placed under an inert atmosphere. 5:1 1,4-dioxane/H₂O solution (1 mL, degassed) was then added via syringe. The resulting mixture was stirred under an inert atmosphere at 100° C. for 2 h, after which time the reaction was cooled to r.t. and solvents were concentrated. The crude residue was taken up in DMSO, and solids were removed by syringe filtration. The crude residue was purified by RP-HPLC (2-32% MeCN in 0.1% TFA aqueous solution over 5 min). Fractions containing product were basified with sat. NaHCO₃, and extracted with 3:1 chloroform/IPA. The combined organic extracts were filtered through a phase separator and concentrated to give the title compound as a white solid (7.3 mg, 28%). ¹H-NMR (400 MHz, CDCl₃) 7.92-7.89 (m, 2H), 7.64-7.55 (m, 4H), 6.71 (d, J=9.4 Hz, 1H), 4.82 (d, J=6.9 Hz, 1H), 4.47-4.38 (m, 1H), 3.96 (dd, J=11.1, 3.5 Hz, 2H), 3.41-3.35 (m, 2H), 2.83-2.68 (m, 4H), 2.35-2.31 (m, 4H), 2.19 (s, 3H), 1.98 (dd, J=11.9, 5.5 Hz, 2H), 1.75-1.67 (m, 5H), 1.36-1.21 (m, 2H). ES-MS [M+H]⁺=436.2.

Example 12. (3aR,5s,6aS)—N-(6-Morpholino-pyridazin-3-yl)-2-((tetrahydro-2H-pyran-4-yl)methyl)octahydrocyclopenta[c]pyrrol-5-amine

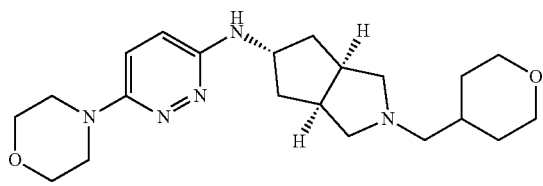 [SMILES: c1cc(N2CCOCC2)nnc1N[C@H]1C[C@@H]2CN(CC3CCOCC3)C[C@@H]2C1]

(3aR,5s,6aS)—N-(6-Morpholinopyridazin-3-yl)-2-((tetrahydro-2H-pyran-4-yl)methyl)octahydrocyclopenta[c]pyrrol-5-amine. (3aR,5s,6aS)—N-(6-Chloropyridazin-3-yl)-2-((tetrahydro-2H-pyran-4-yl)methyl)octahydrocyclopenta[c]pyrrol-5-amine (20 mg, 0.059 mmol) and morpholine (26 μL, 030 mmol) were combined in a microwave vial, and NMP (1 mL) was added, followed by conc. HCl (25 μL, 30 mmol) and N,N-diisopropylethylamine (52 μL, 0.30 mmol). The resulting solution was heated under microwave irradiation at 200° C. for 1 h, after which time the reaction mixture was purified directly by RP-HPLC (20-60% MeCN in 0.05% NH₄OH aqueous solution over 5 min). Fractions containing product were concentrated to give the title compound as a slightly brown solid (13 mg, 55%). ¹H-NMR (400 MHz, CDCl₃) δ 6.86 (d, J=9.6 Hz, 1H), 6.61 (d, J=9.6 Hz, 1H), 4.38-4.30 (m, 1H), 4.20 (d, J=6.8 Hz, 1H), 3.95 (dd, J=11.4, 3.6 Hz, 2H), 3.83-3.81 (m, 4H), 3.40-3.34 (m, 6H), 2.73-2.65 (m, 4H), 2.26-2.24 (m, 4H), 1.93 (dd, J=12.6, 5.6 Hz, 2H), 1.72-1.58 (m, 5H), 1.32-1.21 (m, 2H). ES-MS [M+H]⁺=388.4.

Example 13. N-(4-(5-(((3aR,5s,6aS)-2-(3,3-Dimethylbutyl)octahydrocyclopenta[c]pyrrol-5-yl)amino)pyrazin-2-yl)phenyl)acetamide

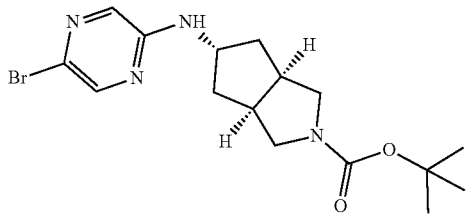 [SMILES: CC(C)(C)OC(=O)N1C[C@H]2C[C@H](Nc3cnc(Br)cn3)C[C@H]2C1]

tert-Butyl (3aR,5s,6aS)-5-((5-bromopyrazin-2-yl)amino)hexahydrocyclopenta[c]pyrrole-2(1H)-carboxylate. To a solution of tert-butyl (3aR,5s,6aS)-5-aminohexahydrocyclopenta[c]pyrrole-2(1H)-carboxylate (274 mg, 1.21 mmol) in NMP (4.5 mL) was added 2-bromo-5-chloropyrazine (585 mg, 3.02 mmol) and N,N-diisopropylethylamine (0.63 mL, 3.63 mmol). The mixture was stirred at 180° C. under microwave irradiation for 1 h. Solids were removed by syringe filtration, and crude residue was purified by RP-HPLC (20-70% MeCN in 0.05% NH₄OH aqueous solution over 20 min). Fractions containing product were combined and concentrated to give the title compound as a brown oil (148 mg, 32%). ES-MS [M+H]⁺=383.2.

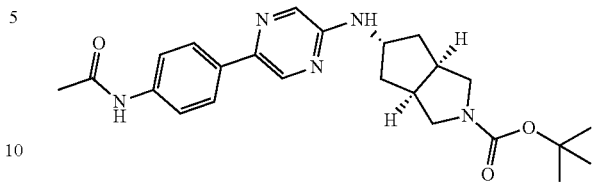

tert-Butyl (3aR,5s,6aS)-5-((5-(4-acetamidophenyl)pyrazin-2-yl)amino)hexahydrocyclopenta[c]pyrrole-2(1H)-carboxylate. tert-Butyl (3aR,5s,6aS)-5-((5-bromopyrazin-2-yl)amino)hexahydrocyclopenta[c]pyrrole-2(1H)-carboxylate (98.2 mg, 0.26 mmol), potassium carbonate (108 mg, 0.77 mmol), RuPhos Pd G3 (21.5 mg, 0.03 mmol), and 4-acetylaminophenyl boronic acid (55 mg, 0.31 mmol) were combined in a 2 mL vial, and 5:1 1,4-dioxane/H₂O solution (1.5 mL, degassed) was added. The solution was stirred at 100° C. for 3 h, after which the reaction was cooled to r.t. and diluted with sat. NaHCO₃ and DCM. The aqueous layer was extracted with DCM, and the combined organic extracts were filtered through a phase separator and concentrated. The crude residue was purified by column chromatography (0-10% MeOH in EtOAc). Fractions containing product were concentrated to give the title compound as a brown oil (70 mg, 62%). ES-MS [M+H]⁺=438.5.

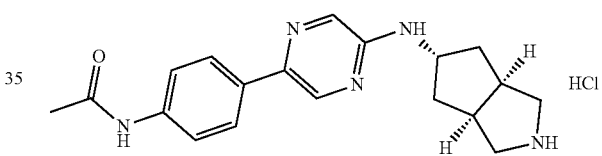

N-(4-(5-(((3aR,5s,6aS)-Octahydrocyclopenta[c]pyrrol-5-yl)amino)pyrazin-2-yl)phenyl)acetamide hydrochloride. tert-Butyl(3aR,5s,6aS)-5-((5-(4-acetamidophenyl)pyrazin-2-yl)amino)hexahydrocyclopenta[c]pyrrole-2(1H)-carboxylate (98.2 mg, 0.26 mmol) was dissolved in 1,4-dioxane (1 mL) and a 4M solution of HCl in dioxanes (4 mL) was added dropwise. The resulting solution was stirred for 2 h at r.t., after which time solvents were concentrated under reduced pressure to give the title compound as a tan solid which was used directly without further purification (59 mg, 100%). ES-MS [M+H]⁺=338.3.

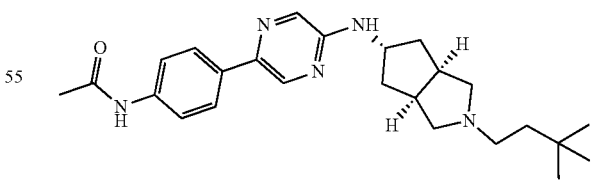

N-(4-(5-(((3aR,5s,6aS)-2-(3,3-Dimethylbutyl)octahydrocyclopenta[c]pyrrol-5-yl)amino)pyrazin-2-yl)phenyl)acetamide. To a solution of N-(4-(5-(((3aR,5s,6aS)-Octahydrocyclopenta[c]pyrrol-5-yl)amino)pyrazin-2-yl)phenyl)acetamide hydrochloride (13.3 mg, 0.04 mmol) in THF (0.25 mL) and DCE (0.25 mL) was added 3,3-dimethylbutyraldehyde (10.7 mg, 0.11 mmol), and the resulting solution was allowed to stir for 6 h. Sodium triacetoxyborohydride (22.6 mg, 0.11 mmol) was then added. The resulting solution was stirred at r.t. overnight, after which time solvents were concentrated, and crude residue was taken up in MeOH. Solids were removed by syringe filtration, and the solution was purified via RP-HPLC (10-50% MeCN in 0.1% aq TFA solution over 5 min). Fractions containing product were basified with NaHCO$_3$, and extracted with 3:1 chloroform/IPA. The organic extracts were combined and passed through a phase separator and concentrated to give the title compound as a white solid (7 mg, 45%). ES-MS [M+H]$^+$=422.4.

Example 14. (3aR,5s,6aS)—N-(5-(1,3-Dimethyl-1H-pyrazol-4-yl)pyridin-2-yl)-2-((tetrahydro-2H-pyran-4-yl)methyl)octahydrocyclopenta[c]pyrrol-5-amine

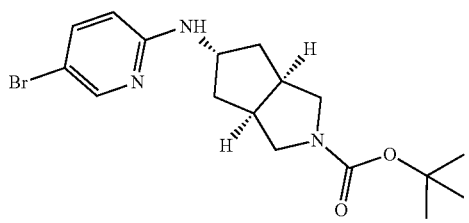 [SMILES: CC(C)(C)OC(=O)N1C[C@H]2C[C@H](Nc3ccc(Br)cn3)C[C@H]2C1]

tert-Butyl (3aR,5s,6aS)-5-((5-bromopyridin-2-yl)amino)hexahydrocyclopenta[c]pyrrole-2(1H)-carboxylate. To a solution of (3aR,5s,6aS)-5-aminohexahydrocyclopenta[c]pyrrole-2(1H)-carboxylate (365 mg, 1.61 mmol) in NMP (10 mL) was added 5-bromo-2-fluoropyridine (851 mg, 4.84 mmol) and N,N-diisopropylethylamine (0.84 mL, 4.83 mmol). The mixture was stirred at 180° C. under microwave irradiation for 1 h. Solids were removed by syringe filtration, and the crude residue was purified via RP-HPLC (20-70% MeCN in 0.05% NH$_4$OH aqueous solution over 20 min). Fractions containing product were combined and concentrated to give the title compound as a colorless oil (119 mg, 19%). ES-MS [M+H]$^+$=382.2

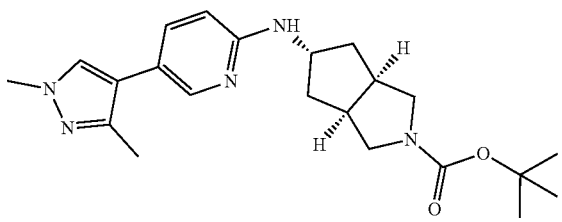 [SMILES: Cc1nn(C)cc1-c1ccc(N[C@H]2C[C@@H]3CN(C(=O)OC(C)(C)C)C[C@@H]3C2)nc1]

tert-Butyl (3aR,5s,6aS)-5-((5-(1,3-dimethyl-1H-pyrazol-4-yl)pyridin-2-yl)amino)hexahydrocyclopenta[c]pyrrole-2(1H)-carboxylate. tert-Butyl (3aR,5s,6aS)-5-((5-bromopyridin-2-yl)amino)hexahydrocyclopenta[c]pyrrole-2(1H)-carboxylate (141 mg, 0.37 mmol), potassium carbonate (156 mg, 1.11 mmol), RuPhos Pd G3 (30.9 mg, 0.04 mmol), and 1,3-dimethyl-1H-pyrazole-4-boronic acid pinacol ester (98.4 mg, 0.44 mmol) were combined in a vial, and 5:1 1,4-dioxane/H$_2$O solution (2 mL, degassed) was added. The resulting mixture was stirred at 100° C. for 3 h, after which time the reaction was cooled to r.t. and diluted with sat. NaHCO$_3$ and DCM. The aqueous layer was extracted with DCM, and the combined organic extracts were filtered through a phase separator and concentrated. The crude residue was purified by column chromatography (0-10% MeOH in EtOAc) and concentrated to give the title compound as a colorless oil (70 mg, 47%). ES-MS [M+H]$^+$=398.5.

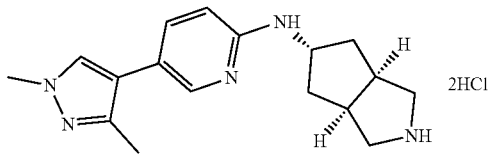 [SMILES: Cc1nn(C)cc1-c1ccc(N[C@@H]2C[C@H]3CNC[C@H]3C2)nc1]

(3aR,5s,6aS)—N-(5-(1,3-Dimethyl-1H-pyrazol-4-yl)pyridin-2-yl)octahydrocyclopenta[c]pyrrol-5-amine dihydrochloride. tert-Butyl (3aR,5s,6aS)-5-((5-(1,3-dimethyl-1H-pyrazol-4-yl)pyridin-2-yl)amino)hexahydrocyclopenta[c]pyrrole-2(1H)-carboxylate (69.5 mg, 0.17 mmol) was dissolved in 1,4-dioxane (1 mL) and a 4M solution of HCl in dioxanes (5 mL) was added dropwise. The resulting solution was stirred at r.t. for 2 h, after which time solvents were concentrated under reduced pressure to give the title compound as a tan solid which was used directly without further purification (65 mg, 100%). ES-MS [M+H]$^+$=298.4.

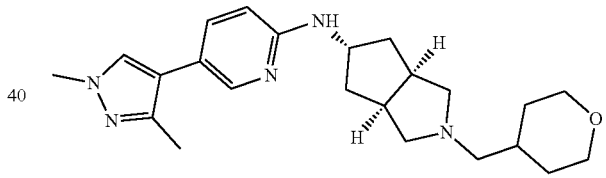

(3aR,5s,6aS)—N-(5-(1,3-Dimethyl-1H-pyrazol-4-yl)pyridin-2-yl)-2-((tetrahydro-2H-pyran-4-yl)methyl)octahydrocyclopenta[c]pyrrol-5-amine. To a solution of (3aR,5s,6aS)—N-(5-(1,3-dimethyl-1H-pyrazol-4-yl)pyridin-2-yl)octahydrocyclopenta[c]pyrrol-5-amine dihydrochloride (16.2 mg, 0.04 mmol) in THF (0.25 mL) and DCE (0.25 mL) was added tetrahydro-2H-pyran-4-carbaldehyde (14.9 mg, 0.13 mmol), and the resulting solution was stirred at r.t. for 6 h. Sodium triacetoxyborohydride (27.8 mg, 0.13 mmol) was then added. The resulting solution was stirred overnight at r.t., at which time the reaction mixture was concentrated, and the crude residue was taken up in MeOH. Solids were removed by syringe filtration, and the solution was purified by RP-HPLC (5-35% MeCN in 0.1% aq TFA solution over 5 min). Fractions containing product were basified with NaHCO$_3$, and extracted with 3:1 chloroform/IPA. The organic extracts were combined and passed through a phase separator and concentrated to yield the title compound as a white solid (3.5 mg, 20%). ES-MS [M+H]$^+$=396.0.

Example 15. 5-Phenyl-N-((3aR,5s,6aS)-2-((tetrahydro-2H-pyran-4-yl)methyl)octahydrocyclopenta[c]pyrrol-5-yl)thiazol-2-amine

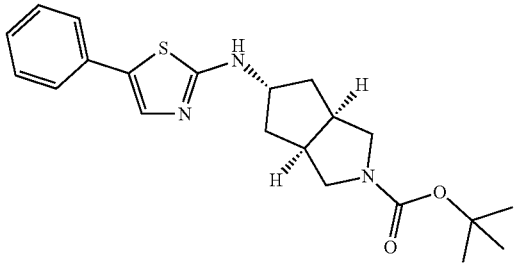 [SMILES: CC(C)(C)OC(=O)N1C[C@H]2C[C@H](Nc3ncc(-c4ccccc4)s3)C[C@H]2C1]

tert-Butyl (3aR,5s,6aS)-5-((5-phenylthiazol-2-yl)amino)hexahydrocyclopenta[c]pyrrole-2(1H)-carboxylate. tert-Butyl (3aR,5s,6aS)-5-aminohexahydrocyclopenta[c]pyrrole-2(1H)-carboxylate (160 mg, 0.71 mmol) and 2-chloro-5-phenylthiazole (277 mg, 1.42 mmol) were dissolved in NMP (2 mL) and DIPEA (0.37 mL, 2.12 mmol) was added. The resulting solution was stirred under microwave irradiation at 180° C. for 1 h, after which time the reaction mixture was purified directly by column chromatography (5-100% EtOAc in hexanes) to give the title compound as an orange oil (56 mg, 20%). ES-MS [M+H]$^+$=386.2.

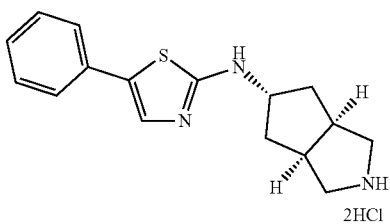 [SMILES: c1ccc(-c2cnc(N[C@@H]3C[C@H]4CNC[C@H]4C3)s2)cc1]

N-((3aR,5s,6aS)-Octahydrocyclopenta[c]pyrrol-5-yl)-5-phenylthiazol-2-amine dihydrochloride. tert-Butyl (3aR,5s,6aS)-5-((5-phenylthiazol-2-yl)amino)hexahydrocyclopenta[c]pyrrole-2(1H)-carboxylate (56 mg, 0.14 mmol) was dissolved in 1,4-dioxane (1 mL) and 4M HCl in dioxanes solution (0.72 mL, 2.88 mmol) was added dropwise. The resulting solution was stirred at r.t. for 1 h, after which time solvents were concentrated under reduced pressure to give the title compound as brown solid which was dried under vacuum and used without further purification (52 mg, 100%). ES-MS [M+H]$^+$=286.2.

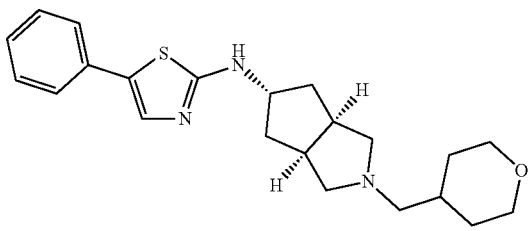 [SMILES: c1ccc(-c2cnc(N[C@H]3C[C@@H]4CN(CC5CCOCC5)C[C@@H]4C3)s2)cc1]

5-Phenyl-N-((3aR,5s,6aS)-2-((tetrahydro-2H-pyran-4-yl)methyl)octahydrocyclopenta[c]pyrrol-5-yl)thiazol-2-amine. N-((3aR,5s,6aS)-Octahydrocyclopenta[c]pyrrol-5-yl)-5-phenylthiazol-2-amine dihydrochloride (17.2 mg, 0.048 mmol) was dissolved in DCM (0.5 mL) and THF (0.5 mL) and tetrahydro-2H-pyran-4-carbaldehyde (27 mg, 0.24 mmol) was added, followed by sodium triacetoxyborohydride (31 mg, 0.14 mmol). The resulting solution was stirred at r.t. for 1.5 h, after which time the reaction mixture was quenched with sat. NaHCO$_3$, and the aqueous layer was extracted with 3:1 chloroform/IPA. The combined organic extracts were filtered through a phase separator and concentrated, and the crude residue was purified by RP-HPLC (5-35% MeCN in 0.1% aq TFA solution over 5 min). Fractions containing product were basified with NaHCO$_3$, and extracted with 3:1 chloroform/IPA. The organic extracts were combined and passed through a phase separator and concentrated to yield the title compound as a white solid (5.4 mg, 29%). $^1$H-NMR (400 MHz, CDCl$_3$) 7.42-7.37 (m, 2H), 7.35-7.31 (m, 3H), 7.23-7.18 (m, 1H), 5.33 (d, J=4.8 Hz, 1H), 4.13-4.04 (m, 1H), 3.98 (dd, J=11.0, 3.9 Hz, 2H), 3.40 (td, J=12.0, 1.6 Hz, 2H), 2.76 (br, 2H), 2.60 (br, 2H), 2.44 (br, 2H), 2.32 (br, 2H), 1.97 (dd, J=12.0, 3.7 Hz, 2H), 1.81-1.73 (m, 5H), 1.36-1.25 (m, 2H). ES-MS [M+H]$^+$=384.4.

Example 16. (3aR,5s,6aS)—N-(6-(4-Fluorophenoxy)pyridazin-3-yl)-2-((tetrahydro-2H-pyran-4-yl)methyl)octahydrocyclopenta[c]pyrrol-5-amine

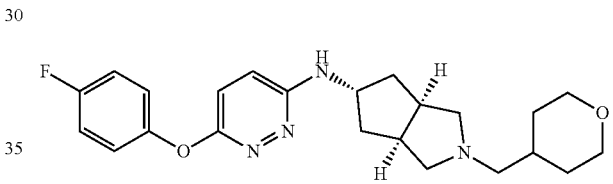

(3aR,5s,6aS)—N-(6-Chloropyridazin-3-yl)-2-((tetrahydro-2H-pyran-4-yl)methyl)octahydrocyclopenta[c]pyrrol-5-amine (25 mg, 0.074 mmol), potassium phosphate tribasic (32 mg, 0.15 mmol), 4-fluorophenol (33 mg, 0.30 mmol), palladium(II) acetate (1.7 mg, 0.007 mmol) and t-butylXPhos (4.7 mg, 0.011 mmol) were combined in a vial, which was sealed and placed under an inert atmosphere. Toluene (1 mL) was then added via syringe, and the resulting mixture was heated to 100° C. overnight, after which time solvents were concentrated, and the crude residue was taken up in DMSO. Solids were removed by syringe filtration, and the crude residue was purified by RP-HPLC (5-35% MeCN in 0.1% aq TFA solution over 5 min). Fractions containing product were basified with NaHCO$_3$, and extracted with 3:1 chloroform/IPA. The organic extracts were combined and passed through a phase separator and concentrated to yield the title compound as a slightly yellow oil (3.3 mg, 11%). $^1$H-NMR (400 MHz, CDCl$_3$) 7.16-7.10 (m, 3H), 7.08-7.02 (m, 2H), 6.98 (d, J=9.4 Hz, 1H), 4.44 (br, 1H), 3.97 (dd, J=11.0, 2.9 Hz, 2H), 3.38 (td, J=12.0, 1.8 Hz, 2H), 3.06 (br, 2H), 2.57 (br, 2H), 2.37 (br, 2H), 2.09-1.97 (m, 2H), 1.94-1.48 (m, 8H), 1.42-1.26 (m, 2H). ES-MS [M+H]$^+$=413.2.

The compounds shown in Table 8 may be prepared similarly to the compounds described above, with appropriate starting materials.

TABLE 8

| Cpd. No. | Name | Structure | ES-MS [M + 1]+ |
|---|---|---|---|
| 128 | (3aR,5s,6aS)-5-(6-chloropyridazin-3-yl)oxy-2-(3,3-dimethylbutyl)-3,3a,4,5,6,6a-hexahydro-1H-cyclopenta[c]pyrrole | 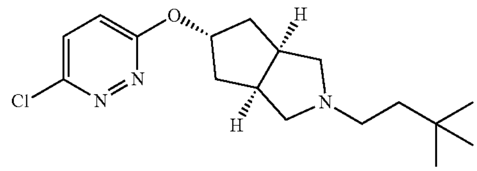 [SMILES: CC(C)(C)CCN1C[C@H]2C[C@H](Oc3ccc(Cl)nn3)C[C@H]2C1] | 324.5 |
| 129 | N-[4-[6-[[(3aR,5s,6aS)-2-(3,3-dimethylbutyl)-3,3a,4,5,6,6a-hexahydro-1H-cyclopenta[c]pyrrol-5-yl]oxy]pyridazin-3-yl]phenyl]acetamide | 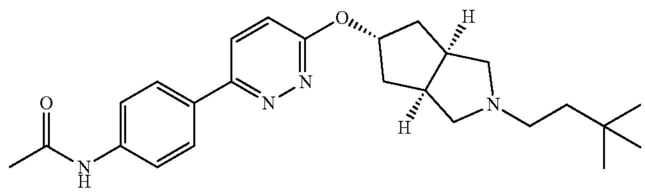 [SMILES: CC(=O)Nc1ccc(-c2ccc(O[C@H]3C[C@@H]4CN(CCC(C)(C)C)C[C@@H]4C3)nn2)cc1] | 423 |
| 130 | N-[4-[6-[[(3aR,5s,6aS)-2-(cyclohexylmethyl)-3,3a,4,5,6,6a-hexahydro-1H-cyclopenta[c]pyrrol-5-yl]oxy]pyridazin-3-yl]phenyl]acetamide | 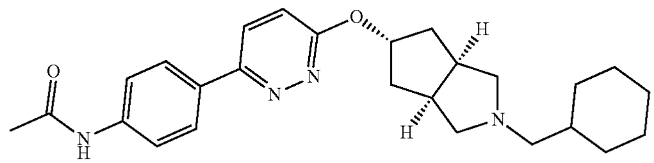 [SMILES: CC(=O)Nc1ccc(-c2ccc(O[C@H]3C[C@@H]4CN(CC5CCCCC5)C[C@@H]4C3)nn2)cc1] | 432 |
| 131 | N-[4-[6-[[(3aR,5s,6aS)-2-[(4-fluorophenyl)methyl]-3,3a,4,5,6,6a-hexahydro-1H-cyclopenta[c]pyrrol-5-yl]oxy]pyridazin-3-yl]phenyl]acetamide | 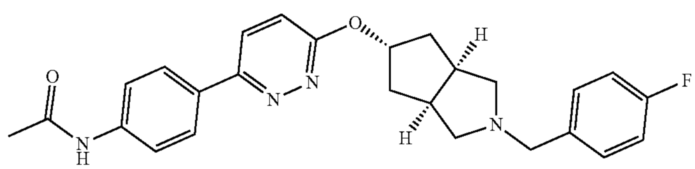 [SMILES: CC(=O)Nc1ccc(-c2ccc(O[C@H]3C[C@@H]4CN(Cc5ccc(F)cc5)C[C@@H]4C3)nn2)cc1] | 447 |
| 132 | N-[4-[6-[[(3aR,5s,6aS)-2-(tetrahydropyran-4-ylmethyl)-3,3a,4,5,6,6a-hexahydro-1H-cyclopenta[c]pyrrol-5-yl]oxy]pyridazin-3-yl]phenyl]acetamide | 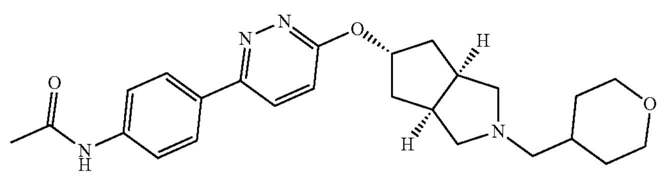 [SMILES: CC(=O)Nc1ccc(-c2ccc(O[C@H]3C[C@@H]4CN(CC5CCOCC5)C[C@@H]4C3)nn2)cc1] | 437 |
| 133 | N-[4-[6-[[(3aR,5s,6aS)-2-[(3-methyl-2-pyridyl)methyl]-3,3a,4,5,6,6a-hexahydro-1H-cyclopenta[c]pyrrol-5-yl]oxy]pyridazin-3-yl]phenyl]acetamide | 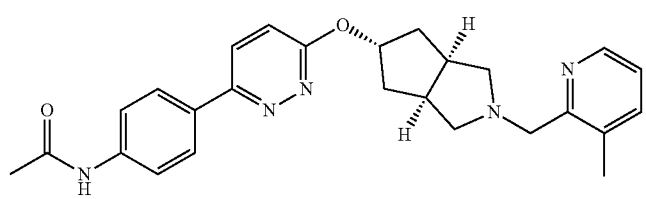 [SMILES: CC(=O)Nc1ccc(-c2ccc(O[C@H]3C[C@@H]4CN(Cc5ncccc5C)C[C@@H]4C3)nn2)cc1] | 444 |
| 134 | (3aR,5s,6aS)-2-(3,3-dimethylbutyl)-5-[6-(1,3-dimethylpyrazol-4-yl)pyridazin-3-yl]oxy-3,3a,4,5,6,6a-hexahydro-1H-cyclopenta[c]pyrrole | 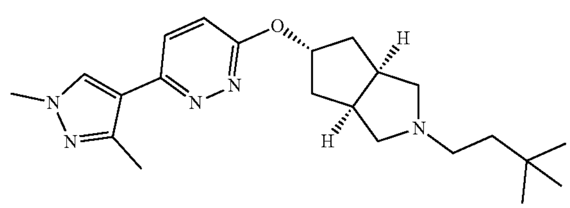 [SMILES: Cc1nn(C)cc1-c1ccc(O[C@H]2C[C@@H]3CN(CCC(C)(C)C)C[C@@H]3C2)nn1] | 384.5 |
| 135 | (3aR,5s,6aS)-2-(3,3-dimethylbutyl)-5-[6-(2,4-dimethylpyrazol-3-yl)pyridazin-3-yl]oxy-3,3a,4,5,6,6a-hexahydro-1H-cyclopenta[c]pyrrole | 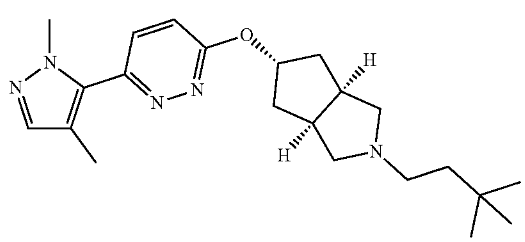 [SMILES: Cc1cnn(C)c1-c1ccc(O[C@H]2C[C@@H]3CN(CCC(C)(C)C)C[C@@H]3C2)nn1] | 384.6 |

TABLE 8-continued

| Cpd. No. | Name | Structure | ES-MS [M + 1]+ |
|---|---|---|---|
| 136 | 4-[6-[[(3aR,5s,6aS)-2-(3,3-dimethylbutyl)-3,3a,4,5,6,6a-hexahydro-1H-cyclopenta[c]pyrrol-5-yl]oxy]pyridazin-3-yl]-3,5-dimethyl-isoxazole | 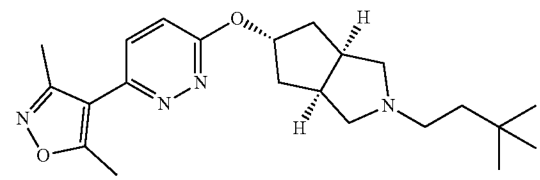 [SMILES: Cc1noc(C)c1-c1ccc(O[C@H]2C[C@@H]3CN(CCC(C)(C)C)C[C@@H]3C2)nn1] | 385.5 |
| 137 | (3aR,5s,6aS)-5-[6-(2-chloro-5-fluoro-phenyl)pyridazin-3-yl]oxy-2-(3,3-dimethylbutyl)-3,3a,4,5,6,6a-hexahydro-1H-cyclopenta[c]pyrrole | 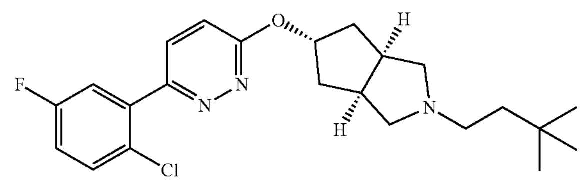 [SMILES: CC(C)(C)CCN1C[C@H]2C[C@H](Oc3ccc(-c4cc(F)ccc4Cl)nn3)C[C@H]2C1] | 418.4 |
| 138 | (3aR,5s,6aS)-5-[6-(1,3-benzodioxol-5-yl)pyridazin-3-yl]oxy-2-(3,3-dimethylbutyl)-3,3a,4,5,6,6a-hexahydro-1H-cyclopenta[c]pyrrole | 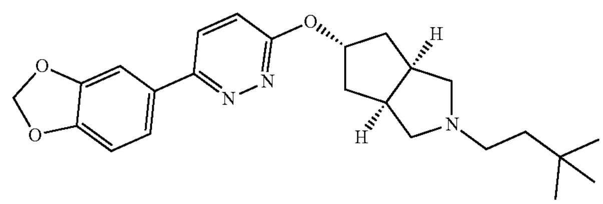 [SMILES: CC(C)(C)CCN1C[C@H]2C[C@H](Oc3ccc(-c4ccc5c(c4)OCO5)nn3)C[C@H]2C1] | 410.4 |
| 139 | (3aR,5s,6aS)-2-(3,3-dimethylbutyl)-5-[6-[4-(trifluoromethyl)phenyl]pyridazin-3-yl]oxy-3,3a,4,5,6,6a-hexahydro-1H-cyclopenta[c]pyrrole | 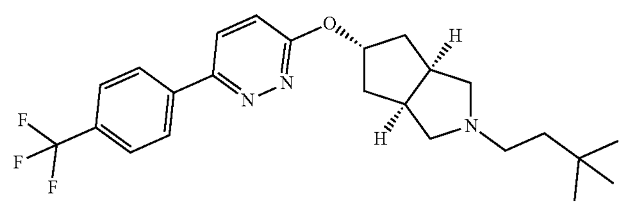 [SMILES: CC(C)(C)CCN1C[C@H]2C[C@H](Oc3ccc(-c4ccc(C(F)(F)F)cc4)nn3)C[C@H]2C1] | 434.4 |
| 140 | N-[4-[6-[[(3aR,5s,6aS)-2-(3,3-dimethylbutyl)-3,3a,4,5,6,6a-hexahydro-1H-cyclopenta[c]pyrrol-5-yl]amino]pyridazin-3-yl]phenyl]acetamide | 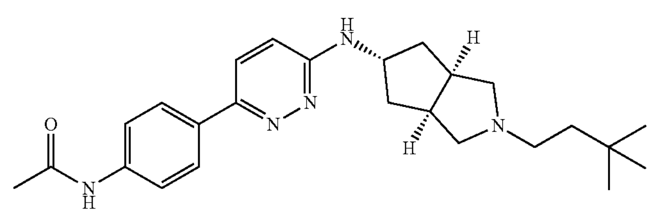 [SMILES: CC(=O)Nc1ccc(-c2ccc(N[C@H]3C[C@@H]4CN(CCC(C)(C)C)C[C@@H]4C3)nn2)cc1] | 422.4 |
| 141 | (3aR,5s,6aS)-N-[6-(2-chloro-4-fluoro-phenyl)pyridazin-3-yl]-2-(3,3-dimethylbutyl)-3,3a,4,5,6,6a-hexahydro-1H-cyclopenta[c]pyrrol-5-amine | 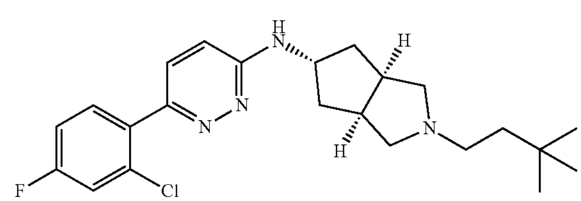 [SMILES: CC(C)(C)CCN1C[C@H]2C[C@H](Nc3ccc(-c4ccc(F)cc4Cl)nn3)C[C@H]2C1] | 417.4 |
| 142 | (3aR,5s,6aS)-2-(3,3-dimethylbutyl)-N-[6-(3,5-dimethylisoxazol-4-yl)pyridazin-3-yl]-3,3a,4,5,6,6a-hexahydro-1H-cyclopenta[c]pyrrol-5-amine | 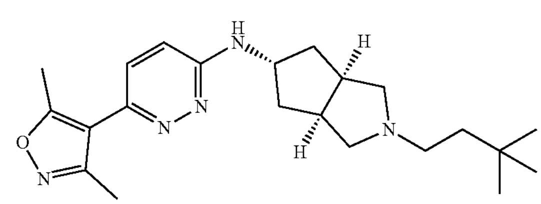 [SMILES: Cc1noc(C)c1-c1ccc(N[C@H]2C[C@@H]3CN(CCC(C)(C)C)C[C@@H]3C2)nn1] | 384.6 |

TABLE 8-continued

| Cpd. No. | Name | Structure | ES-MS [M + 1]+ |
|---|---|---|---|
| 143 | (3aR,5s,6aS)-2-(3,3-dimethylbutyl)-N-(6-morpholinopyridazin-3-yl)-3,3a,4,5,6,6a-hexahydro-1H-cyclopenta[c]pyrrol-5-amine | 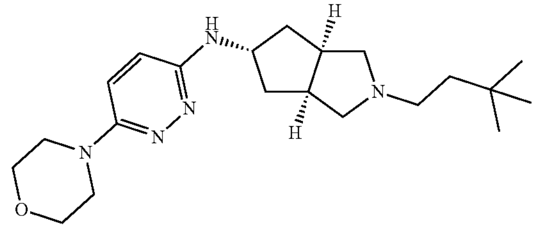 [SMILES: CC(C)(C)CCN1C[C@H]2C[C@H](Nc3ccc(N4CCOCC4)nn3)C[C@H]2C1] | 374.5 |
| 144 | (3aR,5r,6aS)-2-(3,3-dimethylbutyl)-N-[6-(2,4-dimethylpyrazol-3-yl)pyridazin-3-yl]-3,3a,4,5,6,6a-hexahydro-1H-cyclopenta[c]pyrrole-5-carboxamide | 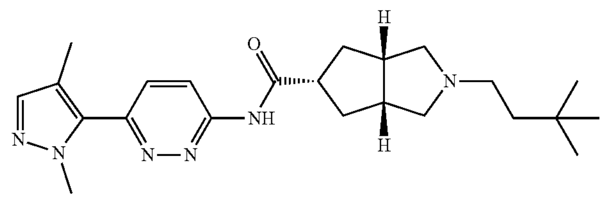 [SMILES: Cc1cnn(C)c1-c1ccc(NC(=O)[C@@H]2C[C@@H]3CN(CCC(C)(C)C)C[C@@H]3C2)nn1] | 411.4 |
| 145 | (3aR,5s,6aS)-2-(3,3-dimethylbutyl)-N-[6-(2,4-dimethylpyrazol-3-yl)pyridazin-3-yl]-3,3a,4,5,6,6a-hexahydro-1H-cyclopenta[c]pyrrole-5-carboxamide | 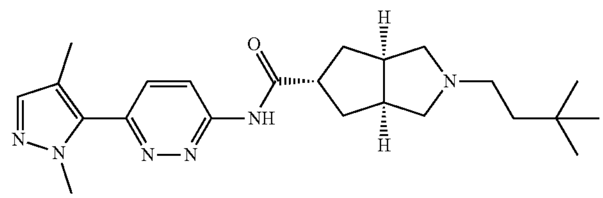 [SMILES: Cc1cnn(C)c1-c1ccc(NC(=O)[C@H]2C[C@@H]3CN(CCC(C)(C)C)C[C@@H]3C2)nn1] | 411.4 |
| 146 | (3aR,5s,6aS)-2-(3,3-dimethylbutyl)-5-[[6-(2,4-dimethylpyrazol-3-yl)pyridazin-3-yl]oxymethyl]-3,3a,4,5,6,6a-hexahydro-1H-cyclopenta[c]pyrrole | 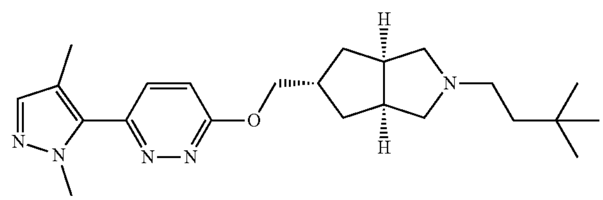 [SMILES: Cc1cnn(C)c1-c1ccc(OC[C@H]2C[C@@H]3CN(CCC(C)(C)C)C[C@@H]3C2)nn1] | 398.4 |
| 147 | (3aR,5r,6aS)-2-(3,3-dimethylbutyl)-5-[[6-(2,4-dimethylpyrazol-3-yl)pyridazin-3-yl]oxymethyl]-3,3a,4,5,6,6a-hexahydro-1H-cyclopenta[c]pyrrole | 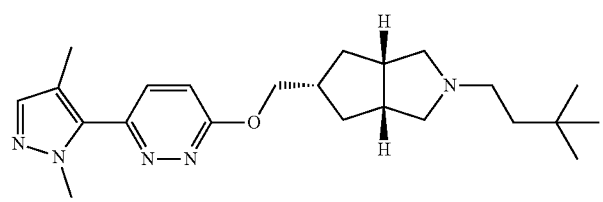 [SMILES: Cc1cnn(C)c1-c1ccc(OC[C@@H]2C[C@@H]3CN(CCC(C)(C)C)C[C@@H]3C2)nn1] | 398.4 |
| 148 | N-[4-[4-[[(3aR,5s,6aS)-2-(3,3-dimethylbutyl)-3,3a,4,5,6,6a-hexahydro-1H-cyclopenta[c]pyrrol-5-yl]amino]-2,3-difluoro-phenyl]phenyl]acetamide | 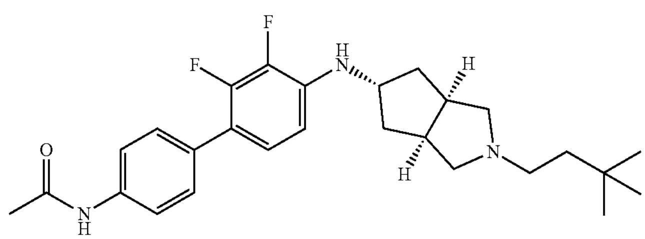 [SMILES: CC(=O)Nc1ccc(-c2ccc(N[C@H]3C[C@@H]4CN(CCC(C)(C)C)C[C@@H]4C3)c(F)c2F)cc1] | 456.4 |
| 149 | (3aR,5s,6aS)-2-(3,3-dimethylbutyl)-N-[5-(1,3-dimethylpyrazol-4-yl)-2-pyridyl]-3,3a,4,5,6,6a-hexahydro-1H-cyclopenta[c]pyrrol-5-amine | 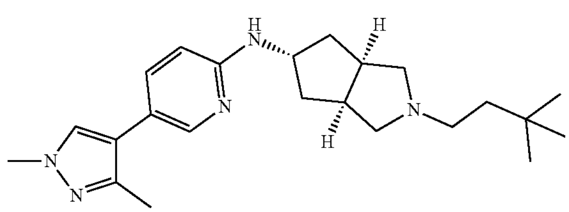 [SMILES: Cc1nn(C)cc1-c1ccc(N[C@H]2C[C@@H]3CN(CCC(C)(C)C)C[C@@H]3C2)nc1] | 382 |

TABLE 8-continued

| Cpd. No. | Name | Structure | ES-MS [M + 1]+ |
|---|---|---|---|
| 150 | (3aR,5s,6aS)-2-(1-adamantylmethyl)-N-[5-(1,3-dimethylpyrazol-4-yl)-2-pyridyl]-3,3a,4,5,6,6a-hexahydro-1H-cyclopenta[c]pyrrol-5-amine | 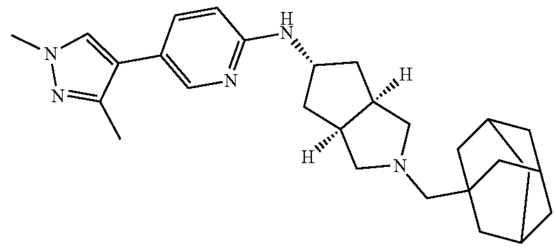 [SMILES: Cc1nn(C)cc1-c1ccc(N[C@H]2C[C@@H]3CN(CC45CC6CC(CC(C6)C4)C5)C[C@@H]3C2)nc1] | 446 |
| 151 | (3aR,5s,6aS)-2-(5-bicyclo[2.2.1]hept-2-enylmethyl)-N-[5-(1,3-dimethylpyrazol-4-yl)-2-pyridyl]-3,3a,4,5,6,6a-hexahydro-1H-cyclopenta[c]pyrrol-5-amine | 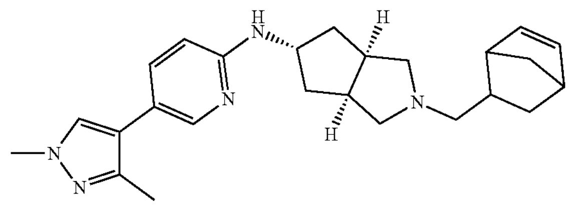 [SMILES: Cc1nn(C)cc1-c1ccc(N[C@H]2C[C@@H]3CN(CC4CC5C=CC4C5)C[C@@H]3C2)nc1] | 404 |
| 152 | (3aR,5s,6aS)-N-[5-(1,3-dimethylpyrazol-4-yl)-2-pyridyl]-2-(tetrahydropyran-4-ylmethyl)-3,3a,4,5,6,6a-hexahydro-1H-cyclopenta[c]pyrrol-5-amine | 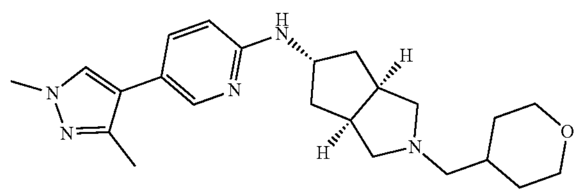 [SMILES: Cc1nn(C)cc1-c1ccc(N[C@H]2C[C@@H]3CN(CC4CCOCC4)C[C@@H]3C2)nc1] | 396 |
| 153 | (3aR,5s,6aS)-2-(3,3-dimethylbutyl)-N-[5-(1,3-dimethylpyrazol-4-yl)pyrazin-2-yl]-3,3a,4,5,6,6a-hexahydro-1H-cyclopenta[c]pyrrol-5-amine | 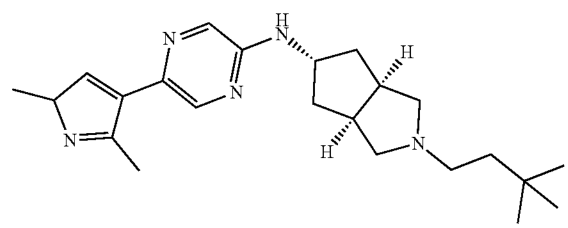 [SMILES: CC1=NC(C)C=C1c1cnc(N[C@H]2C[C@@H]3CN(CCC(C)(C)C)C[C@@H]3C2)cn1] | 383.4 |
| 154 | (3aR,5s,6aS)-2-(5-bicyclo[2.2.1]hept-2-enylmethyl)-N-[5-(1,3-dimethylpyrazol-4-yl)pyrazin-2-yl]-3,3a,4,5,6,6a-hexahydro-1H-cyclopenta[c]pyrrol-5-amine | 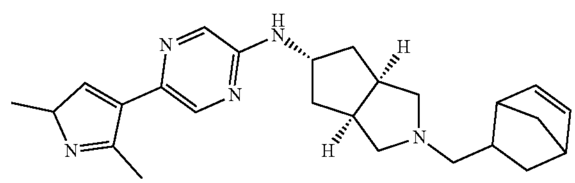 [SMILES: CC1=NC(C)C=C1c1cnc(N[C@H]2C[C@@H]3CN(CC4CC5C=CC4C5)C[C@@H]3C2)cn1] | 405.4 |
| 155 | (3aR,5s6aS)-2-(1-adamantylmethyl)-N-[5-(1,3-dimethylpyrazol-4-yl)pyrazin-2-yl]-3,3a,4,5,6,6a-hexahydro-1H-cyclopenta[c]pyrrol-5-amine | 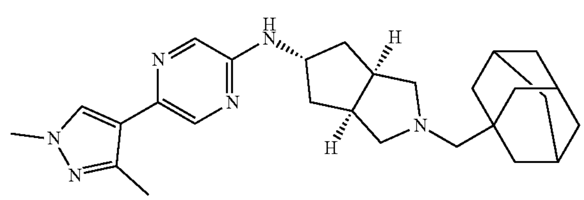 [SMILES: Cc1nn(C)cc1-c1cnc(N[C@H]2C[C@@H]3CN(CC45CC6CC(CC(C6)C4)C5)C[C@@H]3C2)cn1] | 447.4 |
| 156 | N-[4-[5-[[(3aR,5s,6aS)-2-(3,3-dimethylbutyl)-3,3a,4,5,6,6a-hexahydro-1H-cyclopenta[c]pyrrol-5-yl]amino]pyrazin-2-yl]phenyl]acetamide | 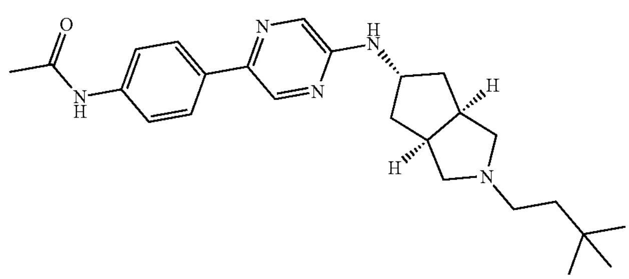 [SMILES: CC(=O)Nc1ccc(-c2cnc(N[C@H]3C[C@@H]4CN(CCC(C)(C)C)C[C@@H]4C3)cn2)cc1] | 422.4 |

TABLE 8-continued

| Cpd. No. | Name | Structure | ES-MS [M + 1]+ |
|---|---|---|---|
| 157 | N-[4-[5-[[(3aR,5s,6aS)-2-(5-bicyclo[2.2.1]hept-2-enylmethyl)-3,3a,4,5,6,6a-hexahydro-1H-cyclopenta[c]pyrrol-5-yl]amino]pyrazin-2-yl]phenyl]acetamide | 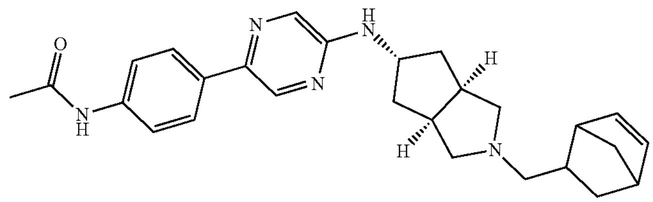 [SMILES: CC(=O)Nc1ccc(-c2cnc(N[C@H]3C[C@@H]4CN(CC5CC6C=CC5C6)C[C@@H]4C3)cn2)cc1] | 444.4 |
| 158 | N-[4-[5-[[(3aR,5s,6aS)-2-(tetrahydropyran-4-ylmethyl)-3,3a,4,5,6,6a-hexahydro-1H-cyclopenta[c]pyrrol-5-yl]amino]pyrazin-2-yl]phenyl]acetamide | 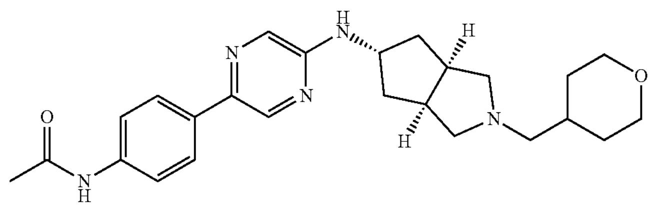 [SMILES: CC(=O)Nc1ccc(-c2cnc(N[C@H]3C[C@@H]4CN(CC5CCOCC5)C[C@@H]4C3)cn2)cc1] | 436.4 |
| 159 | (3aR,5r,6aS)-N-[6-(2-chloro-5-fluoro-phenyl)pyridazin-3-yl]-2-(tetrahydropyran-4-ylmethyl)-3,3a,4,5,6,6a-hexahydro-1H-cyclopenta[c]pyrrol-5-amine | 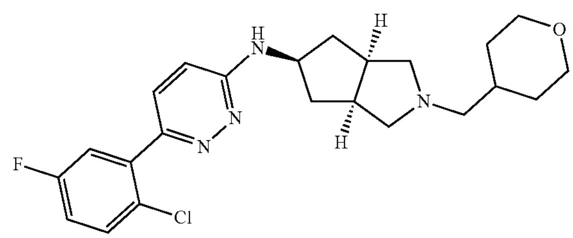 [SMILES: Fc1ccc(Cl)c(-c2ccc(N[C@@H]3C[C@@H]4CN(CC5CCOCC5)C[C@@H]4C3)nn2)c1] | 431.4 |
| 160 | (3aR,5s,6aS)-N-[6-(2-chloro-5-fluoro-phenyl)pyridazin-3-yl]-2-(2-pyridylmethyl)-3,3a,4,5,6,6a-hexahydro-1H-cyclopenta[c]pyrrol-5-amine | 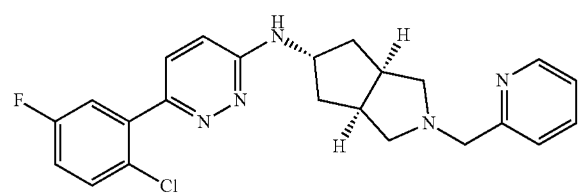 [SMILES: Fc1ccc(Cl)c(-c2ccc(N[C@H]3C[C@@H]4CN(Cc5ccccn5)C[C@@H]4C3)nn2)c1] | 424.4 |
| 161 | (3aR,5s,6aS)-N-[6-(2-chloro-5-fluoro-phenyl)pyridazin-3-yl]-2-(3-pyridylmethyl)-3,3a,4,5,6,6a-hexahydro-1H-cyclopenta[c]pyrrol-5-amine | 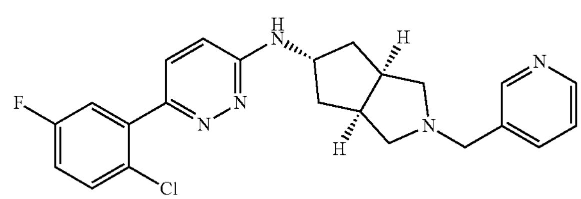 [SMILES: Fc1ccc(Cl)c(-c2ccc(N[C@H]3C[C@@H]4CN(Cc5cccnc5)C[C@@H]4C3)nn2)c1] | 424.4 |
| 162 | (3aR,5s,6aS)-N-[6-(2-chloro-5-fluoro-phenyl)pyridazin-3-yl]-2-(4-pyridylmethyl)-3,3a,4,5,6,6a-hexahydro-1H-cyclopenta[c]pyrrol-5-amine | 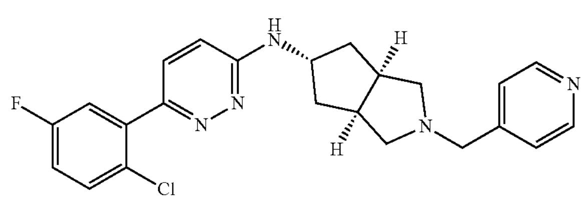 [SMILES: Fc1ccc(Cl)c(-c2ccc(N[C@H]3C[C@@H]4CN(Cc5ccncc5)C[C@@H]4C3)nn2)c1] | 424.4 |
| 163 | (3aR,5s,6aS)-N-[6-(2-chloro-5-fluoro-phenyl)pyridazin-3-yl]-2-[(4-fluorophenyl)methyl]-3,3a,4,5,6,6a-hexahydro-1H-cyclopenta[c]pyrrol-5-amine | 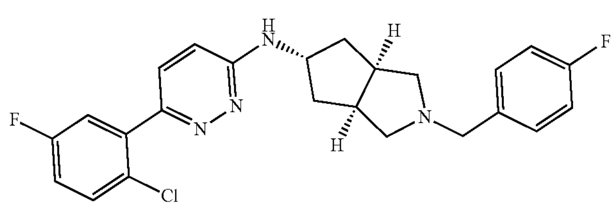 [SMILES: Fc1ccc(CN2C[C@H]3C[C@H](Nc4ccc(-c5cc(F)ccc5Cl)nn4)C[C@H]3C2)cc1] | 441.4 |

TABLE 8-continued

| Cpd. No. | Name | Structure | ES-MS [M + 1]+ |
|---|---|---|---|
| 164 | (3aR,5s,6aS)-N-[6-(2-chloro-5-fluoro-phenyl)pyridazin-3-yl]-2-(3-quinolylmethyl)-3,3a,4,5,6,6a-hexahydro-1H-cyclopenta[c]pyrrol-5-amine | 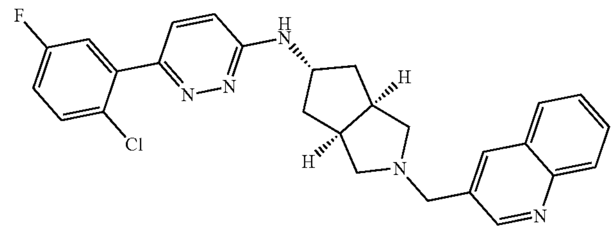 [SMILES: Fc1ccc(Cl)c(-c2ccc(N[C@H]3C[C@@H]4CN(Cc5cnc6ccccc6c5)C[C@@H]4C3)nn2)c1] | 474.4 |
| 165 | (3aR,5s,6aS)-N-[6-(2-chloro-5-fluoro-phenyl)pyridazin-3-yl]-2-(imidazo[1,2-a]pyridin-2-ylmethyl)-3,3a,4,5,6,6a-hexahydro-1H-cyclopenta[c]pyrrol-5-amine | 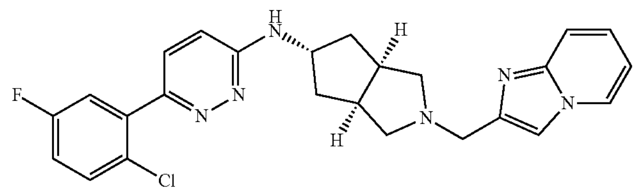 [SMILES: Fc1ccc(Cl)c(-c2ccc(N[C@H]3C[C@@H]4CN(Cc5cn6ccccc6n5)C[C@@H]4C3)nn2)c1] | 463.4 |
| 166 | (3aR,5s,6aS)-2-(1,3-benzodioxol-5-ylmethyl)-N-[6-(2-chloro-5-fluoro-phenyl)pyridazin-3-yl]-3,3a,4,5,6,6a-hexahydro-1H-cyclopenta[c]pyrrol-5-amine | 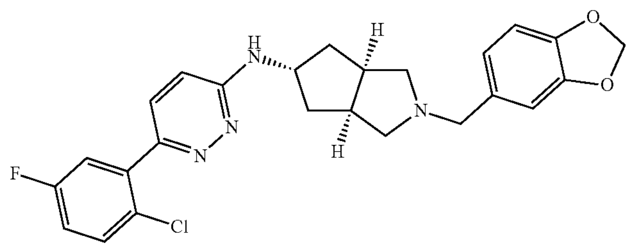 [SMILES: Fc1ccc(Cl)c(-c2ccc(N[C@H]3C[C@@H]4CN(Cc5ccc6c(c5)OCO6)C[C@@H]4C3)nn2)c1] | 467.3 |
| 167 | (3aR,5s,6aS)-2-(1,3-benzodioxol-4-ylmethyl)-N-[6-(2-chloro-5-fluoro-phenyl)pyridazin-3-yl]-3,3a,4,5,6,6a-hexahydro-1H-cyclopenta[c]pyrrol-5-amine | 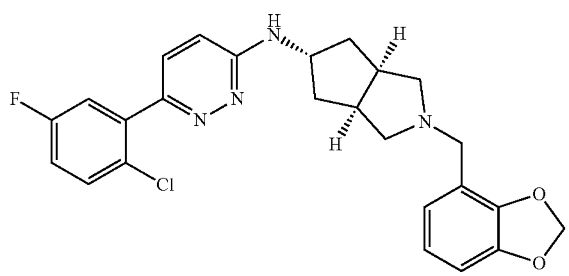 [SMILES: Fc1ccc(Cl)c(-c2ccc(N[C@H]3C[C@@H]4CN(Cc5cccc6c5OCO6)C[C@@H]4C3)nn2)c1] | 467.4 |
| 168 | (3aR,5s,6aS)-N-[6-(2-chloro-5-fluoro-phenyl)pyridazin-3-yl]-2-[(4-methoxyphenyl)methyl]-3,3a,4,5,6,6a-hexahydro-1H-cyclopenta[c]pyrrol-5-amine | 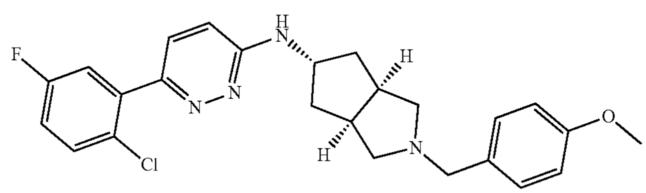 [SMILES: COc1ccc(CN2C[C@H]3C[C@H](Nc4ccc(-c5cc(F)ccc5Cl)nn4)C[C@H]3C2)cc1] | 453.4 |
| 169 | (3aR,5s,6aS)-N-[6-(2-chloro-5-fluoro-phenyl)pyridazin-3-yl]-2-(cyclopropylmethyl)-3,3a,4,5,6,6a-hexahydro-1H-cyclopenta[c]pyrrol-5-amine | 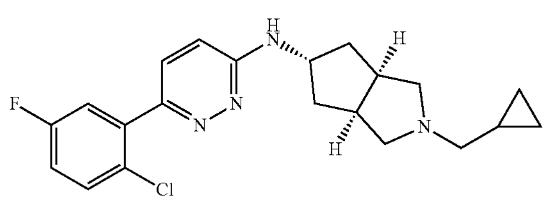 [SMILES: Fc1ccc(Cl)c(-c2ccc(N[C@H]3C[C@@H]4CN(CC5CC5)C[C@@H]4C3)nn2)c1] | 387.4 |
| 170 | (3aR,5s,6aS)-N-[6-(2-chloro-5-fluoro-phenyl)pyridazin-3-yl]-2-(pyrazin-2-ylmethyl)-3,3a,4,5,6,6a-hexahydro-1H-cyclopenta[c]pyrrol-5-amine | 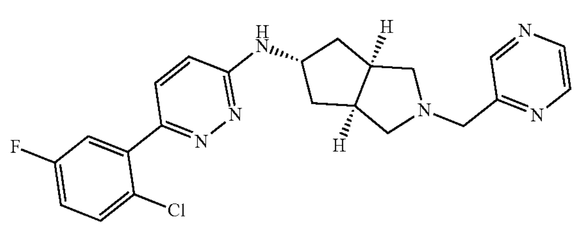 [SMILES: Fc1ccc(Cl)c(-c2ccc(N[C@H]3C[C@@H]4CN(Cc5cnccn5)C[C@@H]4C3)nn2)c1] | 425.3 |

TABLE 8-continued

| Cpd. No. | Name | Structure | ES-MS [M + 1]+ |
|---|---|---|---|
| 171 | (3aR,5s,6aS)-N-[6-(2-chloro-5-fluoro-phenyl)pyridazin-3-yl]-2-[(3-methyloxetan-3-yl)methyl]-3,3a,4,5,6,6a-hexahydro-1H-cyclopenta[c]pyrrol-5-amine | 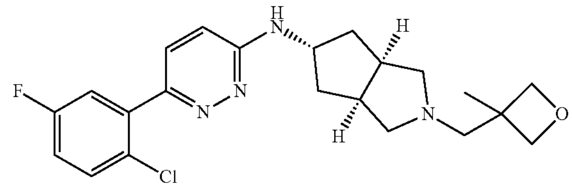 [SMILES: CC1(CN2C[C@H]3C[C@H](Nc4ccc(-c5cc(F)ccc5Cl)nn4)C[C@H]3C2)COC1] | 417.5 |
| 172 | N-[4-[[(3aR,5s,6aS)-5-[[6-(2-chloro-5-fluoro-phenyl)pyridazin-3-yl]amino]-3,3a,4,5,6,6a-hexahydro-1H-cyclopenta[c]pyrrol-2-yl]methyl]phenyl]methanesulfonamide | 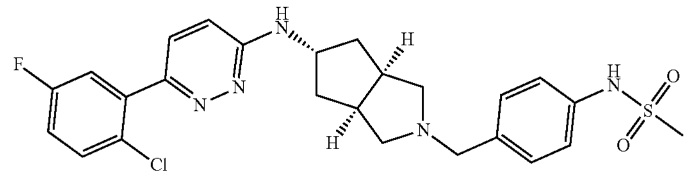 [SMILES: CS(=O)(=O)Nc1ccc(CN2C[C@H]3C[C@H](Nc4ccc(-c5cc(F)ccc5Cl)nn4)C[C@H]3C2)cc1] | 516.1 |
| 173 | (3aR,5s,6aS)-N-[6-(2-chloro-5-fluoro-phenyl)pyridazin-3-yl]-2-[(2,2-dimethyltetrahydropyran-4-yl)methyl]-3,3a,4,5,6,6a-hexahydro-1H-cyclopenta[c]pyrrol-5-amine | 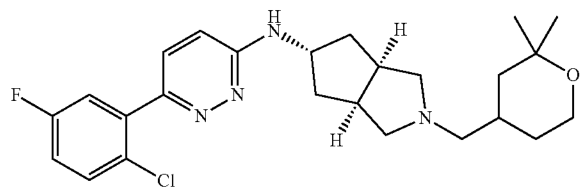 [SMILES: CC1(C)CC(CN2C[C@H]3C[C@H](Nc4ccc(-c5cc(F)ccc5Cl)nn4)C[C@H]3C2)CCO1] | 459.2 |
| 174 | (3aR,5s,6aS)-N-[6-(2-chloro-5-fluoro-phenyl)pyridazin-3-yl]-2-[(2-methoxyphenyl)methyl]-3,3a,4,5,6,6a-hexahydro-1H-cyclopenta[c]pyrrol-5-amine | 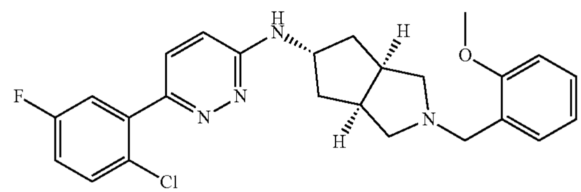 [SMILES: COc1ccccc1CN1C[C@H]2C[C@H](Nc3ccc(-c4cc(F)ccc4Cl)nn3)C[C@H]2C1] | 453.5 |
| 175 | (3aR,5s,6aS)-N-[6-(2-chloro-5-fluoro-phenyl)pyridazin-3-yl]-2-[(3-fluorophenyl)methyl]-3,3a,4,5,6,6a-hexahydro-1H-cyclopenta[c]pyrrol-5-amine | 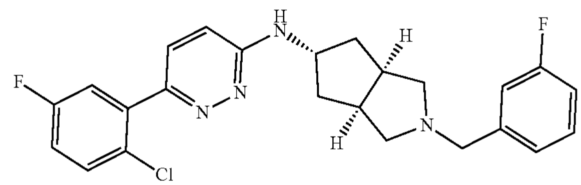 [SMILES: Fc1cccc(CN2C[C@H]3C[C@H](Nc4ccc(-c5cc(F)ccc5Cl)nn4)C[C@H]3C2)c1] | 441.4 |
| 176 | (3aR,5s,6aS)-N-[6-(2-chloro-5-fluoro-phenyl)pyridazin-3-yl]-2-(2-furylmethyl)-3,3a,4,5,6,6a-hexahydro-1H-cyclopenta[c]pyrrol-5-amine | 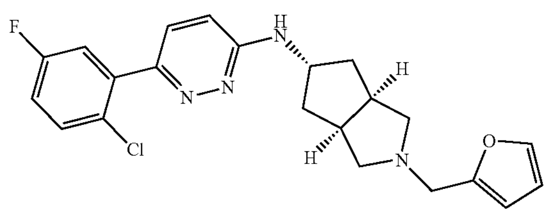 [SMILES: Fc1ccc(Cl)c(-c2ccc(N[C@H]3C[C@@H]4CN(Cc5ccco5)C[C@@H]4C3)nn2)c1] | 413.4 |
| 177 | (3aR,5s,6aS)-N-[6-(2-chloro-5-fluoro-phenyl)pyridazin-3-yl]-2-isobutyl-3,3a,4,5,6,6a-hexahydro-1H-cyclopenta[c]pyrrol-5-amine | 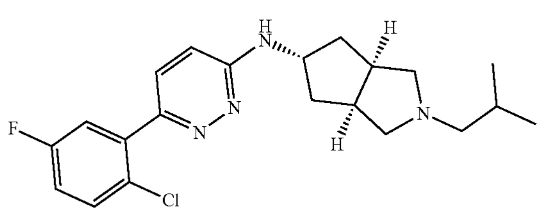 [SMILES: CC(C)CN1C[C@H]2C[C@H](Nc3ccc(-c4cc(F)ccc4Cl)nn3)C[C@H]2C1] | 389.4 |
| 178 | (3aR,5s,6aS)-N-[6-(2-chloro-5-fluoro-phenyl)pyridazin-3-yl]-2-(3-furylmethyl)-3,3a,4,5,6,6a-hexahydro-1H-cyclopenta[c]pyrrol-5-amine | 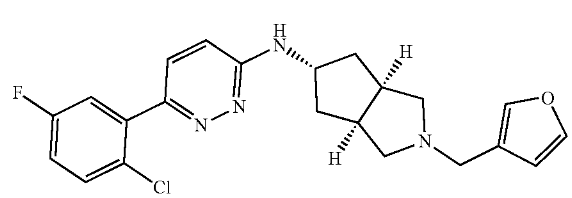 [SMILES: Fc1ccc(Cl)c(-c2ccc(N[C@H]3C[C@@H]4CN(Cc5ccoc5)C[C@@H]4C3)nn2)c1] | 413.4 |

TABLE 8-continued

| Cpd. No. | Name | Structure | ES-MS [M + 1]+ |
|---|---|---|---|
| 179 | (3aR,5s,6aS)-N-(6-chloropyridazin-3-yl)-2-(tetrahydropyran-4-ylmethyl)-3,3a,4,5,6,6a-hexahydro-1H-cyclopenta[c]pyrrol-5-amine | 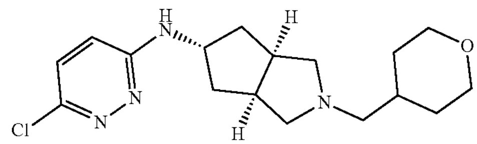 [SMILES: Clc1ccc(N[C@H]2C[C@@H]3CN(CC4CCOCC4)C[C@@H]3C2)nn1] | 337.2 |
| 180 | N-[4-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]phenyl]acetamide | 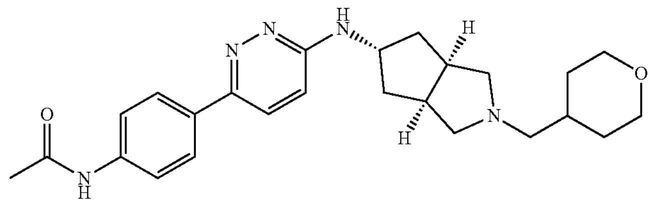 [SMILES: CC(=O)Nc1ccc(-c2ccc(N[C@H]3C[C@@H]4CN(CC5CCOCC5)C[C@@H]4C3)nn2)cc1] | 436.2 |
| 181 | (3aR,5s,6aS)-N-[6-(6-quinolyl)pyridazin-3-yl]-2-(tetrahydropyran-4-ylmethyl)-3,3a,4,5,6,6a-hexahydro-1H-cyclopenta[c]pyrrol-5-amine | 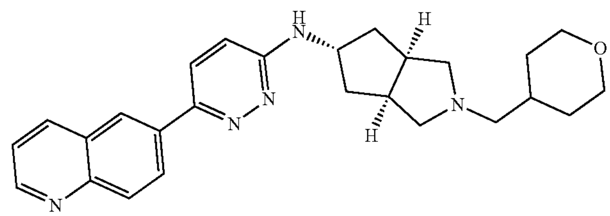 [SMILES: c1cnc2ccc(-c3ccc(N[C@H]4C[C@@H]5CN(CC6CCOCC6)C[C@@H]5C4)nn3)cc2c1] | 430.2 |
| 182 | (3aR,5s,6aS)-N-[6-(1,3-benzodioxol-5-yl)pyridazin-3-yl]-2-(tetrahydropyran-4-ylmethyl)-3,3a,4,5,6,6a-hexahydro-1H-cyclopenta[c]pyrrol-5-amine | 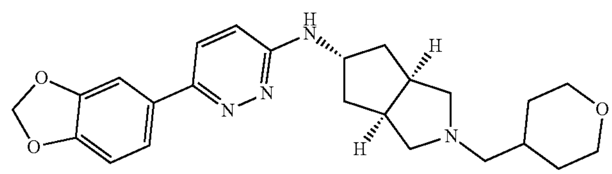 [SMILES: c1cc2c(cc1-c1ccc(N[C@H]3C[C@@H]4CN(CC5CCOCC5)C[C@@H]4C3)nn1)OCO2] | 423.2 |
| 183 | (3aR,5s,6aS)-N-(6-imidazo[1,2-a]pyridin-6-ylpyridazin-3-yl)-2-(tetrahydropyran-4-ylmethyl)-3,3a,4,5,6,6a-hexahydro-1H-cyclopenta[c]pyrrol-5-amine | 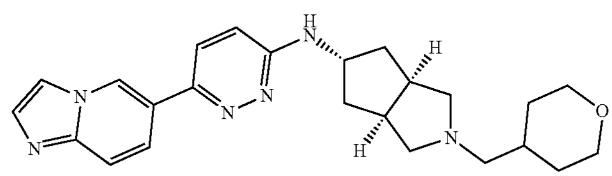 [SMILES: c1cn2cc(-c3ccc(N[C@H]4C[C@@H]5CN(CC6CCOCC6)C[C@@H]5C4)nn3)ccc2n1] | 419.2 |
| 184 | (3aR,5s,6aS)-2-(tetrahydropyran-4-ylmethyl)-N-[6-[4-(trifluoromethoxy)phenyl]pyridazin-3-yl]-3,3a,4,5,6,6a-hexahydro-1H-cyclopenta[c]pyrrol-5-amine | 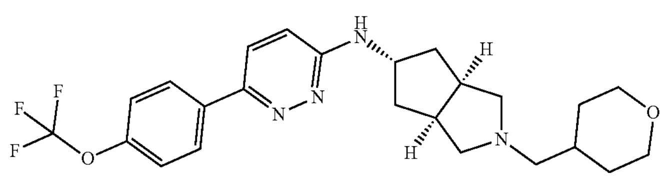 [SMILES: FC(F)(F)Oc1ccc(-c2ccc(N[C@H]3C[C@@H]4CN(CC5CCOCC5)C[C@@H]4C3)nn2)cc1] | 463.2 |
| 185 | (3aR,5s,6aS)-N-[6-(2-fluorophenyl)pyridazin-3-yl]-2-(tetrahydropyran-4-ylmethyl)-3,3a,4,5,6,6a-hexahydro-1H-cyclopenta[c]pyrrol-5-amine | 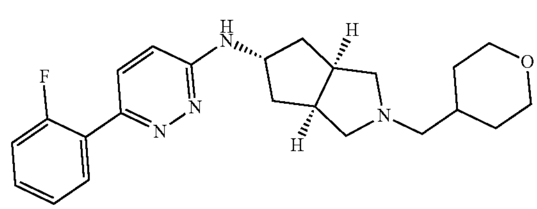 [SMILES: Fc1ccccc1-c1ccc(N[C@H]2C[C@@H]3CN(CC4CCOCC4)C[C@@H]3C2)nn1] | 397.2 |
| 186 | (3aR,5s,6aS)-N-[6-(3-fluorophenyl)pyridazin-3-yl]-2-(tetrahydropyran-4-ylmethyl)-3,3a,4,5,6,6a-hexahydro-1H-cyclopenta[c]pyrrol-5-amine | 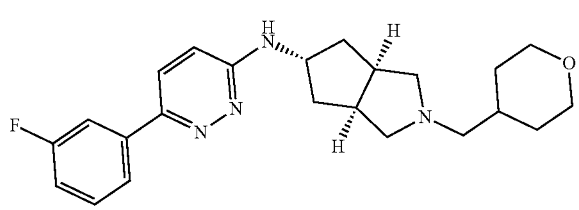 [SMILES: Fc1cccc(-c2ccc(N[C@H]3C[C@@H]4CN(CC5CCOCC5)C[C@@H]4C3)nn2)c1] | 397.2 |

TABLE 8-continued

| Cpd. No. | Name | Structure | ES-MS [M + 1]+ |
|---|---|---|---|
| 187 | (3aR,5s,6aS)-N-[6-(4-fluorophenyl)pyridazin-3-yl]-2-(tetrahydropyran-4-ylmethyl)-3,3a,4,5,6,6a-hexahydro-1H-cyclopenta[c]pyrrol-5-amine | 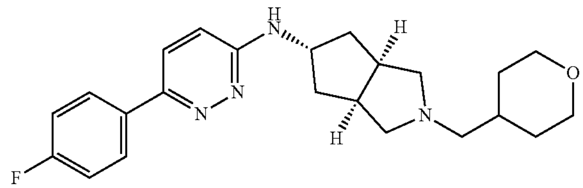 [SMILES: Fc1ccc(-c2ccc(N[C@H]3C[C@@H]4CN(CC5CCOCC5)C[C@@H]4C3)nn2)cc1] | 39.72 |
| 188 | (3aR,5s,6aS)-N-[6-(2-furyl)pyridazin-3-yl]-2-(tetrahydropyran-4-ylmethyl)-3,3a,4,5,6,6a-hexahydro-1H-cyclopenta[c]pyrrol-5-amine | 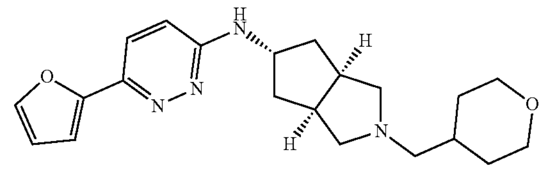 [SMILES: c1coc(-c2ccc(N[C@H]3C[C@@H]4CN(CC5CCOCC5)C[C@@H]4C3)nn2)c1] | 369.2 |
| 189 | (3aR,5s,6aS)-N-[6-(3,3-difluoropyrrolidin-1-yl)pyridazin-3-yl]-2-(tetrahydropyran-4-ylmethyl)-3,3a,4,5,6,6a-hexahydro-1H-cyclopenta[c]pyrrol-5-amine | 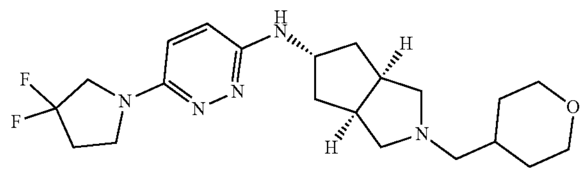 [SMILES: FC1(F)CCN(c2ccc(N[C@H]3C[C@@H]4CN(CC5CCOCC5)C[C@@H]4C3)nn2)C1] | 408.2 |
| 190 | (3aR,5s,6aS)-N-[6-(4,4-difluoro-1-piperidyl)pyridazin-3-yl]-2-(tetrahydropyran-4-ylmethyl)-3,3a,4,5,6,6a-hexahydro-1H-cyclopenta[c]pyrrol-5-amine | 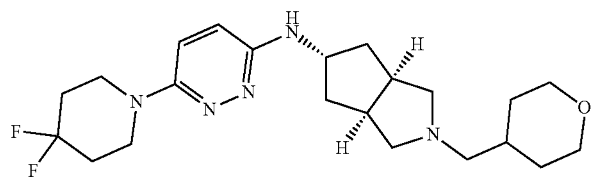 [SMILES: FC1(F)CCN(c2ccc(N[C@H]3C[C@@H]4CN(CC5CCOCC5)C[C@@H]4C3)nn2)CC1] | 422.2 |
| 191 | (3aR,5s,6aS)-N-(6-morpholinopyridazin-3-yl)-2-(tetrahydropyran-4-ylmethyl)-3,3a,4,5,6,6a-hexahydro-1H-cyclopenta[c]pyrrol-5-amine | 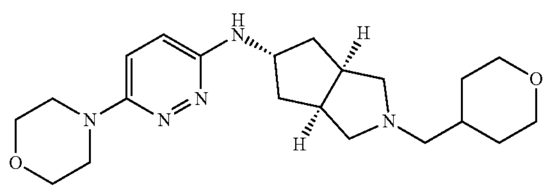 [SMILES: c1cc(N2CCOCC2)nnc1N[C@H]1C[C@@H]2CN(CC3CCOCC3)C[C@@H]2C1] | 388.4 |
| 192 | (3aR,5s,6aS)-N-(6-pyrrolidin-1-ylpyridazin-3-yl)-2-(tetrahydropyran-4-ylmethyl)-3,3a,4,5,6,6a-hexahydro-1H-cyclopenta[c]pyrrol-5-amine | 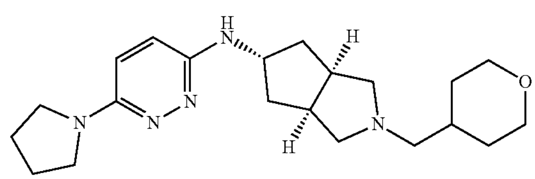 [SMILES: c1cc(N2CCCC2)nnc1N[C@H]1C[C@@H]2CN(CC3CCOCC3)C[C@@H]2C1] | 372.5 |
| 193 | (3aR,5s,6aS)-N-[6-(1-piperidyl)pyridazin-3-yl]-2-(tetrahydropyran-4-ylmethyl)-3,3a,4,5,6,6a-hexahydro-1H-cyclopenta[c]pyrrol-5-amine | 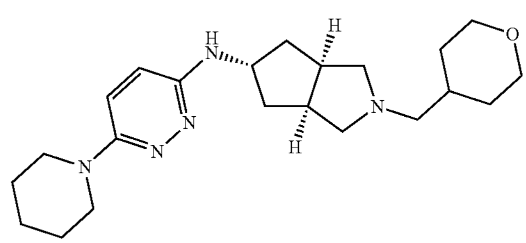 [SMILES: c1cc(N2CCCCC2)nnc1N[C@H]1C[C@@H]2CN(CC3CCOCC3)C[C@@H]2C1] | 386.3 |
| 194 | (3aR,5s,6aS)-N-[6-[(3S)-3-fluoropyrrolidin-1-yl]pyridazin-3-yl]-2-(tetrahydropyran-4-ylmethyl)-3,3a,4,5,6,6a-hexahydro-1H-cyclopenta[c]pyrrol-5-amine | 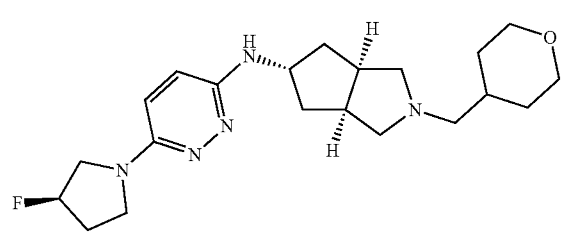 [SMILES: F[C@@H]1CCN(c2ccc(N[C@H]3C[C@@H]4CN(CC5CCOCC5)C[C@@H]4C3)nn2)C1] | 390.2 |

TABLE 8-continued

| Cpd. No. | Name | Structure | ES-MS [M + 1]+ |
|---|---|---|---|
| 195 | (3aR,5s,6aS)-N-[6-[(3R)-3-fluoropyrrolidin-1-yl]pyridazin-3-yl]-2-(tetrahydropyran-4-ylmethyl)-3,3a,4,5,6,6a-hexahydro-1H-cyclopenta[c]pyrrol-5-amine | 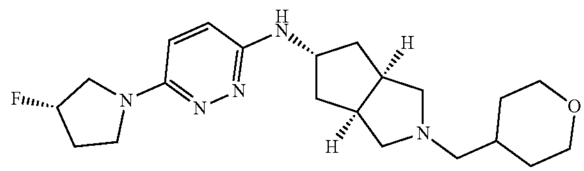 [SMILES: F[C@H]1CCN(c2ccc(N[C@H]3C[C@@H]4CN(CC5CCOCC5)C[C@@H]4C3)nn2)C1] | 390.2 |
| 196 | (3aR,5s,6aS)-N-[6-(3,3-difluoro-1-piperidyl)pyridazin-3-yl]-2-(tetrahydropyran-4-ylmethyl)-3,3a,4,5,6,6a-hexahydro-1H-cyclopenta[c]pyrrol-5-amine | 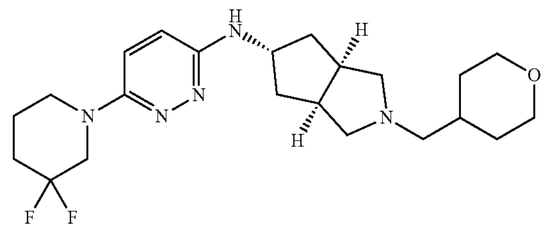 [SMILES: FC1(F)CCCN(c2ccc(N[C@H]3C[C@@H]4CN(CC5CCOCC5)C[C@@H]4C3)nn2)C1] | 422.2 |
| 197 | (3aR,5s,6aS)-N-(6-phenylpyridazin-3-yl)-2-(tetrahydropyran-4-ylmethyl)-3,3a,4,5,6,6a-hexahydro-1H-cyclopenta[c]pyrrol-5-amine | 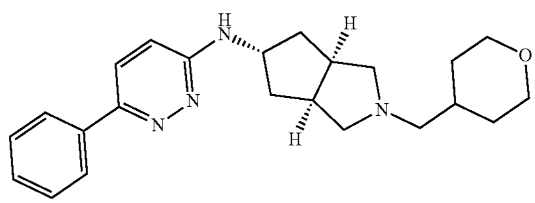 [SMILES: c1ccc(-c2ccc(N[C@H]3C[C@@H]4CN(CC5CCOCC5)C[C@@H]4C3)nn2)cc1] | 379.4 |
| 198 | (3aR,5s,6aS)-N-[6-(p-tolyl)pyridazin-3-yl]-2-(tetrahydropyran-4-ylmethyl)-3,3a,4,5,6,6a-hexahydro-1H-cyclopenta[c]pyrrol-5-amine | 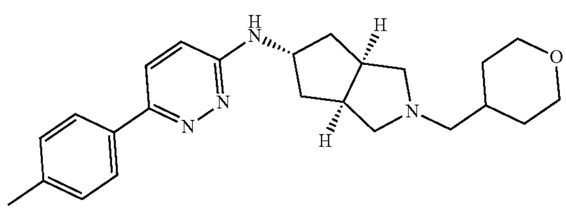 [SMILES: Cc1ccc(-c2ccc(N[C@H]3C[C@@H]4CN(CC5CCOCC5)C[C@@H]4C3)nn2)cc1] | 393.5 |
| 199 | (3aR,5s,6aS)-N-[6-(2-methoxyphenyl)pyridazin-3-yl]-2-(tetrahydropyran-4-ylmethyl)-3,3a,4,5,6,6a-hexahydro-1H-cyclopenta[c]pyrrol-5-amine | 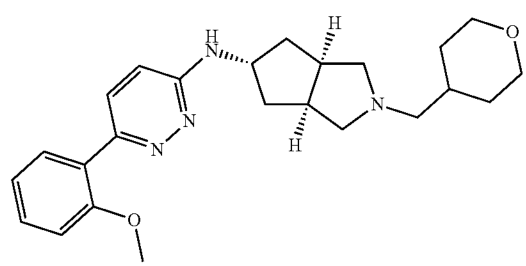 [SMILES: COc1ccccc1-c1ccc(N[C@H]2C[C@@H]3CN(CC4CCOCC4)C[C@@H]3C2)nn1] | 409.5 |
| 200 | (3aR,5s,6aS)-N-[6-(3-methoxyphenyl)pyridazin-3-yl]-2-(tetrahydropyran-4-ylmethyl)-3,3a,4,5,6,6a-hexahydro-1H-cyclopenta[c]pyrrol-5-amine | 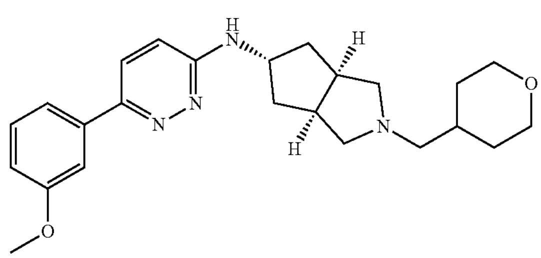 [SMILES: COc1cccc(-c2ccc(N[C@H]3C[C@@H]4CN(CC5CCOCC5)C[C@@H]4C3)nn2)c1] | 409.5 |

TABLE 8-continued

| Cpd. No. | Name | Structure | ES-MS [M + 1]+ |
|---|---|---|---|
| 201 | (3aR,5s,6aS)-N-[6-(4-methoxyphenyl)pyridazin-3-yl]-2-(tetrahydropyran-4-ylmethyl)-3,3a,4,5,6,6a-hexahydro-1H-cyclopenta[c]pyrrol-5-amine | 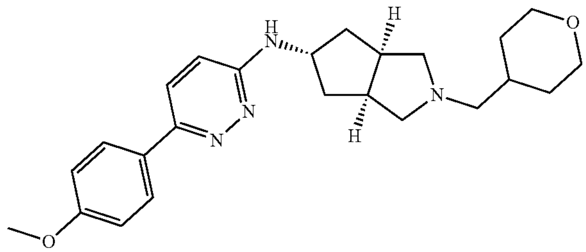 [SMILES: COc1ccc(-c2ccc(N[C@H]3C[C@@H]4CN(CC5CCOCC5)C[C@@H]4C3)nn2)cc1] | 409.3 |
| 202 | (3aR,5s,6aS)-N-[6-(2-chloro-3-fluoro-phenyl)pyridazin-3-yl]-2-(tetrahydropyran-4-ylmethyl)-3,3a,4,5,6,6a-hexahydro-1H-cyclopenta[c]pyrrol-5-amine | 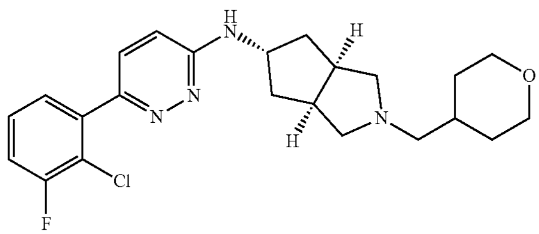 [SMILES: Fc1cccc(-c2ccc(N[C@H]3C[C@@H]4CN(CC5CCOCC5)C[C@@H]4C3)nn2)c1Cl] | 431.4 |
| 203 | (3aR,5s,6aS)-N-[6-(2-chloro-4-fluoro-phenyl)pyridazin-3-yl]-2-(tetrahydropyran-4-ylmethyl)-3,3a,4,5,6,6a-hexahydro-1H-cyclopenta[c]pyrrol-5-amine | 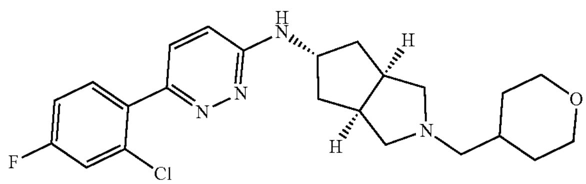 [SMILES: Fc1ccc(-c2ccc(N[C@H]3C[C@@H]4CN(CC5CCOCC5)C[C@@H]4C3)nn2)c(Cl)c1] | 431.4 |
| 204 | (3aR,5s,6aS)-N-[6-(2-chloro-6-fluoro-phenyl)pyridazin-3-yl]-2-(tetrahydropyran-4-ylmethyl)-3,3a,4,5,6,6a-hexahydro-1H-cyclopenta[c]pyrrol-5-amine | 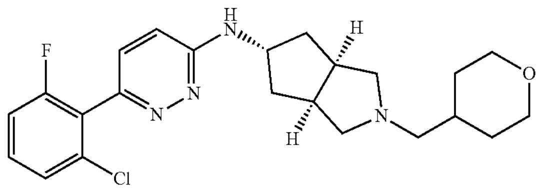 [SMILES: Fc1cccc(Cl)c1-c1ccc(N[C@H]2C[C@@H]3CN(CC4CCOCC4)C[C@@H]3C2)nn1] | 431.4 |
| 205 | (3aR,5s,6aS)-N-[6-(2-chlorophenyl)pyridazin-3-yl]-2-(tetrahydropyran-4-ylmethyl)-3,3a,4,5,6,6a-hexahydro-1H-cyclopenta[c]pyrrol-5-amine | 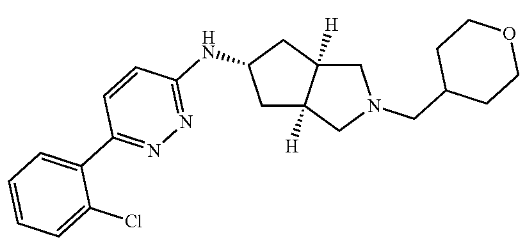 [SMILES: Clc1ccccc1-c1ccc(N[C@H]2C[C@@H]3CN(CC4CCOCC4)C[C@@H]3C2)nn1] | 413.5 |
| 206 | N-[2-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]phenyl]acetamide | 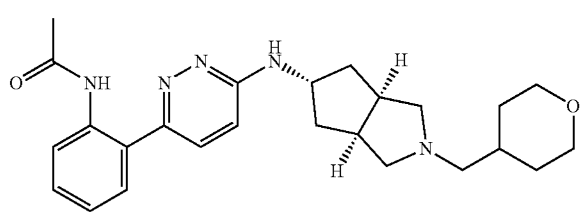 [SMILES: CC(=O)Nc1ccccc1-c1ccc(N[C@H]2C[C@@H]3CN(CC4CCOCC4)C[C@@H]3C2)nn1] | 436.4 |

TABLE 8-continued

| Cpd. No. | Name | Structure | ES-MS [M + 1]+ |
|---|---|---|---|
| 207 | 4-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]-N,N-dimethyl-benzamide | 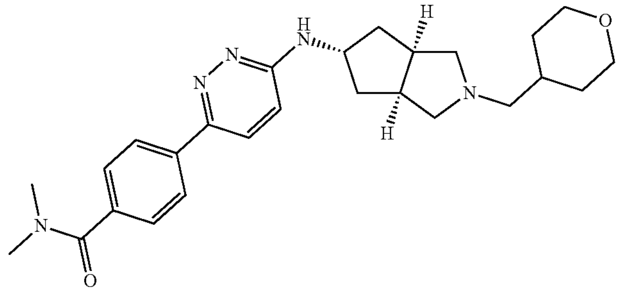 [SMILES: CN(C)C(=O)c1ccc(-c2ccc(N[C@H]3C[C@@H]4CN(CC5CCOCC5)C[C@@H]4C3)nn2)cc1] | 450.2 |
| 208 | (3aR,5s,6aS)-N-[6-(1-methylpyrazol-4-yl)pyridazin-3-yl]-2-(tetrahydropyran-4-ylmethyl)-3,3a,4,5,6,6a-hexahydro-1H-cyclopenta[c]pyrrol-5-amine | 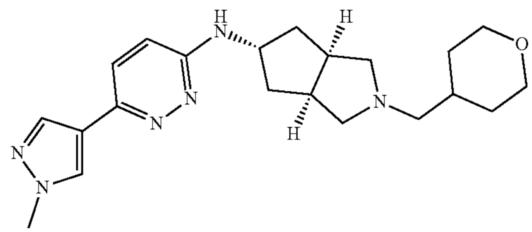 [SMILES: Cn1cc(-c2ccc(N[C@H]3C[C@@H]4CN(CC5CCOCC5)C[C@@H]4C3)nn2)cn1] | 383.2 |
| 209 | (3aR,5s,6aS)-N-[6-(1-cyclopropylpyrazol-4-yl)pyridazin-3-yl]-2-(tetrahydropyran-4-ylmethyl)-3,3a,4,5,6,6a-hexahydro-1H-cyclopenta[c]pyrrol-5-amine | 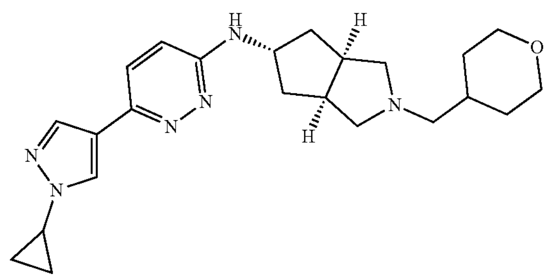 [SMILES: c1nn(C2CC2)cc1-c1ccc(N[C@H]2C[C@@H]3CN(CC4CCOCC4)C[C@@H]3C2)nn1] | 409.3 |
| 210 | (3aR,5s,6aS)-N-[6-(3,5-dimethylisoxazol-4-yl)pyridazin-3-yl]-2-(tetrahydropyran-4-ylmethyl)-3,3a,4,5,6,6a-hexahydro-1H-cyclopenta[c]pyrrol-5-amine | 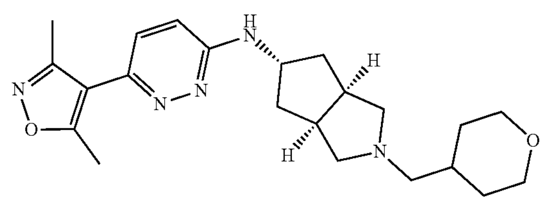 [SMILES: Cc1noc(C)c1-c1ccc(N[C@H]2C[C@@H]3CN(CC4CCOCC4)C[C@@H]3C2)nn1] | 398.2 |
| 211 | (3aR,5s,6aS)-2-(tetrahydropyran-4-ylmethyl)-N-[6-[6-(trifluoromethyl)-3-pyridyl]pyridazin-3-yl]-3,3a,4,5,6,6a-hexahydro-1H-cyclopenta[c]pyrrol-5-amine | 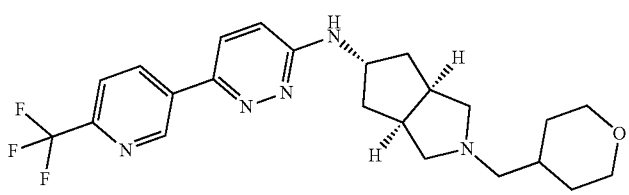 [SMILES: FC(F)(F)c1ccc(-c2ccc(N[C@H]3C[C@@H]4CN(CC5CCOCC5)C[C@@H]4C3)nn2)cn1] | 448.2 |
| 212 | (3aR,5s,6aS)-N-[6-(5-fluoro-2-methoxy-phenyl)pyridazin-3-yl]-2-(tetrahydropyran-4-ylmethyl)-3,3a,4,5,6,6a-hexahydro-1H-cyclopenta[c]pyrrol-5-amine | 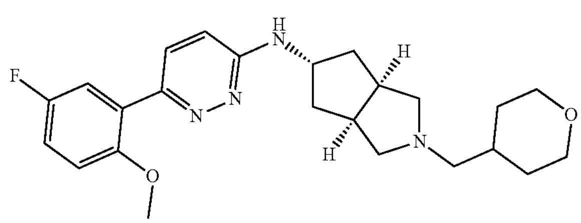 [SMILES: COc1ccc(F)cc1-c1ccc(N[C@H]2C[C@@H]3CN(CC4CCOCC4)C[C@@H]3C2)nn1] | 427.2 |

TABLE 8-continued

| Cpd. No. | Name | Structure | ES-MS [M + 1]+ |
|---|---|---|---|
| 213 | 2-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]-4-fluoro-benzonitrile | 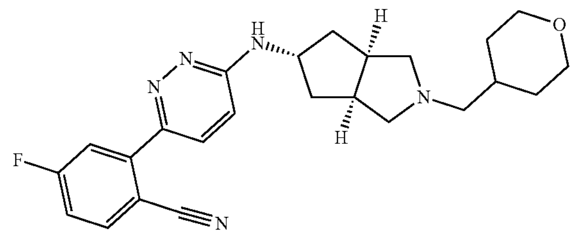 [SMILES: N#Cc1ccc(F)cc1-c1ccc(N[C@H]2C[C@@H]3CN(CC4CCOCC4)C[C@@H]3C2)nn1] | 422.2 |
| 214 | (3aR,5s,6aS)-N-[6-(5-fluoro-2-methyl-phenyl)pyridazin-3-yl]-2-(tetrahydropyran-4-ylmethyl)-3,3a,4,5,6,6a-hexahydro-1H-cyclopenta[c]pyrrol-5-amine | 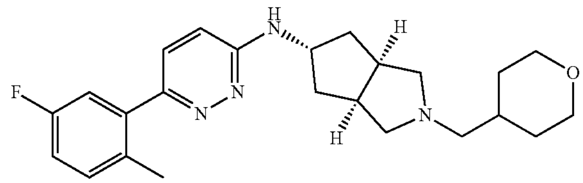 [SMILES: Cc1ccc(F)cc1-c1ccc(N[C@H]2C[C@@H]3CN(CC4CCOCC4)C[C@@H]3C2)nn1] | 411.2 |
| 215 | (3aR,5s,6aS)-N-[6-(2,5-difluorophenyl)pyridazin-3-yl]-2-(tetrahydropyran-4-ylmethyl)-3,3a,4,5,6,6a-hexahydro-1H-cyclopenta[c]pyrrol-5-amine | 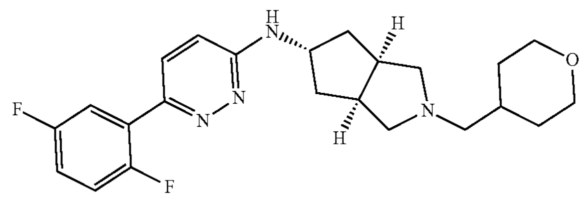 [SMILES: Fc1ccc(F)c(-c2ccc(N[C@H]3C[C@@H]4CN(CC5CCOCC5)C[C@@H]4C3)nn2)c1] | 415.2 |
| 216 | 2-[3-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]phenyl]propan-2-ol | 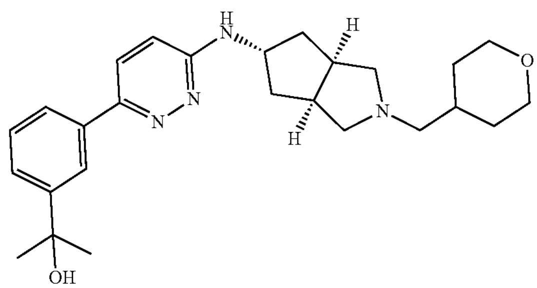 [SMILES: CC(C)(O)c1cccc(-c2ccc(N[C@H]3C[C@@H]4CN(CC5CCOCC5)C[C@@H]4C3)nn2)c1] | 437.2 |
| 217 | N-[3-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]phenyl]methanesulfonamide | 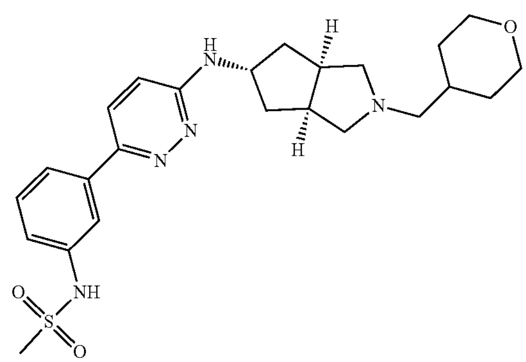 [SMILES: CS(=O)(=O)Nc1cccc(-c2ccc(N[C@H]3C[C@@H]4CN(CC5CCOCC5)C[C@@H]4C3)nn2)c1] | 472.2 |
| 218 | (3aR,5s,6aS)-N-[6-(3-pyridyl)pyridazin-3-yl]-2-(tetrahydropyran-4-ylmethyl)-3,3a,4,5,6,6a-hexahydro-1H-cyclopenta[c]pyrrol-5-amine | 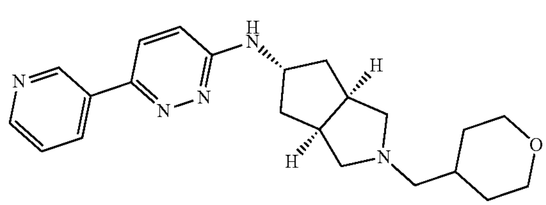 [SMILES: c1cncc(-c2ccc(N[C@H]3C[C@@H]4CN(CC5CCOCC5)C[C@@H]4C3)nn2)c1] | 380.2 |

TABLE 8-continued

| Cpd. No. | Name | Structure | ES-MS [M + 1]+ |
|---|---|---|---|
| 219 | (3aR,5s,6aS)-N-[6-(4-pyridyl)pyridazin-3-yl]-2-(tetrahydropyran-4-ylmethyl)-3,3a,4,5,6,6a-hexahydro-1H-cyclopenta[c]pyrrol-5-amine | 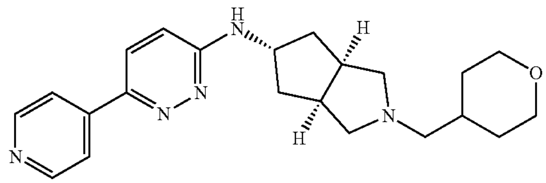 [SMILES: c1cc(-c2ccc(N[C@H]3C[C@@H]4CN(CC5CCOCC5)C[C@@H]4C3)nn2)ccn1] | 380.3 |
| 220 | (3aR,5s,6aS)-N-[6-(2-chloro-5-fluoro-3-pyridyl)pyridazin-3-yl]-2-(tetrahydropyran-4-ylmethyl)-3,3a,4,5,6,6a-hexahydro-1H-cyclopenta[c]pyrrol-5-amine | 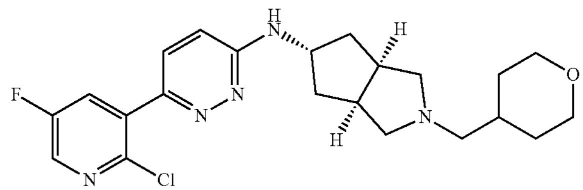 [SMILES: Fc1cnc(Cl)c(-c2ccc(N[C@H]3C[C@@H]4CN(CC5CCOCC5)C[C@@H]4C3)nn2)c1] | 432.2 |
| 221 | (3aR,5s,6aS)-N-[6-(2-methylindazol-5-yl)pyridazin-3-yl]-2-(tetrahydropyran-4-ylmethyl)-3,3a,4,5,6,6a-hexahydro-1H-cyclopenta[c]pyrrol-5-amine | 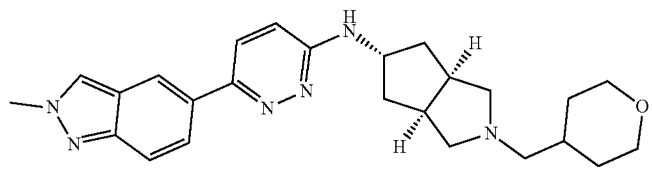 [SMILES: Cn1cc2cc(-c3ccc(N[C@H]4C[C@@H]5CN(CC6CCOCC6)C[C@@H]5C4)nn3)ccc2n1] | 433.2 |
| 222 | (3aR,5s,6aS)-N-[6-(3-fluoro-4-methoxy-phenyl)pyridazin-3-yl]-2-(tetrahydropyran-4-ylmethyl)-3,3a,4,5,6,6a-hexahydro-1H-cyclopenta[c]pyrrol-5-amine | 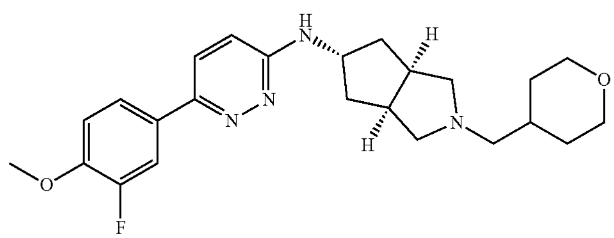 [SMILES: COc1ccc(-c2ccc(N[C@H]3C[C@@H]4CN(CC5CCOCC5)C[C@@H]4C3)nn2)cc1F] | 427.5 |
| 223 | (3aR,5s,6aS)-N-[6-[4-(difluoromethoxy)phenyl]pyridazin-3-yl]-2-(tetrahydropyran-4-ylmethyl)-3,3a,4,5,6,6a-hexahydro-1H-cyclopenta[c]pyrrol-5-amine | 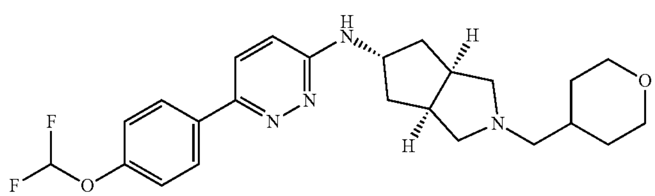 [SMILES: FC(F)Oc1ccc(-c2ccc(N[C@H]3C[C@@H]4CN(CC5CCOCC5)C[C@@H]4C3)nn2)cc1] | 445.4 |
| 224 | (3aR,5s,6aS)-N-[6-(6-methoxy-3-pyridyl)pyridazin-3-yl]-2-(tetrahydropyran-4-ylmethyl)-3,3a,4,5,6,6a-hexahydro-1H-cyclopenta[c]pyrrol-5-amine | 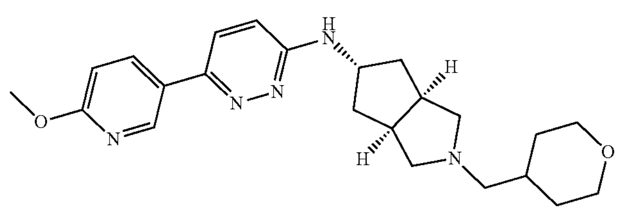 [SMILES: COc1ccc(-c2ccc(N[C@H]3C[C@@H]4CN(CC5CCOCC5)C[C@@H]4C3)nn2)cn1] | 410.4 |
| 225 | (3aR,5s,6aS)-N-[6-(4-fluorophenoxy)pyridazin-3-yl]-2-(tetrahydropyran-4-ylmethyl)-3,3a,4,5,6,6a-hexahydro-1H-cyclopenta[c]pyrrol-5-amine | 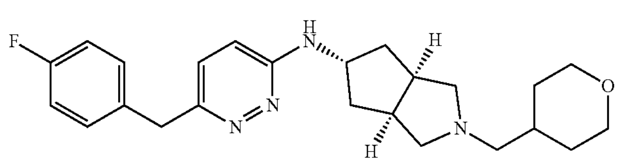 [SMILES: Fc1ccc(Cc2ccc(N[C@H]3C[C@@H]4CN(CC5CCOCC5)C[C@@H]4C3)nn2)cc1] | 413.2 |
| 226 | (3aR,5s,6aS)-2-(tetrahydropyran-4-ylmethyl)-N-[6-(2-thienyl)pyridazin-3-yl]-3,3a,4,5,6,6a-hexahydro-1H-cyclopenta[c]pyrrol-5-amine | 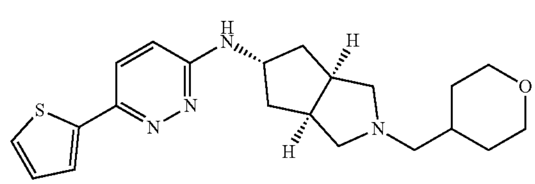 [SMILES: c1csc(-c2ccc(N[C@H]3C[C@@H]4CN(CC5CCOCC5)C[C@@H]4C3)nn2)c1] | 385.5 |

TABLE 8-continued

| Cpd. No. | Name | Structure | ES-MS [M + 1]+ |
|---|---|---|---|
| 227 | (3aR,5s,6aS)-2-(tetrahydropyran-4-ylmethyl)-N-[6-(3-thienyl)pyridazin-3-yl]-3,3a,4,5,6,6a-hexahydro-1H-cyclopenta[c]pyrrol-5-amine | 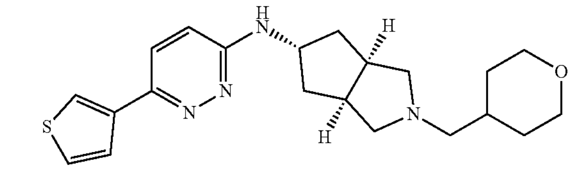 [SMILES: c1cc(-c2ccc(N[C@H]3C[C@@H]4CN(CC5CCOCC5)C[C@@H]4C3)nn2)cs1] | 385.5 |
| 228 | (3aR,5s,6aS)-N-[6-(1-ethylpyrazol-3-yl)pyridazin-3-yl]-2-(tetrahydropyran-4-ylmethyl)-3,3a,4,5,6,6a-hexahydro-1H-cyclopenta[c]pyrrol-5-amine | 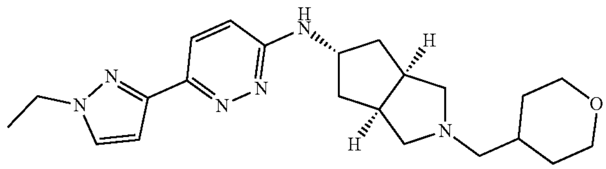 [SMILES: CCn1ccc(-c2ccc(N[C@H]3C[C@@H]4CN(CC5CCOCC5)C[C@@H]4C3)nn2)n1] | 397.5 |
| 229 | (3aR,5s,6aS)-N-[6-(1H-pyrrol-3-yl)pyridazin-3-yl]-2-(tetrahydropyran-4-ylmethyl)-3,3a,4,5,6,6a-hexahydro-1H-cyclopenta[c]pyrrol-5-amine | 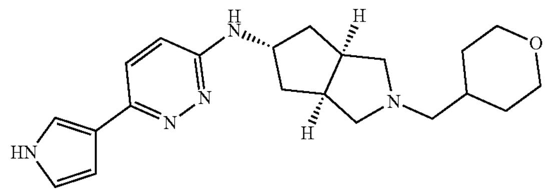 [SMILES: c1cc(-c2ccc(N[C@H]3C[C@@H]4CN(CC5CCOCC5)C[C@@H]4C3)nn2)c[nH]1] | 368.4 |
| 230 | N-[(3aR,5s,6aS)-2-(tetrahydropyran-4-ylmethyl)-3,3a,4,5,6,6a-hexahydro-1H-cyclopenta[c]pyrrol-5-yl]-5-phenyl-thiazol-2-amine | 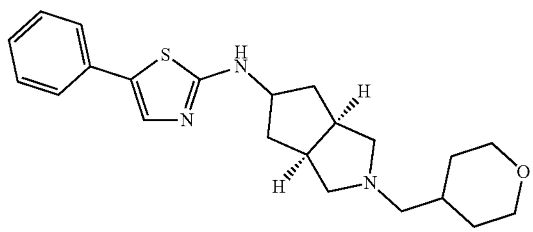 | 384.4 |
| 231 | N-[(3aR,5s,6aS)-2-(4-pyridylmethyl)-3,3a,4,5,6,6a-hexahydro-1H-cyclopenta[c]pyrrol-5-yl]-5-phenyl-thiazol-2-amine | 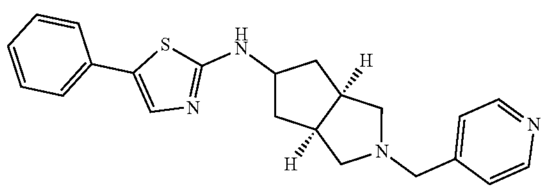 [SMILES: c1ccc(-c2cnc(NC3C[C@@H]4CN(Cc5ccncc5)C[C@@H]4C3)s2)cc1] | 377.2 |
| 232 | (3aR,5s,6aS)-N-[6-(6-cyclopropyl-3-pyridyl)pyridazin-3-yl]-2-(tetrahydropyran-4-ylmethyl)-3,3a,4,5,6,6a-hexahydro-1H-cyclopenta[c]pyrrol-5-amine | 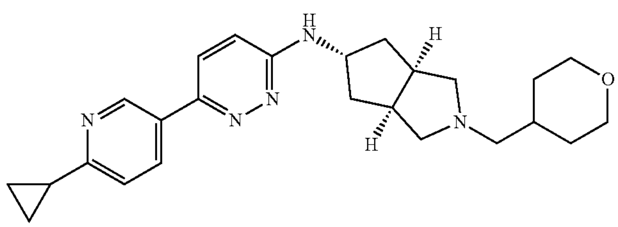 [SMILES: c1cc(C2CC2)ncc1-c1ccc(N[C@H]2C[C@@H]3CN(CC4CCOCC4)C[C@@H]3C2)nn1] | 420.4 |

Biological Activity

A. Cell Lines Expressing Muscarinic Acetylcholine Receptors

Human or rat $M_4$ cDNA, along with the chimeric G protein $G_{qi5}$, were transfected into Chinese hamster ovary (CHO-K1) cells purchased from the American Type Culture Collection using Lipofectamine2000. $M_4/G_{qi5}$/CHO cells were grown in Ham's F-12 medium containing 10% heat-inactivated fetal bovine serum (FBS), 20 mM HEPES, 500 μg/mL G418 sulfate, and 200 μg/mL Hygromycin B.

B. Cell-Based Functional Assay of Muscarinic Acetylcholine Receptor Activity

For high throughput measurement of agonist-evoked increases in intracellular calcium, CHO-K1 cells stably expressing muscarinic receptors were plated in growth medium lacking G418 and hygromycin at 15,000 cells/20 μL/well in Greiner 384-well black-walled, tissue culture (TC)-treated, clear-bottom plates (VWR). Cells were incubated overnight at 37° C. and 5% $CO_2$. The next day, cells were washed using an ELX 405 (BioTek) with assay buffer; the final volume was then aspirated to 20 μL. Next, 20 μL of a 2.3 μM stock of Fluo-4/acetoxymethyl ester (Invitrogen, Carlsbad, Calif.), prepared as a 2.3 mM stock in DMSO and mixed in a 1:1 ratio with 10% (w/v) Pluronic F-127 and diluted in assay buffer, was added to the wells and the cell plates were incubated for 50 min at 37° C. and 5% $C_{O2}$. Dye was removed by washing with the ELX 405 and the final volume was aspirated to 20 μL. Compound master plates were formatted in a 10 point concentration-response curve (CRC) format (1:3 dilutions) in 100% DMSO with a starting concentration of 10 or 1 mM using a BRAVO liquid handler (Agilent). Test compound CRCs were then transferred to daughter plates (240 nL) using the Echo acoustic plate reformatter (Labcyte, Sunnyvale, Calif.) and then diluted into assay buffer (40 µL) to a 2× stock using a Thermo Fisher Combi (Thermo Fisher Scientific, Waltham, Mass.).

Calcium flux was measured using the Functional Drug Screening System (FDSS) 6000 or 7000 (Hamamatsu Corporation, Tokyo, Japan) as an increase in the fluorescent static ratio. Compounds were applied to cells (20 µL, 2×) using the automated system of the FDSS at 2 seconds into the protocol and the data were collected at 1 Hz. At 143 s, 10 µL of an $EC_{20}$ concentration of the muscarinic receptor agonist acetylcholine was added (5×), followed by the addition of 12 µL of an $EC_{80}$ concentration of acetylcholine at the 268 s time point (5×). Agonist activity was analyzed as a concentration-dependent increase in calcium mobilization upon compound addition. Positive allosteric modulator activity was analyzed as a concentration-dependent increase in the $EC_{20}$ acetylcholine response. Antagonist activity was analyzed as a concentration-dependent decrease in the $EC_{80}$ acetylcholine response; for the purposes of the tables herein, an $IC_{50}$ (inhibitory concentration 50) was calculated as a concentration-dependent decrease of the response elicited by an $EC_{80}$ concentration of acetylcholine. Concentration-response curves were generated using a four-parameter logistical equation in XLFit curve fitting software (IDBS, Bridgewater, N.J.) for Excel (Microsoft, Redmond, Wash.) or Prism (GraphPad Software, Inc., San Diego, Calif.) or the Dotmatics software platform (Dotmatics, Bishop's Stortford, UK).

The above described assay was also operated in a second mode where an appropriate fixed concentration of the present compounds were added to the cells after establishment of a fluorescence baseline for about 3 seconds, and the response in cells was measured. 140 s later, a full concentration-response range consisting of increasing concentrations of agonist was added and the calcium response (maximum-local minima response) was measured. The $EC_{50}$ values for the agonist in the presence or absence of test compound were determined by nonlinear curve fitting. A decrease in the $EC_{50}$ value of the agonist with increasing concentrations of the present compounds (a leftward shift of the agonist concentration-response curve) is an indication of the degree of muscarinic positive allosteric modulation at a given concentration of the present compound. An increase in the $EC_{50}$ value of the agonist with increasing concentrations of the present compounds (a rightward shift of the agonist concentration response curve) is an indication of the degree of muscarinic antagonism at a given concentration of the present compound. The second mode also indicates whether the present compounds also affect the maximum response of the muscarinic receptor to agonists.

C. Activity of Compounds in a mAChR $M_4$ Cell-Based Assay

Compounds were synthesized as described above. Activity ($IC_{50}$ and $E_{min}$) was determined in the mAChR $M_4$ cell-based functional assay as described above and the data are shown in Table 9. The compound numbers correspond to the compound numbers used in Examples 1-9 and Tables 1-7.

TABLE 9

| Cpd. No. | Human $M_4$ $IC_{50}$ (nM) | $E_{min}$ (%)* |
|---|---|---|
| 1 | 8.0 | 13.1 |
| 2 | 0.3 | 3.87 |
| 3 | 0.6 | 4.99 |
| 4 | 2.0 | 2.81 |
| 5 | 10.0 | 2.98 |
| 6 | 11.4 | 3.33 |
| 7 | 10.0 | 2.72 |
| 8 | 10.0 | 3.22 |
| 9 | 45.8 | 3.96 |
| 10 | 41.0 | 3.63 |
| 11 | 1.4 | 3.52 |
| 12 | 4.0 | 3.62 |
| 13 | 0.7 | 3.55 |
| 14 | 4.8 | 7.03 |
| 15 | 0.6 | 8.6 |
| 16 | 26.0 | 5.6 |
| 17 | 0.8 | 6.3 |
| 18 | 90.2 | 2.90 |
| 19 | 10.0 | 3.11 |
| 20 | 1.0 | 7.16 |
| 21 | 10.0 | 4.32 |
| 22 | 81.5 | 4.08 |
| 23 | 118 | 3.85 |
| 24 | 37.8 | 5.36 |
| 25 | 193 | 4.92 |
| 26 | 128 | 3.20 |
| 27 | 9.3 | 5.94 |
| 28 | 10.0 | 3.53 |
| 29 | 2.6 | 7.8 |
| 30 | 10.0 | 2.88 |
| 31 | 8.6 | 4.96 |
| 32 | 0.7 | 4.92 |
| 33 | 1.2 | 6.3 |
| 34 | 16.8 | 8.84 |
| 35 | 3.4 | 6.1 |
| 36 | 14.6 | 6.22 |
| 37 | 25.8 | 5.65 |
| 38 | 31.8 | 5.45 |
| 39 | 8278 | 26.8 |
| 40 | ND | ND |
| 41 | 433 | 4.62 |
| 42 | 422 | 4.00 |
| 43 | 1210 | 5.25 |
| 44 | 2145 | 5.01 |
| 45 | 6586 | 12.0 |
| 46 | 1130 | 4.08 |
| 47 | 94.5 | 3.08 |
| 48 | 361 | 3.79 |
| 49 | 272 | 3.17 |
| 50 | 6030 | 15.6 |
| 51 | 7850 | 19.8 |
| 52 | >10 µM | 26.4 |
| 53 | 100 | 3.21 |
| 54 | 222 | 3.07 |
| 55 | 430 | 3.60 |
| 56 | 154 | 3.63 |
| 57 | 3070 | 6.99 |
| 58 | 1460 | 6.11 |
| 59 | >10 µM | 20.7 |
| 60 | >10 µM | 58.2 |
| 61 | 35.6 | 3.12 |
| 62 | 18.9 | 3.32 |
| 63 | 108 | 3.46 |
| 64 | 7.90 | 3.74 |
| 65 | 253 | 4.16 |
| 66 | 3794 | 17.2 |
| 67 | 5305 | 17.2 |
| 68 | 618 | 6.26 |
| 69 | 35.9 | 2.74 |
| 70 | 19.2 | 2.64 |
| 71 | 364 | 3.81 |
| 72 | 201 | 4.02 |
| 73 | 2011 | 9.23 |
| 74 | 263 | 3.37 |
| 75 | 2782 | 3.25 |
| 76 | 1037 | 4.09 |

TABLE 9-continued

| Cpd. No. | Human $M_4$ $IC_{50}$ (nM) | $E_{min}$ (%)* |
|---|---|---|
| 77 | 408 | 3.86 |
| 78 | 105 | 4.35 |
| 79 | 119 | 3.76 |
| 80 | 73.4 | 4.07 |
| 81 | 904 | 4.54 |
| 82 | 538 | 4.50 |
| 83 | 222 | 3.93 |
| 84 | 3088 | 10.9 |
| 85 | 4599 | 14.2 |
| 86 | 2857 | 9.09 |
| 87 | 4006 | 7.39 |
| 88 | 4190 | 9.57 |
| 89 | 8076 | 18.1 |
| 90 | 1427 | 7.98 |
| 91 | 371 | 4.18 |
| 92 | 58.3 | 4.01 |
| 93 | 82.1 | 4.05 |
| 94 | 42.6 | 3.67 |
| 95 | 659 | 4.74 |
| 96 | 301 | 4.62 |
| 97 | 167 | 4.44 |
| 98 | 2232 | 8.70 |
| 99 | 2485 | 7.75 |
| 100 | 2376 | 5.92 |
| 101 | 2535 | 6.60 |
| 102 | 2578 | 6.62 |
| 103 | 9873 | 14.7 |
| 104 | 1531 | 6.78 |
| 105 | 329 | 5.63 |
| 106 | 143 | 3.60 |
| 107 | 1092 | 5.03 |
| 108 | 134 | 3.90 |
| 109 | 583 | 4.62 |
| 110 | 773 | 4.60 |
| 111 | 443 | 3.62 |
| 112 | 609 | 4.59 |
| 113 | 860 | 4.76 |
| 114 | 2501 | 6.02 |
| 115 | 5664 | 9.93 |
| 116 | 3380 | 6.49 |
| 117 | 1462 | 4.82 |
| 118 | 694 | 2.25 |
| 119 | 668 | 4.24 |
| 120 | 2.0 | 3.48 |
| 121 | 47.0 | 3.59 |
| 122 | 27.3 | 4.29 |
| 123 | 6.2 | 2.16 |
| 124 | 20.6 | 3.25 |
| 125 | 28.7 | 4.41 |
| 126 | 23.0 | 3.89 |
| 127 | 57.8 | 4.93 |

*% ACh maximum at 30 μM.

Compounds were synthesized as described above. Activity ($C_{50}$ and $E_{min}$) was determined in the mAChR $M_4$ cell-based functional assay as described above for both human and rat $M_4$ and the data are shown in Table 10. The compound numbers correspond to the compound numbers used in Examples 10-17 and Table 8.

| Cpd. No. | Human $M_4$ | | Rat $M_4$ | |
|---|---|---|---|---|
| | $IC_{50}$ (nM) | $E_{min}$ (%)* | $IC_{50}$ (nM) | $E_{min}$ (%)* |
| 128 | 1090 | 5 | 6330 | 17 |
| 129 | 91.2 | 4 | 195 | 4 |
| 130 | 58.3 | 3 | ND | ND |
| 131 | 977 | 3 | ND | ND |
| 132 | 648 | 6 | 995 | 6 |
| 133 | 1070 | 5 | ND | ND |
| 134 | 17.3 | 4 | ND | ND |
| 135 | 287 | 5 | ND | ND |
| 136 | 174 | 3 | ND | ND |
| 137 | 19.8 | 3 | 313 | 3 |
| 138 | 59.1 | 3 | 382 | 3 |
| 139 | 1560 | 4 | ND | ND |
| 140 | 1.08 | 5 | 17.1 | 3 |
| 141 | 14.8 | 4 | 138 | 3 |
| 142 | 1.82 | 6 | ND | ND |
| 143 | 5020 | 6 | ND | ND |
| 144 | 405 | 5 | ND | ND |
| 145 | 239 | 4 | ND | ND |
| 146 | 167 | 4 | ND | ND |
| 147 | 42.4 | 4 | ND | ND |
| 148 | 997 | 4 | ND | ND |
| 149 | 127 | 4 | ND | ND |
| 150 | 161 | 3 | ND | ND |
| 151 | 77.3 | 3 | ND | ND |
| 152 | 1580 | 8 | ND | ND |
| 153 | 124 | 5 | ND | ND |
| 154 | 30.8 | 4 | ND | ND |
| 155 | 15.9 | 4 | ND | ND |
| 156 | 192 | 5 | ND | ND |
| 157 | 52.9 | 5 | ND | ND |
| 158 | 1090 | 10 | ND | ND |
| 159 | 84.1 | 4 | ND | ND |
| 160 | 4.03 | 3 | ND | ND |
| 161 | 54.1 | 5 | ND | ND |
| 162 | 4.52 | 3 | ND | ND |
| 163 | 19.7 | 3 | ND | ND |
| 164 | 65.0 | 3 | ND | ND |
| 165 | 68.9 | 3 | ND | ND |
| 166 | 6.19 | 2 | ND | ND |
| 167 | 39.1 | 2 | ND | ND |
| 168 | 11.5 | 2 | ND | ND |
| 169 | 18.8 | 3 | ND | ND |
| 170 | 54.3 | 5 | ND | ND |
| 171 | 84.3 | 4 | ND | ND |
| 172 | 42.7 | 3 | ND | ND |
| 173 | 3.32 | 3 | ND | ND |
| 174 | 207 | 4 | ND | ND |
| 175 | 29.7 | 3 | ND | ND |
| 176 | 26.1 | 3 | ND | ND |
| 177 | 5.02 | 3 | ND | ND |
| 178 | 45.1 | 3 | ND | ND |
| 179 | >10 μM | 29 | ND | ND |
| 180 | 1.17 | 8 | ND | ND |
| 181 | 1.42 | 4 | ND | ND |
| 182 | 1.87 | 4 | ND | ND |
| 183 | 1.07 | 7 | ND | ND |
| 184 | 56.7 | 5 | ND | ND |
| 185 | 0.667 | 4 | ND | ND |
| 186 | 3.05 | 5 | ND | ND |
| 187 | 4.60 | 4 | ND | ND |
| 188 | 7.94 | 14 | ND | ND |
| 189 | 2.07 | 8 | ND | ND |
| 190 | 1.67 | 4 | ND | ND |
| 191 | 13.4 | 5 | ND | ND |
| 192 | 40.6 | 6 | ND | ND |
| 193 | 0.8 | 3 | ND | ND |
| 194 | 12.5 | 5 | ND | ND |
| 195 | 9.11 | 4 | ND | ND |
| 196 | 2.09 | 4 | ND | ND |
| 197 | 1.25 | 9 | ND | ND |
| 198 | 3.99 | 6 | ND | ND |
| 199 | 0.579 | 5 | ND | ND |
| 200 | 4.00 | 6 | ND | ND |
| 201 | 3.54 | 7 | ND | ND |
| 202 | 0.517 | 5 | ND | ND |
| 203 | 1.25 | 5 | ND | ND |
| 204 | 0.432 | 4 | ND | ND |
| 205 | 0.365 | 4 | ND | ND |
| 206 | 57.4 | 38 | ND | ND |
| 207 | 44.8 | 16 | ND | ND |
| 208 | 4.14 | 25 | ND | ND |

-continued

| Cpd. No. | Human $M_4$ | | Rat $M_4$ | |
|---|---|---|---|---|
| | $IC_{50}$ (nM) | $E_{min}$ (%)* | $IC_{50}$ (nM) | $E_{min}$ (%)* |
| 209 | 4.41 | 13 | ND | ND |
| 210 | 54.9 | 26 | ND | ND |
| 211 | 85.5 | 24 | ND | ND |
| 212 | 0.486 | 5 | ND | ND |
| 213 | 11.8 | 16 | ND | ND |
| 214 | 0.293 | 4 | ND | ND |
| 215 | 1.40 | 6 | ND | ND |
| 216 | 21.3 | 16 | ND | ND |
| 217 | 7.38 | 16 | ND | ND |
| 218 | 2.77 | 13 | ND | ND |
| 219 | 1.83 | 9 | ND | ND |
| 220 | 0.399 | 4 | ND | ND |
| 221 | 0.270 | 5 | ND | ND |
| 222 | 5.00 | 3 | 63.6 | 6 |
| 223 | 6.39 | 3 | 121 | 6 |
| 224 | 6.93 | 4 | ND | ND |
| 225 | 19.6 | 5 | ND | ND |
| 226 | 22 | 6 | 605 | 14 |
| 227 | 8.4 | 5 | 2230 | 13 |
| 228 | 38 | 28 | ND | ND |
| 229 | 102 | 11 | ND | ND |
| 230 | >10 μM | 41 | ND | ND |
| 231 | >10 μM | 68 | ND | ND |
| 232 | 5.32 | 4 | 490 | 8 |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A compound of formula (I):

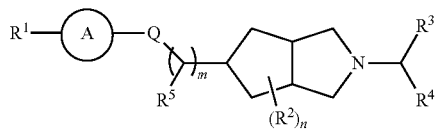

(I)

or a pharmaceutically acceptable salt thereof, wherein:

A is an arylene or a five- or six-membered heteroarylene having 1, 2, or 3 heteroatoms independently selected from N, O, and S;

Q is selected from $NR^a$, O, and $-NR^b-C(O)-$;

m is 0, 1, or 2;

$R^1$ is selected from heteroaryl, aryl, heterocyclyl, cycloalkyl, hydrogen, halo, $-OR^c$, $-NR^dR^e$, and $-NHCOR^f$;

n is 1 or 2;

each $R^2$ is independently selected from hydrogen, $C_1$-$C_4$ alkyl, halo, and $-OR^g$;

$R^3$ is selected from hydrogen and $C_1$-$C_4$ alkyl;

$R^4$ is selected from $-(CR^hR^i)_p-Y'$, hydrogen, $C_1$-$C_8$ alkyl, and $C_2$-$C_8$ alkenyl;

$R^5$ is selected from hydrogen, $C_1$-$C_4$ alkyl, halo, $C_1$-$C_4$ haloalkyl, $C_1$-$C_4$ alkoxy, and $C_1$-$C_4$ haloalkoxy;

Y' is selected from cycloalkyl, cycloalkenyl, heterocycle, aryl, and heteroaryl;

each $R^a$, $R^b$, $R^c$, $R^d$, $R^e$, $R^f$, and $R^g$ is independently selected from hydrogen, $C_1$-$C_4$ alkyl, $C_3$-$C_6$ cycloalkyl, and aryl;

each $R^h$ is independently selected from hydrogen and $C_1$-$C_4$ alkyl;

each $R^i$ is independently selected from hydrogen, $C_1$-$C_4$ alkyl, $C_3$-$C_6$ cycloalkyl, and aryl; and p is 0, 1, 2, 3, or 4;

wherein each aryl, heteroaryl, arylene, heteroarylene, cycloalkyl, cycloalkenyl, and heterocycle is independently unsubstituted or substituted with 1-5 substituents.

Clause 2. The compound of clause 1, or a pharmaceutically acceptable salt thereof, wherein each aryl, heteroaryl, arylene, heteroarylene, cycloalkyl, cycloalkenyl, and heterocycle is independently unsubstituted or substituted with 1, 2, or 3 substituents.

Clause 3. The compound of clause 2, or a pharmaceutically acceptable salt thereof, wherein each aryl, heteroaryl, arylene, heteroarylene, cycloalkyl, cycloalkenyl, and heterocycle is independently unsubstituted or substituted with 1, 2, or 3 substituents independently selected from $C_1$-$C_4$ alkyl, halo, $C_1$-$C_4$ haloalkyl, $C_1$-$C_4$ alkoxy, $C_1$-$C_4$ haloalkoxy, $C_1$-$C_4$ hydroxyalkyl, hydroxy, cyano, $-NHCOR^f$, and benzyl.

Clause 4. The compound of any of clauses 1-3, or a pharmaceutically acceptable salt thereof, wherein A is selected from:

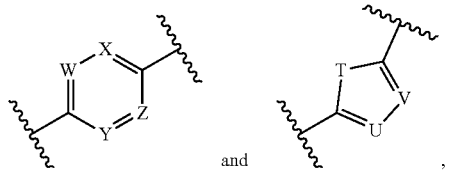

and wherein:

T is selected from O, S and NH;

U, V, W, X, Y and Z are independently selected from N and $CR^j$; and each $R^j$ is independently selected from hydrogen, $C_1$-$C_4$ alkyl, halo, $C_1$-$C_4$ haloalkyl, $C_1$-$C_4$ alkoxy, $C_1$-$C_4$ haloalkoxy, and hydroxy.

Clause 5. The compound of clause 4, or a pharmaceutically acceptable salt thereof, wherein A is

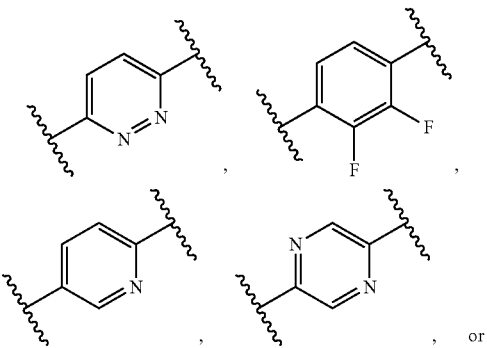

, or

-continued

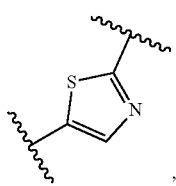

wherein R¹-A- is, respectively,

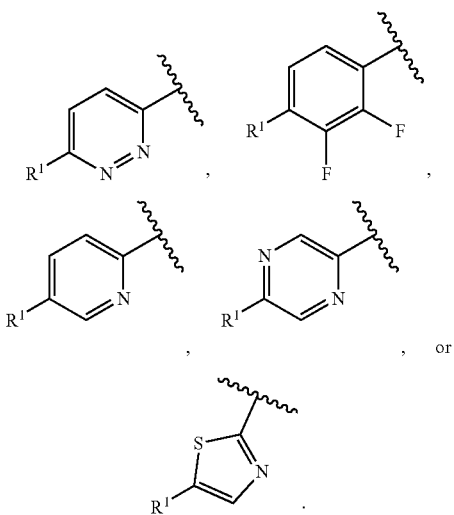

, or

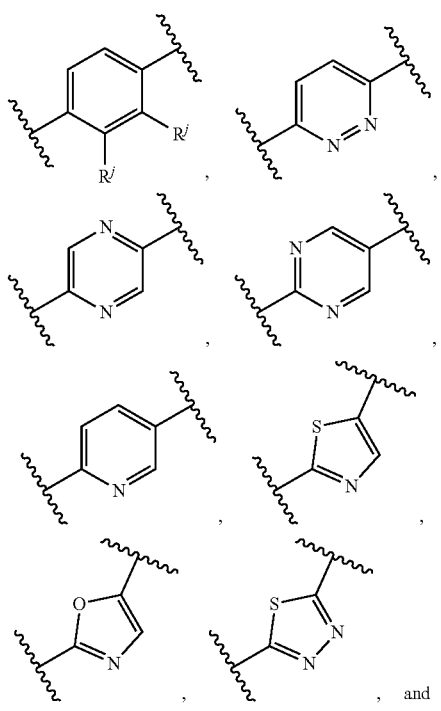

Clause 6. The compound of any of clauses 1-3, or a pharmaceutically acceptable salt thereof, wherein A is selected from:

-continued

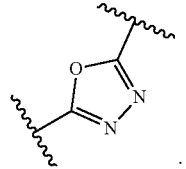

Clause 7. The compound of any one of clauses 1-6, or a pharmaceutically acceptable salt thereof, wherein Q is $NR^a$; and $R^a$ is hydrogen.

Clause 8. The compound of any one of clauses 1-6, or a pharmaceutically acceptable salt thereof, wherein Q is O.

Clause 9. The compound of any one of clauses 1-6, or a pharmaceutically acceptable salt thereof, wherein Q is —$NR^b$—C(O)—; and $R^b$ is hydrogen.

Clause 10. The compound of any one of clauses 1-9, or a pharmaceutically acceptable salt thereof, wherein m is 0.

Clause 11. The compound of any one of clauses 1-9, or a pharmaceutically acceptable salt thereof, wherein m is 1; and $R^5$ is hydrogen.

Clause 12. The compound of any one of clauses 1-9, or a pharmaceutically acceptable salt thereof, wherein m is 2; and each $R^5$ is hydrogen.

Clause 13. The compound of any of clauses 1-12, or a pharmaceutically acceptable salt thereof, wherein $R^1$ is heteroaryl, aryl, heterocyclyl, halo, or —$OR^c$; $R^c$ is $C_1$-$C_4$ alkyl, $C_3$-$C_6$ cycloalkyl, or aryl; wherein the heteroaryl, aryl, heterocyclyl, and cycloalkyl in $R^1$ and/or $R^c$ is optionally substituted with 1-4 substituents independently selected from the group consisting of halo, cyano, $C_1$-$C_4$ alkyl, $C_1$-$C_4$ haloalkyl, —$OR^{10}$, —$NR^{10}R^{10}$, —$NR^{10}COR^{10}$, —$CONR^{10}R^{10}$, —$NR^{10}SO_2R^{11}$, —$C_1$-$C_3$alkylene-$OR^{10}$, $C_3$-$C_6$ cycloalkyl, and —$C_1$-$C_3$alkylene-$C_3$-$C_6$cycloalkyl; $R^{10}$, at each occurrence, is independently hydrogen, $C_1$-$C_4$ alkyl, $C_1$-$C_4$ haloalkyl, $C_3$-$C_6$ cycloalkyl, or —$C_1$-$C_3$alkylene-$C_3$-$C_6$ cycloalkyl; and $R^{11}$, at each occurrence, is independently $C_1$-$C_4$ alkyl, $C_1$-$C_4$ haloalkyl, $C_3$-$C_6$ cycloalkyl, or —$C_1$-$C_3$alkylene-$C_3$-$C_6$ cycloalkyl.

Clause 14. The compound of clause 13, or a pharmaceutically acceptable salt thereof, wherein
$R^1$ is
a) a 5- to 12-membered heteroaryl;
b) a 6- to 12-membered aryl;
c) a 4- to 12-membered heterocyclyl;
d) halo; or
e) —$OR^c$; and
$R^c$ is a 6- to 12-membered aryl;
wherein the heteroaryl, aryl, and heterocyclyl in $R^1$ and/or $R^c$ is optionally substituted as defined in clause 13.

Clause 15. The compound of clause 14, or a pharmaceutically acceptable salt thereof, wherein $R^1$ is a 5- to 6-membered monocyclic heteroaryl or an 8- to 12 membered bicyclic heteroaryl, and $R^1$ is optionally substituted as defined in clause 13.

Clause 16. The compound of clause 15, or a pharmaceutically acceptable salt thereof, wherein $R^1$ is pyrrolyl, pyrazolyl, furanyl, thienyl, isoxazolyl, pyridinyl, or imidazopyridinyl, and $R^1$ is optionally substituted as defined in clause 13.

Clause 17. The compound of clause 15 or 16, or a pharmaceutically acceptable salt thereof, wherein $R^1$ is optionally substituted with 1-3 substituents independently selected from the group consisting of halo, $C_1$-$C_4$ alkyl, $C_1$-$C_4$ haloalkyl, $C_3$-$C_6$ cycloalkyl, and —$OR^{10}$.

Clause 18. The compound of clause 17, or a pharmaceutically acceptable salt thereof, wherein $R^1$ is

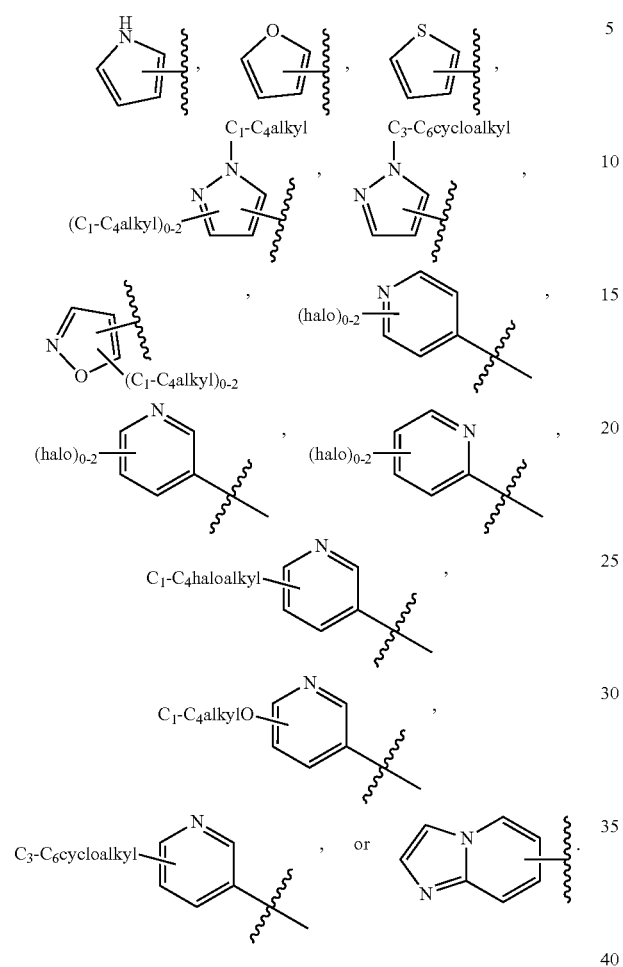

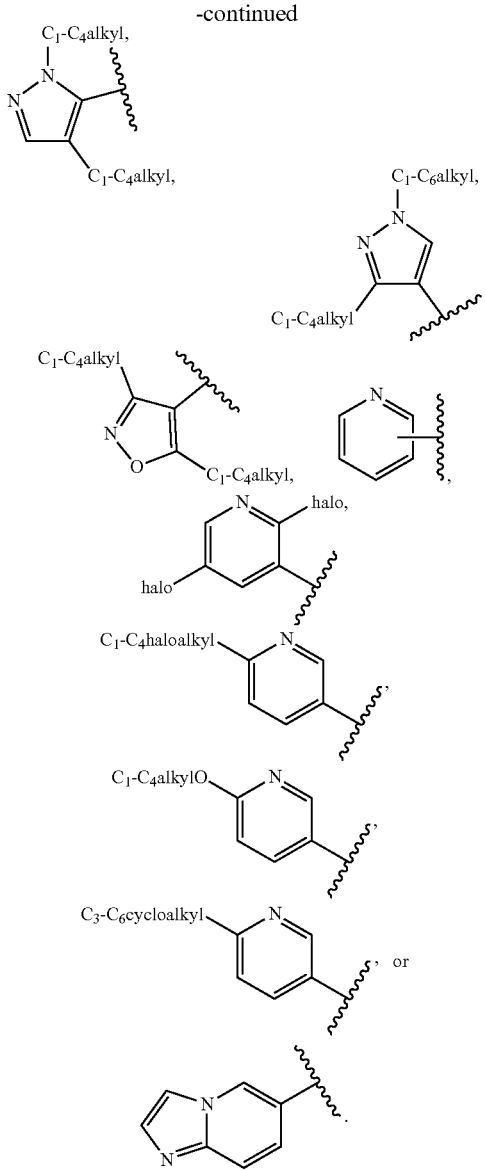

Clause 19. The compound of clause 18, or a pharmaceutically acceptable salt thereof, wherein $R^1$ is

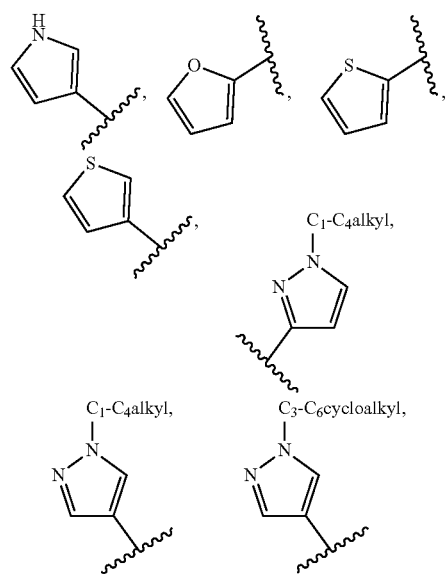

Clause 20. The compound of clause 14, or a pharmaceutically acceptable salt thereof, wherein $R^1$ is phenyl or a 9- to 12-membered aryl, and $R^1$ is optionally substituted as defined in clause 13.

Clause 21. The compound of clause 20, or a pharmaceutically acceptable salt thereof, wherein $R^1$ is phenyl,

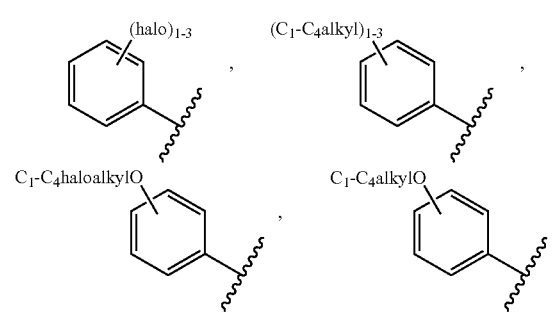

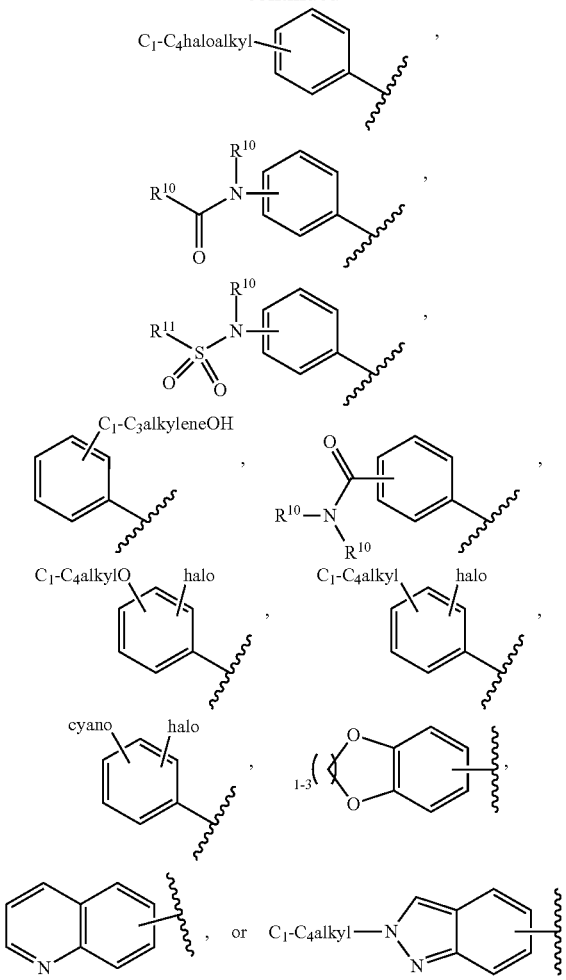
Clause 22. The compound of clause 21, or a pharmaceutically acceptable salt thereof, wherein $R^1$ is phenyl,
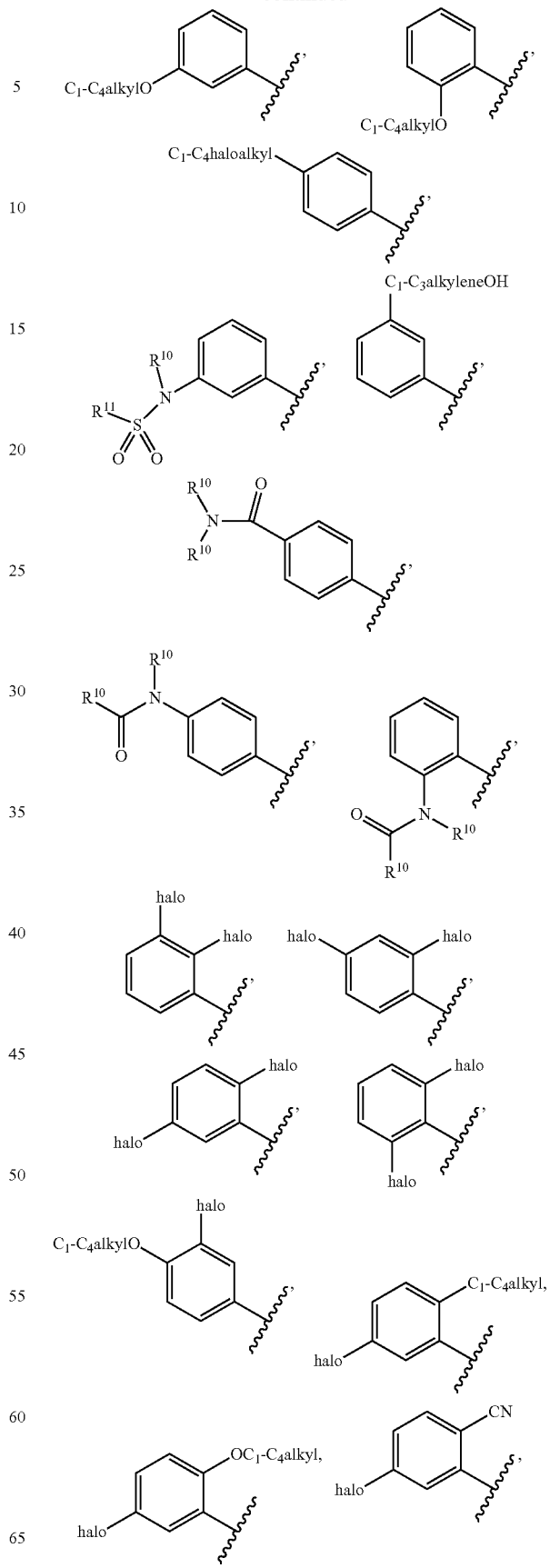

-continued

[structures: benzodioxole, quinoline, and C₁-C₄alkyl-N-indazole]

Clause 23. The compound of clause 14, or a pharmaceutically acceptable salt thereof, wherein $R^1$ is a 4- to 8-membered heterocyclic ring, and optionally substituted as defined in clause 13.

Clause 24. The compound of clause 23, or a pharmaceutically acceptable salt thereof, wherein $R^1$ is a pyrrolindinyl, piperidinyl, or morpholino, optionally with 1-3 substituents independently selected from the group consisting of halo, $C_1$-$C_4$ alkyl, $C_1$-$C_4$ haloalkyl, $C_3$-$C_6$ cycloalkyl, and —$OR^{10}$.

Clause 25. The compound of clause 23, or a pharmaceutically acceptable salt thereof, wherein $R^1$ is

[structures: morpholino and fluoro-substituted pyrrolidinyl]

Clause 26. The compound of clause 14, or a pharmaceutically acceptable salt thereof, wherein $R^1$ is chloro.

Clause 27. The compound of clause 14, or a pharmaceutically acceptable salt thereof, wherein $R^1$ is —OR.

Clause 28. The compound of clause 27, or a pharmaceutically acceptable salt thereof, wherein $R^c$ is phenyl optionally substituted with 1-3 substituents independently selected from the group consisting of halo, cyano, $C_1$-$C_4$ alkyl, $C_1$-$C_4$ haloalkyl, —$OR^{10}$, —$NR^{10}R^{10}$, —$NR^{10}COR^{10}$, —$CONR^{10}R^{10}$, —$NR^{10}SO_2R^{11}$, —$C_1$-$C_3$alkylene-$OR^{10}$, $C_3$-$C_6$ cycloalkyl, and —$C_1$-$C_3$alkylene-$C_3$-$C_6$cycloalkyl.

Clause 29. The compound of any one of clauses 1-12, or a pharmaceutically acceptable salt thereof, wherein $R^1$ is selected from aryl, heteroaryl, heterocyclyl, and cycloalkyl.

Clause 30. The compound of clause 29, or a pharmaceutically acceptable salt thereof, wherein $R^1$ is selected from phenyl and a 5- or 6-membered heteroaryl having 1, 2, or 3 heteroatoms independently selected from N, O, and S; and the phenyl or heteroaryl is unsubstituted or substituted with 1, 2, or 3 substituents independently selected from halo, $C_1$-$C_4$ alkyl, $C_1$-$C_4$ haloalkyl, and —$NHCOR^f$.

Clause 31. The compound of any one of clauses 1-30, or a pharmaceutically acceptable salt thereof, wherein n is 1; and $R^2$ is hydrogen.

Clause 32. The compound of any one of clauses 1-31, or a pharmaceutically acceptable salt thereof, wherein $R^3$ is hydrogen.

Clause 33. The compound of any one of clauses 1-32, or a pharmaceutically acceptable salt thereof, wherein $R^4$ is $C_4$-$C_6$ alkyl.

Clause 34. The compound of any one of clauses 1-32, or a pharmaceutically acceptable salt thereof, wherein $R^4$ is —$(CR^hR^i)_p$—Y';
$R^h$ is hydrogen;
$R^i$ is hydrogen;
p is 0, 1, 2, or 3; and
Y' is selected from: $C_3$-$C_{10}$ cycloalkyl; $C_3$-$C_8$ cycloalkenyl; aryl; a 5- or 6-membered heteroaryl having 1, 2, or 3 heteroatoms independently selected from N, O, and S; and a 5-, 6-, or 7-membered heterocycle having 1, 2, or 3 heteroatoms independently selected from N, O, and S;
wherein Y' is unsubstituted or substituted with one or two substituents independently selected from halo and $C_1$-$C_4$ alkyl.

Clause 35. The compound of any of clauses 1-32, or a pharmaceutically acceptable salt thereof, wherein
$R^4$ is —$(CR^hR^i)_p$—Y';
$R^h$ is hydrogen;
$R^i$ is hydrogen;
p is 0, 1, 2, or 3;
Y' is
a) $C_3$-$C_{10}$ cycloalkyl;
b) $C_3$-$C_8$ cycloalkenyl;
c) a 6- to 12-membered aryl;
d) a 5- to 12-membered heteroaryl; or
e) a 4- to 12-membered heterocyclyl;
wherein Y' is optionally substituted with 1-4 substituents independently selected from the group consisting of halo, $C_1$-$C_4$ alkyl, $C_1$-$C_4$ haloalkyl, —$OR^{12}$, —$NR^{12}R^{12}$, —$NR^{12}COR^{12}$, and —$NR^{12}SO_2R^{13}$;
$R^{12}$ at each occurrence, is independently hydrogen, $C_1$-$C_4$ alkyl, $C_1$-$C_4$ haloalkyl, $C_3$-$C_6$ cycloalkyl, or —$C_1$-$C_3$alkylene-$C_3$-$C_6$ cycloalkyl; and
$R^{13}$ at each occurrence, is independently $C_1$-$C_4$ alkyl, $C_1$-$C_4$ haloalkyl, $C_3$-$C_6$ cycloalkyl, or —$C_1$-$C_3$alkylene-$C_3$-$C_6$ cycloalkyl.

Clause 36. The compound of clause 35, or a pharmaceutically acceptable salt thereof, wherein Y' is a $C_3$-$C_{10}$ cycloalkyl optionally substituted with 1-4 substituents independently selected from the group consisting of halo, $C_1$-$C_4$ alkyl, and $C_1$-$C_4$ haloalkyl.

Clause 37. The compound of clause 35, or a pharmaceutically acceptable salt thereof, wherein Y' is a $C_3$-$C_8$ cycloalkenyl.

Clause 38. The compound of clause 35, or a pharmaceutically acceptable salt thereof, wherein Y' is a phenyl or a 9- to 12-membered aryl, and optionally substituted with 1-4 substituents independently selected from the group consisting of halo, $C_1$-$C_4$ alkyl, $C_1$-$C_4$ haloalkyl, —$OR^{12}$, —$NR^{12}R^{12}$, —$NR^{12}COR^{12}$, and —$NR^{12}SO_2R^{13}$.

Clause 39. The compound of clause 35, or a pharmaceutically acceptable salt thereof, wherein Y' is

[structures: phenyl-halo, phenyl-$OC_1$-$C_4$alkyl, phenyl-$NR^{12}SO_2R^{13}$, or benzodioxole]

Clause 40. The compound of clause 35, or a pharmaceutically acceptable salt thereof, wherein Y' is

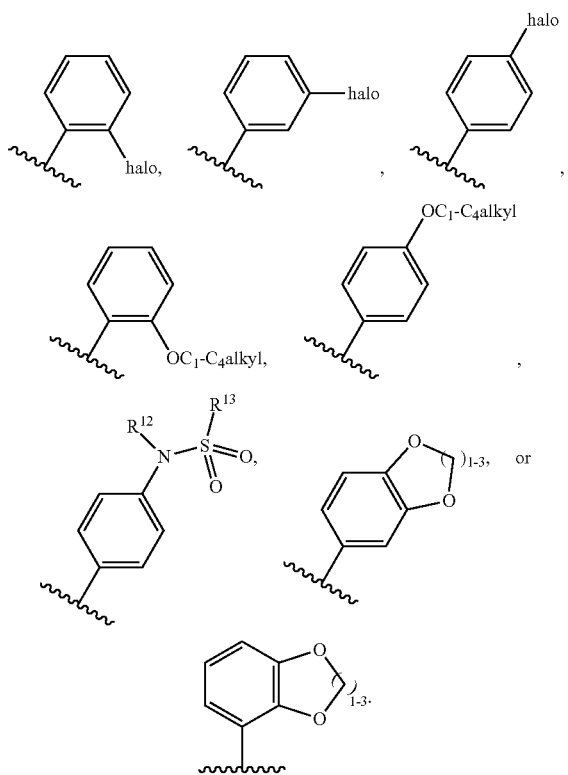

Clause 41. The compound of clause 35, or a pharmaceutically acceptable salt thereof, wherein Y' is a 5- to 6-membered monocyclic heteroaryl or an 8- to 12 membered bicyclic heteroaryl, and optionally substituted with 1-4 substituents independently selected from the group consisting of halo, $C_1$-$C_4$ alkyl, $C_1$-$C_4$ haloalkyl, —$OR^{12}$, —$NR^{12}R^{12}$, —$NR^{12}COR^{12}$, and —$NR^{12}SO_2R^{13}$.

Clause 42. The compound of clause 35, or a pharmaceutically acceptable salt thereof, wherein Y' is

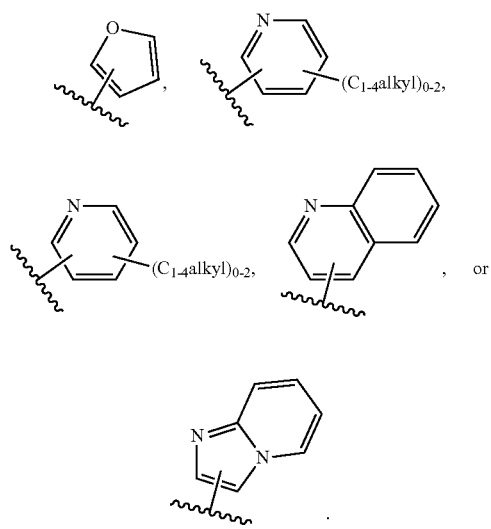

Clause 43. The compound of clause 35, or a pharmaceutically acceptable salt thereof, wherein Y' is

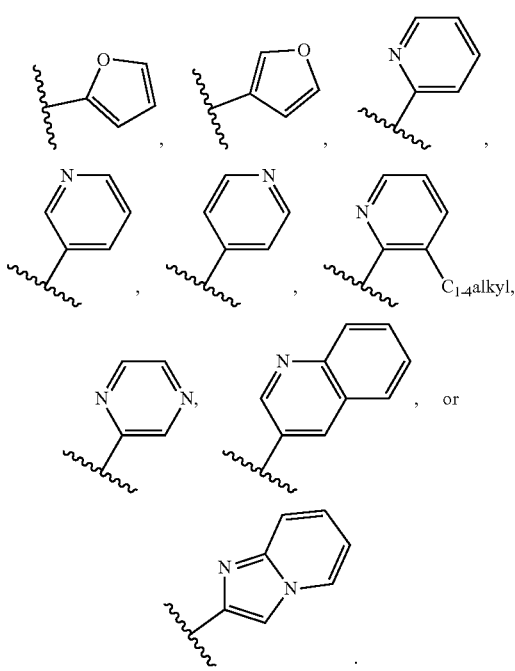

Clause 44. The compound of clause 35, or a pharmaceutically acceptable salt thereof, wherein Y' is 4- to 10-membered monocyclic or bridged bicyclic heterocyclyl containing one oxygen atom and optionally substituted with 1-2 $C_1$-$C_4$alkyl.

Clause 45. The compound of clause 35, or a pharmaceutically acceptable salt thereof, wherein Y' is

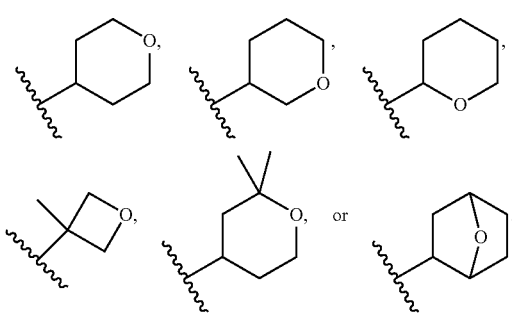

Clause 46. The compound of any of clauses 1-45, wherein the compound is a compound of formula (Ia):

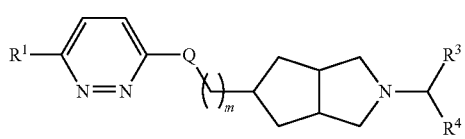

(Ia)

or a pharmaceutically acceptable salt thereof.

Clause 47. The compound of any of clauses 1-45, wherein the compound is a compound of formula (Ib):

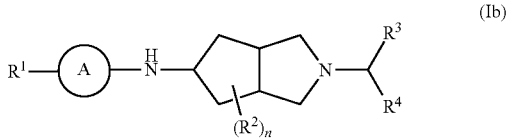

(Ib)

or a pharmaceutically acceptable salt thereof.

Clause 48. The compound of clause 1, wherein the compound is selected from:

(3aR,5s,6aS)-2-(3,3-dimethylbutyl)-N-[6-(2,4-dimethylpyrazol-3-yl)pyridazin-3-yl]-3,3a,4,5,6,6a-hexahydro-1H-cyclopenta[c]pyrrol-5-amine;

(3aR,5s,6aS)-2-(5-bicyclo[2.2.1]hept-2-enylmethyl)-N-[6-(1,3-dimethylpyrazol-4-yl)pyridazin-3-yl]-3,3a,4,5,6,6a-hexahydro-1H-cyclopenta[c]pyrrol-5-amine;

(3aR,5s,6aS)-2-(3,3-dimethylbutyl)-N-[6-(1,3-dimethylpyrazol-4-yl)pyridazin-3-yl]-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-(2,3,3-trimethylbutyl)-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-(tetrahydropyran-3-ylmethyl)-3,3a,4,5,6,6a-hexahydro-1H-cyclopenta[c]pyrrol-5-amine;

(3aR,5s,6aS)-2-(cyclohexylmethyl)-N-[6-(1,3-dimethylpyrazol-4-yl)pyridazin-3-yl]-3,3a,4,5,6,6a-hexahydro-1H-cyclopenta[c]pyrrol-5-amine;

(3aR,5s,6aS)-2-benzyl-N-[6-(1,3-dimethylpyrazol-4-yl)pyridazin-3-yl]-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-(2-pyridylmethyl)-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-[(2-fluorophenyl)methyl]-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-[(3-methyl-2-pyridyl)methyl]-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-(2-phenylethyl)-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-(2-methylbutyl)-3,3a,4,5,6,6a-hexahydro-1H-cyclopenta[c]pyrrol-5-amine;

(3aR,5s,6aS)—N-[6-(1,3-dimethylpyrazol-4-yl)pyridazin-3-yl]-2-(2-methylpentyl)-3,3a,4,5,6,6a-hexahydro-1H-cyclopenta[c]pyrrol-5-amine;

(3aR,5s,6aS)-2-(1,3-benzodioxol-5-ylmethyl)-N-[6-(1,3-dimethylpyrazol-4-yl)pyridazin-3-yl]-3,3a,4,5,6,6a-hexahydro-1H-cyclopenta[c]pyrrol-5-amine;

(3aR,5s,6aS)-2-(1-adamantylmethyl)-N-[6-(2,4-dimethylpyrazol-3-yl)pyridazin-3-yl]-3,3a,4,5,6,6a-hexahydro-1H-cyclopenta[c]pyrrol-5-amine;

(3aR,5s,6aS)-2-(5-bicyclo[2.2.1]hept-2-enylmethyl)-N-[6-(2,4-dimethylpyrazol-3-yl)pyridazin-3-yl]-3,3a,4,5,6,6a-hexahydro-1H-cyclopenta[c]pyrrol-5-amine;

(3aR,5s,6aS)—N-[6-(2,4-dimethylpyrazol-3-yl)pyridazin-3-yl]-2-(2-methylbutyl)-3,3a,4,5,6,6a-hexahydro-1H-cyclopenta[c]pyrrol-5-amine;

(3aR,5s,6aS)—N-[6-(2,4-dimethylpyrazol-3-yl)pyridazin-3-yl]-2-(2-methylpentyl)-3,3a,4,5,6,6a-hexahydro-1H-cyclopenta[c]pyrrol-5-amine;

(3aR,5s,6aS)-2-(cyclohexylmethyl)-N-[6-(2,4-dimethylpyrazol-3-yl)pyridazin-3-yl]-3,3a,4,5,6,6a-hexahydro-1H-cyclopenta[c]pyrrol-5-amine;

(3aR,5s,6aS)—N-[6-(2,4-dimethylpyrazol-3-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2,4-dimethylpyrazol-3-yl)pyridazin-3-yl]-2-(tetrahydropyran-3-ylmethyl)-3,3a,4,5,6,6a-hexahydro-1H-cyclopenta[c]pyrrol-5-amine;

(3aR,5s,6aS)-2-benzyl-N-[6-(2,4-dimethylpyrazol-3-yl)pyridazin-3-yl]-3,3a,4,5,6,6a-hexahydro-1H-cyclopenta[c]pyrrol-5-amine;

(3aR,5s,6aS)—N-[6-(2,4-dimethylpyrazol-3-yl)pyridazin-3-yl]-2-[(3-methyl-2-pyridyl)methyl]-3,3a,4,5,6,6a-hexahydro-1H-cyclopenta[c]pyrrol-5-amine;

(3aR,5s,6aS)—N-[6-(2,4-dimethylpyrazol-3-yl)pyridazin-3-yl]-2-[(2-fluorophenyl)methyl]-3,3a,4,5,6,6a-hexahydro-1H-cyclopenta[c]pyrrol-5-amine;

(3aR,5s,6aS)-2-(1-adamantylmethyl)-N-[6-(2-chloro-5-fluoro-phenyl)pyridazin-3-yl]-3,3a,4,5,6,6a-hexahydro-1H-cyclopenta[c]pyrrol-5-amine;

(3aR,5s,6aS)-2-(5-bicyclo[2.2.1]hept-2-enylmethyl)-N-[6-(2-chloro-5-fluoro-phenyl)pyridazin-3-yl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(3,3-dimethylbutyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(2-methylbutyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(2-methylpentyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(cyclohexylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(tetrahydropyran-3-ylmethyl)-3,3a,4,5,6,6a-hexahydro-1H-cyclopenta[c]pyrrol-5-amine;

(3aR,5s,6aS)-2-benzyl-N-[6-(2-chloro-5-fluoro-phenyl)pyridazin-3-yl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-[(3-methyl-2-pyridyl)methyl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-[(2-fluorophenyl)methyl]-3,3a,4,5,6,6a-hexahydro-1H-cyclopenta[c]pyrrol-5-amine;

(3aR,5s,6aS)-2-(1-adamantylmethyl)-N-[6-(1,3-dimethylpyrazol-4-yl)pyridazin-3-yl]-3,3a,4,5,6,6a-hexahydro-1H-cyclopenta[c]pyrrol-5-amine;

(3aR,5s,6aS)—N-[6-(2,4-dimethylpyrazol-3-yl)pyridazin-3-yl]-2-(tetrahydropyran-2-ylmethyl)-3,3a,4,5,6,6a-hexahydro-1H-cyclopenta[c]pyrrol-5-amine;

N-[4-[6-[[(3aR,5r,6aS)-2-(3,3-dimethylbutyl)-3,3a,4,5,6,6a-hexahydro-1H-cyclopenta[c]pyrrol-5-yl]amino]pyridazin-3-yl]phenyl]acetamide;

(3aR,5s,6aS)—N-[6-(2,4-dimethylpyrazol-3-yl)pyridazin-3-yl]-2-(7-oxabicyclo[2.2.1]heptan-3-ylmethyl)-3,3a,4,5,6,6a-hexahydro-1H-cyclopenta[c]pyrrol-5-amine;

(3aR,5r,6aS)-2-(3,3-dimethylbutyl)-N-[4-(1,3-dimethylpyrazol-4-yl)-2,3-difluoro-phenyl]-3,3a,4,5,6,6a-hexahydro-1H-cyclopenta[c]pyrrol-5-amine;

(3aR,5r,6aS)-2-(5-bicyclo[2.2.1]hept-2-enylmethyl)-N-[4-(1,3-dimethylpyrazol-4-yl)-2,3-difluoro-phenyl]-3,3a,4,5,6,6a-hexahydro-1H-cyclopenta[c]pyrrol-5-amine;

(3aR,5r,6aS)-2-(cyclohexylmethyl)-N-[4-(1,3-dimethylpyrazol-4-yl)-2,3-difluoro-phenyl]-3,3a,4,5,6,6a-hexahydro-1H-cyclopenta[c]pyrrol-5-amine;

(3aR,5r,6aS)-2-(cycloheptylmethyl)-N-[4-(1,3-dimethylpyrazol-4-yl)-2,3-difluoro-phenyl]-3,3a,4,5,6,6a-hexahydro-1H-cyclopenta[c]pyrrol-5-amine;

(3aR,5r,6aS)-2-(1-adamantylmethyl)-N-[4-(1,3-dimethylpyrazol-4-yl)-2,3-difluoro-phenyl]-3,3a,4,5,6,6a-hexahydro-1H-cyclopenta[c]pyrrol-5-amine;

(3aR,5r,6aS)-5-[6-(1,3-dimethylpyrazol-4-yl)pyridazin-3-yl]oxy-2-(2,3,3-trimethylbutyl)-3,3a,4,5,6,6a-hexahydro-1H-cyclopenta[c]pyrrole;

(3aR,5r,6aS)-2-(5-bicyclo[2.2.1]hept-2-enylmethyl)-5-[6-(1,3-dimethylpyrazol-4-yl)pyridazin-3-yl]oxy-3,3a,4,5,6,6a-hexahydro-1H-cyclopenta[c]pyrrole;

(3aR,5r,6aS)-2-(3,3-dimethylbutyl)-5-[6-(1,3-dimethylpyrazol-4-yl)pyridazin-3-yl]oxy-3,3a,4,5,6,6a-hexahydro-1H-cyclopenta[c]pyrrole;

(3aR,5r,6aS)-2-(cyclohexylmethyl)-5-[6-(1,3-dimethylpyrazol-4-yl)pyridazin-3-yl]oxy-3,3a,4,5,6,6a-hexahydro-1H-cyclopenta[c]pyrrole;

(3aR,5r,6aS)-5-[6-(1,3-dimethylpyrazol-4-yl)pyridazin-3-yl]oxy-2-(tetrahydropyran-4-ylmethyl)-3,3a,4,5,6,6a-hexahydro-1H-cyclopenta[c]pyrrole;

(3aR,5r,6aS)-5-[6-(1,3-dimethylpyrazol-4-yl)pyridazin-3-yl]oxy-2-(tetrahydropyran-3-ylmethyl)-3,3a,4,5,6,6a-hexahydro-1H-cyclopenta[c]pyrrole;

(3aR,5r,6aS)-5-[6-(1,3-dimethylpyrazol-4-yl)pyridazin-3-yl]oxy-2-[(3-methyl-2-pyridyl)methyl]-3,3a,4,5,6,6a-hexahydro-1H-cyclopenta[c]pyrrole;

(3aR,5r,6aS)-2-(5-bicyclo[2.2.1]hept-2-enylmethyl)-5-[6-(2-chloro-5-fluoro-phenyl)pyridazin-3-yl]oxy-3,3a,4,5,6,6a-hexahydro-1H-cyclopenta[c]pyrrole;

(3aR,5r,6aS)-5-[6-(2-chloro-5-fluoro-phenyl)pyridazin-3-yl]oxy-2-(3,3-dimethylbutyl)-3,3a,4,5,6,6a-hexahydro-1H-cyclopenta[c]pyrrole;

(3aR,5r,6aS)-5-[6-(2-chloro-5-fluoro-phenyl)pyridazin-3-yl]oxy-2-(2,3,3-trimethylbutyl)-3,3a,4,5,6,6a-hexahydro-1H-cyclopenta[c]pyrrole;

(3aR,5r,6aS)-5-[6-(2-chloro-5-fluoro-phenyl)pyridazin-3-yl]oxy-2-(cyclohexylmethyl)-3,3a,4,5,6,6a-hexahydro-1H-cyclopenta[c]pyrrole;

(3aR,5r,6aS)-5-[6-(2-chloro-5-fluoro-phenyl)pyridazin-3-yl]oxy-2-(tetrahydropyran-3-ylmethyl)-3,3a,4,5,6,6a-hexahydro-1H-cyclopenta[c]pyrrole;

(3aR,5r,6aS)-5-[6-(2-chloro-5-fluoro-phenyl)pyridazin-3-yl]oxy-2-[(3-methyl-2-pyridyl)methyl]-3,3a,4,5,6,6a-hexahydro-1H-cyclopenta[c]pyrrole;

(3aR,5r,6aS)-5-[6-(2-chloro-5-fluoro-phenyl)pyridazin-3-yl]oxy-2-(tetrahydropyran-4-ylmethyl)-3,3a,4,5,6,6a-hexahydro-1H-cyclopenta[c]pyrrole;

[(3aR,5r,6aS)-5-[6-(1,3-dimethylpyrazol-4-yl)pyridazin-3-yl]oxy-3,3a,4,5,6,6a-hexahydro-1H-cyclopenta[c]pyrrol-2-yl]-(1-adamantyl)methanone;

N-[[(3aR,5s,6aS)-2-(3,3-dimethylbutyl)-3,3a,4,5,6,6a-hexahydro-1H-cyclopenta[c]pyrrol-5-yl]methyl]-6-(2,4-dimethylpyrazol-3-yl)pyridazin-3-amine;

N-[[(3aR,6aS)-2-(5-bicyclo[2.2.1]hept-2-enylmethyl)-3,3a,4,5,6,6a-hexahydro-1H-cyclopenta[c]pyrrol-5-yl]methyl]-6-(1,3-dimethylpyrazol-4-yl)pyridazin-3-amine;

N-[[(3aR,6aS)-2-(2,3,3-trimethylbutyl)-3,3a,4,5,6,6a-hexahydro-1H-cyclopenta[c]pyrrol-5-yl]methyl]-6-(1,3-dimethylpyrazol-4-yl)pyridazin-3-amine;

N-[[(3aR,5s,6aS)-2-(5-bicyclo[2.2.1]hept-2-enylmethyl)-3,3a,4,5,6,6a-hexahydro-1H-cyclopenta[c]pyrrol-5-yl]methyl]-6-(2,4-dimethylpyrazol-3-yl)pyridazin-3-amine;

N-[[(3aR,5s,6aS)-2-(2,3,3-trimethylbutyl)-3,3a,4,5,6,6a-hexahydro-1H-cyclopenta[c]pyrrol-5-yl]methyl]-6-(2,4-dimethylpyrazol-3-yl)pyridazin-3-amine;

N-[[(3aR,5s,6aS)-2-(tetrahydropyran-4-ylmethyl)-3,3a,4,5,6,6a-hexahydro-1H-cyclopenta[c]pyrrol-5-yl]methyl]-6-(2,4-dimethylpyrazol-3-yl)pyridazin-3-amine;

N-[[(3aR,5s,6aS)-2-(tetrahydropyran-3-ylmethyl)-3,3a,4,5,6,6a-hexahydro-1H-cyclopenta[c]pyrrol-5-yl]methyl]-6-(2,4-dimethylpyrazol-3-yl)pyridazin-3-amine;

N-[[(3aR,5s,6aS)-2-[(3-methyl-2-pyridyl)methyl]-3,3a,4,5,6,6a-hexahydro-1H-cyclopenta[c]pyrrol-5-yl]methyl]-6-(2,4-dimethylpyrazol-3-yl)pyridazin-3-amine;

N-[[(3aR,5s,6aS)-2-(5-bicyclo[2.2.1]hept-2-enylmethyl)-3,3a,4,5,6,6a-hexahydro-1H-cyclopenta[c]pyrrol-5-yl]methyl]-6-(2-chloro-5-fluoro-phenyl)pyridazin-3-amine;

N-[[(3aR,5s,6aS)-2-(3,3-dimethylbutyl)-3,3a,4,5,6,6a-hexahydro-1H-cyclopenta[c]pyrrol-5-yl]methyl]-6-(2-chloro-5-fluoro-phenyl)pyridazin-3-amine;

N-[[(3aR,5s,6aS)-2-(tetrahydropyran-4-ylmethyl)-3,3a,4,5,6,6a-hexahydro-1H-cyclopenta[c]pyrrol-5-yl]methyl]-6-(2-chloro-5-fluoro-phenyl)pyridazin-3-amine;

N-[[(3aR,5s,6aS)-2-(cyclohexylmethyl)-3,3a,4,5,6,6a-hexahydro-1H-cyclopenta[c]pyrrol-5-yl]methyl]-6-(1,3-dimethylpyrazol-4-yl)pyridazin-3-amine;

N-[[(3aR,5s,6aS)-2-[(3-methyl-2-pyridyl)methyl]-3,3a,4,5,6,6a-hexahydro-1H-cyclopenta[c]pyrrol-5-yl]methyl]-6-(1,3-dimethylpyrazol-4-yl)pyridazin-3-amine;

(3aR,6aS)-2-(3,3-dimethylbutyl)-N-[6-(2,4-dimethylpyrazol-3-yl)pyridazin-3-yl]-3,3a,4,5,6,6a-hexahydro-1H-cyclopenta[c]pyrrole-5-carboxamide;

(3aR,6aS)-2-(5-bicyclo[2.2.1]hept-2-enylmethyl)-N-[6-(2-chloro-4-fluoro-phenyl)pyridazin-3-yl]-3,3a,4,5,6,6a-hexahydro-1H-cyclopenta[c]pyrrole-5-carboxamide;

N-[6-(2,4-dimethylpyrazol-3-yl)pyridazin-3-yl]-2-(2,3,3-trimethylbutyl)-3,3a,4,5,6,6a-hexahydro-1H-cyclopenta[c]pyrrole-5-carboxamide;

2-(5-bicyclo[2.2.1]hept-2-enylmethyl)-N-[6-(2,4-dimethylpyrazol-3-yl)pyridazin-3-yl]-3,3a,4,5,6,6a-hexahydro-1H-cyclopenta[c]pyrrole-5-carboxamide;

(3aR,6aS)-2-(3,3-dimethylbutyl)-5-[[6-(2,4-dimethylpyrazol-3-yl)pyridazin-3-yl]oxymethyl]-3,3a,4,5,6,6a-hexahydro-1H-cyclopenta[c]pyrrole;

(3aR,6aS)-2-(1-adamantylmethyl)-5-[[6-(2,4-dimethylpyrazol-3-yl)pyridazin-3-yl]oxymethyl]-3,3a,4,5,6,6a-hexahydro-1H-cyclopenta[c]pyrrole;

(3aR,6aS)-2-(5-bicyclo[2.2.1]hept-2-enylmethyl)-5-[[6-(2,4-dimethylpyrazol-3-yl)pyridazin-3-yl]oxymethyl]-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-(2-methylbutyl)-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-(2-methylpentyl)-3,3a,4,5,6,6a-hexahydro-1H-cyclopenta[c]pyrrole;

(3aR,6aS)-2-(cyclohexylmethyl)-5-[[6-(2,4-dimethylpyrazol-3-yl)pyridazin-3-yl]oxymethyl]-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-(tetrahydropyran-4-ylmethyl)-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-(tetrahydropyran-3-ylmethyl)-3,3a,4,5,6,6a-hexahydro-1H-cyclopenta[c]pyrrole;

(3aR,6aS)-2-benzyl-5-[[6-(2,4-dimethylpyrazol-3-yl)pyridazin-3-yl]oxymethyl]-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-[(2-fluorophenyl)methyl]-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-[(4-fluorophenyl)methyl]-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-(2-pyridylmethyl)-3,3a,4,5,6,6a-hexahydro-1H-cyclopenta[c]pyrrole;

(3aR,6aS)-5-[[6-(2,4-dimethylpyrazol-3-yl)pyridazin-3-yl]oxymethyl]-2-[(3-methyl-2-pyridyl)methyl]-3,3a,4,5,6,6a-hexahydro-1H-cyclopenta[c]pyrrole;

(3aR,6aS)-2-(1,3-benzodioxol-5-ylmethyl)-5-[[6-(2,4-dimethylpyrazol-3-yl)pyridazin-3-yl]oxymethyl]-3,3a,4,5,6,6a-hexahydro-1H-cyclopenta[c]pyrrole;

(3aR,6aS)-2-(3,3-dimethylbutyl)-5-[[6-(1,3-dimethylpyrazol-4-yl)pyridazin-3-yl]oxymethyl]-3,3a,4,5,6,6a-hexahydro-1H-cyclopenta[c]pyrrole;

(3aR,6aS)-2-(1-adamantylmethyl)-5-[[6-(1,3-dimethylpyrazol-4-yl)pyridazin-3-yl]oxymethyl]-3,3a,4,5,6,6a-hexahydro-1H-cyclopenta[c]pyrrole;

(3aR,6aS)-2-(5-bicyclo[2.2.2]oct-2-enylmethyl)-5-[[6-(1,3-dimethylpyrazol-4-yl)pyridazin-3-yl]oxymethyl]-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-(2-methylbutyl)-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-(2-methylpentyl)-3,3a,4,5,6,6a-hexahydro-1H-cyclopenta[c]pyrrole;

(3aR,6aS)-2-(cyclohexylmethyl)-5-[[6-(1,3-dimethylpyrazol-4-yl)pyridazin-3-yl]oxymethyl]-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-(tetrahydropyran-4-ylmethyl)-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-(tetrahydropyran-3-ylmethyl)-3,3a,4,5,6,6a-hexahydro-1H-cyclopenta[c]pyrrole;

(3aR,6aS)-2-benzyl-5-[[6-(1,3-dimethylpyrazol-4-yl)pyridazin-3-yl]oxymethyl]-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-[(2-fluorophenyl)methyl]-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-[(4-fluorophenyl)methyl]-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-(2-pyridylmethyl)-3,3a,4,5,6,6a-hexahydro-1H-cyclopenta[c]pyrrole;

(3aR,6aS)-5-[[6-(1,3-dimethylpyrazol-4-yl)pyridazin-3-yl]oxymethyl]-2-[(3-methyl-2-pyridyl)methyl]-3,3a,4,5,6,6a-hexahydro-1H-cyclopenta[c]pyrrole;

(3aR,6aS)-2-(1,3-benzodioxol-5-ylmethyl)-5-[[6-(1,3-dimethylpyrazol-4-yl)pyridazin-3-yl]oxymethyl]-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-(3,3-dimethylbutyl)-3,3a,4,5,6,6a-hexahydro-1H-cyclopenta[c]pyrrole;

(3aR,6aS)-2-(1-adamantylmethyl)-5-[[6-(2-chloro-5-fluoro-phenyl)pyridazin-3-yl]oxymethyl]-3,3a,4,5,6,6a-hexahydro-1H-cyclopenta[c]pyrrole;

(3aR,6aS)-2-(5-bicyclo[2.2.1]hept-2-enylmethyl)-5-[[6-(2-chloro-5-fluoro-phenyl)pyridazin-3-yl]oxymethyl]-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-(2-methylbutyl)-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-(2-methylpentyl)-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-(cyclohexylmethyl)-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-(tetrahydropyran-4-ylmethyl)-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-(tetrahydropyran-3-ylmethyl)-3,3a,4,5,6,6a-hexahydro-1H-cyclopenta[c]pyrrole;

(3aR,6aS)-2-benzyl-5-[[6-(2-chloro-5-fluoro-phenyl)pyridazin-3-yl]oxymethyl]-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-[(2-fluorophenyl)methyl]-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-[(4-fluorophenyl)methyl]-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-(2-pyridylmethyl)-3,3a,4,5,6,6a-hexahydro-1H-cyclopenta[c]pyrrole;

(3aR,6aS)-5-[[6-(2-chloro-5-fluoro-phenyl)pyridazin-3-yl]oxymethyl]-2-[(3-methyl-2-pyridyl)methyl]-3,3a,4,5,6,6a-hexahydro-1H-cyclopenta[c]pyrrole;

(3aR,6aS)-2-(1,3-benzodioxol-5-ylmethyl)-5-[[6-(2-chloro-5-fluoro-phenyl)pyridazin-3-yl]oxymethyl]-3,3a,4,5,6,6a-hexahydro-1H-cyclopenta[c]pyrrole;

6-(1,4-dimethyl-1H-pyrazol-5-yl)-N-(2-((3aR,6aS)-2-(3,3-dimethylbutyl)octahydrocyclopenta[c]pyrrol-5-yl)ethyl)pyridazin-3-amine;

N-[2-[(3aR,6aS)-2-(1-adamantylmethyl)-3,3a,4,5,6,6a-hexahydro-1H-cyclopenta[c]pyrrol-5-yl]ethyl]-6-(2,4-dimethylpyrazol-3-yl)pyridazin-3-amine;

N-[2-[(3aR,6aS)-2-(tetrahydropyran-3-ylmethyl)-3,3a,4,5,6,6a-hexahydro-1H-cyclopenta[c]pyrrol-5-yl]ethyl]-6-(2,4-dimethylpyrazol-3-yl)pyridazin-3-amine;

N-[2-[(3aR,6aS)-2-(5-bicyclo[2.2.1]hept-2-enylmethyl)-3,3a,4,5,6,6a-hexahydro-1H-cyclopenta[c]pyrrol-5-yl]ethyl]-6-(2,4-dimethylpyrazol-3-yl)pyridazin-3-amine;

N-[2-[(3aR,6aS)-2-[(3-methyl-2-pyridyl)methyl]-3,3a,4,5,6,6a-hexahydro-1H-cyclopenta[c]pyrrol-5-yl]ethyl]-6-(2,4-dimethylpyrazol-3-yl)pyridazin-3-amine;

N-[2-[(3aR,6aS)-2-(tetrahydropyran-4-ylmethyl)-3,3a,4,5,6,6a-hexahydro-1H-cyclopenta[c]pyrrol-5-yl]ethyl]-6-(2,4-dimethylpyrazol-3-yl)pyridazin-3-amine;

N-[2-[(3aR,6aS)-2-benzyl-3,3a,4,5,6,6a-hexahydro-1H-cyclopenta[c]pyrrol-5-yl]ethyl]-6-(2,4-dimethylpyrazol-3-yl)pyridazin-3-amine;

N-[2-[(3aR,6aS)-2-[(2-fluorophenyl)methyl]-3,3a,4,5,6,6a-hexahydro-1H-cyclopenta[c]pyrrol-5-yl]ethyl]-6-(2,4-dimethylpyrazol-3-yl)pyridazin-3-amine;

(3aR,5s,6aS)-5-(6-chloropyridazin-3-yl)oxy-2-(3,3-dimethylbutyl)-3,3a,4,5,6,6a-hexahydro-1H-cyclopenta[c]pyrrole;

N-[4-[6-[[(3aR,5s,6aS)-2-(3,3-dimethylbutyl)-3,3a,4,5,6,6a-hexahydro-1H-cyclopenta[c]pyrrol-5-yl]oxy]pyridazin-3-yl]phenyl]acetamide;

N-[4-[6-[[(3aR,5s,6aS)-2-(cyclohexylmethyl)-3,3a,4,5,6,6a-hexahydro-1H-cyclopenta[c]pyrrol-5-yl]oxy]pyridazin-3-yl]phenyl]acetamide;

N-[4-[6-[[(3aR,5s,6aS)-2-[(4-fluorophenyl)methyl]-3,3a,4,5,6,6a-hexahydro-1H-cyclopenta[c]pyrrol-5-yl]oxy]pyridazin-3-yl]phenyl]acetamide;

N-[4-[6-[[(3aR,5s,6aS)-2-(tetrahydropyran-4-ylmethyl)-3,3a,4,5,6,6a-hexahydro-1H-cyclopenta[c]pyrrol-5-yl]oxy]pyridazin-3-yl]phenyl]acetamide;

N-[4-[6-[[(3aR,5s,6aS)-2-[(3-methyl-2-pyridyl)methyl]-3,3a,4,5,6,6a-hexahydro-1H-cyclopenta[c]pyrrol-5-yl]oxy]pyridazin-3-yl]phenyl]acetamide;

(3aR,5s,6aS)-2-(3,3-dimethylbutyl)-5-[6-(1,3-dimethylpyrazol-4-yl)pyridazin-3-yl]oxy-3,3a,4,5,6,6a-hexahydro-1H-cyclopenta[c]pyrrole;

(3aR,5s,6aS)-2-(3,3-dimethylbutyl)-5-[6-(2,4-dimethylpyrazol-3-yl)pyridazin-3-yl]oxy-3,3a,4,5,6,6a-hexahydro-1H-cyclopenta[c]pyrrole;

4-[6-[[(3aR,5s,6aS)-2-(3,3-dimethylbutyl)-3,3a,4,5,6,6a-hexahydro-1H-cyclopenta[c]pyrrol-5-yl]oxy]pyridazin-3-yl]-3,5-dimethyl-isoxazole;

(3aR,5s,6aS)-5-[6-(2-chloro-5-fluoro-phenyl)pyridazin-3-yl]oxy-2-(3,3-dimethylbutyl)-3,3a,4,5,6,6a-hexahydro-1H-cyclopenta[c]pyrrole;

(3aR,5s,6aS)-5-[6-(1,3-benzodioxol-5-yl)pyridazin-3-yl]oxy-2-(3,3-dimethylbutyl)-3,3a,4,5,6,6a-hexahydro-1H-cyclopenta[c]pyrrole;

(3aR,5s,6aS)-2-(3,3-dimethylbutyl)-5-[6-[4-(trifluoromethyl)phenyl]pyridazin-3-yl]oxy-3,3a,4,5,6,6a-hexahydro-1H-cyclopenta[c]pyrrole;

N-[4-[6-[[(3aR,5s,6aS)-2-(3,3-dimethylbutyl)-3,3a,4,5,6,6a-hexahydro-1H-cyclopenta[c]pyrrol-5-yl]amino]pyridazin-3-yl]phenyl]acetamide;

(3aR,5s,6aS)—N-[6-(2-chloro-4-fluoro-phenyl)pyridazin-3-yl]-2-(3,3-dimethylbutyl)-3,3a,4,5,6,6a-hexahydro-1H-cyclopenta[c]pyrrol-5-amine;

(3aR,5s,6aS)-2-(3,3-dimethylbutyl)-N-[6-(3,5-dimethylisoxazol-4-yl)pyridazin-3-yl]-3,3a,4,5,6,6a-hexahydro-1H-cyclopenta[c]pyrrol-5-amine;

(3aR,5s,6aS)-2-(3,3-dimethylbutyl)-N-(6-morpholinopyridazin-3-yl)-3,3a,4,5,6,6a-hexahydro-1H-cyclopenta[c]pyrrol-5-amine;

(3aR,5r,6aS)-2-(3,3-dimethylbutyl)-N-[6-(2,4-dimethylpyrazol-3-yl)pyridazin-3-yl]-3,3a,4,5,6,6a-hexahydro-1H-cyclopenta[c]pyrrole-5-carboxamide;

(3aR,5s,6aS)-2-(3,3-dimethylbutyl)-N-[6-(2,4-dimethylpyrazol-3-yl)pyridazin-3-yl]-3,3a,4,5,6,6a-hexahydro-1H-cyclopenta[c]pyrrole-5-carboxamide;

(3aR,5s,6aS)-2-(3,3-dimethylbutyl)-5-[[6-(2,4-dimethylpyrazol-3-yl)pyridazin-3-yl]oxymethyl]-3,3a,4,5,6,6a-hexahydro-1H-cyclopenta[c]pyrrole;

(3aR,5r,6aS)-2-(3,3-dimethylbutyl)-5-[[6-(2,4-dimethylpyrazol-3-yl)pyridazin-3-yl]oxymethyl]-3,3a,4,5,6,6a-hexahydro-1H-cyclopenta[c]pyrrole;

N-[4-[4-[[(3aR,5s,6aS)-2-(3,3-dimethylbutyl)-3,3a,4,5,6,6a-hexahydro-1H-cyclopenta[c]pyrrol-5-yl]amino]-2,3-difluoro-phenyl]phenyl]acetamide;

(3aR,5s,6aS)-2-(3,3-dimethylbutyl)-N-[5-(1,3-dimethylpyrazol-4-yl)-2-pyridyl]-3,3a,4,5,6,6a-hexahydro-1H-cyclopenta[c]pyrrol-5-amine;

(3aR,5s,6aS)-2-(1-adamantylmethyl)-N-[5-(1,3-dimethylpyrazol-4-yl)-2-pyridyl]-3,3a,4,5,6,6a-hexahydro-1H-cyclopenta[c]pyrrol-5-amine;

(3aR,5s,6aS)-2-(5-bicyclo[2.2.1]hept-2-enylmethyl)-N-[5-(1,3-dimethylpyrazol-4-yl)-2-pyridyl]-3,3a,4,5,6,6a-hexahydro-1H-cyclopenta[c]pyrrol-5-amine;

(3aR,5s,6aS)—N-[5-(1,3-dimethylpyrazol-4-yl)-2-pyridyl]-2-(tetrahydropyran-4-ylmethyl)-3,3a,4,5,6,6a-hexahydro-1H-cyclopenta[c]pyrrol-5-amine;

(3aR,5s,6aS)-2-(3,3-dimethylbutyl)-N-[5-(1,3-dimethylpyrazol-4-yl)pyrazin-2-yl]-3,3a,4,5,6,6a-hexahydro-1H-cyclopenta[c]pyrrol-5-amine;

(3aR,5s,6aS)-2-(5-bicyclo[2.2.1]hept-2-enylmethyl)-N-[5-(1,3-dimethylpyrazol-4-yl)pyrazin-2-yl]-3,3a,4,5,6,6a-hexahydro-1H-cyclopenta[c]pyrrol-5-amine;

(3aR,5s,6aS)-2-(1-adamantylmethyl)-N-[5-(1,3-dimethylpyrazol-4-yl)pyrazin-2-yl]-3,3a,4,5,6,6a-hexahydro-1H-cyclopenta[c]pyrrol-5-amine;

N-[4-[5-[[(3aR,5s,6aS)-2-(3,3-dimethylbutyl)-3,3a,4,5,6,6a-hexahydro-1H-cyclopenta[c]pyrrol-5-yl]amino]pyrazin-2-yl]phenyl]acetamide;

N-[4-[5-[[(3aR,5s,6aS)-2-(5-bicyclo[2.2.1]hept-2-enylmethyl)-3,3a,4,5,6,6a-hexahydro-1H-cyclopenta[c]pyrrol-5-yl]amino]pyrazin-2-yl]phenyl]acetamide;

N-[4-[5-[[(3aR,5s,6aS)-2-(tetrahydropyran-4-ylmethyl)-3,3a,4,5,6,6a-hexahydro-1H-cyclopenta[c]pyrrol-5-yl]amino]pyrazin-2-yl]phenyl]acetamide;

(3aR,5r,6aS)—N-[6-(2-chloro-5-fluoro-phenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(2-pyridylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(3-pyridylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(4-pyridylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-[(4-fluorophenyl)methyl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(3-quinolylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(imidazo[1,2-a]pyridin-2-ylmethyl)-3,3a,4,5,6,6a-hexahydro-1H-cyclopenta[c]pyrrol-5-amine;

(3aR,5s,6aS)-2-(1,3-benzodioxol-5-ylmethyl)-N-[6-(2-chloro-5-fluoro-phenyl)pyridazin-3-yl]-3,3a,4,5,6,6a-hexahydro-1H-cyclopenta[c]pyrrol-5-amine;

(3aR,5s,6aS)-2-(1,3-benzodioxol-4-ylmethyl)-N-[6-(2-chloro-5-fluoro-phenyl)pyridazin-3-yl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-[(4-methoxyphenyl)methyl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(cyclopropylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(pyrazin-2-ylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-[(3-methyloxetan-3-yl)methyl]-3,3a,4,5,6,6a-hexahydro-1H-cyclopenta[c]pyrrol-5-amine;

N-[4-[[(3aR,5s,6aS)-5-[[6-(2-chloro-5-fluoro-phenyl)pyridazin-3-yl]amino]-3,3a,4,5,6,6a-hexahydro-1H-cyclopenta[c]pyrrol-2-yl]methyl]phenyl]methanesulfonamide;

(3aR,5s,6aS)—N-[6-(2-chloro-5-fluoro-phenyl)pyridazin-3-yl]-2-[(2,2-dimethyltetrahydropyran-4-yl)methyl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-[(2-methoxyphenyl)methyl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-[(3-fluorophenyl)methyl]-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(2-furylmethyl)-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-isobutyl-3,3a,4,5,6,6a-hexahydro-1H-cyclopenta[c]pyrrol-5-amine;

(3aR,5s,6aS)—N-[6-(2-chloro-5-fluoro-phenyl)pyridazin-3-yl]-2-(3-furylmethyl)-3,3a,4,5,6,6a-hexahydro-1H-cyclopenta[c]pyrrol-5-amine;

(3aR,5s,6aS)—N-(6-chloropyridazin-3-yl)-2-(tetrahydropyran-4-ylmethyl)-3,3a,4,5,6,6a-hexahydro-1H-cyclopenta[c]pyrrol-5-amine;

N-[4-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]phenyl]acetamide;

(3aR,5s,6aS)—N-[6-(6-quinolyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(1,3-benzodioxol-5-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-(6-imidazo[1,2-a]pyridin-6-ylpyridazin-3-yl)-2-(tetrahydropyran-4-ylmethyl)-3,3a,4,5,6,6a-hexahydro-1H-cyclopenta[c]pyrrol-5-amine;

(3aR,5s,6aS)-2-(tetrahydropyran-4-ylmethyl)-N-[6-[4-(trifluoromethoxy)phenyl]pyridazin-3-yl]-3,3a,4,5,6,6a-hexahydro-1H-cyclopenta[c]pyrrol-5-amine;

(3aR,5s,6aS)—N-[6-(2-fluorophenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(3-fluorophenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(4-fluorophenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-furyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(3,3-difluoropyrrolidin-1-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(4,4-difluoro-1-piperidyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-(6-morpholinopyridazin-3-yl)-2-(tetrahydropyran-4-ylmethyl)-3,3a,4,5,6,6a-hexahydro-1H-cyclopenta[c]pyrrol-5-amine;

(3aR,5s,6aS)—N-(6-pyrrolidin-1-ylpyridazin-3-yl)-2-(tetrahydropyran-4-ylmethyl)-3,3a,4,5,6,6a-hexahydro-1H-cyclopenta[c]pyrrol-5-amine;

(3aR,5s,6aS)—N-[6-(1-piperidyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-[(3S)-3-fluoropyrrolidin-1-yl]pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-[(3R)-3-fluoropyrrolidin-1-yl]pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(3,3-difluoro-1-piperidyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-(6-phenylpyridazin-3-yl)-2-(tetrahydropyran-4-ylmethyl)-3,3a,4,5,6,6a-hexahydro-1H-cyclopenta[c]pyrrol-5-amine;

(3aR,5s,6aS)—N-[6-(p-tolyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-methoxyphenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(3-methoxyphenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(4-methoxyphenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-chloro-3-fluoro-phenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-chloro-4-fluoro-phenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-chloro-6-fluoro-phenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2-chlorophenyl)pyridazin-3-yl]-2-(tetrahydropyran-4-ylmethyl)-3,3a,4,5,6,6a-hexahydro-1H-cyclopenta[c]pyrrol-5-amine;

N-[2-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]phenyl]acetamide;

4-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]-N,N-dimethyl-benzamide;

(3aR,5s,6aS)—N-[6-(1-methylpyrazol-4-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(1-cyclopropylpyrazol-4-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(3,5-dimethylisoxazol-4-yl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)-2-(tetrahydropyran-4-ylmethyl)-N-[6-[6-(trifluoromethyl)-3-pyridyl]pyridazin-3-yl]-3,3a,4,5,6,6a-hexahydro-1H-cyclopenta[c]pyrrol-5-amine;

(3aR,5s,6aS)—N-[6-(5-fluoro-2-methoxy-phenyl)pyridazin-3-yl]-2-(tetrahydropyran-4-ylmethyl)-3,3a,4,5,6,6a-hexahydro-1H-cyclopenta[c]pyrrol-5-amine;

2-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]-4-fluoro-benzonitrile;

(3aR,5s,6aS)—N-[6-(5-fluoro-2-methyl-phenyl)pyridazin-3-yl]-2-(tetrahydropyran-4-ylmethyl)-3,3a,4,5,6,6a-hexahydro-1H-cyclopenta[c]pyrrol-5-amine;

(3aR,5s,6aS)—N-[6-(2,5-difluorophenyl)pyridazin-3-yl]-2-(tetrahydropyran-4-ylmethyl)-3,3a,4,5,6,6a-hexahydro-1H-cyclopenta[c]pyrrol-5-amine;

2-[3-[6-[[(3aR,5s,6aS)-2-(tetrahydropyran-4-ylmethyl)-3,3a,4,5,6,6a-hexahydro-1H-cyclopenta[c]pyrrol-5-yl]amino]pyridazin-3-yl]phenyl]propan-2-ol;

N-[3-[6-[[(3aR,5s,6aS)-2-(tetrahydropyran-4-ylmethyl)-3, 3a,4,5,6,6a-hexahydro-1H-cyclopenta[c]pyrrol-5-yl] amino]pyridazin-3-yl]phenyl]methanesulfonamide;
(3aR,5s,6aS)—N-[6-(3-pyridyl)pyridazin-3-yl]-2-(tetrahydropyran-4-ylmethyl)-3,3a,4,5,6,6a-hexahydro-1H-cyclopenta[c]pyrrol-5-amine;
(3aR,5s,6aS)—N-[6-(4-pyridyl)pyridazin-3-yl]-2-(tetrahydropyran-4-ylmethyl)-3,3a,4,5,6,6a-hexahydro-1H-cyclopenta[c]pyrrol-5-amine;
(3aR,5s,6aS)—N-[6-(2-chloro-5-fluoro-3-pyridyl) pyridazin-3-yl]-2-(tetrahydropyran-4-ylmethyl)-3,3a,4,5, 6,6a-hexahydro-1H-cyclopenta[c]pyrrol-5-amine;
(3aR,5s,6aS)—N-[6-(2-methylindazol-5-yl)pyridazin-3-yl]-2-(tetrahydropyran-4-ylmethyl)-3,3a,4,5,6,6a-hexahydro-1H-cyclopenta[c]pyrrol-5-amine;
(3aR,5s,6aS)—N-[6-(3-fluoro-4-methoxy-phenyl) pyridazin-3-yl]-2-(tetrahydropyran-4-ylmethyl)-3,3a,4,5, 6,6a-hexahydro-1H-cyclopenta[c]pyrrol-5-amine;
(3aR,5s,6aS)—N-[6-[4-(difluoromethoxy)phenyl] pyridazin-3-yl]-2-(tetrahydropyran-4-ylmethyl)-3,3a,4,5, 6,6a-hexahydro-1H-cyclopenta[c]pyrrol-5-amine;
(3aR,5s,6aS)—N-[6-(6-methoxy-3-pyridyl)pyridazin-3-yl]-2-(tetrahydropyran-4-ylmethyl)-3,3a,4,5,6,6a-hexahydro-1H-cyclopenta[c]pyrrol-5-amine;
(3aR,5s,6aS)—N-[6-(4-fluorophenoxy)pyridazin-3-yl]-2-(tetrahydropyran-4-ylmethyl)-3,3a,4,5,6,6a-hexahydro-1H-cyclopenta[c]pyrrol-5-amine;
(3aR,5s,6aS)-2-(tetrahydropyran-4-ylmethyl)-N-[6-(2-thienyl)pyridazin-3-yl]-3,3a,4,5,6,6a-hexahydro-1H-cyclopenta[c]pyrrol-5-amine;
(3aR,5s,6aS)-2-(tetrahydropyran-4-ylmethyl)-N-[6-(3-thienyl)pyridazin-3-yl]-3,3a,4,5,6,6a-hexahydro-1H-cyclopenta[c]pyrrol-5-amine;
(3aR,5s,6aS)—N-[6-(1-ethylpyrazol-3-yl)pyridazin-3-yl]-2-(tetrahydropyran-4-ylmethyl)-3,3a,4,5,6,6a-hexahydro-1H-cyclopenta[c]pyrrol-5-amine;
(3aR,5s,6aS)—N-[6-(1H-pyrrol-3-yl)pyridazin-3-yl]-2-(tetrahydropyran-4-ylmethyl)-3,3a,4,5,6,6a-hexahydro-1H-cyclopenta[c]pyrrol-5-amine;
N-[(3aR,5s,6aS)-2-(tetrahydropyran-4-ylmethyl)-3,3a,4,5, 6,6a-hexahydro-1H-cyclopenta[c]pyrrol-5-yl]-5-phenyl-thiazol-2-amine;
N-[(3aR,5s,6aS)-2-(4-pyridylmethyl)-3,3a,4,5,6,6a-hexahydro-1H-cyclopenta[c]pyrrol-5-yl]-5-phenyl-thiazol-2-amine;
(3aR,5s,6aS)—N-[6-(6-cyclopropyl-3-pyridyl)pyridazin-3-yl]-2-(tetrahydropyran-4-ylmethyl)-3,3a,4,5,6,6a-hexahydro-1H-cyclopenta[c]pyrrol-5-amine,
or a pharmaceutically acceptable salt thereof.

Clause 49. The compound of any one of clauses 1-48, or a pharmaceutically acceptable salt thereof, wherein the compound is isotopically labeled.

Clause 50. A pharmaceutical composition comprising a therapeutically effective amount of a compound of any one of clauses 1-49, or a pharmaceutically acceptable salt thereof, and a pharmaceutically acceptable carrier.

Clause 51. A method for antagonizing mAChR M₄ in a subject, comprising a step of administering to the subject a therapeutically effective amount of a compound of any one of clauses 1-49, or a pharmaceutically acceptable salt thereof, or the pharmaceutical composition of clause 50.

Clause 52. A method for treating a disorder in a subject, wherein the subject would benefit from antagonism of mAChR M₄, comprising a step of administering to the mammal a therapeutically effective amount of a compound of any one of clauses 1-49, or a pharmaceutically acceptable salt thereof, or the pharmaceutical composition of clause 50.

Clause 53. The method of clause 52, wherein the disorder is a neurodegenerative disorder, a movement disorder, or a brain disorder.

Clause 54. The method of clause 53, wherein the disorder is a movement disorder.

Clause 55. The method of clause 53, wherein the disorder is selected from Parkinson's disease, drug-induced Parkinsonism, dystonia, Tourette's syndrome, dyskinesias, schizophrenia, cognitive deficits associated with schizophrenia, excessive daytime sleepiness, attention deficit hyperactivity disorder (ADHD), Huntington's disease, chorea, cerebral palsy, and progressive supranuclear palsy.

Clause 56. A method for treating motor symptoms in a subject, comprising administering to a subject in need thereof a therapeutically effective amount of the compound of any one of clauses 1-49, or a pharmaceutically acceptable salt thereof, or the pharmaceutical composition of clause 50.

Clause 57. The method of clause 56, wherein the subject has a disorder selected from Parkinson's disease, drug-induced Parkinsonism, dystonia, Tourette's syndrome, dyskinesias, schizophrenia, cognitive deficits associated with schizophrenia, excessive daytime sleepiness, attention deficit hyperactivity disorder (ADHD), Huntington's disease, chorea, cerebral palsy, and progressive supranuclear palsy.

Clause 58. A compound of any of clauses 1-49, or a pharmaceutically acceptable salt thereof, or the pharmaceutical composition of clause 50, for use in the treatment of a neurodegenerative disorder, a movement disorder, or a brain disorder.

Clause 59. The use of a compound of any of clauses 1-49, or a pharmaceutically acceptable salt thereof, or the pharmaceutical composition of clause 50, for the preparation of a medicament for the treatment of a neurodegenerative disorder, a movement disorder, or a brain disorder.

What is claimed is:
1. A compound of formula (I):

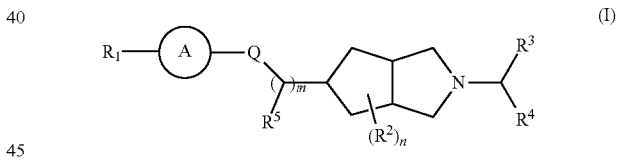

or a pharmaceutically acceptable salt thereof, wherein:
A is an arylene or a five- or six-membered heteroarylene having 1, 2, or 3 heteroatoms independently selected from N, O, and S;
Q is selected from $NR^a$, O, and —$NR^b$—C(O)—;
m is 0, 1, or 2;
$R^1$ is aryl;
n is 1 or 2;
each $R^2$ is independently selected from hydrogen, $C_1$-$C_4$ alkyl, halo, and —$OR^g$;
$R^3$ is selected from hydrogen and $C_1$-$C_4$ alkyl;
$R^4$ is selected from —$(CR^hR^i)_p$—Y', hydrogen, $C_1$-$C_8$ alkyl, and $C_2$-$C_8$ alkenyl;
$R^5$ is selected from hydrogen, $C_1$-$C_4$ alkyl, halo, $C_1$-$C_4$ haloalkyl, $C_1$-$C_4$ alkoxy, and $C_1$-$C_4$ haloalkoxy;
Y' is selected from cycloalkyl, cycloalkenyl, heterocycle, aryl, and heteroaryl;
each $R^a$, $R^b$, and $R^g$ is independently selected from hydrogen, $C_1$-$C_4$ alkyl, $C_3$-$C_6$ cycloalkyl, and aryl;
each $R^h$ is independently selected from hydrogen and $C_1$-$C_4$ alkyl;

each $R^i$ is independently selected from hydrogen, $C_1$-$C_4$ alkyl, $C_3$-$C_6$ cycloalkyl, and aryl; and p is 0, 1, 2, 3, or 4;

wherein each aryl, heteroaryl, arylene, heteroarylene, cycloalkyl, cycloalkenyl, and heterocycle is independently unsubstituted or substituted with 1-5 substituents.

2. The compound of claim 1, or a pharmaceutically acceptable salt thereof, wherein
A is selected from:

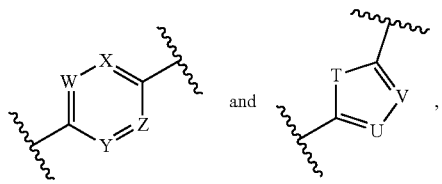

and wherein:

T is selected from O, S and NH;

U, V, W, X, Y and Z are independently selected from N and $CR^j$;

each $R^j$ is independently selected from hydrogen, $C_1$-$C_4$ alkyl, halo, $C_1$-$C_4$ haloalkyl, $C_1$-$C_4$ alkoxy, $C_1$-$C_4$ haloalkoxy, and hydroxy;

$R^a$ and $R^b$ are independently selected from hydrogen and $C_1$-$C_4$ alkyl;

$R^1$ is phenyl or a 9- to 12-membered aryl, and $R^1$ is optionally substituted with 1-4 substituents independently selected from the group consisting of halo, cyano, $C_1$-$C_4$ alkyl, $C_1$-$C_4$ haloalkyl, —$OR^{10}$, —$NR^{10}COR^{10}$, —$CONR^{10}R^{10}$, —$C_1$-$C_3$alkylene-$OR^{10}$, $C_3$-$C_6$ cycloalkyl, and —$C_1$-$C_3$alkylene-$C_3$-$C_6$cycloalkyl;

each $R^2$ is independently selected from hydrogen and $C_1$-$C_4$ alkyl;

$R^4$ is $C_4$-$C_6$ alkyl or —$(CR^hR^i)_p$—Y';

$R^h$ is hydrogen;

$R^i$ is hydrogen;

p is 0, 1, 2, or 3;

Y' is
a) $C_3$-$C_{10}$ cycloalkyl;
b) $C_3$-$C_8$ cycloalkenyl;
c) a 6- to 12-membered aryl;
d) a 5- to 12-membered heteroaryl; or
e) a 4- to 12-membered heterocyclyl;

wherein Y' is optionally substituted with 1-4 substituents independently selected from the group consisting of halo, $C_1$-$C_4$ alkyl, $C_1$-$C_4$ haloalkyl, —$OR^{12}$, —$NR^{12}R^{12}$, —$NR^{12}COR^{12}$, and —$NR^{12}SO_2R^{13}$;

$R^5$ is selected from hydrogen and $C_1$-$C_4$ alkyl;

$R^{10}$, at each occurrence, is independently hydrogen, $C_1$-$C_4$ alkyl, $C_1$-$C_4$ haloalkyl, $C_3$-$C_6$ cycloalkyl, or —$C_1$-$C_3$alkylene-$C_3$-$C_6$ cycloalkyl;

$R^{11}$, at each occurrence, is independently $C_1$-$C_4$ alkyl, $C_1$-$C_4$ haloalkyl, $C_3$-$C_6$ cycloalkyl, or —$C_1$-$C_3$alkylene-$C_3$-$C_6$ cycloalkyl;

$R^{12}$, at each occurrence, is independently hydrogen, $C_1$-$C_4$ alkyl, $C_1$-$C_4$ haloalkyl, $C_3$-$C_6$ cycloalkyl, or —$C_1$-$C_3$alkylene-$C_3$-$C_6$ cycloalkyl; and $R^{13}$, at each occurrence, is independently $C_1$-$C_4$ alkyl, $C_1$-$C_4$ haloalkyl, $C_3$-$C_6$ cycloalkyl, or —$C_1$-$C_3$alkylene-$C_3$-$C_6$ cycloalkyl.

3. The compound of claim 1, or a pharmaceutically acceptable salt thereof, wherein
A is

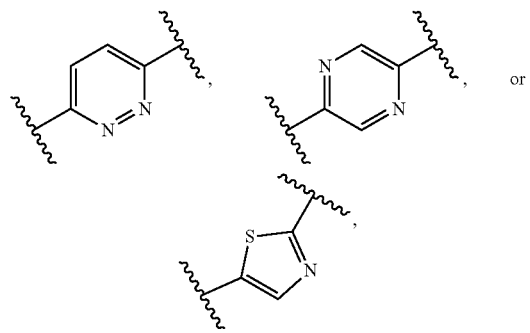

wherein $R^1$-A- is, respectively,

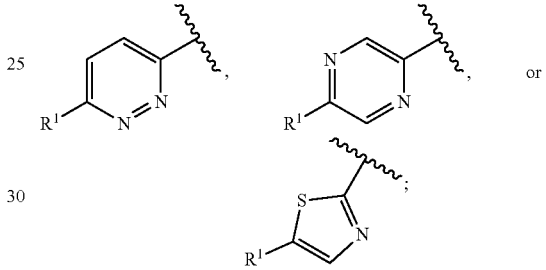

$R^a$ and $R^b$ are hydrogen;
$R^2$ is hydrogen;
$R^3$ is hydrogen; and
$R^5$ is hydrogen.

4. The compound of claim 3, or a pharmaceutically acceptable salt thereof, wherein:

$R^1$ is phenyl or a 9- to 12-membered aryl, and $R^1$ is optionally substituted with 1-4 substituents independently selected from the group consisting of halo, cyano, $C_1$-$C_4$ alkyl, $C_1$-$C_4$ haloalkyl, —$OR^{10}$, —$NR^{10}COR^{10}$, —$CONR^{10}R^{10}$, —$C_1$-$C_3$alkylene-$OR^{10}$, $C_3$-$C_6$ cycloalkyl, and —$C_1$-$C_3$alkylene-$C_3$-$C_6$cycloalkyl;

$R^{10}$, at each occurrence, is independently hydrogen, $C_1$-$C_4$ alkyl, $C_1$-$C_4$ haloalkyl, $C_3$-$C_6$ cycloalkyl, or —$C_1$-$C_3$alkylene-$C_3$-$C_6$ cycloalkyl; and $R^{11}$, at each occurrence, is independently $C_1$-$C_4$ alkyl, $C_1$-$C_4$ haloalkyl, $C_3$-$C_6$ cycloalkyl, or —$C_1$-$C_3$alkylene-$C_3$-$C_6$ cycloalkyl.

5. The compound of claim 4, or a pharmaceutically acceptable salt thereof, wherein
$R^4$ is $C_4$-$C_6$ alkyl.

6. The compound of claim 4, or a pharmaceutically acceptable salt thereof, wherein
$R^4$ is —$(CR^hR^i)_p$—Y';
$R^h$ is hydrogen;
$R^i$ is hydrogen;
p is 0, 1, 2, or 3;
Y' is
a) $C_3$-$C_{10}$ cycloalkyl;
b) $C_3$-$C_8$ cycloalkenyl;

c) a 6- to 12-membered aryl;
d) a 5- to 12-membered heteroaryl; or
e) a 4- to 12-membered heterocyclyl;
wherein Y' is optionally substituted with 1-4 substituents independently selected from the group consisting of halo, $C_1$-$C_4$ alkyl, $C_1$-$C_4$ haloalkyl, —$OR^{12}$, —$NR^{12}R^{12}$, —$NR^{12}COR^{12}$, and —$NR^{12}SO_2R^{13}$;

$R^{12}$, at each occurrence, is independently hydrogen, $C_1$-$C_4$ alkyl, $C_1$-$C_4$ haloalkyl, $C_3$-$C_6$ cycloalkyl, or —$C_1$-$C_3$alkylene-$C_3$-$C_6$ cycloalkyl; and $R^{13}$, at each occurrence, is independently $C_1$-$C_4$ alkyl, $C_1$-$C_4$ haloalkyl, $C_3$-$C_6$ cycloalkyl, or —$C_1$-$C_3$alkylene-$C_3$-$C_6$ cycloalkyl.

7. The compound of claim 6, or a pharmaceutically acceptable salt thereof, wherein Y' is a $C_3$-$C_{10}$ cycloalkyl optionally substituted with 1-4 substituents independently selected from the group consisting of halo, $C_1$-$C_4$ alkyl, and $C_1$-$C_4$ haloalkyl.

8. The compound of claim 6, or a pharmaceutically acceptable salt thereof, wherein Y' is a $C_3$-$C_8$ cycloalkenyl.

9. The compound of claim 6, or a pharmaceutically acceptable salt thereof, wherein Y' is a phenyl or a 9- to 12-membered aryl, and optionally substituted with 1-4 substituents independently selected from the group consisting of halo, $C_1$-$C_4$ alkyl, $C_1$-$C_4$ haloalkyl, —$OR^{12}$, —$NR^{12}R^{12}$, —$NR^{12}COR^{12}$, and —$NR^{12}SO_2R^{13}$.

10. The compound of claim 6, or a pharmaceutically acceptable salt thereof, wherein Y' is a 5- to 6-membered monocyclic heteroaryl or an 8- to 12 membered bicyclic heteroaryl, and optionally substituted with 1-4 substituents independently selected from the group consisting of halo, $C_1$-$C_4$ alkyl, $C_1$-$C_4$ haloalkyl, —$OR^{12}$, —$NR^{12}R^{12}$, —$NR^{12}COR^{12}$, and —$NR^{12}SO_2R^{13}$.

11. A method for antagonizing mAChR $M_4$ in a subject, comprising a step of administering to a subject in need thereof a therapeutically effective amount of a compound of claim 1, or a pharmaceutically acceptable salt thereof.

12. A method for treating a disorder in a subject, wherein the subject would benefit from antagonism of mAChR $M_4$, comprising a step of administering to a subject in need thereof a therapeutically effective amount of a compound of claim 1, or a pharmaceutically acceptable salt thereof.

13. A method for treating motor symptoms in a subject, comprising administering to a subject in need thereof a therapeutically effective amount of the compound of claim 1, or a pharmaceutically acceptable salt thereof.

14. The compound of claim 6, or a pharmaceutically acceptable salt thereof, wherein p is 0.

15. The compound of claim 5, or a pharmaceutically acceptable salt thereof, wherein Q is $NR^a$ and m is 0.

16. The compound of claim 14, or a pharmaceutically acceptable salt thereof, wherein Q is $NR^a$ and m is 0.

17. The compound of claim 5, or a pharmaceutically acceptable salt thereof, wherein Q is $NR^a$ and m is 1.

18. The compound of claim 14, or a pharmaceutically acceptable salt thereof, wherein Q is $NR^a$ and m is 1.

19. The compound of claim 5, or a pharmaceutically acceptable salt thereof, wherein Q is O and m is 0.

20. The compound of claim 14, or a pharmaceutically acceptable salt thereof, wherein Q is O and m is 0.

* * * * *